US011197926B2

(12) United States Patent
Kawaoka et al.

(10) Patent No.: US 11,197,926 B2
(45) Date of Patent: Dec. 14, 2021

(54) RECOMBINANT INFLUENZA VIRUSES WITH STABILIZED HA FOR REPLICATION IN EGGS

(71) Applicants: Wisconsin Alumni Research Foundation (WARF), Madison, WI (US); The University of Tokyo, Tokyo (JP)

(72) Inventors: Yoshihiro Kawaoka, Middleton, WI (US); Shinya Yamada, Bunkyo-ku (JP); Shiho Chiba, Madison, WI (US)

(73) Assignees: Wisconsin Alumni Research Foundation (WARF), Madison, WI (US); The University of Tokyo, Tokyo (JP)

( * ) Notice: Subject to any disclaimer, the term of this patent is extended or adjusted under 35 U.S.C. 154(b) by 0 days.

(21) Appl. No.: 16/170,321

(22) Filed: Oct. 25, 2018

(65) Prior Publication Data
US 2019/0167781 A1 Jun. 6, 2019

Related U.S. Application Data

(60) Provisional application No. 62/577,049, filed on Oct. 25, 2017, provisional application No. 62/633,400, filed on Feb. 21, 2018.

(51) Int. Cl.
| *A61K 39/145* | (2006.01) |
| *A61K 9/00* | (2006.01) |
| *A61P 31/16* | (2006.01) |
| *C07K 14/005* | (2006.01) |
| *C12N 7/00* | (2006.01) |
| *C12N 15/63* | (2006.01) |
| *C12N 9/24* | (2006.01) |

(52) U.S. Cl.
CPC .......... *A61K 39/145* (2013.01); *A61K 9/0019* (2013.01); *A61K 9/0043* (2013.01); *A61P 31/16* (2018.01); *C07K 14/005* (2013.01); *C12N 7/00* (2013.01); *C12N 9/2402* (2013.01); *C12N 15/63* (2013.01); *C12N 2760/16021* (2013.01); *C12N 2760/16022* (2013.01); *C12N 2760/16034* (2013.01); *C12N 2760/16051* (2013.01); *C12Y 302/01018* (2013.01)

(58) Field of Classification Search
None
See application file for complete search history.

(56) References Cited

U.S. PATENT DOCUMENTS

2007/0231348 A1* 10/2007 Kawaoka ............. A61K 39/145
424/209.1
2011/0159031 A1 6/2011 Falkner et al.

FOREIGN PATENT DOCUMENTS

| JP | 2009-523252 A | 6/2009 |
| JP | 2013-507990 A | 3/2013 |
| JP | 2016-500007 A | 1/2016 |
| JP | 2016-524915 A | 8/2016 |
| WO | WO-2011/087839 A1 | 7/2011 |
| WO | WO-2016/207853 A2 | 12/2016 |
| WO | WO-2017/143236 A1 | 8/2017 |

OTHER PUBLICATIONS

"International Application Serial No. PCT US2018 057576, Invitation to Pay Additional Fees and Partial Search Report dated Jan. 31, 2019", 16 pgs.
Ramanunninair, M., "Molecular Signature of High Yield (Growth) Influenza A Virus Reassortants Prepared as Candidate Vaccine Seeds", PLOS ONE, 8(6): e65955, (2013), 1-16.
Wang, W, "Identification of Critical Residues in the Hemagglutinin and Neuraminidase of Influenza Virus H1N1pdm for Vaccine Virus Replication in Embryonated Chicken Eggs", Journal Of Virology., vol. 87, No. 8, (Feb. 13, 2013), 4642-4649.
Yen, H L, "Neuraminidase Inhibitor-Resistant Recombinant A Vietnam 1203 04 (K5N1) Influenza Viruses Retain Their Replication Efficiency and Pathogenicity In Vitro and In Vivo", Journal Of Virology., vol. 81, No. 22, (Nov. 15, 2007), 12418-12426.
"International Application Serial No. PCT/US2018/057576, International Search Report dated Mar. 25, 2019", 7 pgs.
"International Application Serial No. PCT/US2018/057576, Written Opinion dated Mar. 25, 2019", 10 pgs.
Kuwahara, Tomoko, "Characterization of cell-derived and egg-passaged influenza A Saitama 103 2014 (H3N2) strain", The 65th Annual Meeting of the Japanese Society of Virology, (2017), 1 pg.
"International Application Serial No. PCT/US2018/057576, International Preliminary Report on Patentability dated May 7, 2020", 12 pgs.
"European Application Serial No. 18800815.5, Response to Communication pursuant to Rules 161(1) and 162 EPC filed Dec. 15, 2020", 14 pgs.
"Japanese Application Serial No. 2020-523276, Notification of Reasons for Refusal dated Jul. 27, 2021", (w/ English Translation), 12 pgs.

* cited by examiner

*Primary Examiner* — Nicole Kinsey White
(74) *Attorney, Agent, or Firm* — Schwegman Lundberg & Woessner, P.A.

(57) ABSTRACT

Modified influenza virus neuraminidases are described herein that improve viral replication, thus improving the yield of vaccine viruses. Expression of such modified neuraminidases by influenza virus may also stabilize co-expressed hemagglutinins so that the hemagglutinins do not undergo mutation.

18 Claims, 46 Drawing Sheets

Specification includes a Sequence Listing.

A/Yokohama/2017/03 PB2

AGCAAAAGCAGGTCAATTATATTCAGTATGGAAAGAATAAAAGAACTACGGAACCTGATGTCGCAGTCTCGCACT
CGCGA
GATACTGACAAAAACCACAGTGGACCATATGGCCATAATTAAGAAGTACACATCGGGGAGACAGGAAAAGAACC
CGTCAC
TTAGGATGAAATGGATGATGGCAATGAAATACCCAATCACTGCTGACAAAAGGATAACAGAAATGGTTCCGGAGA
GAAAT
GAACAAGGACAAACTCTATGGAGTAAAATGAGTGATGCTGGATCAGATCGAGTGATGGTATCACCTTTGGCTGTG
ACATG
GTGGAATAGAAATGGACCCGTGACAAGTACGGTCCATTACCCAAAAGTATACAAGACTTATTTTGACAAAGTCGA
AAGGT
TAAAACATGGAACCTTTGGCCCTGTTCATTTTAGAAATCAAGTCAAGATACGCCGAAGAGTAGACACAAACCCTGG
TCAT
GCGGACCTCAGTGCCAAGGAGGCACAAGATGTAATTATGGAAGTTGTTTTTCCCAATGAAGTGGGAGCCAGGATA
CTAAC
ATCAGAATCGCAATTAACAATAACTAAAGAGAAAAAAGAAGAACTCCGAGATTGCAAAATTTCTCCCTTGATGGTT
GCAT
ACATGTTAGAGAGAGAACTTGTCCGAAAAACAAGATTTCTCCCAGTTGCTGGCGGAACAAGCAGTATATACATTG
AAGTT
TTACATTTGACTCAAGGGACGTGTTGGGAACAAATGTACACTCCAGGTGGAGAAGTGAGGAATGACGATGTTGAC
CAAAG
CCTAATTATTGCAGCCAGGAACATAGTAAGAAGAGCCGCAGTATCAGCAGATCCACTAGCATCTTTATTGGAGATG
TGCC
ACAGCACACAAATTGGCGGGACAAGGATGGTGGACATTCTTAGACAGAACCCGACTGAAGAACAAGCTGTGGAT
ATATGC
AAGGCTGCAATGGGATTGAGAATCAGCTCATCCTTCAGCTTTGGTGGGTTTACATTTAAAAGAACAAGCGGGTCAT
CAGT
CAAAAAGAGGAAGAAGTGCTTACAGGCAATCTCCAAACATTGAAGATAAGAGTACATGAGGGGTATGAGGAGT
TCACAA
TGGTGGGGAAAAGAGCAACAGCTATACTCAGAAAAGCAACCAGAAGATTGGTTCAGCTCATAGTGAGTGGAAGA
GACGAA

FIG. 1

CAGTCAATAGCCGAAGCAATAATTGTGGCCATGGTGTTTTCACAAGAGGATTGCATGATAAAAGCAGTTAGAGGTGACCT

GAATTTCGTCAACAGAGCAAATCAGCGGTTGAACCCCATGCATCAGCTTTTAAGGCATTTTCAGAAAGATGCGAAAGTGC

TTTTTCAGAATTGGGGAATTGAACACATCGACAGTGTAATGGGAATGGTTGGAGTATTACCAGATATGACTCCAAGCACA

GAGATGTCAATGAGAGGAATAAGAGTCAGCAAAATGGGTGTGGATGAATACTCCAGTACAGAGAGGGTGGTGGTTAGCAT

TGATCGGTTTTTGAGAGTTCGAGACCAACGCGGGAATGTATTATTATCTCCTGAAGAGGTTAGTGAAACACAGGGAACTG

AGAGACTGACAATAACTTATTCATCGTCGATGATGTGGGAGATTAACGGTCCTGAGTCGGTTTTGGTCAATACTTATCAA

TGGATCATCAGAAATTGGGAAGCTGTCAAAATTCAATGGTCTCAGAATCCTGCAATGTTGTACAACAAAATGGAATTTGA

ACCATTTCAATCTTTAGTCCCCAAGGCCATTAGAAGCCAATACAGTGGGTTTGTCAGAACTCTATTCCAACAAATGAGAG

ACGTACTTGGGACATTTGACACCACCCAGATAATAAAGCTTCTCCCTTTTGCAGCCGCTCCACCAAAGCAAAGCAGAATG

CAGTTCTCTTCACTGACTGTAAATGTGAGGGGATCAGGGATGAGAATACTTGTAAGGGGCAATTCTCCTGTATTCAACTA

CAACAAGACCACTAAAAGACTAACAATTCTCGGAAAAGATGCCGGCACTTTAATTGAAGACCCAGATGAAAGCACATCCG

GAGTGGAGTCCGCTGTATTGAGAGGGTTTCTCATTATAGGTAAGGAAGACAGAAGATACGGGCCAGCATTAAGCATCAAT

GAACTGAGTAACCTTGCAAAAGGGGAAAAGGCTAATGTGCTAATCGGGCAAGGAGACGTGGTGTTGGTAATGAAACGAAA

ACGGGACTCTAGCATACTTACTGACAGCCAGACAGCGACCAAAAGAATTCGGATGGCCATCAATTAATGTTGAATAGTTT

AAAAACGACCTTGTTTCTACT (SEQ ID NO:4)

<u>A/Yokohama/2017/03 PB1</u>

AGCAAAAGCAGGCAAACCATTTGAATGGATGTCAATCCGACTCTACTGTTCCTAAAGGTTCCAGCGCAAAATGCCATAAG

```
CACCACATTCCCTTATACTGGAGATCCTCCATACAGCCATGGAACAGGAACAGGGTACACCATGGACACAGTCAAC
AGAA
CACACCAATATTCAGATAAGGGGAAGTGGACGACAAATACAGAAACTGGGGCACCCCAACTCAACCCAATTGATG
GACCA
CTACCTGAGGATAATGAGCCAAGTGGATATGCACAAACAGACTGTGTCCTGGAGGCTATGGCCTTCCTTGAAGAA
TCCCA
CCCAGGTATCTTTGAGAACTCATGCCTTGAAACAATGGAAGTCGTTCAACAAACAAGGGTGGACAAACTAACCCA
AGGTC
GCCAGACTTATGATTGGACATTAAACAGAAATCAACCGGCAGCAACTGCATTAGCCAACACCATAGAAGTTTTTAG
ATCG
AATGGACTAACAGCTAATGAATCAGGAAGGCTAATAGATTTCCTCAAGGATGTGATGGAATCAATGGATAAAGAG
GAAAT
GGAGATAACAACACACTTTCAAAGAAAAAGGAGAGTAAGAGACAACATGACCAAGAAAATGGTCACACAAAGAA
CAATAG
GGAAGAAAAACAAAGAGTGAATAAGAGAGGCTATCTAATAAGAGCTTTGACATTGAACACGATGACCAAAGAT
GCAGAG
AGAGGTAAATTAAAAA GAAGGGCTATTGCAACACCCGGGATGCAAATTAGAGGGTTCGTGTACTTCGTTGAAACT
TTAGC
TAGAAGCATTTGCGAAAAGCTTGAACAGTCTGGACTTCCGGTTGGGGGTAATGAAAAGAAGGCCAAACTGGCAA
ATGTTG
TGAGAAAAATGATGACTAATTCACAAGACACAGAGCTTTCTTTCACAATCACTGGGGACAACACTAAGTGGAATG
AAAAT
CAAAACCCTCGAATGTTTTTGGCGATGATTACATATATCACAAAAAATCAACCTGAGTGGTTCAGAAACATCCTGA
GCAT
CGCACCAATAATGTTCTCAAACAAAATGGCAAGACTGGGAAAAGGATACATGTTCGAGAGTAAGAGAATGAAACT
CCGAA
CACAAATACCCGCAGAAATGCTAGCAAACATTGACCTGAAGTATTTCAATGAATCAACAAGGAAGAAAATTGAGA
AAATA
AGGCCTCTTCTAATAGATGGCACAGCATCATTGAGCCCTGGGATGATGATGGGCATGTTCAACATGCTAAGTACG
GTTTT
AGGAGTCTCGATACTGAATCTTGGGCAAAAGAAATACACCAAGACAACATACTGGTGGGATGGGCTCCAATCCTC
CGACG
ATTTTGCCCTCATAGTGAATGCACCAAATCATGAGGGAATACAAGCAGGAGTGGATAGATTTTACAGGACCTGCA
AGTTA
```

FIG. 1(Continued)

GTGGGAATCAACATGAGCAAAAAGAAGTCCTATATAAATAAAACAGGGACATTTGAATTCACAAGCTTTTTTTATCGATA

TGGATTTGTGGCTAATTTTAGCATGGAGCTGCCCAGTTTTGGAGTGTCTGGAATAAACGAGTCAGCTGATATGAGCATTG

GAGTAACAGTGATAAAGAACAACATGATAAACAATGACCTTGGACCAGCAACAGCCCAGATGGCTCTCCAATTGTTCATC

AAAGACTACAGATATACATATAGGTGCCATAGAGGAGACACACAAATTCAGACGAGAAGATCATTCGAGCTAAAGAAGCT

GTGGGATCAAACCCAATCAAGGGCAGGACTATTGGTATCAGATGGGGGACCAAACTTATACAATATCCGGAATCTTCACA

TCCCTGAAGTCTGCTTAAAGTGGGAGCTAATGGATGAGAATTATCGGGGAAGACTTTGTAATCCCCTGAATCCCTTTGTC

AGCCATAAAGAAATTGAGTCTGTAAACAATGCTGTAGTGATGCCAGCCCATGGTCCGGCCAAAAGTATGGAATATGATGC

CGTTGCAACTACACACTCCTGGATTCCCAAGAGGAACCGCTCTATTCTCAACACAAGCCAAAGGGGAATTCTTGAGGATG

AACAGATGTACCAGAAGTGCTGCAACTTGTTCGAGAAATTTTTCCCTAGTAGTTCATATAGGAGACCGATTGGAATTTCT

AGCATGGTGGAGGCCATGGTGTCTAGGGCCCGGATTGATGCCAGAATTGACTTCGAGTCTGGACGGATTAAGAAGGAAGA

GTTCTCTGAGATCATGAAGATCTGTTCCACCATTGAAGAACTCAGACGGCAAAAATAATGAATTTAGCTTGTCCTTCATG

AAAAAATGCCTTGTTTCTACT (SEQ ID NO:5)

<u>A/Yokohama/2017/03 PA</u>

AGCAAAAGCAGGTACTGATTCGAAATGGAAGATTTTGTGCGACAATGCTTCAACCCGATGATTGTCGAACTTGCAGAAAA

AGCAATGAAAGAGTATGGGGAGGATCTGAAAATTGAAACAAACAAATTTGCAGCAATATGCACTCACTTGGAGGTATGTT

TCATGTATTCAGATTTTCATTTCATCAATGAACAAGGCGAATCAATAGTGGTAGAACTTGATGATCCAAATGCACTGTTA

AAGCACAGATTTGAAATAATCGAGGGGAGAGACAGAACAATGGCCTGGACAGTAGTAAACAGTATCTGCAACACTACTGG

```
AGCTGAAAAACCGAAGTTTCTACCAGATTTGTATGATTACAAGGAGAACAGATTCATCGAAATTGGAGTGACAAG
GAGAG
AAGTCCACATATATTACCTTGAAAAGGCCAATAAGATTAAATCTGAGAACACACACATTCACATTTTCTCATTCACT
GGG
GAGGAAATGGCCACAAAGGCAGACTACACTCTCGACGAGGAAAGCAGGGCTAGGATTAAGACCAGGCTATTTAC
CATAAG
ACAAGAAATGGCCAACAGAGGCCTCTGGGATTCCTTTCGTCAGTCCGAAAGAGGCGAAGAAACAATTGAAGAAA
AATTTG
AAATCTCAGGAACTATGCGTAGGCTTGCCGACCAAAGTCTCCCACCGAACTTCTCCTGCCTTGAGAATTTTAGAGC
CTAT
GTGGATGGATTCGAACCGAACGGCTGCATTGAGGGCAAGCTTTCTCAAATGTCCAAAGAAGTGAATGCCCAAATT
GAACC
TTTTCTGAAGACAACACCAAGACCAATCAAACTTCCGAATGGACCTCCTTGTTATCAGCGGTCCAAGTTCCTCCTGA
TGG
ATGCTTTAAAATTGAGCATTGAAGACCCAAGTCACGAAGGAGAAGGGATCCCATTATATGATGCGATCAAGTGCA
TAAAA
ACATTCTTTGGATGGAAAGAACCTTATATAGTCAAACCACACGAAAAGGGAATAAATTCAAATTACCTGCTGTCAT
GGAA
GCAAGTATTGTCAGAATTGCAGGACATTGAAAATGAGGAGAAGATTCCAAGGACTAAAAACATGAAGAAAACGA
GTCAAC
TAAAGTGGGCTCTTGGTGAGAACATGGCACCAGAGAAAGTAGACTTTGAAAACTGCAGAGACATAAGCGATTTGA
AGCAA
TATGATAGTGACGAACCTGAATTAAGGTCACTTTCAAGCTGGATACAGAATGAGTTCAACAAGGCCTGCGAGCTA
ACTGA
TTCAATCTGGATAGAGCTCGATGAAATTGGAGAGGACGTAGCCCCAATTGAATACATTGCAAGCATGAGGAGGAA
TTATT
TCACAGCAGAGGTGTCCCATTGTAGAGCCACTGAGTACATAATGAAGGGGGTATACATTAATACTGCCCTGCTCAA
TGCA
TCCTGTGCAGCAATGGACGATTTTCAACTAATTCCCATGATAAGCAAGTGCAGAACTAAAGAGGGAAGGCGAAAA
ACCAA
TTTATATGGATTCATCATAAAGGGAAGATCTCATTTAAGGAATGACACAGATGTGGTAAACTTTGTGAGCATGGAG
TTTT
CTCTCACTGACCCGAGACTTGAGCCACATAAATGGGAGAAATACTGTGTCCTTGAGATAGGAGATATGTTACTAAG
AAGT
```

FIG. 1(Continued)

GCCATAGGCCAAATTTCAAGGCCTATGTTCTTGTATGTGAGGACAAACGGAACATCAAAGGTCAAAATGAAATGGGGAAT

GGAGATGAGACGTTGCCTCCTTCAGTCACTCCAGCAGATCGAGAGCATGATTGAAGCCGAGTCCTCGGTTAAAGAGAAAG

ACATGACCAAAGAGTTTTTTGAGAATAAATCAGAAGCATGGCCCATTGGGGAGTCCCCCAAGGGAGTGGAAGAAGGTTCC

ATTGGGAAAGTCTGTAGGACTCTATTGGCTAAGTCAGTGTTCAATAGCCTGTATGCATCACCACAATTGGAAGGATTTTC

AGCGGAGTCAAGAAAACTGCTCCTTGTTGTTCAGGCTCTTAGGGACAACCTCGAACCTGGGACCTTTGATCTTGGGGGGC

TATATGAAGCAATTGAGGAGTGCCTGATTAATGATCCCTGGGTTTTGCTCAATGCGTCTTGGTTCAACTCCTTCCTGACA

CATGCATTAAAATAGTTATGGCAGTGCTACTATTTGTTATCCGTACTGTCCAAAAAAGTACCTTGTTTCTACT (SEQ ID NO:6)

A/Yokohama/2017/03 HA

AGCAAAAGCAGGGGATAATTCTATTAACCATGAAGACTATCATTGCTTTGAGCTACATTCTATGTCTGGTTTTCGCTCAA

AAGCTTCCCGGAAATGACAACAGCACGGCAACGCTGTGCCTTGGGCACCATGCAGTACCAAACGGAACGATAGTGAAAAC

AATCACGAATGACCAAATTGAAGTTACTAATGCTACTGAGCTGGTTCAGAGTTCCTCAACAGGTGGAATATGCGACAGTC

CTCATCAGATCCTTGATGGAGAAAACTGCACACTAATAGATGCTCTATTGGGAGACCCTCAGTGTGATGGCTTCCAAAAT

AAGAAATGGGACCTTTTTGTTGAACGCAGCAAAGCCTACAGCAACTGTTACCCTTATGATGTGCCGGATTATGCCTCCCT

TAGGTCACTAGTTGCCTCATCCGGCACACTGGAGTTTAACAATGAAAGCTTCAATTGGACTGGAGTCACTCAGAATGGAA

CAAGCTCTGCTTGCAAAAGGAGATCTAATAAAAGTTTCTTTAGTAGATTGAATTGGTTGACCCACTTAAAATACAAATAC

CCAGCATTGAACGTGACTATGCCAAACAATGAAAAATTTGACAAATTGTACATTTGGGGGGTTCACCACCCGGGTACGGA

CAGTGATCAAATCAGCCTATATGCTCAAGCATCAGGAAGAATCACAGTCTCTACCAAAAGAAGCCAACAAACTGTAATCC
CGAATATCGGATCTAGACCCAGGGTAAGGGATGTCTCCAGCAGAATAAGCATCTATTGGACAATAGTAAAACCGGGAGAC
ATACTTTTGATTAACAGCACAGGGAATCTAATTGCTCCTCGGGGTTACTTCAAAATACGAAGTGGGAAAAGCTCAATAAT
GAGATCAGATGCACCCATTGGCAAATGCAATTCTGAATGCATCACTCCAAATGGAAGCATTCCCAATGACAAACCATTTC
AAAATGTAAACAGGATCACATATGGGGCCTGTCCCAGATATGTTAAGCAAAACACTCTGAAATTGGCAACAGGGATGCGA
AATGTACCAGAGAAACAAACTAGAGGCATATTTGGCGCAATCGCGGGTTTCATAGAAAATGGTTGGGAGGGAATGGTGGA
CGGTTGGTACGGTTTCAGGCATCAAAATTCTGAGGGCACAGGACAAGCAGCAGATCTCAAAAGCACTCAAGCAGCAATCA
ACCAAATCAATGGGAAACTGAATAGGTTAATCGGGAAAACAAACGAGAAATTCCATCAGATTGAAAAGAATTCTCAGAA
GTAGAAGGGAGAATTCAGGACCTCGAGAAATATGTTGAGGACACTAAAATAGATCTCTGGTCATACAACGCGGAGCTTCT
TGTTGCCCTGGAGAACCAACATACAATTGATCTAACTGACTCAGAAATGAACAAACTGTTTGAAAGAACAAAGAAGCAAC
TGAGGGAAAATGCTGAGGATATGGGCAATGGTTGTTTCAAAATATACCACAAATGTGACAATGCCTGCATAGAGTCAATC
AGAAATGGAACTTATGACCATGATGTATACAGAGATGAAGCATTAAACAACCGGTTCCAGATCAAAGGTGTTGAGCTGAA
GTCAGGATACAAAGATTGGATCCTATGGATTTCCTTTGCCATATCATGTTTTTTGCTCTGTGTTGCTTTGTTGGGGTTCA
TCATGTGGGCCTGCCAAAAAGGCAACATTAGGTGCAACATTTGCATTTGAGTGCATTAATTAAAAACACCCTTGTTTCTACT (SEQ ID NO:7)

<u>A/Yokohama/2017/03 NP</u>

AGCAAAAGCAGGGTTAATAATCACTCACTGAGTGACATCAAAATCATGGCGTCCCAAGGCACCAAACGGTCTTATGAACA

GATGGAAACTGATGGGGATCGCCAGAATGCAACTGAGATTAGGGCATCCGTCGGGAAGATGATTGATGGAATTGGGAGAT

TCTACATCCAAATGTGCACTGAACTTAAACTCAGTGATTATGAAGGGCGGTTGATCCAGAACAGCTTGACAATAGAGAAA

ATGGTGCTCTCTGCTTTTGATGAAAGAAGGAATAAATATCTGGAAGAACACCCCAGCGCGGGGAAAGATCCTAAGAAAAC

TGGGGGGCCCATATACAGGAGAGTAGATGGAAAATGGATGAGGGAACTCGTCCTTTATGACAAAGAAGAAATAAGGCGAA

TCTGGCGCCAAGCCAACAATGGTGAGGATGCGACAGCTGGTCTAACTCACATAATGATCTGGCATTCCAATTTGAATGAT

GCAACATACCAGAGGACAAGAGCTCTTGTTCGAACCGGAATGGATCCCAGAATGTGCTCTCTGATGCAGGGCTCGACTCT

CCCTAGAAGGTCCGGAGCTGCAGGTGCTGCAGTCAAAGGAATCGGGACAATGGTGATGGAGCTGATCAGAATGGTCAAAC

GGGGGATCAACGATCGAAATTTCTGGAGAGGTGAGAATGGGCGGAAAACAAGAAGTGCTTATGAGAGAATGTGCAACATT

CTTAAAGGAAAATTTCAAACAGCTGCACAAAGAGCAATGGTGGATCAAGTGAGAGAAAGTCGGAACCCAGGAAATGCTGA

GATCGAAGATCTCATATTTTTGGCAAGATCTGCATTGATATTGAGAGGATCAGTTGCTCACAAATCTTGCCTACCTGCCT

GTGTGTATGGACCTGCAGTATCCAGTGGGTACGACTTCGAAAAGAGGGATATTCCTTGGTGGGAATAGACCCTTTCAAA

CTACTTCAAAATAGCCAAGTATACAGCCTAATCAGACCTAACGAGAATCCAGCACACAAGAGTCAGCTGGTATGGATGGC

ATGCCATTCTGCTGCATTTGAAGATTTAAGATTGTTAAGCTTCATCAGAGGGACAAAAGTATCTCCACGAGGGAAACTTT

CAACTAGAGGAGTACAAATTGCTTCAAATGAGAACATGGATAATATGGGATCGAGCACTCTTGAACTGAGAAGCGGGTAC

TGGGCCATAAGGACCAGGAGTGGAGGAAACACTAATCAACAGAGGGCCTCCGCAGGCCAAACCAGTGTGCAACCTACGTT

TTCTGTACAAAGAAACCTCCCATTTGAAAAGTCAACCATCATGGCAGCATTCACTGGAAATACGGAGGGAAGAACTTCAG

ACATGAGGGCAGAAATCATAAGAATGATGGAAGGTGCAAAACCAGAAGAAGTGTCGTTCCGGGGGAGGGGAGTTTTCGAG

FIG. 1(Continued)

CTCTCAGACGAGAAGGCAACGAACCCGATCGTGCCCTCTTTTGATATGAGTAATGAAGGATCTTATTTCTTCGGAGACAA
TGCAGAAGAGTACGACAATTAAGGAAAAATACCCTTGTTTCTACT (SEQ ID NO:8)

A/Yokohama/2017/03 NA

AGCAAAAGCAGGAGTAAAGATGAATCCAAATCAAAAGATAATAACGATTGGCTCTGTTTCCCTCACCATTTCCACAATAT
GCTTCTTCATGCAAATTGCCATCCTGATAACTACTGTAACATTGCATTTCAAGCAATATGAATTCAACTCCCCCCCAAAC
AACCAAGTGATGCTGTGTGAACCAACAATAATAGAAAGAAACATAACAGAGATAGTGTATCTGACCAACACCACCATAGA
GAAGGAAATATGCCCCAAACTAGCAGAATACAGAAATTGGTCAAAGCCGCAATGTAACATTACAGGATTTGCACCTTTTT
CTAAGGACAATTCGATTCGGCTTTCCGCTGGTGGGGACATCTGGGTGACAAGAGAACCTTATGTGTCATGCGATCCTGAC
AAGTGTTATCAATTTGCCCTTGGACAGGGAACAACACTAAACAACGTGCATTCAAATGACATAGTACATGATAGGACCCC
TTATCGGACCCTATTGATGAATGAGTTGGGTGTTCCATTTCATCTGGGGACCAAGCAAGTGTGCATAGCATGGTCCAGCT
CAAGTTGTCACGATGGAAAAGCATGGCTGCATGTTTGTGTAACGGGGGATGATGAAAATGCAACTGCTAGCTTCATTTAC
AATGGGAGGCTTGCAGATAGTATTGTTTCATGGTCCAAAAAAATCCTCAGGACCCAGGAGTCAGAATGCGTTTGTATCAA
TGGAACTTGTACAGTAGTAATGACTGATGGGAGTGCTTCAGGAAAAGCTGATACTAAAATACTATTCATTGAGGAGGGGA
AAATTGTTCATACTAGCACATTATCAGGAAGTGCTCAGCATGTCGAGGAGTGCTCCTGTTATCCTCGATATCCTGGTGTC
AGATGTGTCTGCAGAGACAACTGGAAAGGCTCCAATAGGCCCATCGTAGATATAAACATAAAGGATTATAGCATTGTTTC
CAGTTATGTGTGCTCAGGACTTGTTGGAGACACACCCAGAAAAAACGACAGCTCCAGCAGTAGCCATTGCTTGGATCCAA
ACAATGAGGAAGGTGGTCATGGAGTGAAAGGCTGGGCCTTTGATGATGGAAATGACGTGTGGATGGGAAGAACGATCAGC

FIG. 1(Continued)

GAGAAGTTACGCTCAGGATATGAAACCTTCAAAGTCATTGAAGGCTGGTCCAACCCTAACTCCAAATTGCAGATAA
ATAG

GCAAGTCATAGTTGACAGAGGTAACAGGTCCGGTTATTCTGGTATTTTCTCTGTTGAAGGCAAAAGCTGCATCAAT
CGGT

GCTTTTATGTGGAGTTGATAAGGGGAAGAAAACAGGAAACTGAAGTCTTGTGGACCTCAAACAGTATTGTTGTGT
TTTGT

GGCACCTCAGGTACATATGGAACAGGCTCATGGCCTGATGGGGCGGACATCAATCTCATGCCTATATAAGCTTTCG
CAAT

TTTAGAAAAAACTCCTTGTTTCTACT (SEQ ID NO:9)

Which encodes M N P N Q K I I T I G S V S L T I S T I C F F M Q I A I L I T T V T L H F K Q Y E
F N S P P N N Q V M L C E P T I I E R N I T E I V Y L T N T T I E K E I C P K L A E Y R N W S
K P Q C N I T G F A P F S K D N S I R L S A G G D I W V T R E P Y V S C D P D K C Y Q F A L
G Q G T T L N N V H S N D I V H D R T P Y R T L L M N E L G V P F H L G T K Q V C I A W
S S S S C H D G K A W L H V C V T G D D E N A T A S F I Y N G R L A D S I V S W S K K I L
R T Q E S E C V C I N G T C T V V M T D G S A S G K A D T K I L F I E E G K I V H T S L S
G S A Q H V E E C S C Y P R Y P G V R C V C R D N W K G S N R P I V D I N I K D Y S I V S S
Y V C S G L V G D T P R K N D S S S S H C L D P N N E E G G H G V K G W A F D D G N D
V W M G R T I S E K L R S G Y E T F K V I E G W S N P N S K L Q I N R Q V I V D R G N R S
G Y S G I F S V E G K S C I N R C F Y V E L I R G R K Q E T E V L W T S N S I V V F C G T S G
T Y G T G S W P D G A D I N L M P I (SEQ ID NO:3)

A/Yokohama/2017/03 M

AGCAAAAGCAGGTAGATATTGAAAGATGAGCCTTCTAACCGAGGTCGAAACGTATGTTCTCTCTATCGTTCCATCA
GGCC

CCCTCAAAGCCGAGATCGCGCAGAGACTTGAAGATGTCTTTGCTGGGAAAAACACAGATCTTGAGGCTCTCATGG
AATGG

CTAAAGACAAGACCAATTCTGTCACCTCTGACTAAGGGGATTCTGGGGTTTGTGTTCACGCTCACCGTGCCCAGTG
AGCG

AGGACTGCAGCGTAGACGCTTTGTCCAAAATGCCCTCAATGGGAATGGAGATCCAAATAACATGGACAAAGCAGT
TAAAC

TGTATAGGAAACTTAAGAGGGAGATAACGTTCCATGGGGCCAAAGAAATAGCTCTCAGTTATTCTGCTGGTGCAC
TTGCC

FIG. 1(Continued)

AGTTGCATGGGCCTCATATACAATAGGATGGGGGCTGTAACCACTGAAGTGGCATTTGGCCTGGTATGTGCAACATGTGA
GCAGATTGCTGACTCCCAGCACAGGTCTCATAGGCAAATGGTGGCAACAACCAATCCATTAATAAGGCATGAGAACAGAA
TGGTTTTGGCCAGCACTACAGCTAAGGCTATGGAGCAAATGGCTGGATCAAGTGAGCAGGCAGCGGAGGCCATGGAGATT
GCTAGTCAGGCCAGGCAAATGGTGCAGGCAATGAGAGCCATTGGGACTCATCCTAGCTCCAGTACTGGTCTAAGAGATGA
TCTTCTTGAAAATTTGCAGACCTATCAGAAACGAATGGGGGTGCAGATGCAACGATTCAAGTGACCCACTTGTTGTTGCC
GCGAGTATCATTGGGATCTTGCACTTGATATTGTGGATTCTTGATCGTCTTTTTTTCAAATGCGTCTATCGACTCTTCAA
ACACGGCCTTAAAAGAGGCCCTTCTACGGAAGGAGTACCTGAGTCTATGAGGGAAGAGTATCGAAAGGAACAGCAGAATG (SEQ ID NO:10)

CTGTGGATGCTGACGACAGTCATTTTGTCAGCATAGAGTTGGAGTAAAAAACTACCTTGTTTCTACT

A/Yokohama/2017/03 NS

AGCAAAAGCAGGGTGACAAAGACATAATGGATTCCAACACTGTGTCAAGTTTCCAGGTAGATTGCTTTCTTTGGCATATC
CGGAAACAAGTTGTAGACCAAGAACTGAGTGATGCCCCATTCCTTGATCGGCTTCGCCGAGATCAGAGGTCCCTAAGGGG
AAGAGGCAATACTCTCGGTCTAGACATCAAAGCAGCCACCCATGTTGGAAAGCAAATTGTAGAAAAGATTCTGAAAGAAG
AATCTGATGAGGCACTTAAAATGACCATGGTCTCCACACCTGCTTCGCGATACATAACTGACATGACTATTGAGGAATTG
TCAAGAAACTGGTTCATGCTAATGCCCAAGCAGAAAGTGGAAGGACCTCTTTGCATCAGAATGGACCAGGCAATCATGGA
GAAAAACATCATGTTGAAAGCGAATTTCAGTGTGATTTTTGACCGACTAGAGACCATAGTATTACTAAGGGCTTTCACCG
AAGAGGGAGCAATTGTTGGCGAAATCTCACCATTGCCTTCTTTTCCAGGACATACTATTGAGGATGTCAAAAATGCAATT

GGGGTCCTCATCGGAGGACTTGAATGGAATGATAACACAGTTCGAGTCTCTAAAAATCTACAGAGATTCGCTTGG
AGAAG
CAGTAATGAGAATGGGGGACCTCCACTTACTCCAAAACAGAAACGGAAAATGGCGAGAACAGCTAGGTCAAAAG
TTTGAA
GAGATAAGATGGCTGATTGAAGAAGTGAGACACAGACTAAAAACAACTGAAAATAGCTTTGAACAAATAACATTC
ATGCA
AGCATTACAACTGCTGTTTGAAGTGGAACAGGAGATAAGAACTTTCTCATTTCAGCTTATTTAATGATAAAAAACA
CCCT
TGTTTCTACT (SEQ ID NO:11)

FIG. 1(Continued)

MNPNQKIITIGSVSLTISTICFFMQIAILITTVTLHFKQYEFNSPPNNQVMLCEPTIIERNVTEIVYLTNTTIEKEI
CPKPAEYRNWSKPQCGITGFAPFSKDNSIRLSAGGDIWVTREPYVSCDPDKCYQFALGQGTTLNNVHSNNTVRDRTP
YRTLLMNELGVPFHLGTKQVCIAWSSSSCHDGKAWLHVCITGDDKNATASFIYNGRLVDSVVSWSKDILRTQESECV
CINGTCTVVMTDGSASGKADTKILFIEEGKIVHTSKLSGSAQHVEECSCYPRYPGVRCVCRDNWKGSNRPIVDINIK
DHSIVSSYVCSGLVGDTPRKNDSSSSSHCLDPNNEEGGHGVKGWAFDDGNDVWMGRTINETSRLGYETFKVVEGWSN
PKSKLQINRQVIVDRGDRSGYSGIFSVEGKSCINRCFYVELIRGRKEETEVLWTSNSIVVFCGTSGTYGTGSWPDGA
DLNLMPI (SEQ ID NO:2)

FIG. 2

>Y2017M3L4-NA(32A, 147N, 329D, 347Q, del46-50aa)
ATGAATCCAAATCAAAAGATAATAACGATTGGCTCTGTTTCCCTCACCATTTCCACAATA
TGCTTCTTCATGCAAATTGCCATCCTGATAACTGCTGTAACATTGCATTTCAAGCAATAT
GAATTCAACTCCCCCATGCTGTGTGAACCAACAATAATAGAAAGAAACATAACAGAGATA
GTGTATCTGACCAACACCACCATAGAGAAGGAAATATGCCCCAAACTAGCAGAATACAGA
AATTGGTCAAAGCCGCAATGTAACATTACAGGATTTGCACCTTTTTCTAAGGACAATTCG
ATTCGGCTTTCCGCTGGTGGGGACATCTGGGTGACAAGAGAACCTTATGTGTCATGCGAT
CCTGACAAGTGTTATCAATTTGCCCTTGGACAGGGAACAACACTAAACAACGTGCATTCA
AATAACATAGTACATGATAGGACCCCTTATCGGACCCTATTGATGAATGAGTTGGGTGTT
CCATTTCATCTGGGGACCAAGCAAGTGTGCATAGCATGGTCCAGCTCAAGTTGTCACGAT
GGAAAAGCATGGCTGCATGTTTGTGTAACGGGGGATGATGAAAATGCAACTGCTAGCTTC
ATTTACAATGGGAGGCTTGCAGATAGTATTGTTTCATGGTCCAAAAAAATCCTCAGGACC
CAGGAGTCAGAATGCGTTTGTATCAATGGAACTTGTACAGTAGTAATGACTGATGGGAGT
GCTTCAGGAAAAGCTGATACTAAATACTATTCATTGAGGAGGGGAAAATTGTTCATACT
AGCACATTATCAGGAAGTGCTCAGCATGTCGAGGAGTGCTCCTGTTATCCTCGATATCCT
GGTGTCAGATGTGTCTGCAGAGACAACTGGAAAGGCTCCAATAGGCCCATCGTAGATATA
AACATAAAGGATTATAGCATTGTTTCCAGTTATGTGTGCTCAGGACTTGTTGGAGACACA
CCCAGAAAAGACGACAGCTCCAGCAGTAGCCATTGCTTGGATCCAAACAATGAGGAAGGT
GGTCAAGGAGTGAAAGGCTGGGCCTTTGATGATGGAAATGACGTGTGGATGGGAAGAACG
ATCAGCGAGAAGTTACGCTCAGGATATGAAACCTTCAAAGTCATTGAAGGCTGGTCCAAC
CCTAACTCCAAATTGCAGATAAATAGGCAAGTCATAGTTGACAGAGGTAACAGGTCCGGT
TATTCTGGTATTTTCTCTGTTGAAGGCAAAAGCTGCATCAATCGGTGCTTTTATGTGGAG
TTGATAAGGGGAAGAAAACAGGAAACTGAAGTCTTGTGGACCTCAAACAGTATTGTTGTG
TTTTGTGGCACCTCAGGTACATATGGAACAGGCTCATGGCCTGATGGGGCGGACATCAAT
CTCATGCCTATATAAGCTTTCGCAATTTTAGAAAAAAACTCCTTGTTTCTACT (SEQ ID NO:12)

M N P N Q K I I T I G S V S L T I S T I C F F M Q I A I L I T A V T L H F K Q
Y E F N S P M L C E P T I I E R N I T E I V Y L T N T T I E K E I C P K L A E
Y R N W S K P Q C N I T G F A P F S K D N S I R L S A G G D I W V T R E P
Y V S C D P D K C Y Q F A L G Q G T T L N N V H S N N I V H D R T P Y R
T L L M N E L G V P F H L G T K Q V C I A W S S S C H D G K A W L H V
C V T G D D E N A T A S F I Y N G R L A D S I V S W S K K I L R T Q E S E
C V C I N G T C T V V M T D G S A S G K A D T K I L F I E E G K I V H T S
T L S G S A Q H V E E C S C Y P R Y P G V R C V C R D N W K G S N R P I
V D I N I K D Y S I V S S Y V C S G L V G D T P R K D D S S S S H C L D
P N N E E G G Q G V K G W A F D D G N D V W M G R T I S E K L R S G Y
E T F K V I E G W S N P N S K L Q I N R Q V I V D R G N R S G Y S G I F S
V E G K S C I N R C F Y V E L I R G R K Q E T E V L W T S N S I V V F C G
T S G T Y G T G S W P D G A D I N L M P I (SEQ ID NO:1)

>Y2017M3L4HA
ATGAAGACTATCATTGCTTTGAGCTACATTCTATGTCTGGTTTTCGCTCAAAAGCTTCCC
GGAAATGACAACAGCACGGCAACGCTGTGCCTTGGGCACCATGCAGTACCAAACGGAACG
ATAGTGAAAACAATCACGAATGACCAAATTGAAGTTACTAATGCTACTGAGCTGGTTCAG
AGTTCCTCAACAGGTGGAATATGCGACAGTCCTCATCAGATCCTTGATGGAGAAAACTGC
ACACTAATAGATGCTCTATTGGGAGACCCTCAGTGTGATGGCTTCCAAAATAAGAAATGG

FIG. 3

GACCTTTTTGTTGAACGCAGCAAAGCCTACAGCAACTGTTACCCTTATGATGTGCCGGAT
TATGCCTCCCTTAGGTCACTAGTTGCCTCATCCGGCACACTGGAGTTTAACAATGAAAGC
TTCAATTGGACTGGAGTCACTCAGAATGGAACAAGCTCTGCTTGCAAAAGGAGATCTAAT
AAAAGTTTCTTTAGTAGATTGAATTGGTTGACCCACTTAAAATACAAATACCCAGCATTG
AACGTGACTATGCCAAACAATGAAAAATTTGACAATTGTACATTTGGGGGGTTCACCAC
CCGGGTACGGACAGTGATCAAATCAGCCTATATGCTCAAGCATCAGGAAGAATCACAGTC
TCTACCAAAAGAAGCCAACAAACTGTAATCCCGAATATCGGATCTAGACCCAGGGTAAGG
GATGTCTCCAGCAGAATAAGCATCTATTGGACAATAGTAAAACCGGGAGACATACTTTTG
ATTAACAGCACAGGGAATCTAATTGCTCCTCGGGGTTACTTCAAAATACGAAGTGGGAAA
AGCTCAATAATGAGATCAGATGCACCCATTGGCAAATGCAATTCTGAATGCATCACTCCA
AATGGAAGCATTCCCAATGACAAACCATTTCAAAATGTAAACAGGATCACATATGGGGCC
TGTCCCAGATATGTTAAGCAAAACACTCTGAAATTGGCAACAGGGATGCGAAATGTACCA
GAGAAACAAACTAGAGGCATATTTGGCGCAATCGCGGGTTTCATAGAAATGGTTGGGAG
GGAATGGTGGACGGTTGGTACGGTTTCAGGCATCAAAATTCTGAGGGCACAGGACAAGCA
GCAGATCTCAAAAGCACTCAAGCAGCAATCAACCAAATCAATGGGAAACTGAATAGGTTA
ATCGGGAAAACAAACGAGAAATTCCATCAGATTGAAAAGAATTCTCAGAAGTAGAAGGG
AGAATTCAGGACCTCGAGAAATATGTTGAGGACACTAAAATAGATCTCTGGTCATACAAC
GCGGAGCTTCTTGTTGCCCTGGAGAACCAACATACAATTGATCTAACTGACTCAGAAATG
AACAAACTGTTTGAAAGAACAAAGAAGCAACTGAGGGAAAATGCTGAGGATATGGGCAAT
GGTTGTTTCAAAATATACCACAAATGTGACAATGCCTGCATAGAGTCAATCAGAAATGGA
ACTTATGACCATGATGTATACAGAGATGAAGCATTAAACAACCGGTTCCAGATCAAAGGT
GTTGAGCTGAAGTCAGGATACAAAGATTGGATCCTATGGATTTCCTTTGCCATATCATGT
TTTTTGCTCTGTGTTGCTTTGTTGGGGTTCATCATGTGGGCCTGCCAAAAAGGCAACATT
AGGTGCAACATTTGCATTTGAGTGCATTAATTAAAAACACCCTTGTTTCTACT (SEQ ID NO:13)

>Y2017M3L4-M(M1-23Q)
ATGAGCCTTCTAACCGAGGTCGAAACGTATGTTCTCTCTATCGTTCCATCAGGCCCCCTC
AAAGCCCAGATCGCGCAGAGACTTGAAGATGTCTTTGCTGGGAAAAACACAGATCTTGAG
GCTCTCATGGAATGGCTAAAGACAAGACCAATTCTGTCACCTCTGACTAAGGGGATTCTG
GGGTTTGTGTTCACGCTCACCGTGCCCAGTGAGCGAGGACTGCAGCGTAGACGCTTTGTC
CAAAATGCCCTCAATGGGAATGGAGATCCAAATAACATGGACAAAGCAGTTAAACTGTAT
AGGAAACTTAAGAGGGAGATAACGTTCCATGGGGCCAAAGAAATAGCTCTCAGTTATTCT
GCTGGTGCACTTGCCAGTTGCATGGGCCTCATATACAATAGGATGGGGGCTGTAACCACT
GAAGTGGCATTTGGCCTGGTATGTGCAACATGTGAGCAGATTGCTGACTCCCAGCACAGG
TCTCATAGGCAAATGGTGGCAACAACCAATCCATTAATAAGGCATGAGAACAGAATGGTT
TTGGCCAGCACTACAGCTAAGGCTATGGAGCAAATGGCTGGATCAAGTGAGCAGGCAGCG
GAGGCCATGGAGATTGCTAGTCAGGCCAGGCAAATGGTGCAGGCAATGAGAGCCATTGGG
ACTCATCCTAGCTCCAGTACTGGTCTAAGAGATGATCTTCTTGAAAATTTGCAGACCTAT
CAGAAACGAATGGGGGTGCAGATGCAACGATTCAAGTGACCCACTTGTTGTTGCCGCGAG
TATCATTGGGATCTTGCACTTGATATTGTGGATTCTTGATCGTCTTTTTTCAAATGCGT
CTATCGACTCTTCAAACACGGCCTTAAAAGAGGCCCTTCTACGGAAGGAGTACCTGAGTC
TATGAGGGAAGAGTATCGAAAGGAACAGCAGAATGCTGTGGATGCTGACGACAGTCATTT
TGTCAGCATAGAGTTGGAGTAAAAAACTACCTTGTTTCTACT (SEQ ID NO:14)

>Y2017M3L4-NP(101N)
ATGGCGTCCCAAGGCACCAAACGGTCTTATGAACAGATGGAAACTGATGGGGATCGCCAG
AATGCAACTGAGATTAGGGCATCCGTCGGGAAGATGATTGATGGAATTGGGAGATTCTAC
ATCCAAATGTGCACTGAACTTAAACTCAGTGATTATGAAGGGCGGTTGATCCAGAACAGC
TTGACAATAGAGAAATGGTGCTCTCTGCTTTTGATGAAAGAAGGAATAAATATCTGGAA
GAACACCCCAGCGCGGGGAAGATCCTAAGAAAACTGGGGGCCCATATACAGGAGAGTA
AATGGAAAATGGATGAGGGAACTCGTCCTTTATGACAAGAAGAAATAAGGCGAATCTGG
CGCCAAGCCAACAATGGTGAGGATGCGACAGCTGGTCTAACTCACATAATGATCTGGCAT

TCCAATTTGAATGATGCAACATACCAGAGGACAAGAGCTCTTGTTCGAACCGGAATGGAT
CCCAGAATGTGCTCTCTGATGCAGGGCTCGACTCTCCCTAGAAGGTCCGGAGCTGCAGGT
GCTGCAGTCAAAGGAATCGGGACAATGGTGATGGAGCTGATCAGAATGGTCAAACGGGGG
ATCAACGATCGAAATTCTGGAGAGGTGAGAATGGGCGGAAAACAAGAAGTGCTTATGAG
AGAATGTGCAACATTCTTAAAGGAAAATTTCAAACAGCTGCACAAGAGCAATGGTGGAT
CAAGTGAGAGAAAGTCGGAACCCAGGAAATGCTGAGATCGAAGATCTCATATTTTTGGCA
AGATCTGCATTGATATTGAGAGGATCAGTTGCTCACAAATCTTGCCTACCTGCCTGTGTG
TATGGACCTGCAGTATCCAGTGGGTACGACTTCGAAAAGAGGGATATTCCTTGGTGGGA
ATAGACCCTTTCAAACTACTTCAAAATAGCCAAGTATACAGCCTAATCAGACCTAACGAG
AATCCAGCACACAAGAGTCAGCTGGTATGGATGGCATGCCATTCTGCTGCATTTGAAGAT
TTAAGATTGTTAAGCTTCATCAGAGGGACAAAAGTATCTCCACGAGGGAAACTTTCAACT
AGAGGAGTACAAATTGCTTCAAATGAGAACATGGATAATATGGGATCGAGCACTCTTGAA
CTGAGAAGCGGGTACTGGGCCATAAGGACCAGGAGTGGAGGAAACACTAATCAACAGAGG
GCCTCCGCAGGCCAAACCAGTGTGCAACCTACGTTTTCTGTACAAAGAAACCTCCCATTT
GAAAAGTCAACCATCATGGCAGCATTCACTGGAAATACGGAGGGAAGAACTTCAGACATG
AGGGCAGAAATCATAAGAATGATGGAAGGTGCAAAACCAGAAGAAGTGTCGTTCCGGGGG
AGGGGAGTTTTCGAGCTCTCAGACGAGAAGGCAACGAACCCGATCGTGCCCTCTTTTGAT
ATGAGTAATGAAGGATCTTATTTCTTCGGAGACAATGCAGAAGAGTACGACAATTAAGGA
AAAATACCCTTGTTTCTACT (SEQ ID NO:15)

>Y2017M3L4-NS
ATGGATTCCAACACTGTGTCAAGTTTCCAGGTAGATTGCTTTCTTTGGCATATCCGGAAA
CAAGTTGTAGACCAAGAACTGAGTGATGCCCCATTCCTTGATCGGCTTCGCCGAGATCAG
AGGTCCCTAAGGGGAAGAGGCAATACTCTCGGTCTAGACATCAAAGCAGCCACCCATGTT
GGAAAGCAAATTGTAGAAAGATTCTGAAAGAAGAATCTGATGAGGCACTTAAAATGACC
ATGGTCTCCACACCTGCTTCGCGATACATAACTGACATGACTATTGAGGAATTGTCAAGA
AACTGGTTCATGCTAATGCCCAAGCAGAAAGTGGAAGGACCTCTTTGCATCAGAATGGAC
CAGGCAATCATGGAGAAAACATCATGTTGAAAGCGAATTTCAGTGTGATTTTGACCGA
CTAGAGACCATAGTATTACTAAGGGCTTTCACCGAAGAGGGAGCAATTGTTGGCGAAATC
TCACCATTGCCTTCTTTTCCAGGACATACTATTGAGGATGTCAAAAATGCAATTGGGGTC
CTCATCGGAGGACTTGAATGGAATGATAACACAGTTCGAGTCTCTAAAAATCTACAGAGA
TTCGCTTGGAGAAGCAGTAATGAGAATGGGGGACCTCCACTTACTCCAAAACAGAAACGG
AAAATGGCGAGAACAGCTAGGTCAAAAGTTTGAAGAGATAAGATGGCTGATTGAAGAAGT
GAGACACAGACTAAAAACAACTGAAAATAGCTTTGAACAAATAACATTCATGCAAGCATT
ACAACTGCTGTTTGAAGTGGAACAGGAGATAAGAACTTTCTCATTTCAGCTTATTTAATG
ATAAAAAACACCCTTGTTTCTACT (SEQ ID NO:16)

>Y2017M3L4-PB1
ATGGATGTCAATCCGACTCTACTGTTCCTAAAGGTTCCAGCGCAAAATGCCATAAGCACC
ACATTCCCTTATACTGGAGATCCTCCATACAGCCATGGAACAGGAACAGGGTACACCATG
GACACAGTCAACAGAACACACCAATATTCAGATAAGGGGAAGTGGACGACAAATACAGAA
ACTGGGGCACCCCAACTCAACCCAATTGATGGACCACTACCTGAGGATAATGAGCCAAGT
GGATATGCACAAACAGACTGTGTCCTGGAGGCTATGGCCTTCCTTGAAGAATCCCACCCA
GGTATCTTTGAGAACTCATGCCTTGAAACAATGGAAGTCGTTCAACAAACAAGGGTGGAC
AAACTAACCCAAGGTCGCCAGACTTATGATTGGACATTAAACAGAAATCAACCGGCAGCA
ACTGCATTAGCCAACACCATAGAAGTTTTTAGATCGAATGGACTAACAGCTAATGAATCA
GGAAGGCTAATAGATTTCCTCAAGGATGTGATGGAATCAATGGATAAAGAGGAAATGGAG
ATAACAACACTTTCAAAGAAAAGGAGAGTAAGAGACAACATGACCAAGAAAATGGTC
ACACAAGAACAATAGGGAAGAAAAACAAAGAGTAAATAAGAGAGGCTATCTAATAAGA
GCTTTGACATTGAACACGATGACCAAAGATGCAGAGAGAGGTAAATTAAAAGAAGGGCT
ATTGCAACACCCGGGATGCAAATTAGAGGGTTCGTGACTTCGTTGAAACTTTAGCTAGA
AGCATTTGCGAAAAGCTTGAACAGTCTGGACTTCCGGTTGGGGGTAATGAAAAGAAGGCC

FIG. 3(Continued)

```
AAACTGGCAAATGTTGTGAGAAAATGATGACTAATTCACAAGACACAGAGCTTTCTTTC
ACAATCACTGGGGACAACACTAAGTGGAATGAAAATCAAAACCCTCGAATGTTTTGGCG
ATGATTACATATATCACAAAAAATCAACCTGAGTGGTTCAGAAACATCCTGAGCATCGCA
CCAATAATGTTCTCAAACAAATGGCAAGACTGGGAAAAGGATACATGTTCGAGAGTAAG
AGAATGAAACTCCGAACACAAATACCCGCAGAAATGCTAGCAAACATTGACCTGAAGTAT
TTCAATGAATCAACAAGGAAGAAAATTGAGAAAATAAGGCCTCTTCTAATAGATGGCACA
GCATCATTGAGCCCTGGGATGATGATGGGCATGTTCAACATGCTAAGTACGGTTTTAGGA
GTCTCGATACTGAATCTTGGGCAAAAGAAATACACCAAGACAACATACTGGTGGGATGGG
CTCCAATCCTCCGACGATTTTGCCCTCATAGTGAATGCACCAAATCATGAGGGAATACAA
GCAGGAGTGGATAGATTTTACAGGACCTGCAAGTTAGTGGGAATCAACATGAGCAAAAAG
AAGTCCTATATAAATAAAACAGGGACATTTGAATTCACAAGCTTTTTTATCGATATGGA
TTTGTGGCTAATTTTAGCATGGAGCTGCCCAGTTTTGGAGTGTCTGGAATAAACGAGTCA
GCTGATATGAGCATTGGAGTAACAGTGATAAAGAACAACATGATAAACAATGACCTTGGA
CCAGCAACAGCCCAGATGGCTCTCCAATTGTTCATCAAGACTACAGATACATATAGG
TGCCATAGAGGAGACACACAAATTCAGACGAGAAGATCATTCGAGCTAAAGAAGCTGTGG
GATCAAACCCAATCAAGGGCAGGACTATTGGTATCAGATGGGGACCAAACTTATACAAT
ATCCGGAATCTTCACATCCCTGAAGTCTGCTTAAAGTGGGAGCTAATGGATGAGAATTAT
CGGGGAAGACTTTGTAATCCCCTGAATCCCTTTGTCAGCCATAAAGAAATTGAGTCTGTA
AACAATGCTGTAGTGATGCCAGCCCATGGTCCGGCCAAAAGTATGGAATATGATGCCGTT
GCAACTACACACTCCTGGATTCCCAAGAGGAACCGCTCTATTCTCAACACAAGCCAAAGG
GGAATTCTTGAGGATGAACAGATGTACCAGAAGTGCTGCAACTTGTTCGAGAAATTTTTC
CCTAGTAGTTCATATAGGAGACCGATTGGAATTTCTAGCATGGTGGAGGCCATGGTGTCT
AGGGCCCGGATTGATGCCAGAATTGACTTCGAGTCTGGACGGATTAAGAAGGAAGAGTTC
TCTGAGATCATGAAGATCTGTTCCACCATTGAAGAACTCAGACGGCAAAAATAATGAATT
TAGCTTGTCCTTCATGAAAAAATGCCTTGTTTCTACT (SEQ ID NO:17)

>Y2017M3L4-PA
ATGGAAGATTTTGTGCGACAATGCTTCAACCCGATGATTGTCGAACTTGCAGAAAAAGCA
ATGAAGAGTATGGGGAGGATCTGAAAATTGAAACAAACAAATTTGCAGCAATATGCACT
CACTTGGAGGTATGTTTCATGTATTCAGATTTTCATTTCATCAATGAACAAGGCGAATCA
ATAGTGGTAGAACTTGATGATCCAAATGCACTGTTAAAGCACAGATTTGAAATAATCGAG
GGGAGAGACAGAACAATGGCCTGGACAGTAGTAAACAGTATCTGCAACACTACTGGAGCT
GAAAAACCGAAGTTTCTACCAGATTTGTATGATTACAAGGAGAACAGATTCATCGAAATT
GGAGTGACAAGGAGAGAAGTCCACATATATTACCTTGAAAAGGCCAATAAGATTAAATCT
GAGAACACACACATTCACATTTTCTCATTCACTGGGGAGGAAATGGCCACAAAGGCAGAC
TACACTCTCGACGAGGAAAGCAGGGCTAGGATTAAGACCAGGCTATTTACCATAAGACAA
GAAATGGCCAACAGAGGCCTCTGGGATTCCTTTCGTCAGTCCGAAAGAGGCGAAGAAACA
ATTGAAGAAAATTTGAAATCTCAGGAACTATGCGTAGGCTTGCCGACCAAAGTCTCCCA
CCGAACTTCTCCTGCCTTGAGAATTTTAGAGCCTATGTGGATGGATTCGAACCGAACGGC
TGCATTGAGGGCAAGCTTTCTCAAATGTCCAAAGAAGTGAATGCCCAAATTGAACCTTTT
CTGAAGACAACACCAAGACCAATCAAACTTCCGAATGGACCTCCTTGTTATCAGCGGTCC
AAGTTCCTCCTGATGGATGCTTTAAATTGAGCATTGAGACCCAAGTCACGAAGGAGAA
GGGATCCATTATATGATGCGATCAAGTGCATAAAAACATTCTTTGGATGGAAAGAACCT
TATATAGTCAAACCACACGAAAGGGAATAAATTCAAATTACCTGCTGTCATGGAAGCAA
GTATTGTCAGAATTGCAGGACATTGAAAATGAGGAGAAGATTCCAAGGACTAAAACATG
AAGAAAACGAGTCAACTAAAGTGGGCTCTTGGTGAGAACATGGCACCAGAGAAAGTAGAC
TTTGAAAACTGCAGAGACATAAGCGATTTGAAGCAATATGATAGTGACGAACCTGAATTA
AGGTCACTTTCAAGCTGGATACAGAATGAGTTCAACAAGGCCTGCGAGCTAACTGATTCA
ATCTGGATAGAGCTCGATGAAATTGGAGAGGACGTAGCCCCAATTGAATACATTGCAAGC
ATGAGGAGGAATTATTTCACAGCAGAGGTGTCCATTGTAGAGCCACTGAGTACATAATG
AAGGGGGTATACATTAATACTGCCCTGCTCAATGCATCCTGTGCAGCAATGGACGATTTT
CAACTAATTCCCATGATAAGCAAGTGCAGAACTAAAGAGGGAAGGCGAAAACCAATTTA
TATGGATTCATCATAAAGGGAAGATCTCATTTAAGGAATGACACAGATGTGGTAAACTTT
```

```
GTGAGCATGGAGTTTTCTCTCACTGACCCGAGACTTGAGCCACATAAATGGGAGAAATAC
TGTGTCCTTGAGATAGGAGATATGTTACTAAGAAGTGCCATAGGCCAAATTTCAAGGCCT
ATGTTCTTGTATGTGAGGACAAACGGAACATCAAGGTCAAAATGAAATGGGGAATGGAG
ATGAGACGTTGCCTCCTTCAGTCACTCCAGCAGATCGAGAGCATGATTGAAGCCGAGTCC
TCGGTTAAAGAGAAAGACATGACCAAAGAGTTTTTTGAGAATAAATCAGAAGCATGGCCC
ATTGGGGAGTCCCCCAAGGGAGTGGAAGAAGGTTCCATTGGGAAAGTCTGTAGGACTCTA
TTGGCTAAGTCAGTGTTCAATAGCCTGTATGCATCACCACAATTGGAAGGATTTTCAGCG
GAGTCAAGAAACTGCTCCTTGTTGTTCAGGCTCTTAGGGACAACCTCGAACCTGGGACC
TTTGATCTTGGGGGCTATATGAAGCAATTGAGGAGTGCCTGATTAATGATCCCTGGGTT
TTGCTCAATGCGTCTTGGTTCAACTCCTTCCTGACACATGCATTAAATAGTTATGGCAG
TGCTACTATTTGTTATCCGTACTGTCCAAAAAAGTACCTTGTTTCTACT (SEQ ID NO:18)

>M3L4-PB2(147I)
ATGGAAAGAATAAAAGAACTACGGAACCTGATGTCGCAGTCTCGCACTCGCGAGATACTG
ACAAAAACCACAGTGGACCATATGGCCATAATTAAGAAGTACACATCGGGGAGACAGGAA
AAGAACCCGTCACTTAGGATGAAATGGATGATGGCAATGAAATACCCAATCACTGCTGAC
AAAAGGATAACAGAAATGGTTCCGGAGAGAAATGAACAAGGACAAACTCTATGGAGTAAA
ATGAGTGATGCTGGATCAGATCGAGTGATGGTATCACCTTTGGCTGTGACATGGTGGAAT
AGAAATGGACCCGTGACAAGTACGGTCCATTACCCAAAAGTATACAAGACTTATTTTGAC
AAAGTCGAAAGGTTAAAACATGGAACCTTTGGCCCTGTTCATTTTAGAAATCAAGTCAAG
ATACGCCGAAGAGTAGACATAAACCCTGGTCATGCGGACCTCAGTGCCAAGGAGGCACAA
GATGTAATTATGGAAGTTGTTTTTCCCAATGAAGTGGGAGCCAGGATACTAACATCAGAA
TCGCAATTAACAATAACTAAAGAGAAAAAGAAGAACTCCGAGATTGCAAAATTTCTCCC
TTGATGGTTGCATACATGTTAGAGAGAGAACTTGTCCGAAAACAAGATTTCTCCCAGTT
GCTGGCGGAACAAGCAGTATATACATTGAAGTTTTACATTTGACTCAAGGGACGTGTTGG
GAACAAATGTACACTCCAGGTGGAGAAGTGAGGAATGACGATGTTGACCAAAGCCTAATT
ATTGCAGCCAGGAACATAGTAAGAAGAGCCGCAGTATCAGCAGATCCACTAGCATCTTTA
TTGGAGATGTGCCACAGCACACAAATTGGCGGGACAAGGATGGTGGACATTCTTAGACAG
AACCCGACTGAAGAACAAGCTGTGGATATATGCAAGGCTGCAATGGGATTGAGAATCAGC
TCATCCTTCAGCTTTGGTGGGTTTACATTTAAAAGAACAAGCGGGTCATCAGTCAAAAAA
GAGGAAGAAGTGCTTACAGGCAATCTCCAAACATTGAAGATAAGAGTACATGAGGGGTAT
GAGGAGTTCACAATGGTGGGGAAAAGAGCAACAGCTATACTCAGAAAAGCAACCAGAAGA
TTGGTTCAGCTCATAGTGAGTGGAAGAGACGAACAGTCAATAGCCGAAGCAATAATTGTG
GCCATGGTGTTTTCACAAGAGGATTGCATGATAAAAGCAGTTAGAGGTGACCTGAATTTC
GTCAACAGAGCAAATCAGCGGTTGAACCCCATGCATCAGCTTTTAAGGCATTTTCAGAAA
GATGCGAAAGTGCTTTTTCAGAATTGGGGAATTGAGCACATCGACAGTGTAATGGGAATG
GTTGGAGTATTACCAGATATGACTCCAAGCACAGAGATGTCAATGAGAGGAATAAGAGTC
AGCAAAATGGGTGTGGATGAATACTCCAGTACAGAGAGGGTGGTGGTTAGCATTGATCGG
TTTTTGAGAGTTCGAGACCAACGCGGGAATGTATTATTATCTCCTGAAGAGGTTAGTGAA
ACACAGGGAACTGAGAGACTGACAATAACTTATTCATCGTCGATGATGTGGGAGATTAAC
GGTCCTGAGTCGGTTTTGGTCAATACTTATCAATGGATCATCAGAAATTGGGAAGCTGTC
AAAATTCAATGGTCTCAGAATCCTGCAATGTTGTACAACAAAATGGAATTTGAACCATTT
CAATCTTTAGTCCCCAAGGCCATTAGAAGCCAATACAGTGGGTTTGTCAGAACTCTATTC
CAACAAATGAGAGACGTACTTGGACATTTGACACCACCCAGATAATAAAGCTTCTCCCT
TTTGCAGCCGCTCCACCAAAGCAAAGCAGAATGCAGTTCTCTTCACTGACTGTAAATGTG
AGGGGATCAGGGATGAGAATACTTGTAAGGGCAATTCTCCTGTATTCAACTACAACAAG
ACCACTAAAAGACTAACAATTCTCGGAAAGATGCCGGCACTTTAATTGAAGACCCAGAT
GAAAGCACATCCGGAGTGGAGTCCGCTGTATTGAGAGGGTTTCTCATTATAGGTAAGGAA
GACAGAAGATACGGGCCAGCATTAAGCATCAATGAACTGAGTAACCTTGCAAAGGGGAA
AAGGCTAATGTGCTAATCGGGCAAGGAGACGTGGTGTTGGTAATGAAACGAAAACGGGAC
TCTAGCATACTTACTGACAGCCAGACAGCGACCAAAAGAATTCGGATGGCCATCAATTAA
TGTTGAATAGTTTAAAAACGACCTTGTTTCTACT (SEQ ID NO:19)
```

FIG. 3(Continued)

>M3L4-PB2(147I,344L)
ATGGAAAGAATAAAAGAACTACGGAACCTGATGTCGCAGTCTCGCACTCGCGAGATACTG
ACAAAAACCACAGTGGACCATATGGCCATAATTAAGAAGTACACATCGGGGAGACAGGAA
AAGAACCCGTCACTTAGGATGAAATGGATGATGGCAATGAAATACCCAATCACTGCTGAC
AAAAGGATAACAGAAATGGTTCCGGAGAGAAATGAACAAGGACAAACTCTATGGAGTAAA
ATGAGTGATGCTGGATCAGATCGAGTGATGGTATCACCTTTGGCTGTGACATGGTGGAAT
AGAAATGGACCCGTGACAAGTACGGTCCATTACCCAAAAGTATACAAGACTTATTTTGAC
AAAGTCGAAAGGTTAAAACATGGAACCTTTGGCCCTGTTCATTTTAGAAATCAAGTCAAG
ATACGCCGAAGAGTAGACATAAACCCTGGTCATGCGGACCTCAGTGCCAAGGAGGCACAA
GATGTAATTATGGAAGTTGTTTTTCCCAATGAAGTGGGAGCCAGGATACTAACATCAGAA
TCGCAATTAACAATAACTAAAGAGAAAAAGAAGAACTCCGAGATTGCAAAATTTCTCCC
TTGATGGTTGCATACATGTTAGAGAGAGAACTTGTCCGAAAAACAAGATTCCTCCCAGTT
GCTGGCGGAACAAGCAGTATATACATTGAAGTTTTACATTTGACTCAAGGGACGTGTTGG
GAACAAATGTACACTCCAGGTGGAGAAGTGAGGAATGACGATGTTGACCAAAGCCTAATT
ATTGCAGCCAGGAACATAGTAAGAAGAGCCGCAGTATCAGCAGATCCACTAGCATTTTA
TTGGAGATGTGCCACAGCACACAAATTGGCGGGACAAGGATGGTGGACATTCTTAGACAG
AACCCGACTGAAGAACAAGCTGTGGATATATGCAAGGCTGCAATGGGATTGAGAATCAGC
TCATCCTTCAGCTTTGGTGGGTTTACATTTAAAAGAACAAGCGGGTCATCAGTCAAAAAA
GAGGAAGAACTGCTTACAGGCAATCTCCAAACATTGAAGATAAGAGTACATGAGGGGTAT
GAGGAGTTCACAATGGTGGGAAAAGAGCAACAGCTATACTCAGAAAAGCAACCAGAAGA
TTGGTTCAGCTCATAGTGAGTGGAAGAGACGAACAGTCAATAGCCGAAGCAATAATTGTG
GCCATGGTGTTTTCACAAGAGGATTGCATGATAAAAGCAGTTAGAGGTGACCTGAATTTC
GTCAACAGAGCAAATCAGCGGTTGAACCCCATGCATCAGCTTTTAAGGCATTTTCAGAAA
GATGCGAAAGTGCTTTTTCAGAATTGGGGAATTGAGCACATCGACAGTGTAATGGGAATG
GTTGGAGTATTACCAGATATGACTCCAAGCACAGAGATGTCAATGAGAGGAATAAGAGTC
AGCAAAATGGGTGTGGATGAATACTCCAGTACAGAGAGGGTGGTGGTTAGCATTGATCGG
TTTTTGAGAGTTCGAGACCAACGCGGGAATGTATTATTATCTCCTGAAGAGGTTAGTGAA
ACACAGGGAACTGAGAGACTGACAATAACTTATTCATCGTCGATGATGTGGGAGATTAAC
GGTCCTGAGTCGGTTTTGGTCAATACTTATCAATGGATCATCAGAAATTGGGAAGCTGTC
AAAATTCAATGGTCTCAGAATCCTGCAATGTTGTACAACAAATGGAATTTGAACCATTT
CAATCTTTAGTCCCCAAGGCCATTAGAAGCCAATACAGTGGGTTTGTCAGAACTCTATTC
CAACAAATGAGAGACGTACTTGGGACATTTGACACCACCCAGATAATAAAGCTTCTCCCT
TTTGCAGCCGCTCCACCAAAGCAAAGCAGAATGCAGTTCTCTTCACTGACTGTAAATGTG
AGGGGATCAGGGATGAGAATACTTGTAAGGGGCAATTCTCCTGTATTCAACTACAACAAG
ACCACTAAAAGACTAACAATTCTCGGAAAAGATGCCGGCACTTTAATTGAAGACCCAGAT
GAAAGCACATCCGGAGTGGAGTCCGCTGTATTGAGAGGGTTTCTCATTATAGGTAAGGAA
GACAGAAGATACGGGCCAGCATTAAGCATCAATGAACTGAGTAACCTTGCAAAAGGGGAA
AAGGCTAATGTGCTAATCGGGCAAGGAGACGTGGTGTTGGTAATGAAACGAAAACGGGAC
TCTAGCATACTTACTGACAGCCAGACAGCGACCAAAAGAATTCGGATGGCCATCAATTAA
TGTTGAATAGTTTAAAAACGACCTTGTTTCTACT (SEQ ID NO:20)

>M3L4-PB2(147I,344L,358K)
ATGGAAAGAATAAAAGAACTACGGAACCTGATGTCGCAGTCTCGCACTCGCGAGATACTG
ACAAAAACCACAGTGGACCATATGGCCATAATTAAGAAGTACACATCGGGGAGACAGGAA
AAGAACCCGTCACTTAGGATGAAATGGATGATGGCAATGAAATACCCAATCACTGCTGAC
AAAAGGATAACAGAAATGGTTCCGGAGAGAAATGAACAAGGACAAACTCTATGGAGTAAA
ATGAGTGATGCTGGATCAGATCGAGTGATGGTATCACCTTTGGCTGTGACATGGTGGAAT
AGAAATGGACCCGTGACAAGTACGGTCCATTACCCAAAAGTATACAAGACTTATTTTGAC
AAAGTCGAAAGGTTAAAACATGGAACCTTTGGCCCTGTTCATTTTAGAAATCAAGTCAAG
ATACGCCGAAGAGTAGACATAAACCCTGGTCATGCGGACCTCAGTGCCAAGGAGGCACAA
GATGTAATTATGGAAGTTGTTTTTCCCAATGAAGTGGGAGCCAGGATACTAACATCAGAA
TCGCAATTAACAATAACTAAAGAGAAAAAGAAGAACTCCGAGATTGCAAAATTTCTCCC
TTGATGGTTGCATACATGTTAGAGAGAGAACTTGTCCGAAAAACAAGATTCCTCCCAGTT

FIG. 3(Continued)

```
GCTGGCGGAACAAGCAGTATATACATTGAAGTTTTACATTTGACTCAAGGGACGTGTTGG
GAACAAATGTACACTCCAGGTGGAGAAGTGAGGAATGACGATGTTGACCAAAGCCTAATT
ATTGCAGCCAGGAACATAGTAAGAAGAGCCGCAGTATCAGCAGATCCACTAGCATCTTTA
TTGGAGATGTGCCACAGCACACAAATTGGCGGGACAAGGATGGTGGACATTCTTAGACAG
AACCCGACTGAAGAACAAGCTGTGGATATATGCAAGGCTGCAATGGGATTGAGAATCAGC
TCATCCTTCAGCTTTGGTGGGTTTACATTTAAAAGAACAAGCGGGTCATCAGTCAAAAAA
GAGGAAGAACTGCTTACAGGCAATCTCCAAACATTGAAGATAAGAGTACATAAGGGGTAT
GAGGAGTTCACAATGGTGGGGAAAAGAGCAACAGCTATACTCAGAAAAGCAACCAGAAGA
TTGGTTCAGCTCATAGTGAGTGGAAGAGACGAACAGTCAATAGCCGAAGCAATAATTGTG
GCCATGGTGTTTTCACAAGAGGATTGCATGATAAAAGCAGTTAGAGGTGACCTGAATTTC
GTCAACAGAGCAAATCAGCGGTTGAACCCCATGCATCAGCTTTTAAGGCATTTTCAGAAA
GATGCGAAAGTGCTTTTTCAGAATTGGGGAATTGAGCACATCGACAGTGTAATGGGAATG
GTTGGAGTATTACCAGATATGACTCCAAGCACAGAGATGTCAATGAGAGGAATAAGAGTC
AGCAAAATGGGTGTGGATGAATACTCCAGTACAGAGAGGGTGGTGGTTAGCATTGATCGG
TTTTTGAGAGTTCGAGACCAACGCGGGAATGTATTATTATCTCCTGAAGAGGTTAGTGAA
ACACAGGGAACTGAGAGACTGACAATAACTTATTCATCGTCGATGATGTGGGAGATTAAC
GGTCCTGAGTCGGTTTTGGTCAATACTTATCAATGGATCATCAGAAATTGGGAAGCTGTC
AAAATTCAATGGTCTCAGAATCCTGCAATGTTGTACAACAAATGGAATTTGAACCATTT
CAATCTTTAGTCCCCAAGGCCATTAGAAGCCAATACAGTGGGTTTGTCAGAACTCTATTC
CAACAAATGAGAGACGTACTTGGGACATTTGACACCACCCAGATAATAAAGCTTCTCCCT
TTTGCAGCCGCTCCACCAAAGCAAAGCAGAATGCAGTTCTCTTCACTGACTGTAAATGTG
AGGGGATCAGGGATGAGAATACTTGTAAGGGGCAATTCTCCTGTATTCAACTACAACAAG
ACCACTAAAAGACTAACAATTCTCGGAAAGATGCCGGCACTTTAATTGAAGACCCAGAT
GAAAGCACATCCGGAGTGGAGTCCGCTGTATTGAGAGGGTTTCTCATTATAGGTAAGGAA
GACAGAAGATACGGGCCAGCATTAAGCATCAATGAACTGAGTAACCTTGCAAAAGGGGAA
AAGGCTAATGTGCTAATCGGGCAAGGAGACGTGGTGTTGGTAATGAAACGAAAACGGGAC
TCTAGCATACTTACTGACAGCCAGACAGCGACCAAAAGAATTCGGATGGCCATCAATTAA
TGTTGAATAGTTTAAAAACGACCTTGTTTCTACT (SEQ ID NO:21)
```

FIG. 3 (Continued)

| | | | | |
|---|---|---|---|---|
| HA | HK4801 | HK4801 | HK4801 | HK4801 |
| NA | HK4801 | Y2017-M3L4 | HK4801 | Y2017-M3L4 |
| Backbone | Y2017 | Y2017 | HY-PR8 | HY-PR8 |

FIG. 7

Yokohama/2017/2003 NA

Upper: wild-type
Lower: Y2017-M3L4

```
  1 MNPNQKIITIGSVSLTISTICFFMQIAILITTVTLHFKQYEFNSPPNNQVMLCEPTIIER  60
                                A
    ...............................................-----...........
                               T32A        del 46-50aa 61 NITEIVYLTNTTIEKEICPKLAEYRNWSKPQCNITGFAPFSKDNSIRLSAGGDIWVTREP 120
    ............................................................

121 YVSCDPDKCYQFALGQGTTLNNVHSNDIVHDRTPYRTLLMNELGVPFHLGTKQVCIAWSS 180
                              N
    ............................................................
                            D147N

181 SSCHDGKAWLHVCVTGDDENATASFIYNGRLADSIVSWSKKILRTQESECVCINGTCTVV 240
    ............................................................

241 MTDGSASGKADTKILFIEEGKIVHTSTLSGSAQHVEECSCYPRYPGVRCVCRDNWKGSNR 300
    ............................................................

301 PIVDINIKDYSIVSSYVCSGLVGDTPRKNDSSSSSHCLDPNNEEGGHGVKGWAFDDGNDV 360
                                 D                 Q
    ............................................................
                               N329D             H347Q

361 WMGRTISEKLRSGYETFKVIEGWSNPNSKLQINRQVIVDRGNRSGYSGIFSVEGKSCINR 420
    ............................................................

421 CFYVELIRGRKQETEVLWTSNSIVVFCGTSGTYGTGSWPDGADINLMPI*           470
    ............................................................
```

FIG. 8

N3 (Accession No. AAO62039.1)

```
  1 mnpnqkiiti gvvnttlsti alligvgnli fntvihekig dhqtvihptt ttpaipncsd
 61 tiitynntvi nnittiitea erlfkpplpl cpfrgffpfh kdnairlgen kdvivtrepy
121 vscdndncws falaqgallg tkhsngtikd rtpyrsliqf pigtapvlgn ykeiciawss
181 sscfdgkewm hvcmtgndnd asaqiiyagr mtdsikswkr dilrtqesec qcidgtcvva
241 vtdgpaansa dhrvywireg rivkyenvpk tkiqhleecs cyvdidvyci crdnwkgsnr
301 pwmrinneti letgyvcskf hsdtprpadp stvscdspsn vnggpgvkgf gfkvgndvwl
361 grtmstsgrs gfeiikvaeg winspnhaks vtqtlvsnnd wsgysgsfiv ktkacfqpcf
421 yvelirgrpn knddvswtsn sivtfcgldn epgsgnwpdg snigfmpk  (SEQ ID NO:30)
```

N4 (Accession No. AAO62043.1

```
  1 mnpnqkiiti gsvsiiltti glllqitslc siwfshynqv tqtheqpcsn nttnyynetf
 61 vnvtnvqnny ttviepsapd vvhyssgrdl cpirgwapls kdngirigsr gevfvirepf
121 iscsisecrt ffltqgallin dkhsngtvkd rspfrtlmsc pigvapspsn srfesvawsa
181 tacsdgpgwl tlgitgpdat avavlkyngi itdtlkswkg nimrtqesec vcqdefcytl
241 itdgpsdaga fykilkirkg kivsmkdvda tgfhfeecsc ypsgtdiecv crdnwrgsnr
301 pwirfnsdld yqigyvcsgi fgdnprpvdg tgscnspvnn gkgrygvkgf sfrygdgvwi
361 grtkslesrs gfemvwdang wvstdkdsng vqdiidndnw sgysgsfsir gettgrnctv
421 pcfwvemirg qpkektiwts gssiafcgvn sdttgwswpd gallpfdidk (SEQ ID NO:31)
```

N6 (Accession No. AAO62070.1)

```
  1 mnpnqkiici satgmtlsvv slligianlg lniglhykmg dtpdvnipnm netnstttii
 61 nnhtqnnftn itniivnkne egtflnltkp lcevnswhil skdnairige dahilvtrep
121 ylscdpqgcr mfalsqgttl rgrhangtih drspfralis wemgqapspy nvrvecigws
181 stschdgisr msicmsgann nasavvwygg rpvteipswa gnilrtqese cvchkgicpv
241 vmtdgpannr aatkiiyfke gkiqkieela gntqhieecs cygavgvikc icrdnwkgan
301 rpvitidpem mthtskylcs kiltdtsrpn dptngncdap itggspdpgv kqfafldren
361 swlgrtiskd srsgyemlkv pnaetdtqsg pishqvivnn gnwsgysgaf idywankecf
421 npcfyvelir grpkessvlw tsnsivalcg skerlgswsw hdgaeiiyfk (SEQ ID NO:32)
```

N7 (Accession No. AIK26357.1)

```
  1 mnpnqklfal sqvaialsil nlligisnvg lnvslhlkgs sdqdknwtct svtqnnttli
 61 entyvnnttv idketgtakp nylminkslc kvegwvvvak dnairfgese qiivtrepyv
121 scdplgckmy alhqgttirn khsngtihdr tafrglistp lgsppvvsns dflcvgwsst
181 schdgigrmt icvggnndna tatvyydrrl tttiktwagn iirtqesecv chngtcvvim
241 tdgsassqay tkvlyfhkgl vikeealkgs arhieecscy ghnskvtcvc rdnwqganrp
301 vieidmname htsqylctgv ltdtsrpsdk smgdcnnpit gspgapgvkg fgfldssntw
361 lgrtisprsr sgfemlkipn aetdpnskit erqeivdnnn wsgysgsfid ywdessecyn
421 pcfyvelirg rpeeakyvgw tsnslialcg spisvgsgsf pdgaqiqyfs (SEQ ID NO:33)
```

FIG. 9

N8 (Accession No. AIK26315.1)

```
  1 mnpnqkiitv gsvslglvvl nillhivsit vtvlvlpgng nnkncnetvi reynetvrie
 61 kvtqwhntnv ieyiekpesg hfmnntealc dakgfapfsk dngirigsrg hvfvirepfv
121 scsptecrtf fltqgsllnd khsngtvkdr spyrtlmsve igqspnvyqa rfeavawsat
181 achdgkkwmt igvtgpdaka vavvhyggip tdvinswagd ilrtqessct ciqgecywvm
241 tdgpanrqaq yrafkakqgk ivgqteisfn gshieecscy pnegkvecvc rdnwtgtnrp
301 vlvispdlsy ragylcaglp sdtprgedsq ftgsctspvg nqgygvkgfg frqgndvwmg
361 rtisrtsrsg feilkvrngw vqnskeqikr qvvvdnlkws gysgsftlpv eltkrnclvp
421 cfwvemirgk peektiwtss ssivmcgvdh eiadwswhdg ailpfdidkm (SEQ ID NO:34)
```

N9 (Accession No. ALH21371)

```
  1 mnpnqkilct sataiiigai avligianlg lniglhlkpg cncshsqpet tntsqtiinn
 61 yynetnitni qmeertsrnf nnltkglcti nswhiygkdn avrigessdv lvtrepyvsc
121 dpdecrfyal sqgttirgkh sngtihdrsq yraliswpls spptvynsrv ecigwsstsc
181 hdgksrmsic isgpnnnasa vvwynrrpvt eintwarnil rtqesecvch ngvcpvvftd
241 gsatgpadtr iyyfkegkil kwesltgtak hieecscyge rtgitctcrd nwqgsnrpvi
301 qidpvamtht sqyicspvlt dnprpndpni gkcndpypgn nnngvkgfsy ldgantwlgr
361 tistasrsgy emlkvpnalt ddrskpiqgq tivlnadwsg ysgsfmdywa egdcyracfy
421 velirgrpke dkvwwtsnsi vsmcsstefl gqwnwpdgak ieyfl (SEQ ID NO:35)
```

FIG. 9(Continued)

agcgaaagca ggtcaattat attcaatatg gaaagaataa aagaactaag aaatctaatg
tcgcagtctc gcacccgcga gatactcaca aaaaccaccg tggaccatat ggccataatc
aagaagtaca catcaggaag acaggagaag aacccagcac ttaggatgaa atggatgatg
gcaatgaaat atccaattac agcagacaag aggataacgg aaatgattcc tgagagaaat
gagcaaggac aaactttatg gagtaaaatg aatgatgccg gatcagaccg agtgatggta
tcacctctgg ctgtgacatg gtggaatagg aatggaccaa tgacaaatac agttcattat
ccaaaaatct acaaaactta ttttgaaaga gtcgaaaggc taaagcatgg aacctttggc
cctgtccatt ttagaaacca agtcaaaata cgtcggagag ttgacataaa tcctggtcat
gcagatctca gtgccaagga ggcacaggat gtaatcatgg aagttgtttt ccctaacgaa
gtgggagcca ggatactaac atcggaatcg caactaacga taaccaaaga gaagaaagaa
gaactccagg attgcaaaat ttctcctttg atggttgcat acatgttgga gagagaactg
gtccgcaaaa cgagattcct cccagtggct ggtggaacaa gcagtgtgta cattgaagtg
ttgcatttga ctcaaggaac atgctgggaa cagatgtata ctccaggagg ggaagtgaag
aatgatgatg ttgatcaaag cttgattatt gctgctagga acatagtgag aagagctgca
gtatcagcag acccactagc atctttattg gagatgtgcc acagcacaca gattggtgga
attaggatgg tagacatcct taagcagaac ccaacagaag agcaagccgt ggatatatgc
aaggctgcaa tgggactgag aattagctca tccttcagtt ttggtggatt cacatttaag
agaacaagcg gatcatcagt caagagagag gaagaggtgc ttacgggcaa tcttcaaaca
ttgaagataa gagtgcatga gggatctgaa gagttcacaa tggttgggag aagagcaaca
gccatactca gaaaagcaac caggagattg attcagctga tagtgagtgg gagagacgaa
cagtcgattg ccgaagcaat aattgtggcc atggtatttt cacaagagga ttgtatgata
aaagcagtta gaggtgatct gaatttcgtc aatagggcga atcagcgact gaatcctatg
catcaacttt taagacattt tcagaaggat gcgaaagtgc ttttttcaaaa ttggggagtt
gaacctatcg acaatgtgat gggaatgatt gggatattgc ccgacatgac tccaagcatc
gagatgtcaa tgagaggagt gagaatcagc aaaatgggtg tagatgagta ctccagcacg
gagagggtag tggtgagcat tgaccggttc ttgagagtca gggaccaacg aggaaatgta
ctactgtctc ccgaggaggt cagtgaaaca cagggaacag agaaactgac aataacttac
tcatcgtcaa tgatgtggga gattaatggt cctgaatcag tgttggtcaa tacctatcaa
tggatcatca gaaactggga aactgttaaa attcagtggt cccagaaccc tacaatgcta
tacaataaaa tggaatttga accatttcag tctttagtac ctaaggccat tagaggccaa
tacagtgggt ttgtaagaac tctgttccaa caaatgaggg atgtgcttgg gacatttgat
accgcacaga taataaaact tcttcccttc gcagccgctc caccaaagca aagtagaatg
cagttctcct catttactgt gaatgtgagg ggatcaggaa tgagaatact tgtaaggggc
aattctcctg tattcaacta caacaaggcc acgaagagac tcacagttct cggaaaggat
gctggcactt taaccgaaga cccagatgaa ggcacagctg agtggagtc cgctgttctg
agggggattcc tcattctggg caaagaagac aggagatatg gccagcatt aagcatcaat
gaactgagca accttgcgaa aggagagaag gctaatgtgc taattgggca aggagacgtg
gtgttggtaa tgaaacgaaa acgggactct agcatactta ctgacagcca gacagcgacc
aaaagaattc ggatggccat caattagtgt cgaatagttt aaaaacgacc ttgtttctac
t (SEQ ID NO:39)which encodes

```
agcgaaagca ggcaaaccat ttgaatggat gtcaatccga ccttactttt cttaaaagtg
ccagcacaaa atgctataag cacaactttc ccttataccg gagaccctcc ttacagccat
gggacaggaa caggatacac catggatact gtcaacagga cacatcagta ctcagaaaag
ggaagatgga caacaaacac cgaaactgga gcaccgcaac tcaacccgat tgatgggcca
ctgccagaag acaatgaacc aagtggttat gcccaaacag attgtgtatt ggaagcaatg
gctttccttg aggaatccca tcctggtatt tttgaaaact cgtgtattga acgatggag
gttgttcagc aaacacgagt agacaagctg acacaaggcc gacagaccta tgactggact
ttaaatagaa accagcctgc tgcaacagca ttggccaaca caatagaagt gttcagatca
aatggcctca cggccaatga gtcaggaagg ctcatagact tccttaagga tgtaatggag
tcaatgaaaa aagaagaaat ggggatcaca actcattttc agagaaagag acgggtgaga
gacaatatga ctaagaaaat gataacacag agaacaatag gtaaaaggaa acagagattg
aacaaaaggg gttatctaat tagagcattg accctgaaca caatgaccaa agatgctgag
agagggaagc taaaacggag agcaattgca accccaggga tgcaaataag ggggtttgta
tactttgttg agacactggc aaggagtata tgtgagaaac ttgaacaatc agggttgcca
gttggaggca atgagaagaa agcaaagttg gcaaatgttg taaggaagat gatgaccaat
tctcaggaca ccgaactttc tttcaccatc actggagata acaccaaatg gaacgaaaat
cagaatcctc ggatgttttt ggccatgatc acatatatga ccagaaatca gcccgaatgg
ttcagaaatg ttctaagtat tgctccaata atgttctcaa acaaaatggc gagactggga
aaagggtata tgtttgagag caagagtatg aaacttagaa ctcaaatacc tgcagaaatg
ctagcaagca ttgatttgaa atatttcaat gattcaacaa gaaagaagat tgaaaaaatc
cgaccgctct taatagaggg gactgcatca ttgagccctg gaatgatgat gggcatgttc
aatatgttaa gcactgtatt aggcgtctcc atcctgaatc ttggacaaaa gagatacacc
aagactactt actggtggga tggtcttcaa tcctctgacg attttgctct gattgtgaat
gcacccaatc atgaagggat tcaagccgga gtcgacaggt tttatcgaac tgtaagcta
cttggaatca atatgagcaa gaaaaagtct tacataaaca gaacaggtac atttgaattc
acaagttttt tctatcgtta tgggtttgtt gccaatttca gcatggagct tcccagtttt
ggggtgtctg ggatcaacga gtcagcggac atgagtattg gagttactgt catcaaaaac
aatatgataa acaatgatct tggtccagca acagctcaaa tggcccttca gttgttcatc
aaagattaca ggtacacgta ccgatgccat agaggtgaca cacaaataca aacccgaaga
tcatttgaaa taaagaaact gtgggagcaa acccgttcca aagctggact gctggtctcc
gacggaggcc caaatttata caacattaga aatctccaca ttcctgaagt ctgcctaaaa
tgggaattga tggatgagga ttaccagggg cgtttatgca acccactgaa cccatttgtc
agccataaag aaattgaatc aatgaacaat gcagtgatga tgccagcaca tggtccagcc
aaaaacatgg agtatgatgc tgttgcaaca acacactcct ggatccccaa aagaaatcga
tccatcttga atacaagtca aagaggagta cttgaagatg aacaaatgta ccaaaggtgc
tgcaatttat ttgaaaaatt cttccccagc agttcataca gaagaccagt cgggatatcc
agtatggtgg aggctatggt ttccagagcc cgaattgatg cacggattga tttcgaatct
```
ggaaggataa agaaagaaga gttcactgag atcatgaaga tctgttccac cattgaagag
ctcagacggc aaaaatagtg aatttagctt gtccttcatg aaaaaatgcc ttgtttctac t(SEQ ID
NO:40) which encodes

```
M D V N P T L L F L K V P A Q N A I S T T F P Y T G D P P Y S H G T G T G Y
T M D T V N R T H Q Y S E K G R W T T N T E T G A P Q L N P I D G P L P E D
N E P S G Y A Q T D C V L E A M A F L E E S H P G I F E N S C I E T M E V V
Q Q T R V D K L T Q G R Q T Y D W T L N R N Q P A A T A L A N T I E V F R
S N G L T A N E S G R L I D F L K D V M E S M K K E E M G I T T H F Q R K R
R V R D N M T K K M I T Q R T I G K R K Q R L N K R G Y L I R A L T L N T M
T K D A E R G K L K R R A I A T P G M Q I R G F V Y F V E T L A R S I C E K
L E Q S G L P V G G N E K K A K L A N V V R K M M T N S Q D T E L S F T I T
G D N T K W N E N Q N P R M F L A M I T Y M T R N Q P E W F R N V L S I A
P I M F S N K M A R L G K G Y M F E S K S M K L R T Q I P A E M L A S I D L
K Y F N D S T R K K I E K I R P L L I E G T A S L S P G M M M G M F N M L S
T V L G V S I L N L G Q K R Y T K T T Y W W D G L Q S S D D F A L I V N A P
N H E G I Q A G V D R F Y R T C K L L G I N M S K K K S Y I N R T G T F E F
T S F F Y R Y G F V A N F S M E L P S F G V S G I N E S A D M S I G V T V I K
N N M I N N D L G P A T A Q M A L Q L F I K D Y R Y T Y R C H R G D T Q I Q
T R R S F E I K K L W E Q T R S K A G L L V S D G G P N L Y N I R N L H I P E
V C L K W E L M D E D Y Q G R L C N P L N P F V S H K E I E S M N N A V M
M P A H G P A K N M E Y D A V A T T H S W I P K R N R S I L N T S Q R G V L
E D E Q M Y Q R C C N L F E K F F P S S S Y R R P V G I S S M V E A M V S R
A R I D A R I D F E S G R I K K E E F T E I M K I C S T I E E L R R Q K
```
agcgaaagca ggtactgatt caaaatggaa gattttgtgc gacaatgctt caatccgatg
attgtcgagc ttgcggaaaa aacaatgaaa gagtatgggg aggacctgaa aatcgaaaca
aacaaatttg cagcaatatg cactcacttg gaagtatgct tcatgtattc agatttccac
ttcatcaatg agcaaggcga gtcaataatc gtagaacttg gtgatcctaa tgcacttttg
aagcacagat tgaaataat cgagggaaga gatcgcacaa tggcctggac agtagtaaac
agtatttgca acactacagg ggctgagaaa ccaaagtttc taccagattt gtatgattac
aaggaaaata gattcatcga aattggagta acaaggagag aagttcacat atactatctg
gaaaaggcca ataaaattaa atctgagaaa acacacatcc acattttctc gttcactggg
gaagaaatgg ccacaagggc cgactacact ctcgatgaag aaagcagggc taggatcaaa
accaggctat tcaccataag acaagaaatg gccagcagag gcctctggga ttcctttcgt
cagtccgaga gaggagaaga gacaattgaa gaaaggtttg aaatcacagg aacaatgcgc
aagcttgccg accaaagtct cccgccgaac ttctccagcc ttgaaaattt tagagcctat
gtggatggat tcgaaccgaa cggctacatt gagggcaagc tgtctcaaat gtccaaagaa
gtaaatgcta gaattgaacc ttttttgaaa acaacaccac gaccacttag acttccgaat
gggcctccct gttctcagcg gtccaaattc ctgctgatgg atgccttaaa attaagcatt
gaggacccaa gtcatgaagg agagggaata ccgctatatg atgcaatcaa atgcatgaga
acattctttg gatggaagga acccaatgtt gttaaaccac acgaaaaggg aataaatcca
aattatcttc tgtcatggaa gcaagtactg cagaactgc aggacattga gaatgaggag
aaaattccaa agactaaaaa tatgaaaaaa acaagtcagc taaagtgggc acttggtgag
aacatggcac cagaaaaggt agactttgac gactgtaaag atgtaggtga tttgaagcaa
tatgatagtg atgaaccaga attgaggtcg cttgcaagtt ggattcagaa tgagttcaac
```

FIG. 10(Continued)

aaggcatgcg aactgacaga ttcaagctgg atagagcttg atgagattgg agaagatgtg
gctccaattg aacacattgc aagcatgaga aggaattatt tcacatcaga ggtgtctcac
tgcagagcca cagaatacat aatgaagggg gtgtacatca atactgcctt acttaatgca
tcttgtgcag caatggatga tttccaatta attccaatga taagcaagtg tagaactaag
gagggaaggc gaaagaccaa cttgtatggt ttcatcataa aaggaagatc ccacttaagg
aatgacaccg acgtggtaaa ctttgtgagc atggagtttt ctctcactga cccaagactt
gaaccacaca aatgggagaa gtactgtgtt cttgagatag gagatatgct tctaagaagt
gccataggcc aggtttcaag gcccatgttc ttgtatgtga ggacaaatgg aacctcaaaa
attaaaatga aatggggaat ggagatgagg cgttgtctcc tccagtcact tcaacaaatt
gagagtatga ttgaagctga gtcctctgtc aaagagaaag acatgaccaa agagttcttt
gagaacaaat cagaaacatg gcccattgga gagtctccca aaggagtgga ggaaagttcc
attgggaagg tctgcaggac tttattagca aagtcggtat ttaacagctt gtatgcatct
ccacaactag aaggattttc agctgaatca agaaaactgc ttcttatcgt tcaggctctt
agggacaatc tggaacctgg gacctttgat cttgggggc tatatgaagc aattgaggag
tgcctaatta atgatccctg ggttttgctt aatgcttctt ggttcaactc cttccttaca
catgcattga gttagttgtg gcagtgctac tatttgctat ccatactgtc caaaaaagta
ccttgtttct act (SEQ ID NO:41) which encodes M E D F V R Q C F N P M I V E L A E K T M K E Y G E D L K I E T N K F A A I
C T H L E V C F M Y S D F H F I N E Q G E S I I V E L G D P N A L L K H R F E
I I E G R D R T M A W T V V N S I C N T T G A E K P K F L P D L Y D Y K E N
R F I E I G V T R R E V H I Y Y L E K A N K I K S E K T H I H I F S F T G E E M
A T R A D Y T L D E E S R A R I K T R L F T I R Q E M A S R G L W D S F R Q
S E R G E E T I E E R F E I T G T M R K L A D Q S L P P N F S S L E N F R A Y
V D G F E P N G Y I E G K L S Q M S K E V N A R I E P F L K T T P R P L R L P
N G P P C S Q R S K F L L M D A L K L S I E D P S H E G E G I P L Y D A I K C
M R T F F G W K E P N V V K P H E K G I N P N Y L L S W K Q V L A E L Q D
I E N E E K I P K T K N M K K T S Q L K W A L G E N M A P E K V D F D D C
K D V G D L K Q Y D S D E P E L R S L A S W I Q N E F N K A C E L T D S S W
I E L D E I G E D V A P I E H I A S M R R N Y F T S E V S H C R A T E Y I M K
G V Y I N T A L L N A S C A A M D D F Q L I P M I S K C R T K E G R R K T N
L Y G F I I K G R S H L R N D T D V V N F V S M E F S L T D P R L E P H K W
E K Y C V L E I G D M L L R S A I G Q V S R P M F L Y V R T N G T S K I K M
K W G M E M R R C L L Q S L Q Q I E S M I E A E S S V K E K D M T K E F F E
N K S E T W P I G E S P K G V E E S S I G K V C R T L L A K S V F N S L Y A S
P Q L E G F S A E S R K L L L I V Q A L R D N L E P G T F D L G G L Y E A I E
E C L I N D P W V L L N A S W F N S F L T H A L S agcaaaagca gggtagataa tcactcactg agtgacatca aaatcatggc gtcccaaggc
accaaacggt cttacgaaca gatggagact gatggagaac gccagaatgc cactgaaatc
agagcatccg tcggaaaaat gattggtgga attggacgat ctacatcca aatgtgcaca
gaacttaaac tcagtgatta tgagggacgg ttgatccaaa acagcttaac aatagagaga
atggtgctct ctgcttttga cgaaggaga aataaatacc tggaagaaca tcccagtgcg
gggaaagatc ctaagaaaac tggaggacct atatacagaa gagtaaacgg aaagtggatg
agagaactca tcctttatga caaagaagaa ataaggcgaa tctggcgcca agctaataat
ggtgacgatg caacggctgg tctgactcac atgatgatct ggcattccaa tttgaatgat
gcaacttatc agaggacaag ggctcttgtt cgcaccggaa tggatcccag gatgtgctct ctgatgcaag gttcaactct ccctaggagg tctggagccg caggtgctgc agtcaaagga
gttggaacaa tggtgatgga attggtcagg atgatcaaac gtgggatcaa tgatcggaac
ttctggaggg gtgagaatgg acgaaaaaca agaattgctt atgaaagaat gtgcaacatt
ctcaaaggga aatttcaaac tgctgcacaa aaagcaatga tggatcaagt gagagagagc
cggaacccag ggaatgctga gttcgaagat ctcactttc tagcacggtc tgcactcata
ttgagagggt cggttgctca caagtcctgc ctgcctgcct gtgtgtatgg acctgccgta
gccagtgggt acgactttga aagagaggga tactctctag tcggaataga ccctttcaga
ctgcttcaaa acagccaagt gtacagccta atcagaccaa atgagaatcc agcacacaag
agtcaactgg tgtggatggc atgccattct gccgcatttg aagatctaag agtattgagc
ttcatcaaag ggacgaaggt ggtcccaaga gggaagcttt ccactagagg agttcaaatt
gcttccaatg aaaatatgga gactatggaa tcaagtacac ttgaactgag aagcaggtac
tgggccataa ggaccagaag tggaggaaac accaatcaac agagggcatc tgcgggccaa
atcagcatac aacctacgtt ctcagtacag agaaatctcc cttttgacag aacaaccgtt
atggcagcat tcactgggaa tacagagggg agaacatctg acatgaggac cgaaatcata
aggatgatgg aaagtgcaag accagaagat gtgtctttcc aggggcgggg agtcttcgag
ctctcggacg aaaaggcagc gagcccgatc gtgccttcct tgacatgag taatgaagga
tcttatttct tcggagacaa tgcagaggag tacgacaatt aaagaaaaat accttgttt
ctact (SEQ ID NO:42) which encodes M A S Q G T K R S Y E Q M E T D G E R Q N A T E I R A S V G K M I G G I G R
F Y I Q M C T E L K L S D Y E G R L I Q N S L T I E R M V L S A F D E R R N K
Y L E E H P S A G K D P K K T G G P I Y R R V N G K W M R E L I L Y D K E E
I R R I W R Q A N N G D D A T A G L T H M M I W H S N L N D A T Y Q R T R
A L V R T G M D P R M C S L M Q G S T L P R R S G A A G A A V K G V G T M
V M E L V R M I K R G I N D R N F W R G E N G R K T R I A Y E R M C N I L K
G K F Q T A A Q K A M M D Q V R E S R N P G N A E F E D L T F L A R S A L I
L R G S V A H K S C L P A C V Y G P A V A S G Y D F E R E G Y S L V G I D P
F R L L Q N S Q V Y S L I R P N E N P A H K S Q L V W M A C H S A A F E D L
R V L S F I K G T K V V P R G K L S T R G V Q I A S N E N M E T M E S S T L
E L R S R Y W A I R T R S G G N T N Q Q R A S A G Q I S I Q P T F S V Q R N L
P F D R T T V M A A F T G N T E G R T S D M R T E I I R M M E S A R P E D V
S F Q G R G V F E L S D E K A A S P I V P S F D M S N E G S Y F F G D N A E E
Y D N agcaaaagca ggtagatatt gaaagatgag tcttctaacc gaggtcgaaa cgtacgttct
ctctatcatc ccgtcaggcc ccctcaaagc cgagatcgca cagagacttg aagatgtctt
tgcagggaag aacaccgatc ttgaggttct catggaatgg ctaaagacaa gaccaatcct
gtcacctctg actaagggga tttaggatt tgtgttcacg ctcaccgtgc ccagtgagcg
aggactgcag cgtagacgct ttgtccaaaa tgcccttaat gggaacgggg atccaaataa
catggacaaa gcagttaaac tgtataggaa gctcaagagg gagataacat tccatgggc
caaagaaatc tcactcagtt attctgctgg tgcacttgcc agttgtatgg cctcatata
caacaggatg ggggctgtga ccactgaagt ggcatttggc ctggtatgtg caacctgtga
acagattgct gactcccagc atcggtctca taggcaaatg gtgacaacaa ccaacccact
aatcagacat gagaacagaa tggttttagc cagcactaca gctaaggcta tggagcaaat
ggctggatcg agtgagcaag cagcagaggc catggaggtt gctagtcagg ctaggcaaat
ggtgcaagcg atgagaacca ttgggactca tcctagctcc agtgctggtc tgaaaaatga
tcttcttgaa aatttgcagg cctatcagaa acgaatgggg gtgcagatgc aacggttcaa
gtgatcctct cgctattgcc gcaaatatca ttgggatctt gcacttgata ttgtggattc
ttgatcgtct tttttcaaa tgcatttacc gtcgctttaa atacggactg aaaggagggc

```
cttctacgga aggagtgcca aagtctatga gggaagaata tcgaaaggaa cagcagagtg
ctgtggatgc tgacgatggt cattttgtca gcatagagct ggagtaaaaa actaccttgt
ttctact (SEQ ID NO:43) which encodes
```

MS L L T E V E T Y V L S I I P S G P L K A E I A Q R L E D V F A G K N T D L
E V L M E W L K T R P I L S P L T K G I L G F V F T L T V P S E R G L Q R R R
F V Q N A L N G N G D P N N M D K A V K L Y R K L K R E I T F H G A K E I S
L S Y S A G A L A S C M G L I Y N R M G A V T T E V A F G L V C A T C E Q I
A D S Q H R S H R Q M V T T T N P L I R H E N R M V L A S T T A K A M E Q
M A G S S E Q A A E A M E V A S Q A R Q M V Q A M R T I G T H P S S A G
L K N D L L E N L Q A Y Q K R M G V Q M Q R F K

```
agcaaaagca gggtgacaaa gacataatgg atccaaacac tgtgtcaagc tttcaggtag   60
attgctttct ttggcatgtc cgcaaacgag ttgcagacca agaactaggt gatgccccat  120
tccttgatcg gcttcgccga gatcagaaat ccctaagagg aaggggcagc actcttggtc  180
tggacatcga gacagccaca cgtgctggaa agcagatagt ggagcggatt ctgaaagaag  240
aatccgatga ggcacttaaa atgaccatgg cctctgtacc tgcgtcgcgt tacctaaccg  300
acatgactct tgaggaaatg tcaagggaat ggtccatgct catacccaag cagaaagtgg  360
caggccctct ttgtatcaga atggaccagg cgatcatgga taaaaacatc atactgaaag  420
cgaacttcag tgtgattttt gaccggctgg agactctaat attgctaagg gctttcaccg  480
aagagggagc aattgttggc gaaatttcac cattgccttc tcttccagga catactgctg  540
aggatgtcaa aaatgcagtt ggagtcctca tcggaggact tgaatggaat gataacacag  600
ttcgagtctc tgaaactcta cagagattcg cttggagaag cagtaatgag aatgggagac  660
ctccactcac tccaaaacag aaacgagaaa tggcgggaac aattaggtca gaagtttgaa  720
gaaataagat ggttgattga agaagtgaga cacaaactga aggtaacaga gaatagtttt  780
gagcaaataa catttatgca agccttacat ctattgcttg aagtggagca agagataaga  840
actttctcat ttcagcttat
ttaataataa aaaacaccct
tgtttctact
(SEQ ID NO:44)
```

```
  1 mnpnqkiiti gsvcmtigma nlilqignii siwishsiql gnqnqietcn qsvityennt
 61 wvnqtyvnis ntnfaagqsv vsvklagnss lcpvsgwaiy skdnsvrigs kgdvfvirep
121 fiscsplecr tffltqgall ndkhsngtik drspyrtlms cpigevpspy nsrfesvaws
181 asachdginw ltigisgpdn gavavlkyng iitdtikswr nnilrtqese cacvngscft
241 vmtdgpsngq asykifriek gkivksvemn apnyhyeecs cypdsseitc vcrdnwhgsn
301 rpwvsfnqnl eyqigyicsg ifgdnprpnd ktgscgpvss ngangvkgfs fkygngvwig
361 rtksissrng femiwdpngw tgtdnnfsik qdivginews gysgsfvqhp eltgldcirp
421 cfwvelirgr pkentiwtsg ssisfcgvns dtvgwswpdg aelpftidk
```

N7

```
  1 mnpnqklfal sgvaialsil nlligisnvg lnvslhlkgs sdqdknwtct svtqnnttli
 61 entyvnnttv idketgtakp nylmlnkslc kvegwvvvak dnairfgese qiivtrepyv
121 scdplgckmy alhqgttirn khsngtihdr tafrglistp lgsppvvsns dflcvgwsst
181 schdgigrmt icvqgnndna tatvyydrrl tttiktwagn ilrtqesecv chngtcvvim
241 tdgsassqay tkvlyfhkgl vikeealkgs arhieecscy ghnskvtcvc rdnwqganrp
301 vieidmname htsqylctgv ltdtsrpsdk smgdcnnpit gspgapgvkq fgfldssntw
361 lgrtisprsr sgfemlkipn aetdpnskit erqeivdnnn wsgysgsfid ywdessecyn
421 pcfyvelirg rpeeakyvgw tsnslialcg spisvgsgsf pdgaqiqyfs
```

N9

```
    mnpnqkilct sataiiigai avligianlg lniglhlkpg cncshsqpet tntsqtiinn
 61 yynetnitni qmeertsrnf nnltkglcti nswhiygkdn avrigessdv lvtrepyvsc
121 dpdecrfyal sqgttirgkh sngtihdrsq yraliswpls spptvynsrv ecigwsstsc
181 hdgksrmsic isgpnnnasa vvwynrrpva eintwarnil rtqesecvch ngvcpvvftd
241 gsatgpadtr iyyfkegkil kwesltgtak hieecscyge rtgitctcrd nwqgsnrpvi
301 qidpvamtht sqyicspvlt dnprpndpni gkcndpypgn nnngvkgfsy ldgantwlgr
361 tistasrsgy emlkvpnalt ddrskpiqgq tivlnadwsg ysgsfmdywa egdcyracfy
421 velirgrpke dkvwwtsnsi vsmcsstefl gqwnwpdgak ieyfl
```

N2

```
  1 mnpnqkiiti gsvsltisti cffmqiaili ttvtlhfkqy efnsppnnqv mlceptiier
 61 niteivyltn ttiekeicpk laeyrnwskp qcnitgfapf skdnsirlsa ggdiwvtrep
121 yvscdpdkcy qfalgqgttl nnvhsndivh drtpyrtllm nelgvpfhlg tkqvciawss
181 sschdgkawl hvcvtgdden atasfiyngr ladsivswsk kilrtqesec vcingtctvv
241 mtdgsasgka dtkilfieeg kivhtstlsg saqhveecsc yprypgvrcv crdnwkgsnr
```

FIG. 11

```
301 pivdinikdy sivssyvcsg lvgdtprknd ssssshcldp nneegghgvk gwafddgndv
361 wmgrtisekl rsgyetfkvi egwsnpnskl qinrqvivdr gnrsgysgif svegkscinr
421 cfyvelirgr kqetevlwts nsivvfcgts gtygtgswpd gadinlmpi
```

FIG. 11(Continued)

| Passage 1 | | | Passage 2 | | | Passage 3 | | |
|---|---|---|---|---|---|---|---|---|
| Egg | Virus Titer (pfu/ml) | HA Mutation | Egg | Virus Titer (pfu/ml) | HA Mutation | Egg | Virus Titer (pfu/ml) | HA Mutation |
| A | $2.6\times10^6$ | none | A1 | $6.6\times10^6$ | none | A1a | $5.3\times10^7$ | none |
| | | | | | | A1b | $1.2\times10^8$ | none |
| | | | | | | A1c | $3.7\times10^7$ | none |
| | | | A2 | $3.5\times10^7$ | none | A2a | $5.8\times10^7$ | none |
| | | | |

| AM: amniotic cavity | | | | | | | | | | | | | | | | | | | |
|---|---|---|---|---|---|---|---|---|---|---|---|---|---|---|---|---|---|---|---|
| AL: allantoic cavity | | | | | | | | | | | | | | | | | | | |
| | AM1 | | | AM1AL1 | | | AM1AL2 | | | | AM1AL3 | | | | AM1AL4 | | | | AM1AL5 | | | |
| | Titer pfu/ml | Mutation HA | Mutation NA | Titer pfu/ml | Mutation HA | Mutation NA | Egg | Titer pfu/ml | Mutation HA | Mutation NA | Egg | Titer pfu/ml | Mutation HA | Mutation NA | Egg | Titer pfu/ml | Mutation HA | Mutation NA | Egg | Titer pfu/ml | Mutation HA | Mutation NA |
| Virus generated by reverse genetics | | | | | | | | | | | | | | | | | | | | | | |
| HA: A/HK/4801/2014 | | | | | | | | | | | | | | | | | | | | | | |
| NA: A/HK/4801/2014NA(T148K, N329X, 347X) | | | | | | | | | | | | | | | | | | | | | | |
| backbone: High Yield-PR8 | | | | | | | | | | | | | | | | | | | | | | |
| | | | | | | | a | 1.2x10⁶ | none | T148K, D151E, H347G | a | 1.5x10⁸ | none | 4M* | | | | | a | 1.1x10⁷ | none | 4M |
| titer: 4x10⁴ (pfu/ml) | 1.1x10⁸ | nd | nd | 9.4x10⁶ | none | T148K, D151E, H347G | | | | | | | | | a | 1.1x10⁸ | none | 4M | b | 2.6x10⁷ | none | 4M |
| | | | | | | | | | | | | | | | | | | | c | 3.2x10⁷ | none | 4M |
| | | | | | | | | | | | | | | | | | | | d | 1.1x10⁷ | none | 4M |
| | | | | | | | b | 1.1x10⁷ | none | T148K, D151E, H347G | a | 2.3x10⁷ | none | 4M | | | | | a | 7.5x10⁶ | none | 4M |
| | | | | | | | | | | | | | | | b | 1.1x10⁸ | none | 4M | a | 1.6x10⁷ | none | 4M |
| | | | | | | | | | | | | | | | | | | | b | 1.6x10⁷ | none | 4M |
| | | | | | | | | | | | | | | | a | 1.2x10⁸ | none | 4M | c | 7.3x10⁶ | none | 4M |
| | | | | | | | | | | | | | | | | | | | d | 1.9x10⁷ | none | 4M |
| | | | | | | | | | | | b | 3.1x10⁷ | none | 4M* | | | | | e | 2.5x10⁷ | none | 4M |
| | | | | | | | | | | | | | | | | | | | a | 1.3x10⁷ | none | 4M |
| | | | | | | | | | | | | | | | b | 6.6x10⁸ | none | 4M | b | 1.3x10⁷ | none | 4M |
| | | | | | | | | | | | | | | | | | | | c | 1.0x10⁷ | none | 4M |
| | | | | | | | | | | | | | | | a | 3.3x10⁸ | none | 4M | d | 3.2x10⁷ | none | 4M |
| | | | | | | | | | | | | | | | | | | | a | 8.0x10⁶ | none | 4M |
| | | | | | | | | | | | | | | | b | 5.8x10⁸ | none | 4M | b | 1.7x10⁷ | none | 4M |
| | | | | | | | | | | | | | | | | | | | c | 6.9x10⁷ | none | 4M |
| | | | | | | | | | | | | | | | | | | | a | 2.7x10⁷ | none | 4M |

FIG. 14

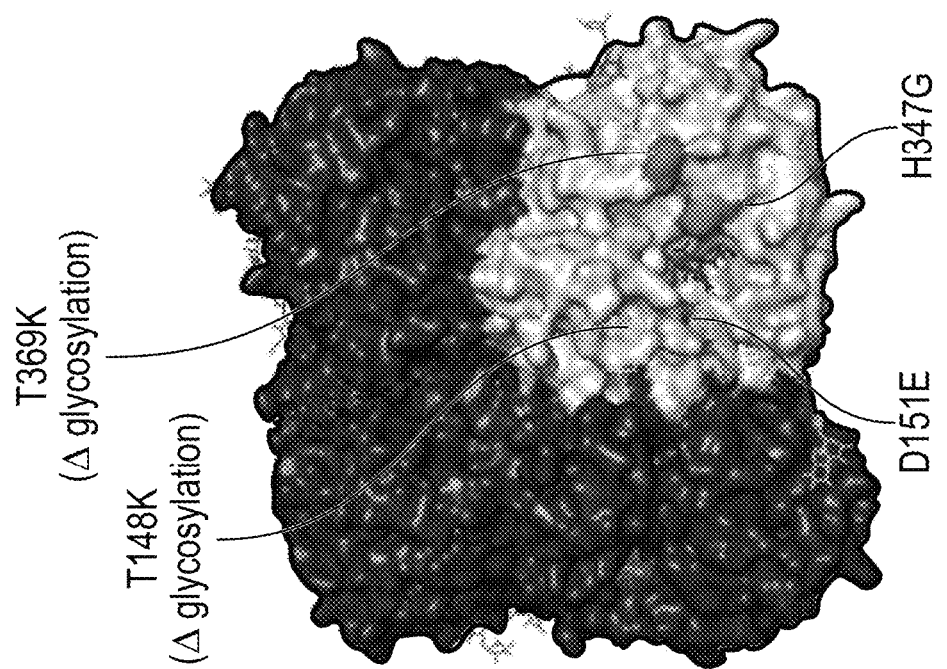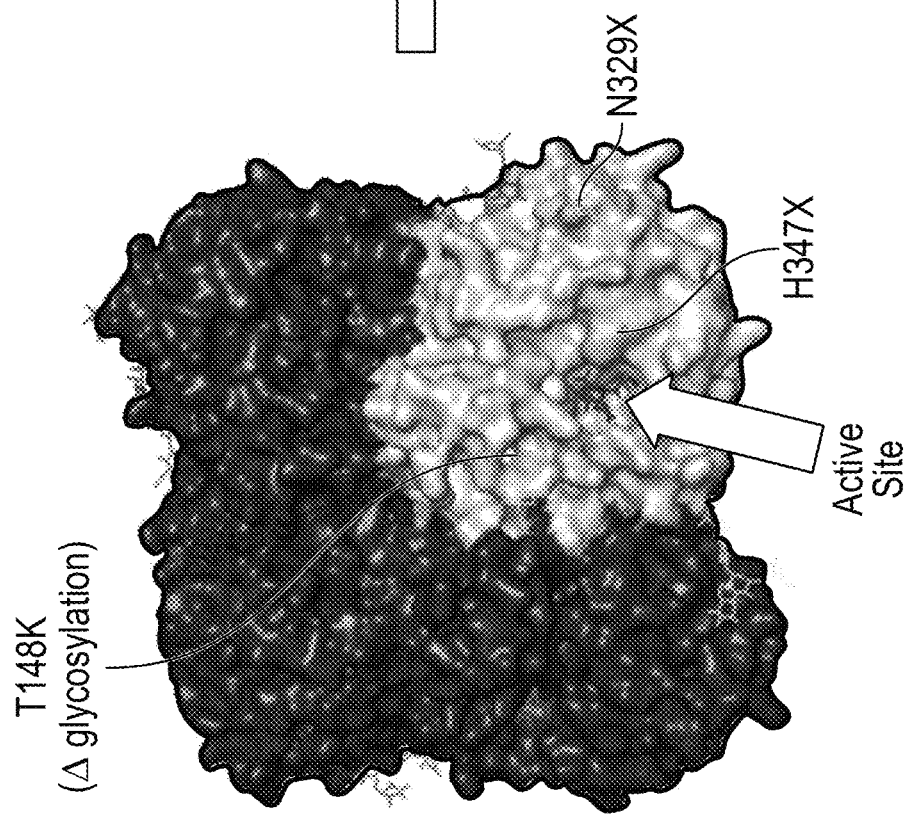
FIG. 15

| Egg | Passage 1 | | Egg | Passage 2 | | Egg | Passage 3 | |
|---|---|---|---|---|---|---|---|---|
| | Virus Titer (pfu/ml) | HA Mutation | | Virus Titer (pfu/ml) | HA Mutation | | Virus Titer (pfu/ml) | HA Mutation |
| A | 2.6x10$^6$ | none | A1 | 6.6x10$^6$ | none | A1a | 5.3x10$^7$ | none |
| | | | | | | A1b | 1.2x10$^8$ | none |
| | | | | | | A1c | 3.7x10$^7$ | none |
| | | | A2 | 3.5x10$^7$ | none | A2a | 5.8x10$^7$ | none |
| | | | | | | A2b | 1.0x10$^8$ | none |
| | | | A3 | 2.

| | | AM1 | | AM1AL1 | | | AM1AL2 | | | | AM1AL3 | | | | AM1AL4 | | | | AM1AL5 | | |
|---|---|---|---|---|---|---|---|---|---|---|---|---|---|---|---|---|---|---|---|---|---|
| | | Titer pfu/ml | Mutation HA / NA | Titer Pfu/ml | Mutation HA / NA | Egg | Titer pfu/ml | Mutation HA | Mutation NA | Egg | Titer pfu/ml | Mutation HA | Mutation NA | Egg | Titer pfu/ml | Mutation HA | Mutation NA | Egg | Titer pfu/ml | Mutation

K189E-N158K-A212T

| | | Inoculation | Egg1 | Egg2 | Egg3 |
|---|---|---|---|---|---|
| P4 | Inoculation | 4.3 | 6.0 | 5.0 | N.D. |
| | Harvested | 6.5 | 2.6 | N.D. | 3.0 |
| P5 | Inoculation | 6.3 | 6.0 | 5.0 | N.D. |
| | Harvested | 7.3 | 2.6 | 5.9 | 4.0 |
| P6 | Inoculation | 6.3 | 6.1 | 5.1 | 4.2 |
| | Harvested | 5.5 | 7.7 | 6.0 | 4.1 |
| P7 | Inoculation | 4.5 | 6.6 | 6.1 | 4.7 |
| | Harvested | 6.3 | 5.8 | 3.5 | 2.5 |
| P8 | Inoculation | 3.4 | 6.2 | 7.3 | 7.8 |
| | Harvested | 8.0 | 7.9 | 2.4 | 1.4 |
| P9 | Inoculation | 2.3 | 7.1 | 4.6 | 8.2 |
| | Harvested | 8.2 | 5.1 | 1.3 | 4.8 |
| P10 | Inoculation | 3.1 | 3.5 | 1.8 | 1.3 |
| | Harvested | 3.9 | 2.9 | 2.1 | N.D. |
| P11 | Inoculation | 4.0 | 8.8 | 5.4 | 4.3 |
| | Harvested | 6.9 | 4.6 | 3.0 | 2.0 |

Legend:
- Inoculation
- Egg1 / Egg2 / Egg3
- ←Titer (log10 PFU/egg)
- ←Titer (log10 PFU/mL)

FIG. 21

HA/NA Mutations (HA-K189E/N158K/A212T Mutant Virus)

| | | HA | | NA | | | |
|---|---|---|---|---|---|---|---|
| | | | | 148 | 151 | 245 | 346 |
| | Passage | | | T | D | N | G |
| K189E/N158K/A212T | E4 | No Mutation | | K | E | S | |
| | E6 | No Mutation | | K | E | S | V |
| | E7 | No Mutation | | K | E | S | V |
| | E10 | No Mutation | | K | E | S | V |

FIG. 22

Allantoic Titer (35C 3days) 2x10^3pfu/egg Inoculation

| | | WT | WT | NA Mutants | | |
|---|---|---|---|---|---|---|
| Alaska NA | 148 | T | T | K | T | K |
| | 151 | D | D | E | D | E |
| | 245 | N | N | S | N | S |
| | 346 | G | G | G | V | V |
| Alaska HA | | | WT | WT | WT | WT |

FIG. 23A

RECOMBINANT INFLUENZA VIRUSES WITH STABILIZED HA FOR REPLICATION IN EGGS

CROSS-REFERENCE TO RELATED APPLICATIONS

This application claims the benefit of the filing date of U.S. application Ser. No. 62/577,049, filed on Oct. 25, 2017, and U.S. application Ser. No. 62/633,400, filed on Feb. 21, 2018, the disclosures of which are incorporated by reference herein.

STATEMENT OF GOVERNMENT FUNDING

This invention was made with government support under HHSO100201500033C awarded by the Biomedical Advanced Research and Development Authority. The government has certain rights in the invention.

BACKGROUND

Influenza is a major respiratory disease in some mammals including horses and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. Most commonly, inactivated virus vaccines are used. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective in response against the predominant and expected influenza virus strains.

There are four general types of influenza viruses, Type A, Type B, Type C and Type D, which are defined by the absence of serological crossreactivity between their internal proteins. Influenza Type A viruses are further classified into subtypes based on antigenic and genetic differences of their glycoproteins, the HA and NA proteins. All the known HA and NA subtypes (H1 to H18 and N1 to N11) have been isolated from aquatic birds, which are though to act as a natural reservoir for influenza.

Most influenza vaccines are produced in embryonated chicken eggs. However, the WHO-recommended influenza vaccine strains often do not replicate efficiently in embryonated chicken eggs, requiring serial passages in eggs in order to allow for adaptation of the virus. During adaptation and amplification in eggs, the hemagglutinin (HA) protein of influenza viruses often acquires egg-adapting mutations. These egg-adapting mutations in HA often alter the antigenicity of the viruses, resulting in vaccine viruses that are no longer optimally matched to the circulating virus strains.

SUMMARY

As described herein, an influenza virus was passaged 7 times in eggs (in triplicate) to study the mutations that occurred in the 6 non-immunogenic viral segments during adaptation. Surprisingly, the virus acquired no HA mutations and instead had mutations in the NA, PB2, NP, and M1 proteins. The NA mutations were identical in all three experiments, and they included a deletion and 4 amino acid mutations. The NA mutations were tested alone and it was found that they, e.g., alone or in various combinations, were responsible for the effect, which permitted efficient growth in eggs without HA mutations.

The present disclosure thus relates to influenza mutations that prevent the acquisition of antigenicity-compromising mutations in the hemagglutinin (HA) segment of influenza virus during growth in eggs. The mutations in the neuraminidase (NA) protein of human influenza viruses were found to 'stabilize' the HA during egg-passages, e.g., in the presence of the mutations in NA, the HA protein did not acquire egg-adapting mutations. Those NA mutations may also increase the vaccine virus yield.

The disclosure provides isolated recombinant, e.g., reassortant, influenza viruses with selected amino acid residues or deletions at specified positions in NA. In one embodiment, the NA is selected to not encode a threonine at residue 32. In one embodiment, the NA is selected to not encode an aspartic acid at position 147. In one embodiment, the NA is selected to not encode an asparagine at residue 329. In one embodiment, the NA is selected to not encode a threonine at residue 329. In one embodiment, the NA is selected to not encode a histidine at residue 347. In one embodiment, the NA is selected to not encode an arginine or an asparagine at residue 347. In one embodiment, the NA is selected to not encode a NA having a threonine at position 148. In one embodiment, the NA is selected to not encode a NA having an aspartic acid at position 151. In one embodiment, the NA is selected to not encode a NA having an asparagine at position 245. In one embodiment, the NA is selected to not encode a NA having a glycine at position 346. In one embodiment, the NA is selected to have a deletion of one or more of residues 46 to 50. The numbering for NA is based on N2. In one embodiment, the disclosure provides an isolated recombinant reassortant influenza virus having six "internal" viral segments from a vaccine influenza virus, e.g., PR8UW, a NA viral segment with one or more of the specified residues at particular positions or a deletion of specified residues, or any combination thereof, and a HA viral segment, e.g., any of H1-H18, e.g., from a circulating influenza virus. Also provided are compositions comprising the recombinant influenza virus, pharmaceutical compositions such as vaccines.

Thus, for vaccine viruses that are to be grown or passaged in cells, e.g., in eggs, replacement of the residue at position 32, 147, 329, 347, or a deletion of one or more of residues 46 to 50, or any combination thereof, in NA, e.g., by mutation, or selection of a NA viral segment for a NA to not encode a threonine at residue 32, to not encode an aspartic acid at position 147, to not encode an asparagine at residue 329, to not encode a histidine at residue 347, or to have a deletion of one or more of residues 46 to 50, or any combination thereof, wherein the numbering is based on N2, may result in stabilization of HA and/or higher viral titers. In one embodiment, for vaccine viruses that are to be grown or passaged in cells, e.g., in eggs, replacement of the residue at position 147, 329, 347, or a deletion of one or more of residues 46 to 50, or any combination thereof, in NA, e.g., by mutation, or selection of a NA viral segment for a NA to not encode an aspartic acid at position 147, to not encode an asparagine at residue 329, to not encode a histidine at residue 347, 369, or any combination thereof, or optionally not encode a threonine at residue 369, or any combination thereof, wherein the numbering is based on N2, may result in stabilization of HA and/or higher viral titers. In one embodiment, for vaccine viruses that are to be grown or passaged in cells, e.g., in eggs, replacement of the residue at position 148, 151, 245, 346, or any combination thereof, in NA, e.g., by mutation, or selection of a NA viral segment for a NA to not encode a threonine at residue 148, to not encode an aspartic acid at position 151, to not encode an asparagine at residue 245, to not encode a glycine at residue 346, or any combination thereof, wherein the numbering is based on N2, may result in stabilization of HA and/or higher viral titers. In one embodiment, for vaccine viruses that are to be grown or passaged in cells, e.g., in eggs, replacement of the residue at position 148, 151, 347, or any combination thereof, in NA, e.g., by mutation, or selection of a NA viral segment for a NA to not encode a threonine at residue 148, to not encode an aspartic acid at position 151, to not encode a histidine at residue 347, or any combination thereof, wherein the numbering is based on N2, may result in stabilization of HA and/or higher viral titers.

In one embodiment, the disclosure provides an isolated recombinant influenza virus comprising PA, PB1, PB2, NP, NS, M, and HA viral segments and a NA viral segment that encodes an NA selected to not encode a threonine at residue 32, to not encode an aspartic acid at position 147, to not encode an asparagine at residue 329, to not encode a histidine at residue 347, or to have a deletion of one or more of residues 46 to 50, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 32 does not have a deletion of residues 46 or 50, encodes an aspartic acid at position 147, encodes an asparagine at residue 329, encodes a histidine at residue 347, or any combination thereof. In one embodiment, the disclosure provides an isolated recombinant influenza virus comprising PA, PB1, PB2, NP, NS, M, and HA viral segments and a NA viral segment that encodes an NA selected to not encode a threonine at residue 148, to not encode an aspartic acid at position 151, to not encode an asparagine at residue 245, to not encode a glycine at residue 346, to not encode a histidine at residue 347, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 148, encodes an aspartic acid at position 151, encodes an asparagine at residue 245, encodes a glycine at residue 346, encodes a histidine at residue 347, or any combination thereof. In one embodiment, the isolated recombinant influenza virus is a reassortant. In one embodiment, the NA viral segment encodes a NA that has at least 80%, 85%, 90%, 95%, or 99% amino acid sequence identity to any one of SEQ ID Nos. 1-3, 30-38, 48-50, or 54. In one embodiment, the NA viral segment encodes a NA that has less than 100% amino acid sequence identity to SEQ ID NO:2 or SEQ ID NO:3. In one embodiment, the NA viral segment encodes a N2, N3, N7, or N9 and the positions in N3, N7, or N9 with the specified residue(s) correspond to the specified positions in N2. In one embodiment, the NA viral segment encodes a N1, N4, N5, N6, N8, N10 or N11 and the positions in N1, N4, N5, N6, N8, N10 or N11 with the specified residue(s) correspond to the specified positions in N2. In one embodiment, the residue at position 32 is A, I, G, or L. In one embodiment, the deletion is a deletion of residues 46 to 50. In one embodiment, the residue at position 147 is N or Q. In one embodiment, the residue at position 329 is D or E. In one embodiment, the residue at position 347 is Q, N, S, T, Y, C or W. In one embodiment, the HA is H1, H3, H5, H7, or H9. In one embodiment, the virus is an influenza A virus. In one embodiment, the PA, PB1, PB2, NP, M, and NS viral segments have at least 85% nucleic acid sequence identity to SEQ ID Nos. 24 to 29 or encode a polypeptide having at least 80%, 85%, 90%, 95%, or 99 amino acid sequence identity to a polypeptide encoded by SEQ ID Nos. 24 to 29 or 39-44. In one embodiment, the PB2 has I, A, L, or G at residue 147. In one embodiment, the virus is an influenza B virus.

Further provided is an isolated recombinant nucleic acid, e.g., a vector such as a viral vector, comprising a nucleic acid sequence that encodes an influenza virus NA selected to not encode a threonine at residue 32, to have a deletion of one or more of residues 46-50, to not encode an aspartic acid at position 147, to not encode an asparagine at residue 329, or to not encode a histidine at residue 347, or any combination thereof, wherein the numbering is based on N2. In one embodiment, the isolated recombinant nucleic acid does not encode a threonine at residue 148, to not encode an aspartic acid at position 151, to not encode an asparagine at residue 245, to not encode a glycine at residue 346, or any combination thereof. In one embodiment, the NA has at least 95% amino acid sequence identity to SEQ ID NO:1, SEQ ID NO:3, SEQ ID NO:48, or SEQ ID NO:49. In one embodiment, the NA has less than 100% amino acid sequence identity to SEQ ID NO:2 or SEQ ID NO:3. In one embodiment, the NA is a N2, N3, N7, or N9. In one embodiment, the NA is a N1, N4, N5, N6, N8, N10 or N11. In one embodiment, the residue at position 32 is A, I, G, or L. In one embodiment, the deletion is a deletion of residues 46 to 50. In one embodiment, the residue at position 147 is N or Q. In one embodiment, the residue at position 329 is D or E. In one embodiment, the residue at position 347 is Q, N, S, T, Y, C or W. In one embodiment, the residue at position 148 is K, R or H. In one embodiment, the residue at position 151 is E, N or Q. In one embodiment, the residue at position 245 is S, T, I, L, A, N, or V.

Also provided is a method to prepare influenza virus. The method includes contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes an NA selected to not encode a threonine at residue 32, to not encode an aspartic acid at position 147, to not encode an asparagine at residue 329, to not encode a histidine at residue 347, to not encode a threonine at residue 148, to not encode an aspartic acid at position 151, to not encode an asparagine at residue 245, to not encode a glycine at residue 346, or to have a deletion of one or more of residues 46 to 50, or any combination thereof, wherein the numbering for NA residues is that for N2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally comprising one or more of: a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, a vector for mRNA production comprising a promoter operably linked to a DNA segment encoding influenza virus NS1, or a vector for mRNA production comprising a promoter operably linked to a DNA segment encoding influenza virus NS2; in an amount effective to yield infectious influenza virus. In one embodiment, the NA has at least 80%, 85%, 90%, 95%, or 99% amino acid sequence identity to SEQ ID NO:1 SEQ ID NO:2, SEQ ID NO:3, SEQ ID NO:48 or SEQ ID NO:49. In one embodiment, the NA has less than 100% amino acid sequence identity to SEQ ID NO:2 or SEQ ID NO:3. In one embodiment, the NA is N2, N3, N7, or N9. In one embodiment, the NA is N1, N4, N5, N6, N8, N10 or N11. In one embodiment, the residue at position 32 is A, I, G, or L. In one embodiment, the deletion is a deletion of residues 46 to 50. In one embodiment, the residue at position 147 is N or Q. In one embodiment, the residue at position 329 is D or E. In one embodiment, the residue at position 346 is S, T, P, Y, W, A, N, I, L, or V. In one embodiment, the residue at position 347 is Q, N, S, T, Y, C or W. In one embodiment, the residue at position 148 is K, R or H. In one embodiment, the residue at position 151 is E, N or Q. In one embodiment, the residue at position 245 is S, T, I, L, A, N, or V.

In one embodiment, the HA is H1, H3, H5, H7, or H9. In one embodiment, the virus is an influenza A virus. In one embodiment, PA, PB1, PB2, NP, M, and NS viral segments have at least 85%, 85%, 90%, 95%, or 99% nucleic acid sequence identity to SEQ ID Nos. 24 to 29 or 39 to 44 or encode a polypeptide having at least 80%, 85%, 90%, 95%, or 99% amino acid sequence identity to a polypeptide encoded by SEQ ID Nos. 24 to 29 or 39 to 44. In one embodiment, PB2 has I, A, L, or G at residue 147. In one embodiment, HA is H2, H4, H5, H6, H8, or any of H10-H18. In one embodiment, the virus is an influenza B virus.

Further provided is a method of immunizing an avian or a mammal with a composition having an effective amount of the virus described herein. In one embodiment, the composition comprises at least one other different influenza virus. In one embodiment, the mammal is a human. In one embodiment, the composition is administered intranasally or via injection.

Thus, the invention provides a method to select for influenza viruses with enhanced replication in cell culture, e.g., in embryonated avian eggs. The method includes providing cells suitable for influenza vaccine production; serially culturing one or more influenza virus isolates in eggs; and isolating serially cultured virus with enhanced growth relative to the one or more isolates prior to serial culture. Also provided is a method to identify a NA that stabilizes HA and/or that confers altered growth of a recombinant influenza virus, e.g., in eggs. The method includes introducing one or more substitutions or deletions as described herein into a NA viral segment to yield a mutant NA viral segment; and optionally identifying whether the mutant NA viral segment, when present in a replication competent recombinant influenza virus, results in enhanced replication of the recombinant influenza virus in eggs and optionally inhibits HA mutations, relative to a corresponding replication competent influenza virus without the one or more substitutions and/or deletions in NA.

In one embodiment, the disclosure provides isolated influenza type A virus with a characteristic residue(s) and/or deletion, or a combination thereof, in NA described herein. In one embodiment, the isolated influenza type A virus with a characteristic residue(s) and/or deletion, or a combination thereof, has an NA amino acid sequence with at least 80%, e.g., 90%, 92%, 95%, 97% or 99%, including any integer between 80 and 99, contiguous amino acid sequence identity to a polypeptide encoded by one of SEQ ID NOs:1, 2, 3, or 30-38. In one embodiment, the isolated influenza type A virus of the invention with a characteristic residue(s) and/or deletion, or a combination thereof, has an HA from any one of subtypes 1-18 of HA. In one embodiment the characteristic residue is a conservative substitution, e.g., relative to SEQ ID NO:2 or SEQ ID NO:3. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

In one embodiment, a mutation is introduced into a NA viral segment of an influenza virus isolate, e.g., via recombinant DNA techniques including site-specific mutagenesis, or replacing a portion of the NA coding sequence with a portion that includes the characteristic residue(s) or deletion. In one embodiment, a NA viral segment with a characteristic residue and/or deletion described herein is combined with a HA segment, and internal viral segments of an influenza vaccine virus.

The disclosure provides a plurality of influenza virus vectors of the invention, e.g., those useful to prepare reassortant viruses including 6:1:1 reassortants, 6:2 reassortants and 7:1 reassortants. A 6:1:1 reassortant is an influenza virus with 6 internal viral segments from a vaccine virus, a HA viral segment that is from a different (second) viral isolate than the vaccine virus, and a NA viral segment with a characteristic residue(s) and/or deletion, or a combination thereof, as described herein, which is from a different viral source than the HA segment and the vaccine virus; a 6:2 reassortant is an influenza virus with 6 internal viral segments from a vaccine virus, and a NA viral segment having a characteristic residue(s) and/or deletion, or a combination thereof, which segment is from the same source as the HA segment, and a HA viral segment from a different viral isolate than the vaccine virus; and a 7:1 reassortant, in one embodiment, is an influenza virus with 6 internal viral segments and a HA segment from a vaccine virus, and a NA segment that is modified to include the characteristic residue(s) and/or deletion, or a combination thereof, which NA segment is from a different viral source than the vaccine virus.

In one embodiment of the invention, the plurality includes vectors for vRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as Vero cells, MDCK cells, or PER.C6® cells, or embryonated eggs, and/or from a vaccine virus, e.g., one that does not cause significant disease in humans. The DNA for vRNA production of NA may be from any NA, any of N1-N9, and the DNA for vRNA production of HA may be from any HA, e.g., H1-H18. In one embodiment, the DNAs for vRNA production may be for an influenza B or C virus. For example, the DNAs for vRNA production include influenza B virus PA, PB1, PB2, NP, NS, and M or influenza B virus PA, PB1, PB2, NP, NS, M, and NA, wherein the vRNA for NA has a NA with a characteristic residue and/or deletion as described herein. The DNAs for vRNA production of NA and HA may be from different strains or isolates (6:1:1 reassortants) or from the same strain or isolate (6:2 reassortants), or the NA or HA may be from the same strain or isolate as that for the internal genes (7:1 reassortant). The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Viruses that may provide the internal genes for reassortants within the scope of the invention include viruses that have high titers, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ $EID_{50}$/mL, e.g., at least $10^8$ $EID_{50}$/mL, $10^9$ $EID_{50}$/mL or $10^{10}$ $EID_{50}$/mL; high titers in MDCK cells, e.g., titers of at least about $10^7$ PFU/mL, e.g., at least $10^8$ PFU/mL, or high titers in two of more of those host cells.

Other reassortants with internal genes from other PR8 isolates or vaccine viruses may be employed in recombinant reassortant viruses.

In one embodiment, the DNAs for the internal genes for PB1, PB2, PA, NP, M, and NS encode proteins with substantially the same activity as a corresponding polypeptide encoded by one of SEQ ID NOs:24-29 or 39 to 44. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:24-29 or 39 to 44. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:24-29 and, in one embodiment, also encodes a polypeptide having at least 80%, e.g., 90%, 92%, 95%, 97% or 99%, including any integer between 80 and 99, contiguous amino acid sequence identity to a polypeptide encoded by one of SEQ ID NOs:24-29 or 39 to 44. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs:24-29 or 39 to 44. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:24-29.

In one embodiment, the nucleic acid a sequence encoding a NA polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:1, 3, 30-35, 48-49, or one of Accession Nos. ACP41107.1 (N1) (SEQ ID NO:36) AIK26357.1 (N7) (SEQ ID NO:37), ALH21372.1 (N9) (SEQ ID NO:45), or BAK86313.1 (N2) (SEQ ID NO:50), the sequences of which are incorporated by reference herein. In one embodiment, the isolated and/or purified nucleic acid molecule encodes a polypeptide having at least 80%, e.g., 90%, 92%, 95%, 97% or 99%, including any integer between 80 and 99, contiguous amino acid sequence identity to a polypeptide encoded by SEQ ID NOs:1, 3, 30-35, 48-49, or one of Accession Nos. ACP41107.1 (N1) AIK26357.1 (N7), ALH21372.1 (N9), or BAK86313.1 (N2), the sequences of which are incorporated by reference herein. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs:1, 3, 30-35, 48-49, or one of Accession Nos. ACP41107.1 (N1) AIK26357.1 (N7), ALH21372.1 (N9), or BAK86313.1 (N2), the sequences of which are incorporated by reference herein. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:1, 3, 30-35, 48-49, or one of Accession Nos. ACP41107.1 (N1) AIK26357.1 (N7), ALH21372.1 (N9), or BAK86313.1 (N2), the sequences of which are incorporated by reference herein.

The invention thus includes the use of isolated and purified vectors or plasmids, which express or encode influenza virus proteins, or express or encode influenza vRNA, both native and recombinant vRNA. The vectors comprise influenza cDNA, e.g., influenza. A (e.g., any influenza A gene including any of the 18 HA or 11 NA subtypes), B or C DNA (see Fields *Virology* (Fields et al. (eds.), Lippincott, Williams and Wickens (2013), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, at least one vector comprises sequences corresponding to those encoding PB1, PB2, PA, NP, M, or NS, or a portion thereof, having substantially the same activity as a corresponding polypeptide encoded by one of SEQ ID NOs:24-29 or 39 to 44, a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:24-29. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., may be administered separately in conjunction with those anti-virals, for instance, administered before, during and/or after.

Thus, the modified neuraminidase comprises at least one, or at least two, or at least three modifications, wherein the modification comprise one or more amino acids within positions 29-35, one or more amino acids within positions 44-52, one or more amino acids within positions 144-154, one or more amino acid positions within 240-250, one or more amino acids within positions 326-333, one or more amino acid positions within 344-350, one or more amino acid positions within 365-375, or combinations thereof, wherein the numbering is that for N2. In one embodiment, the NA comprises a deletion of at least one proline, asparagine, glutamine, valine, or a combination of a proline, one or more asparagine(s), a glutamine, and a valine within positions 44-52; a substitution (replacement) of a threonine within positions 29-35; a substitution (replacement) of an threonine or an aspartic acid within positions 145-155; a substitution (replacement) of an asparagine within positions 240 to 250 or 326-333; a substitution (replacement) of a histidine within positions 345-350; or a combination thereof.

BRIEF DESCRIPTION OF FIGURES

FIG. 1. Nucleotide sequences for the viral segments of A/Yokohama/2017/2003 (SEQ ID Nos. 4-11), and amino acid sequence of the NA of A/Yokohama/2017/2003 (SEQ ID NO:3).

FIG. 2. Amino acid sequence for the NA of A/Saitama/103/2014 (SEQ ID NO:2)

FIG. 3. Nucleotide sequence of NA viral segment (SEQ ID NO:12) and amino acid sequences for NA of mutant of A/Yokohama/2017/2003 (SEQ ID NO:1), and nucleotide sequence of other viral segments of the mutant (SEQ ID Nos.12-21)

FIG. 7. Graph of virus titer in eggs for reassortants with two different backbones (PA, PB1, PB2, NP, NS and M) and two different HA and NA combinations (e.g., PB2-1504V, PB1-M40L/G180W, PA-R401K, NP-I116L, NS1-A30P/R118K; and NA of Y2017-M3L4 contains mutations; NA-T32A, D147N, N329D, H347Q and deletion of 46-50aa). Virus inoculation: $2 \times 10^3$ pfu/egg into allantoic fluid, 72 h incubation at 37° C.

FIG. 8. Amino acid sequence comparison of Yokohama/2017/2003 NA wild-type (SEQ ID NO:3) and Y2017-M3L4 (SEQ ID NO:1).

FIG. 9. Exemplary NA sequences for N3, N4, N6, N7, N8, and N9 (SEQ ID Nos. 30-35).

FIG. 10. Exemplary sequences for the internal viral segments for a master vaccine strain (SEQ ID Nos. 39-44 and 58-62).

FIG. 11. Exemplary NA sequences (SEQ ID Nos:51-54).

FIG. 13. Titers of HK4801HA, Y2017-M3L4NA and HY-PR8 (PB2 C4U, 1504V; PB1 C4U, M40L/G180W; PA C4U, R401K; NP I116L; NS A30P/R118K) and analyses for HA mutations in infected eggs over time.

FIG. 14 shows data for viruses passaged in eggs that had certain NA mutants but did not result in substitutions in HA.

FIG. 15 is a schematic of the positions of certain NA residues.

FIG. 19 summarizes virus titers and HA status over time (HK4801HA, Y2017-M3L4NA and HY-PR8 (PB2 C4U, I504V; PB1 C4U, M40L/G180W; PA C4U, R401K; NP I116L; NS A30P/R118K)).

FIG. 20 summarizes virus titers and HA status for viruses with different NAs.

FIG. 21 provides inoculation and harvested virus titers in allantoic passages (HA-K189E/N158K/A212T mutant virus).

FIG. 22 shows detection of HA status after multiple passages.

DETAILED DESCRIPTION

Definitions

Figure 4:
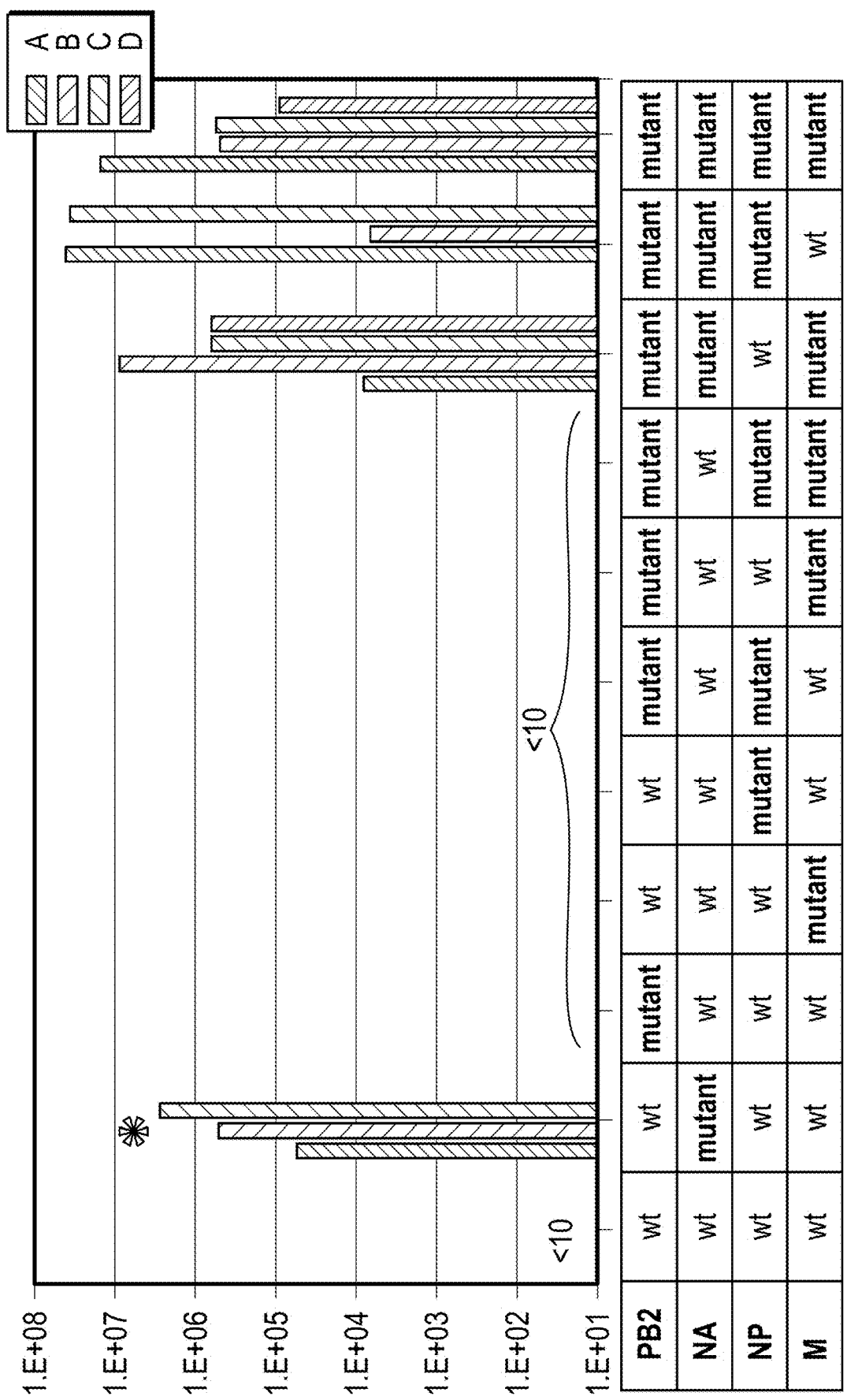
FIG. 4. Graph showing titers in eggs of various reassortants with the PB2, M, NA and NP segments of mutant and wild-type A/Yokohama/2017/2003. Virus inoculation: $2 \times 10^3$ pfu/egg into allantoic fluid, 72 h incubation at 37° C.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the disclosure, by the methodology of genetic engineering.

As used herein, a "heterologous" influenza virus gene or viral segment is from an influenza virus source that is different than a majority of the other influenza viral genes or viral segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a frill-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a viral segment with both NA and NB sequences. Influenza C virus has only seven viral segments.

Cells That Can Be Used to Produce Virus

Any cell, e.g., any avian or mammalian cell, such as avian eggs, a human, e.g., 293T or PER.C6® cells, or canine, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 µg, e.g., 30 to 100 µg, 0.1 to 2 µg, 0.5 to 5 µg, 1 to 10 µg, 10 µg to 20 µg, 15 µg to 30 µg, or 10 to 30 µg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-$\alpha$, interferon-$\beta$, interferon-$\gamma$, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{20}$, e.g., $10^3$-$10^{12}$, $10^2$-$10^{10}$, $10^5$-$10^{11}$, $10^6$-$10^{15}$, $10^2$-$10^{10}$, or $10^{15}$-$10^{20}$ plaque forming units (PFU)/kg, or any range or value therein. The dose of one viral isolate vaccine, e.g., in an inactivated vaccine, may range from about 0.1 to 1000, e.g., 0.1 to 10 µg, 1 to 20 µg, 30 to 100 µg, 10 to 50 µg, 50 to 200 µg, or 150 to 300 µg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 0.1 µg to 1 µg, 0.5 µg to 5 µg, 1 µg to 10 µg, 10 µg to 20 µg, 15 µg to 30 µg, or 30 µg to 100 µg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 µg or any range or value therein, or the amount recommended by the U.S. Public Health Service (PHS), which is usually 15 µg, per component for older children >3 years of age, and 7.5 µg per component for children <3 years of age. The quantity of NA can also be standardized, however, this glycoprotein can be labile during the processor purification and storage (Kendal et al., 1980; Kerr et al., 1975). Each 0.5-ml dose of vaccine may contain approximately 0.1 to 0.5 billion viral particles, 0.5 to 2 billion viral particles, 1 to 50 billion virus particles, 1 to 10 billion viral particles, 20 to 40 billion viral particles, 1 to 5 billion viral particles, or 40 to 80 billion viral particles.

Exemplary Viruses

Useful modifications of influenza neuraminidase (NA) proteins are described herein that stabilize hemagglutinin (HA) protein during egg-passages of influenza viruses that express those modified neuraminidase proteins. Modified nucleic acids are also described that encode such modified neuraminidase proteins. The modifications can include deletions, substitutions and combinations thereof within the neuraminidase protein and nucleic acid sequences. Viruses that express such modified neuraminidase proteins exhibit significantly reduced acquisition of antigenicity-compromising mutations in hemagglutinin (HA) during growth of influenza in eggs.

For example, in some cases the modified neuraminidase can have at least one, or at least two, or at least three modifications. Amino acid positions within influenza neuraminidase proteins that can be modified include, for example, one or more amino acids within positions 29-35, one or more amino acids within positions 44-52, one or more amino acids within positions 144-154, one or more amino acid positions within 240-250, one or more amino acid positions within 326-333, one or more amino acid positions within 344-350, one or more amino acid positions within 365-375, and combinations thereof, based on N2 numbering.

For example, the amino acid(s) can be any amino acid within these positions such as any of the amino acids listed in the table below.

| Original Residue | Exemplary Substitutions | Alternative Substitutions |
|---|---|---|
| Ala (A) | val; leu; ile | Val |
| Arg (R) | lys; gln; asn | Lys |
| Asn (N) | gln; his; lys; arg | Gln |
| Asp (D) | Glu, Asn | Glu, Asn |
| Cys (C) | Ser | Ser |
| Gln (Q) | Asn | Asn |
| Glu (E) | Asp | Asp |
| Gly (G) | Pro | Pro |
| His (H) | asn; gln; lys; arg; gln; | Arg; Gln |
| Ile (I) | leu; val; met; ala; phe norleucine | Leu |
| Leu (L) | norleucine; ile; val; met; ala; phe | Ile |
| Lys (K) | arg; gln; asn | Arg |
| Met (M) | leu; phe; ile | Leu |
| Phe (F) | leu; val; ile; ala | Leu |
| Pro (P) | Gly | Gly |
| Ser (S) | Thr | Thr |
| Thr (T) | Ser, Ala | Ser, Als |
| Trp (W) | Tyr | Tyr |
| Tyr (Y) | trp; phe; thr; ser | Phe |
| Val (V) | ile; leu; met; phe; ala; norleucine | Leu |

In some cases, a selected amino acid within positions 29-35, positions 44-52, positions 144-154, positions 326-333, positions within 344-350, positions within 365-375, can have a conservative substitution. However, in other cases, the selected amino acid within positions 29-35, positions 44-52, positions 144-150, positions 326-333, positions within 344-350, positions within 365-375, can have a non-conservative substitution.

For example, a modified neuraminidase can have a deletion of at least one praline, asparagine, glutamine, valine, or a combination of a proline, one or more asparagine(s), a glutamine, and a valine within positions 44-52 of the modified neuraminidase. A modified neuraminidase can have a substitution (replacement) of a threonine within positions 29-35, where the replacement is any amino acid. A modified neuraminidase can have a substitution (replacement) of a threonine or an aspartic acid within positions 145-154 or 365 to 375, where the replacement is any amino acid. A modified neuraminidase can have a substitution (replacement) of an asparagine within positions 326-333, where the replacement is any amino acid. A modified neuraminidase can have a substitution (replacement) of a histidine within positions 345-350, where the replacement is any amino acid. Exemplary substitutions (replacements) for various types of amino acids are provided in the table above.

One example of an influenza A virus (A/Yokohama/2013/2003(H3N2)) neuraminidase protein sequence is provided below

```
                                          (SEQ ID NO: 55)
  1    MNPNQKIITI GSVSLTISTI CFFMQIAILI TTVTLHFKQY
 41    EFNSPPNNQV MLCEPTIIER NITEIVYLTN TTIEKEICPK
 81    LAEYRNWSKP QCNITGFAPF SKDNSIRLSA GGDIWVTREP
121    YVSCDPDKCY QFALGQGTTL NNVHSNDIVH DRTPYRTLLM
161    NELGVPFHLG TKQVCIAWSS SSCHDGKAWL HVCVTGDDEN
```

```
201 ATASFIYNGR LADSIVSWSK KILRTQESEC VCINGTCTVV

241 MTDGSASGKA DTKILFIEEG KIVHTSTLSG SAQHVEECSC

281 YPRYPGVRCV CRDNWKGSNR PIVDINIKDY SIVSSYVCSG

321 LVGDTPRKND SSSSSHCLDP NNEEGGHGVK GWAFDDGNDV

361 WMGRTISEKL RSGYETFKVI EGWSNPNSKL QINRQVIVDR

401 GNRSGYSGIF SVEGKSCINR CFYVELIRGR KQETEVLWTS

441 NSIVVFCGTS GTYGTGSWPD GADINLMPI
```

Amino acids that can be modified to improve the stability of co-expressed HA are highlighted in bold and with underlining within the sequence shown above. A nucleic acid that encodes such an influenza A virus (A/Yokohama/2013/2003 (H3N2)) neuraminidase protein sequence is shown below

```
                                          (SEQ ID NO: 56)
   1 AGCAAAAGCA GGAGTAAAGA TGAATCCAAA TCAAAAGATA

41 ATAACGATTG GCTCTGTTTC CCTCACCATT TCCACAATAT

81 GCTTCTTCAT GCAAATTGCC ATCCTGATAA CTACTGTAAC

121 ATTGCATTTC AAGCAATATG AATTCAACTC CCCCCCAAAC

161 AACCAAGTGA TGCTGTGTGA ACCAACAATA ATAGAAAGAA

201 ACATAACAGA GATAGTGTAT CTGACCAACA CCACCATAGA

241 GAAGGAAATA TGCCCCAAAC TAGCAGAATA CAGAAATTGG

281 TCAAAGCCGC AATGTAACAT TACAGGATTT GCACCTTTTT

321 CTAAGGACAA TTCGATTCGG CTTTCCGCTG GTGGGGACAT

361 CTGGGTGACA AGAGAACCTT ATGTGTCATG CGATCCTGAC

401 AAGTGTTATC AATTTGCCCT TGGACAGGGA ACAACACTAA

441 ACAACGTGCA TTCAAATGAC ATAGTACATG ATAGGACCCC

481 TTATCGGACC CTATTGATGA ATGAGTTGGG TGTTCCATTT

521 CATCTGGGGA CCAAGCAAGT GTGCATAGCA TGGTCCAGCT

561 CAAGTTGTCA CGATGGAAAA GCATGGCTGC ATGTTTGTGT

601 AACGGGGGAT GATGAAAATG CAACTGCTAG CTTCATTTAC

641 AATGGGAGGC TTGCAGATAG TATTGTTTCA TGGTCCAAAA

681 AAATCCTCAG GACCCAGGAG TCAGAATGCG TTTGTATCAA

721 TGGAACTTGT ACAGTAGTAA TGACTGATGG GAGTGCTTCA

761 GGAAAAGCTG ATACTAAAAT ACTATTCATT GAGGAGGGGA

801 AAATTGTTCA TACTAGCACA TTATCAGGAA GTGCTCAGCA

841 TGTCGAGGAG TGCTCCTGTT ATCCTCGATA TCCTGGTGTC

881 AGATGTGTCT GCAGAGACAA CTGGAAAGGC TCCAATAGGC

921 CCATCGTAGA TATAAACATA AAGGATTATA GCATTGTTTC

961 CAGTTATGTG TGCTCAGGAC TTGTTGGAGA CACACCCAGA

1001 AAAAACGACA GCTCCAGCAG TAGCCATTGC TTGGATCCAA

1041 ACAATGAGGA AGGTGGTCAT GGAGTGAAAG GCTGGGCCTT

1081 TGATGATGGA AATGACGTGT GGATGGGAAG AACGATCAGC

1121 GAGAAGTTAC GCTCAGGATA TGAAACCTTC AAAGTCATTG
```

```
1161 AAGGCTGGTC CAACCCTAAC TCCAAATTGC AGATAAATAG

1201 GCAAGTCATA GTTGACAGAG GTAACAGGTC CGGTTATTCT

1241 GGTATTTTCT CTGTTGAAGG CAAAAGCTGC ATCAATCGGT

1281 GCTTTTATGT GGAGTTGATA AGGGGAAGAA AACAGGAAAC

1321 TGAAGTCTTG TGGACCTCAA ACAGTATTGT TGTGTTTTGT

1361 GGCACCTCAG GTACATATGG AACAGGCTCA TGGCCTGATG

1401 GGGCGGACAT CAATCTCATG CCTATATAAG CTTTCGCAAT

1441 TTTAGAAAAA AACTCCTTGT TTCTACT
```

Modifications at the specified positions in neuraminidase can confer enhanced growth of the virus.

Another example of an influenza A virus (A/Yokohama/47/2002(H1N2)) neuraminidase sequence is shown below, with positions of modifications highlighted in bold and with underlining.

```
                                          (SEQ ID NO: 57)
          10         20         30         40
    MNPNQKIITI GSVSLTIATI CFLMQIAILV TTVTLHFKQY 50         60         70         80
    ECNSPPNNQV MLCEPTIIER NITEIVYLTN TTIEKEICPK 90        100        110        120
    LAEYRNWSKP QCNITGFAPF SKDNSIRLSA GGDIWVTREP 130        140        150        160
    YVSCDPDKCY QFALGQGTTL NNGHSNDTVH DRTPYRTLLM 170        180        190        200
    NELGVPFHLG TKQVCIAWSS SSCHDGKAWL HVCVTGDDGN 210        220        230        240
    ATASFIYNGR LVDSIGSWSK KILRTQESEC VCINGTCTVV 250        260        270        280
    MTDGSASGKA DTKILFIEEG KIVHTSLLSG SAQHVEECSC 290        300        310        320
    YPRYPGVRCV CRDNWKGSNR PIVDINVKDY SIVSSYVCSG 330        340        350        360
    LVGDTPRKND SSSSSHCLDP NNEEGGHGVK GWAFDDGNDV 370        380        390        400
    WMGRTISEKL RSGYETFKVI EGWSKPNSKL QINRQVIVDR 410        420        430        440
    GNRSGYSGIF SVEGKSCINR CFYVELIRGR NQETEVLWTS 450        460
    NSIVVFCGTS GTYGTGSWPD GADINLMPI
```

Amino acids that can be modified to improve the stability of co-expressed HA are highlighted in bold and with underlining within the sequence shown above.

In some cases, in one or more modifications can also be introduced into HA, PA, PB1, PB2, NP, M1, M2, NS2, PB1-F2, PA-X, and/or NS1 proteins (and nucleic acids encoding such proteins).

Enhanced growth of the virus when passaged through embryonated chicken eggs or cultured cells is observed when the modified NA proteins are expressed and such expression can result in significantly higher viral titers. Thus, the invention provides a method for making influenza viruses with enhanced replication in cell culture or in embryonated chicken eggs. The method includes providing cells suitable for influenza vaccine production; modifying nucleic acids encoding the neuraminidase; and isolating virus strains with enhanced growth relative to the one or more unmodified viral isolates. In some cases, a method for making influenza viruses with enhanced replication in cell culture can involve, serially culturing one or more influenza virus isolates in embryonated chicken eggs; and isolating serially cultured virus with enhanced growth relative to the one or more isolates prior to serial culture. In some cases, the viruses can be grown or passaged within cells in culture, e.g., MDCK or Vero cells.

The modified neuraminidases can be expressed in a variety of influenza strains. For example, A/Puerto Rico/8/34 (H1N1), "PR8," virus often serves as the genetic backbone for generation of inactivated influenza vaccines. Some vaccine strains based on PR8 backbone can replicate to relatively low titers in eggs and cell culture, resulting in delayed vaccine production and vaccine shortage. However, expression of the modified neuraminidases described herein can improve replication of the PR8 (and other) influenza strains.

In one embodiment of the invention, vectors for vRNA production can include a vector comprising a promoter operably linked to a modified NA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1. PB2, PA, NP, M, and NS, have sequences from an influenza virus that replicates to high titers in cultured mammalian cells such as MDCK cells, Vero cells or PER.C6® cells or embryonated eggs, and/or from a vaccine virus, e.g., one that does not cause significant disease in humans. The DNA for vRNA production of NA may be from any NA, e.g., any of N1-N11, and the DNA for vRNA production of HA may be from any HA, e.g., H1-H18. In one embodiment, the DNAs for vRNA production may be for an influenza B or C virus. The DNAs for vRNA production of NA and HA may be from different strains or isolates (6:1:1 reassortants) or from the same strain or isolate (6:2 reassortants), or the NA may be from the same strain or isolate as that for the internal genes (7:1 reassortant). Vectors for mRNA production can include a vector encoding a modified NA, a vector encoding influenza virus PA, a vector encoding influenza virus PB1, a vector encoding influenza virus PB2, and a vector encoding influenza virus NP, and optionally one or more vectors encoding NP, NS, M, e.g., M1 and M2, HA or NA. The vectors encoding viral proteins may further include a transcription termination sequence.

Other reassortants with internal genes from other PR8 isolates or vaccine viruses may be employed in recombinant reassortant viruses of the invention. In particular, 5:1:2 reassortants having UW-PR8 PB1, PB2, PA, NP, and M ("5") and PR8(Cam) NS ("1"); 6:1:1 reassortants having UW-PR8 (modified) NA, PB1, PB2, PA, NP, and M ("6") and PR8(Cam) NS ("1"); and 7:1 reassortants having UW-PR8 PB1, PB2, PA, NP, M, (modified) NA, and NS ("7") may be employed.

The neuraminidases that can be modified can have sequences that vary from those described herein. However, in some cases, the modified neuraminidases can have substantially the same activity as a corresponding polypeptide described by sequence herein. As used herein, "substantially the same activity" includes an activity that is about 0.1%, 1%, 10%, 30%, 50%, 90%, e.g., up to 100% or more activity, or a detectable protein level that is about 80%, 90% or more protein level, of the corresponding protein described herein. In one embodiment, the nucleic acid encodes a polypeptide which is substantially the same as, e.g., having at least 80%, e.g., 90%, 92%, 95%, 97%, 98%, or 99%, including any integer between 80 and 99, contiguous amino acid sequence identity to a polypeptide encoded by one of sequences described herein. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of the nucleic acid sequences described herein. In one embodiment, a nucleic acid also encodes a polypeptide having at least 80%, e.g., 90%, 92%, 95%, 97%, 98%, or 99%, including any integer between 80 and 99, contiguous amino acid sequence identity to a polypeptide described herein.

In one embodiment, a modified influenza virus neuraminidase polypeptide has one or more, for instance, 2, 5, 10, 15, 20 or more, conservative amino acids substitutions, e.g., conservative substitutions of up to 10% or 20% of 2, 5, 10, 15, 20 or more, of a combination of conservative and non-conservative amino acids substitutions, e.g., conservative substitutions of up to 10% or 20% of the residues, or relative to a polypeptide with one of the sequences disclosed herein.

The invention thus includes the use of isolated and purified vectors or plasmids, which express or encode influenza virus proteins, or express or encode influenza vRNA, both native and recombinant vRNA. The vectors comprise influenza cDNA, influenza. A (e.g., any influenza A gene including any of the 18 HA or 11 NA subtypes), B or C DNA (see Fields Virology (Fields et al. (eds.), Lippincott, Williams and Wickens (2006), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, for instance, may encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, the invention provides a plurality of influenza virus vectors for a reassortant, comprising a vector for vRNA production comprising a promoter operably linked to a modified influenza virus NA DNA linked to a transcription termination sequence, a vector for vRNA production comprising a promoter operably linked to an influenza vines PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the DNAs for the modified NA, PB1 PB2 PA, NP, NS, and M are from one or more influenza vaccine seed viruses and contain two or more of the characteristic residues at the specified position(s); and a vector for mRNA production comprising a promoter operably linked to a DNA segment encoding influenza virus NA, a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, a vector for mRNA production comprising a promoter operably linked to a DNA segment encoding influenza virus NS1, or a vector for mRNA production comprising a promoter operably linked to a DNA segment encoding influenza virus NS2. In one embodiment, at least one vector comprises sequences corresponding to those encoding PB1, PB2, PA, NP, M, or NS, or a portion thereof, having substantially the same activity as a corresponding polypeptide described herein or encoded by a nucleic acid described herein. Optionally, two vectors may be employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1 PB2 and NP employed in the method are on one plasmid or on two or three different plasmids.

Exemplary Embodiments

An isolated recombinant influenza virus comprising a selected NA viral segment encoding a plurality of selected residues or a deletion of residues in NA is provided. In one embodiment, the selected NA viral segment does not encode a NA having a threonine at residue 32, does not encode a NA having an aspartic acid at position 147, does not encode a NA having a threonine at position 148, does not encode a NA having an aspartic acid at position 151, does not encode a NA having an asparagine at position 245, does not encode a NA having an asparagine at residue 329, does not encode a NA having a glycine at position 346, does not encode a NA having a histidine at residue 347, or encodes a NA having a deletion of one or more of residues 46 to 50, or any combination thereof, wherein the numbering is based on N2, wherein the recombinant influenza virus has enhanced replication in avian eggs or has a reduction in HA mutations when grown in avian eggs relative to a corresponding influenza virus that has a NA that encodes a threonine at residue 32, does not have a deletion of residues 46 to 50, encodes an aspartic acid at position 147, encodes a threonine at residue 148, encodes an aspartic acid at residue 151, encodes an asparagine at residue 245, encodes an asparagine at residue 329, encodes a histidine at residue 347, or any combination thereof. In one embodiment, the selected NA viral segment does not have an aspartic acid at position 147, does not have an asparagine at residue 329, and does not have an arginine or a histidine at residue 347. In one embodiment, the selected NA viral segment does not a threonine at position 148, does not have an aspartic acid at position 151, and does not have an asparagine at position 245. In one embodiment, the selected NA viral segment does not have an aspartic acid at position 147, does not have an asparagine at residue 329, and does not have an arginine or a histidine at residue 347. In one embodiment, the selected NA viral segment does not a threonine at position 148, does not have an aspartic acid at position 151, and does not have an asparagine at position 245. In one embodiment, the selected NA viral segment has at least two of: N or Q at position 147, D or E at residue 329, or Q or G at residue 347. In one embodiment, the selected NA viral segment has at least two of: K, R or H at position 148, E or Q at position 151, or S, I, T, V or G at position 245. In one embodiment, the selected NA viral segment has N or Q at position 147, D or E at residue 329, and Q or G at residue 347. In one embodiment, the selected NA viral segment has K, R or H at position 148, E or Q at position 151, and S, I, T, V or G at position 245. In one embodiment, the isolated recombinant influenza virus is a reassortant. In one embodiment, the NA viral segment encodes a NA that has at least 90% amino acid sequence identity to SEQ ID NO:1, SEQ ID NO:3, SEQ ID NO:48, SEQ ID NO:49, SEQ ID NO:50 or SEQ ID NO:54. In one embodiment, the NA viral segment encodes a NA that has at least 90% amino acid sequence identity to SEQ ID NO:2. In one embodiment, the NA viral segment encodes a N2, N3, N7, or N9. In one embodiment, the NA viral segment encodes a N1, N4, N5, N6, N8, N10 or N11. In one embodiment, the residue at position 32 is A, I, G, or L. In one embodiment, the deletion is a deletion of residues 46 to 50. In one embodiment, the residue at position 147 is N or Q. In one embodiment, the residue at position 148 is K, R or H. In one embodiment, the residue at position 151 is E, N or Q. In one embodiment, the residue at position 245 is S, T, I, L, A, N, W, Y, P, V, or G. In one embodiment, the residue at position 329 is D or E. In one embodiment, the residue at position 346 is S, T, P, Y, W, A, N, I, L, or V. In one embodiment, the residue at position 347 is G, Q, S, T, Y, C or W. In one embodiment, the residue at position 147 is N or Q, the residue at position 329 is D or E, the residue at position 347 is G, Q, S, T, Y, C or W, or any combination thereof. In one embodiment, the residue at position 147 is N or Q, the residue at position 329 is D or E, the residue at position 347 is G or Q, or any combination thereof. In one embodiment, the residue at position 148 is K, R or H, the residue at position 151 is E, N or Q, the residue at position 245 is S, T, I, L, A, W, Y, P, V, or G, or any combination thereof. In one embodiment, the residue at position 148 is K, R or H, the residue at position 151 is E, N or Q, the residue at position 245 is S, T, I, L, A, or V, or any combination thereof. In one embodiment, the selected NA viral segment does not encode a NA having an aspartic acid at position 147, does not encode a NA having a threonine at position 148, does not encode a NA having an aspartic acid at position 151, does not encode a NA having an asparagine at position 245, does not encode a NA having an asparagine or threonine at residue 329, does not encode a NA having a glycine at position 346, does not encode a NA having a histidine, arginine or an asparagine at residue 347, or any combination thereof. In one embodiment the selected NA viral segment does not encode a NA having an aspartic acid at position 147, does not encode a NA having an asparagine at residue 329, does not encode a NA having a histidine, arginine or asparagine at residue 347, or any combination thereof. In one embodiment, the selected NA viral segment does not encode a NA having a threonine at position 148, does not encode a NA having an aspartic acid at position 151, does not encode a NA having an asparagine at position 245, does not encode a NA having a glycine at position 346, or any combination thereof. In one embodiment, the virus has HA H1, H3, H7, or H9. In one embodiment, the virus is an influenza A virus. In one embodiment, the virus comprises PA, PB1, PB2, NP, M, and NS viral segments with at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44. In one embodiment, the virus comprises PB2 having I, A, L, or G at residue 147.

In one embodiment, an isolated recombinant nucleic acid is provided comprising a nucleic acid sequence for an influenza virus NA viral segment that encodes a NA having a plurality of selected residues or a deletion of residues, wherein the NA viral segment does not encode a NA having a threonine at residue 32, does not encode a NA having an aspartic acid at position 147, does not encode a NA having a threonine at position 148, does not encode a NA having an aspartic acid at position 151, does not encode a NA having an asparagine at position 245, does not encode a NA having an asparagine or a threonine at residue 329, does not encode a NA having a histidine, arginine or asparagine at residue 347, or encodes a NA having a deletion of one or more of residues 46 to 50, or any combination thereof, wherein the numbering is based on N2. In one embodiment, the NA has at least 90% amino acid sequence identity to SEQ ID NO:1 or SEQ ID NO:3. In one embodiment, the NA has at least 90% amino acid sequence identity to SEQ ID NO:2. In one embodiment, the NA is a N2, N3, N7, or N9. In one embodiment, the NA is a N1, N4, N5, N6, N8, N10 or N11. In one embodiment, the residue at position 32 is A, I, G, or L. In one embodiment, the residue at position 147 is N or Q. In one embodiment, the residue at position 329 is D or E. In one embodiment, the residue at position 151 is E, N or Q. In one embodiment, the residue at position 148 is K, R or H. In one embodiment, the residue at position 245 is S, T, I, L, A, W, Y, P, V, or G. In one embodiment, the residue at position 347 is G, Q, S, or T.

In one embodiment, a method to prepare influenza virus is provided. The method includes contacting a cell with: a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes a NA having a plurality of selected residues or a deletion of residues, wherein the NA does not encode a NA having a threonine at residue 32, does not encode a NA having an aspartic acid at position 147, does not encode a NA having a threonine at position 148, does not encode a NA having an aspartic acid at position 151, does not encode a NA having an asparagine at position 245, does not encode a NA having an asparagine at residue 329, does not encode a NA having a glycine at position 346, does not encode a NA having a histidine at residue 347, or encodes a NA having a deletion of one or more of residues 46 to 50, or any combination thereof, wherein the numbering for NA residues is that for N2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus. In one embodiment, the NA has at least 90% amino acid to SEQ ID NO:1, SEQ ID NO:2, SEQ ID NO:3, SEQ ID NO:48, or SEQ ID NO:49. In one embodiment, the NA is N2, N3, N7, or N9. In one embodiment, the residue at position 147 is N or Q. In one embodiment, the residue at position 329 is D or E. In one embodiment, the residue at position 347 is Q, N, S, T, Y, C or W. In one embodiment, the residue at position 151 is E, N or Q. In one embodiment, the residue at position 148 is K, R or H. In one embodiment, the residue at position 245 is S, T, I, L, A, N, W, Y, P, V, or G. In one embodiment, the virus HA is H1, H3, H7, or H9. In one embodiment, The PA, PB1, PB2, NP, M, and NS viral segments have at least 85% nucleic acid sequence identity to SEQ ID Nos. 24 to 29 or 39 to 44 or encode a polypeptide having at least 80% amino acid sequence identity to a polypeptide encoded by SEQ ID Nos. 24 to 29 or 39 to 44. In one embodiment, HA is H2, H4, H5, H6, H8, or any of H10-H18. In one embodiment, virus prepared by the method is isolated. In one embodiment, virus is passaged through avian eggs.

In one embodiment, a method of immunizing an avian or a mammal is provided. The method includes administering to the avian or the mammal, e.g., a bovine, ovine, caprine, feline, canine, equine or human, a composition having an effective amount of the virus described above. In one embodiment, the composition comprises at least one other different influenza virus. In one embodiment, the composition is administered intranasally or via injection.

The invention will be described by the following non-limiting examples.

EXAMPLE 1

Exemplary viral sequences for a master vaccine strain (PR8UW)

HA (SEQ ID NO: 22)
AGCAAAAGCAGGGGAAAATAAAAACAACCAAAATGAAGGCAAACCTACTG

GTCCTGTTATGTGCACTTGCAGCTGCAGATGCAGACACAATATGTATAGG

CTACCATGCGAACAATTCAACCGACACTGTTGACACAGTACTCGAGAAGA

ATGTGACAGTGACACACTCTGTTAACCTGCTCGAAGACAGCCACAACGGA

AAACTATGTAGATTAAAAGGAATAGCCCCACTACAATTGGGGAAATGTAA

CATCGCCGGATGGCTCTTGGGAAACCCAGAATGCGACCCACTGCTTCCAG

TGAGATCATGGTCCTACATTGTAGAAACACCAAACTCTGAGAATGGAATA

TGTTATCCAGGAGATTTCATCGACTATGAGGAGCTGAGGGAGCAATTGAG

CTCAGTGTCATCATTCGAAAGATTCGAAATATTTCCCAAAGAAAGCTCAT

GGCCCAACCACAACACAAACGGAGTAACGGCAGCATGCTCCCATGAGGGG

AAAAGCAGTTTTTACAGAAATTTGCTATGGCTGACGGAGAAGGAGGGCTC

ATACCCAAAGCTGAAAAATTCTTATGTGAACAAAAAAGGGAAAGAAGTCC

TTGTACTGTGGGGTATTCATCACCCGCCTAACAGTAAGGAACAACAGAAT

CTCTATCAGAATGAAAATGCTTATGTCTCTGTAGTGACTTCAAATTATAA

CAGGAGATTTACCCCGGAAATAGCAGAAAGACCCAAAGTAAGAGATCAAG

-continued
```
CTGGGAGGATGAACTATTACTGGACCTTGCTAAAACCCGGAGACACAATA
ATATTTGAGGCAAATGGAAATCTAATAGCACCAATGTATGCTTTCGCACT
GAGTAGAGGCTTTGGGTCCGGCATCATCACCTCAAACGCATCAATGCATG
AGTGTAACACGAAGTGTCAAACACCCCTGGGAGCTATAAACAGCAGTCTC
CCTTACCAGAATATACACCCAGTCACAATAGGAGAGTGCCCAAAATACGT
CAGGAGTGCCAAATTGAGGATGGTTACAGGACTAAGGAACATTCCGTCCA
TTCAATCCAGAGGTCTATTTGGAGCCATTGCCGGTTTTATTGAAGGGGGA
TGGACTGGAATGATAGATGGATGGTATGGTTATCATCATCAGAATGAACA
GGGATCAGGCTATGCAGCGGATCAAAAAGCACACAAAATGCCATTAACG
GGATTACAAACAAGGTGAACACTGTTATCGAGAAAATGAACATTCAATTC
ACAGCTGTGGGTAAAGAATTCAACAAATTAGAAAAAAGGATGGAAAATTT
AAATAAAAAAGTTGATGATGGATTTCTGGACATTTGGACATATAATGCAG
AATTGTTAGTTCTACTGGAAAATGAAAGGACTCTGGATTTCCATGACTCA
AATGTGAAGAATCTGTATGAGAAAGTAAAAAGCCAATTAAAGAATAATGC
CAAAGAAATCGGAAATGGATGTTTTGAGTTCTACCACAAGTGTGACAATG
AATGCATGGAAAGTGTAAGAAATGGGACTTATGATTATCCCAAATATTCA
GAAGAGTCAAAGTTGAACAGGGAAAAGGTAGATGGAGTGAAATTGGAATC
AATGGGGATCTATCAGATTCTGGCGATCTACTCAACTGTCGCCAGTTCAC
TGGTGCTTTTGGTCTCCCTGGGGGCAATCAGTTTCTGGATGTGTTCTAAT
GGATCTTTGCAGTGCAGAATATGCATCTGAGATTAGAATTTCAGAGATAT
GAGGAAAAACACCCTTGTTTCTACT
```
NA
```
                                (SEQ ID NO: 23)
AGCAAAAGCAGGGGTTTAAAATGAATCCAAATCAGAAATAATAACCATT
GGATCAATCTGTCTGGTAGTCGGACTAATTAGCCTAATATTGCAAATAGG
GAATATAATCTCAATATGGATTAGCCATTCAATTCAAACTGGAAGTCAAA
ACCATACTGGAATATGCAACCAAAACATCATTACCTATAAAAATAGCACC
TGGGTAAAGGACACAACTTCAGTGATATTAACCGGCAATTCATCTCTTTG
TCCCATCCGTGGGTGGGCTATATACAGCAAAGACAATAGCATAAGAATTG
GTTCCAAAGGAGACGTTTTTGTCATAAGAGAGCCCTTTATTTCATGTTCT
CACTTGGAATGCAGGACCTTTTTTCTGACCCAAGGTGCCTTACTGAATGA
CAAGCATTCAAGTGGGACTGTTAAGGACAGAAGCCCTTATAGGGCCTTAA
TGAGCTGCCCTGTCGGTGAAGCTCCGTCCCCGTACAATTCAAGATTTGAA
TCGGTTGCTTGGTCAGCAAGTGCATGTCATGATGGCATGGGCTGGCTAAC
AATCGGAATTTCAGGTCCAGATAATGGAGCAGTGGCTGTATTAAAATACA
ACGGCATAATAACTGAAACCATAAAAAGTTGGAGGAAGAAAATATTGAGG
ACACAAGAGTCTGAATGTGCCTGTGTAAATGGTTCATGTTTTACTATAAT
GACTGATGGCCCGAGTGATGGGCTGGCCTCGTACAAAATTTTCAAGATCG
AAAAGGGGAAGGTTACTAAATCAATAGAGTTGAATGCACCTAATTCTCAC
TATGAGGAATGTTCCTGTTACCCTGATACCGGCAAAGTGATGTGTGTGTG
CAGAGACAATTGGCATGGTTCGAACCGGCCATGGGTGTCTTTCGATCAAA
ACCTGGATTATCAAATAGGATACATCTGCAGTGGGGTTTTCGGTGACAAC
```
-continued
```
CCGCGTCCCGAAGATGGAACAGGCAGCTGTGGTCCAGTGTATGTTGATGG
AGCAAACGGAGTAAAGGGATTTTCATATAGGTATGGTAATGGTGTTTGGA
TAGGAAGGACCAAAAGTCACAGTTCCAGACATGGGTTTGAGATGATTTGG
GATCCTAATGGATGGACAGAGACTGATAGTAAGTTCTCTGTGAGGCAAGA
TGTTGTGGCAATGACTGATTGGTCAGGGTATAGCGGAAGTTTCGTTCAAC
ATCCTGAGCTGACAGGGCTAGACTGTATGAGGCCGTGCTTCTGGGTTGAA
TTAATCAGGGGACGACCTAAAGAAAAAACAATCTGGACTAGTGCGAGCAG
CATTTCTTTTGTGGCGTGAATAGTGATACTGTAGATTGGTCTTGGCCAG
ACGGTGCTGAGTTGCCATTCAGCATTGACAAGTAGTCTGTTCAAAAAACT
CCTTGTTTCTACT
```
PA
```
                                (SEQ ID NO: 24)
AGCGAAAGCA GGTACTGATC CAAAATGGAA GATTTTGTGC
GACAATGCTT CAATCCGATG ATTGTCGAGC TTGCGGAAAA
AACAATGAAA GAGTATGGGG AGGACCTGAA AATCGAAACA
AACAAATTTG CAGCAATATG CACTCACTTG GAAGTATGCT
TCATGTATTC AGATTTTCAC TTCATCAATG AGCAAGGCGA
GTCAATAATC GTAGAACTTG GTGATCCAAA TGCACTTTTG
AAGCACAGAT TTGAAATAAT CGAGGGAAGA GATCGCACAA
TGGCCTGGAC AGTAGTAAAC AGTATTTGCA ACACTACAGG
GGCTGAGAAA CCAAAGTTTC TACCAGATTT GTATGATTAC
AAGGAGAATA GATTCATCGA AATTGGAGTA ACAAGGAGAG
AAGTTCACAT ATACTATCTG GAAAAGGCCA ATAAAATTAA
ATCTGAGAAA ACACACATCC ACATTTTCTC GTTCACTGGG
GAAGAAATGG CCACAAAGGC AGACTACACT CTCGATGAAG
AAAGCAGGGC TAGGATCAAA ACCAGACTAT TCACCATAAG
ACAAGAAATG GCCAGCAGAG GCCTCTGGGA TTCCTTTCGT
CAGTCCGAGA GAGGAGAAGA GACAATTGAA GAAAGGTTTG
AAATCACAGG AACAATGCGC AAGCTTGCCG ACCAAAGTCT
CCCGCCGAAC TTCTCCAGCC TTGAAAATTT TAGAGCCTAT
GTGGATGGAT TCGAACCGAA CGGCTACATT GAGGGCAAGC
TGTCTCAAAT GTCCAAAGAA GTAAATGCTA GAATTGAACC
TTTTTTGAAA ACAACACCAC GACCACTTAG ACTTCCGAAT
GGGCCTCCCT GTTCTCAGCG GTCCAAATTC CTGCTGATGG
ATGCCTTAAA ATTAAGCATT GAGGACCCAA GTCATGAAGG
AGAGGGAATA CCGCTATATG ATGCAATCAA ATGCATGAGA
ACATTCTTTG GATGGAAGGA ACCCAATGTT GTTAAACCAC
ACGAAAAGGG AATAAATCCA AATTATCTTC TGTCATGGAA
GCAAGTACTG GCAGAACTGC AGGACATTGA GAATGAGGAG
AAAATTCCAA AGACTAAAAA TATGAAGAAA ACAAGTCAGC
TAAAGTGGGC ACTTGGTGAG AACATGGCAC CAGAAAAGGT
```

-continued

AGACTTTGAC GACTGTAAAG ATGTAGGTGA TTTGAAGCAA
TATGATAGTG ATGAACCAGA ATTGAGGTCG CTTGCAAGTT
GGATTCAGAA TGAGTTTAAC AAGGCATGCG AACTGACAGA
TTCAAGCTGG ATAGAGCTCG ATGAGATTGG AGAAGATGTG
GCTCCAATTG AACACATTGC AAGCATGAGA AGGAATTATT
TCACATCAGA GGTGTCTCAC TGCAGAGCCA CAGAATACAT
AATGAAGGGA GTGTACATCA ATACTGCCTT GCTTAATGCA
TCTTGTGCAG CAATGGATGA TTTCCAATTA ATTCCAATGA
TAAGCAAGTG TAGAACTAAG GAGGGAAGGC GAAAGACCAA
CTTGTATGGT TTCATCATAA AAGGAAGATC CCACTTAAGG
AATGACACCG ACGTGGTAAA CTTTGTGAGC ATGGAGTTTT
CTCTCACTGA CCCAAGACTT GAACCACATA ATGGGAGAA
GTACTGTGTT CTTGAGATAG GAGATATGCT TATAAGAAGT
GCCATAGGCC AGGTTTCAAG GCCCATGTTC TTGTATGTGA
GAACAAATGG AACCTCAAAA ATTAAAATGA ATGGGGAAT
GGAGATGAGG CGTTGCCTCC TCCAGTCACT TCAACAAATT
GAGAGTATGA TTGAAGCTGA GTCCTCTGTC AAAGAGAAAG
ACATGACCAA AGAGTTCTTT GAGAACAAAT CAGAAACATG
GCCCATTGGA GAGTCCCCCA AAGGAGTGGA GGAAAGTTCC
ATTGGGAAGG TCTGCAGGAC TTTATTAGCA AAGTCGGTAT
TCAACAGCTT GTATGCATCT CCACAACTAG AAGGATTTTC
AGCTGAATCA AGAAAACTGC TTCTTATCGT TCAGGCTCTT
AGGGACAACC TGGAACCTGG GACCTTTGAT CTTGGGGGGC
TATATGAAGC AATTGAGGAG TGCCTGATTA ATGATCCCTG
GGTTTTGCTT AATGCTTCTT GGTTCAACTC CTTCCTTACA
CATGCATTGA GTTAGTTGTG GCAGTGCTAC TATTTGCTAT
CCATACTGTC CAAAAAAGTA CCTTGTTTCT ACT

PB1

(SEQ ID NO: 25)

AGCGAAAGCAGGCAAACCATTTGAATGGATGTCAATCCGACCTTACTTTT
CTTAAAAGTGCCAGCACAAAATGCTATAAGCACAACTTTCCCTTATACTG
GAGACCCTCCTTACAGCCATGGGACAGGAACAGGATACACCATGGATACT
GTCAACAGGACACATCAGTACTCAGAAAAGGGAAGATGGACAACAAACAC
CGAAACTGGAGCACCGCAACTCAACCCGATTGATGGGCCACTGCCAGAAG
ACAATGAACCAAGTGGTTATGCCCAAACAGATTGTGTATTGGAGGCGATG
GCTTTCCTTGAGGAATCCCATCCTGGTATTTTTGAAAACTCGTGTATTGA
AACGATGGAGGTTGTTCAGCAAACACGAGTAGACAAGCTGACACAAGGCC
GACAGAGACCTATGACTGGACTCTAAATAGAAACCAACCTGCTGCAACAGCA
TTGGCCAACACAATAGAAGTGTTCAGATCAAATGGCCTCACGGCCAATGA
GTCTGGAAGGCTCATAGACTTCCTTAAGGATGTAATGGAGTCAATGAACA
AAGAAGAAATGGGGATCACAACTCATTTTCAGAGAAAGAGACGGGTGAGA
GACAATATGACTAAGAAAATGATAACACAGAGAACAATGGGTAAAAAGAA

GCAGAGATTGAACAAAAGGAGTTATCTAATTAGAGCATTGACCCTGAACA
CAATGACCAAAGATGCTGAGAGAGGGAAGCTAAAACGGAGAGCAATTGCA
ACCCCAGGGATGCAAATAAGGGGGTTTGTATACTTTGTTGAGACACTGGC
AAGGAGTATATGTGAGAAACTTGAACAATCAGGGTTGCCAGTTGGAGGCA
ATGAGAAGAAAGCAAAGTTGGCAAATGTTGTAAGGAAGATGATGACCAAT
TCTCAGGACACCGAACTTTCTTTCACCATCACTGGAGATAACACCAAATG
GAACGAAAATCAGAATCCTCGGATGTTTTTGGCCATGATCACATATATGA
CCAGAAATCAGCCCGAATGGTTCAGAAATGTTCTAAGTATTGCTCCAATA
ATGTTCTCAAACAAAATGGCGAGACTGGGAAAAGGGTATATGTTTGAGAG
CAAGAGTATGAAACTTAGAACTCAAATACCTGCAGAAATGCTAGCAAGCA
TCGATTTGAAATATTTCAATGATTCAACAAGAAAGAAGATTGAAAAAATC
CGACCGCTCTTAATAGAGGGGACTGCATCATTGAGCCCTGGAATGATGAT
GGGCATGTTCAATATGTTAAGCACTGTATTAGGCGTCTCCATCCTGAATC
TTGGACAAAAGAGATACACCAAGACTACTTACTGGTGGGATGGTCTTCAA
TCCTCTGACGATTTTGCTCTGATTGTGAATGCACCCAATCATGAAGGGAT
TCAAGCCGGAGTCGACAGGTTTTATCGAACCTGTAAGCTACTTGGAATCA
ATATGAGCAAGAAAAGTCTTACATAAACAGAACAGGTACATTTGAATTC
ACAAGTTTTTTCTATCGTTATGGGTTTGTTGCCAATTTCAGCATGGAGCT
TCCCAGTTTTGGGGTGTCTGGGATCAACGAGTCAGCGGACATGAGTATTG
GAGTTACTGTCATCAAAAACAATATGATAAACAATGATCTTGGTCCAGCA
ACAGCTCAAATGGCCCTTCAGTTGTTCATCAAAGATTACAGGTACACGTA
CCGATGCCATATAGGTGACACACAAATACAAACCCGAAGATCATTTGAAA
TAAAGAAACTGTGGGAGCAAACCCGTTCCAAAGCTGGACTGCTGGTCTCC
GACGGAGGCCCAAATTTATACAACATTAGAAATCTCCACATTCCTGAAGT
CTGCCTAAAATGGGAATTGATGGATGAGGATTACCAGGGGCGTTTATGCA
ACCCACTGAACCCATTTGTCAGCCATAAAGAAATTGAATCAATGAACAAT
GCAGTGATGATGCCAGCACATGGTCCAGCCAAAAACATGGAGTATGATGC
TGTTGCAACAACACACTCCTGGATCCCCAAAAGAAATCGATCCATCTTGA
ATACAAGTCAAAGAGGAGTACTTGAGGATGAACAAATGTACCAAAGGTGC
TGCAATTTATTTGAAAAATTCTTCCCCAGCAGTTCATACAGAAGACCAGT
CGGGATATCCAGTATGGTGGAGGCTATGGTTTCCAGAGCCCGAATTGATG
CACGGATTGATTTCGAATCTGGAAGGATAAAGAAAGAAGAGTTCACTGAG
ATCATGAAGATCTGTTCCACCATTGAAGAGCTCAGACGGCAAAAATAGTG
AATTTAGCTTGTCCTTCATGAAAAAATGCCTTGTTTCTACT

PB2

(SEQ ID NO: 26)

AGCGAAAGCA GGTCAATTAT ATTCAATATG GAAAGAATAA
AAGAACTACG AAATCTAATG TCGCAGTCTC GCACCCGCGA
GATACTCACA AAAACCACCG TGGACCATAT GGCCATAATC
AAGAAGTACA CATCAGGAAG ACAGGAGAAG AACCCAGCAC
TTAGGATGAA ATGGATGATG GCAATGAAAT ATCCAATTAC

-continued

AGCAGACAAG AGGATAACGG AAATGATTCC TGAGAGAAAT

GAGCAAGGAC AAACTTTATG GAGTAAAATG AATGATGCCG

GATCAGACCG AGTGATGGTA TCACCTCTGG CTGTGACATG

GTGGAATAGG AATGGACCAA TAACAAATAC AGTTCATTAT

CCAAAAATCT ACAAAACTTA TTTTGAAAGA GTCGAAAGGC

TAAAGCATGG AACCTTTGGC CCTGTCCATT TTAGAAACCA

AGTCAAAATA CGTCGGAGAG TTGACATAAA TCCTGGTCAT

GCAGATCTCA GTGCCAAGGA GGCACAGGAT GTAATCATGG

AAGTTGTTTT CCCTAACGAA GTGGGAGCCA GGATACTAAC

ATCGGAATCG CAACTAACGA TAACCAAAGA GAAGAAAGAA

GAACTCCAGG ATTGCAAAAT TTCTCCTTTG ATGGTTGCAT

ACATGTTGGA GAGAGAACTG GTCCGCAAAA CGAGATTCCT

CCCAGTGGCT GGTGGAACAA GCAGTGTGTA CATTGAAGTG

TTGCATTTGA CTCAAGGAAC ATGCTGGGAA CAGATGTATA

CTCCAGGAGG GGAAGTGAGG AATGATGATG TTGATCAAAG

CTTGATTATT GCTGCTAGGA ACATAGTGAG AAGAGCTGCA

GTATCAGCAG ATCCACTAGC ATCTTTATTG GAGATGTGCC

ACAGCACACA GATTGGTGGA ATTAGGATGG TAGACATCCT

TAGGCAGAAC CCAACAGAAG AGCAAGCCGT GGATATATGC

AAGGCTGCAA TGGGACTGAG AATTAGCTCA TCCTTCAGTT

TTGGTGGATT CACATTTAAG AGAACAAGCG ATCATCAGT

CAAGAGAGAG GAAGAGGTGC TTACGGGCAA TCTTCAAACA

TTGAAGATAA GAGTGCATGA GGGATATGAA GAGTTCACAA

TGGTTGGGAG AAGAGCAACA GCCATACTCA GAAAAGCAAC

CAGGAGATTG ATTCAGCTGA TAGTGAGTGG GAGAGACGAA

CAGTCGATTG CCGAAGCAAT AATTGTGGCC ATGGTATTTT

CACAAGAGGA TTGTATGATA AAAGCAGTCA GAGGTGATCT

GAATTTCGTC AATAGGGCGA ATCAACGATT GAATCCTATG

CATCAACTTT TAAGACATTT TCAGAAGGAT GCGAAAGTGC

TTTTTCAAAA TTGGGGAGTT GAACCTATCG ACAATGTGAT

GGGAATGATT GGGATATTGC CCGACATGAC TCCAAGCATC

GAGATGTCAA TGAGAGGAGT GAGAATCAGC AAAATGGGTG

TAGATGAGTA CTCCAGCACG GAGAGGGTAG TGGTGAGCAT

TGACCGTTTT TTGAGAATCC GGGACCAACG AGGAAATGTA

CTACTGTCTC CCGAGGAGGT CAGTGAAACA CAGGGAACAG

AGAAACTGAC AATAACTTAC TCATCGTCAA TGATGTGGGA

GATTAATGGT CCTGAATCAG TGTTGGTCAA TACCTATCAA

TGGATCATCA GAAACTGGGA AACTGTTAAA ATTCAGTGGT

CCCAGAACCC TACAATGCTA CAATAAAAA TGGAATTTGA

ACCATTTCAG TCTTTAGTAC CTAAGGCCAT TAGAGGCCAA

TACAGTGGGT TTGTAAGAAC TCTGTTCCAA CAAATGAGGG

ATGTGCTTGG GACATTTGAT ACCGCACAGA TAATAAAACT

TCTTCCCTTC GCAGCCGCTC CACCAAAGCA AAGTAGAATG

CAGTTCTCCT CATTTACTGT GAATGTGAGG GGATCAGGAA

TGAGAATACT TGTAAGGGGC AATTCTCCTG TATTCAACTA

TAACAAGGCC ACGAAGAGAC TCACAGTTCT CGGAAAGGAT

GCTGGCACTT TAACTGAAGA CCCAGATGAA GGCACAGCTG

GAGTGGAGTC CGCTGTTCTG AGGGGATTCC TCATTCTGGG

CAAAGAAGAC AAGAGATATG GGCCAGCACT AAGCATCAAT

GAACTGAGCA ACCTTGCGAA AGGAGAGAAG GCTAATGTGC

TAATTGGGCA AGGAGACGTG GTGTTGGTAA TGAAACGGAA

ACGGGACTCT AGCATACTTA CTGACAGCCA GACAGCGACC

AAAAGAATTC GGATGGCCAT CAATTAGTGT CGAATAGTTT

AAAAACGACC TTGTTTCTAC T

NP
(SEQ ID NO: 27)

AGCAAAAGCA GGGTAGATAA TCACTCACTG AGTGACATCA

AAATCATGGC GTCTCAAGGC ACCAAACGAT CTTACGAACA

GATGGAGACT GATGGAGAAC GCCAGAATGC CACTGAAATC

AGAGCATCCG TCGGAAAAAT GATTGGTGGA ATTGGACGAT

TCTACATCCA AATGTGCACC GAACTCAAAC TCAGTGATTA

TGAGGGACGG TTGATCCAAA ACAGCTTAAC AATAGAGAGA

ATGGTGCTCT CTGCTTTTGA CGAAAGGAGA AATAAATACC

TTGAAGAACA TCCCAGTGCG GGAAAGATC CTAAGAAAAC

TGGAGGACCT ATATACAGGA GAGTAAACGG AAAGTGGATG

AGAGAACTCA TCCTTTATGA CAAAGAAGAA ATAAGGCGAA

TCTGGCGCCA AGCTAATAAT GGTGACGATG CAACGGCTGG

TCTGACTCAC ATGATGATCT GGCATTCCAA TTTGAATGAT

GCAACTTATC AGAGGACAAG AGCTCTTGTT CGCACCGGAA

TGGATCCCAG GATGTGCTCT CTGATGCAAG GTTCAACTCT

CCCTAGGAGG TCTGGAGCCG CAGGTGCTGC AGTCAAGGA

GTTGGAACAA TGGTGATGGA ATTGGTCAGA ATGATCAAAC

GTGGGATCAA TGATCGGAAC TTCTGGAGGG GTGAGAATGG

ACGAAAAACA GAATTGCTT ATGAAAGAAT GTGCAACATT

CTCAAAGGGA AATTTCAAAC TGCTGCACAA AAAGCAATGA

TGGATCAAGT GAGAGAGAGC CGGAACCCAG GAATGCTGA

GTTCGAAGAT CTCACTTTTC TAGCACGGTC TGCACTCATA

TTGAGAGGGT CGGTTGCTCA CAAGTCCTGC CTGCCTGCCT

GTGTGTATGG ACCTGCCGTA GCCAGTGGGT ACGACTTTGA

AAGGGAGGGA TACTCTCTAG TCGGAATAGA CCCTTTCAGA

CTGCTTCAAA ACAGCCAAGT GTACAGCCTA ATCAGACCAA

ATGAGAATCC AGCACACAAG AGTCAACTGG TGTGGATGGC

-continued

```
ATGCCATTCT GCCGCATTTG AAGATCTAAG AGTATTAAGC

TTCATCAAAG GGACGAAGGT GCTCCCAAGA GGGAAGCTTT

CCACTAGAGG AGTTCAAATT GCTTCCAATG AAAATATGGA

GACTATGGAA TCAAGTACAC TTGAACTGAG AAGCAGGTAC

TGGGCCATAA GGACCAGAAG TGGAGGAAAC ACCAATCAAC

AGAGGGCATC TGCGGGCCAA ATCAGCATAC AACCTACGTT

CTCAGTACAG AGAAATCTCC CTTTTGACAG AACAACCATT

ATGGCAGCAT TCAATGGGAA TACAGAGGGG AGAACATCTG

ACATGAGGAC CGAAATCATA AGGATGATGG AAAGTGCAAG

ACCAGAAGAT GTGTCTTTCC AGGGGCGGGG AGTCTTCGAG

CTCTCGGACG AAAAGGCAGC GAGCCCGATC GTGCCTTCCT

TTGACATGAG TAATGAAGGA TCTTATTTCT TCGGAGACAA

TGCAGAGGAG TACGACAATT AAAGAAAAAT ACCCTTGTTT CTACT
```

M (SEQ ID NO: 28)

```
AGCAAAAGCA GGTAGATATT GAAAGATGAG TCTTCTAACC

GAGGTCGAAA CGTACGTACT CTCTATCATC CCGTCAGGCC

CCCTCAAAGC CGAGATCGCA CAGAGACTTG AAGATGTCTT

TGCAGGGAAG AACACCGATC TTGAGGTTCT CATGGAATGG

CTAAAGACAA GACCAATCCT GTCACCTCTG ACTAAGGGGA

TTTTAGGATT TGTGTTCACG CTCACCGTGC CCAGTGAGCG

AGGACTGCAG CGTAGACGCT TTGTCCAAAA TGCCCTTAAT

GGGAACGGGG ATCCAAATAA CATGGACAAA GCAGTTAAAC

TGTATAGGAA GCTCAAGAGG GAGATAACAT TCCATGGGGC

CAAAGAAATC TCACTCAGTT ATTCTGCTGG TGCACTTGCC

AGTTGTATGG GCCTCATATA CAACAGGATG GGGGCTGTGA

CCACTGAAGT GGCATTTGGC CTGGTATGTG CAACCTGTGA

ACAGATTGCT GACTCCCAGC ATCGGTCTCA TAGGCAAATG

GTGACAACAA CCAATCCACT AATCAGACAT GAGAACAGAA

TGGTTTTAGC CAGCACTACA GCTAAGGCTA TGGAGCAAAT

GGCTGGATCG AGTGAGCAAG CAGCAGAGGC CATGGAGGTT

GCTAGTCAGG CTAGACAAAT GGTGCAAGCG ATGAGAACCA

TTGGGACTCA TCCTAGCTCC AGTGCTGGTC TGAAAAATGA

TCTTCTTGAA AATTTGCAGG CCTATCAGAA ACGAATGGGG

GTGCAGATGC AACGGTTCAA GTGATCCTCT CACTATTGCC

GCAAATATCA TTGGGATCTT GCACTTGACA TTGTGGATTC

TTGATCGTCT TTTTTTCAAA TGCATTTACC GTCGCTTTAA

ATACGGACTG AAAGGAGGGC CTTCTACGGA AGGAGTGCCA

AAGTCTATGA GGGAAGAATA TCGAAAGGAA CAGCAGAGTG
```

```
CTGTGGATGC TGACGATGGT CATTTTGTCA GCATAGAGCT

GGAGTAAAAA ACTACCTTGT TTCTACT
```

NS (SEQ ID NO: 29)

```
AGCAAAAGCA GGGTGACAAA AACATAATGG ATCCAAACAC

TGTGTCAAGC TTTCAGGTAG ATTGCTTTCT TTGGCATGTC

CGCAAACGAG TTGCAGACCA AGAACTAGGC GATGCCCCAT

TCCTTGATCG GCTTCGCCGA GATCAGAAAT CCCTAAGAGG

AAGGGGCAGT ACTCTCGGTC TGGACATCAA GACAGCCACA

CGTGCTGGAA AGCAGATAGT GGAGCGGATT CTGAAAGAAG

AATCCGATGA GGCACTTAAA ATGACCATGG CCTCTGTACC

TGCGTCGCGT TACCTAACTG ACATGACTCT TGAGGAAATG

TCAAGGGACT GGTCCATGCT CATACCCAAG CAGAAAGTGG

CAGGCCCTCT TTGTATCAGA ATGGACCAGG CGATCATGGA

TAAGAACATC ATACTGAAAG CGAACTTCAG TGTGATTTTT

GACCGGCTGG AGACTCTAAT ATTGCTAAGG GCTTTCACCG

AAGAGGGAGC AATTGTTGGC GAAATTTCAC CATTGCCTTC

TCTTCCAGGA CATACTGCTG AGGATGTCAA AAATGCAGTT

GGAGTCCTCA TCGGAGGACT TGAATGGAAT GATAACACAG

TTCGAGTCTC TGAAACTCTA CAGAGATTCG CTTGGAGAAG

CAGTAATGAG AATGGGAGAC CTCCACTCAC TCCAAAACAG

AAACGAGAAA TGGCGGGAAC AATTAGGTCA GAAGTTTGAA

GAAATAAGAT GGTTGATTGA AGAAGTGAGA CACAAACTGA

AGATAACAGA GAATAGTTTT GAGCAAATAA CATTTATGCA

AGCCTTACAT CTATTGCTTG AAGTGGAGCA AGAGATAAGA

ACTTTCTCGT TTCAGCTTAT TTAGTACTAA AAACACCCT

TGTTTCTACT
```

EXAMPLE 2

Neuraminidase Modifications

Materials

Viruses:
Y2017: A/Yokohama12017/2003 (H3N2)
HK4801: A/Hong Kong/4801/2014(H3N2)
Y2017-M3L4: Y2017 passaged 7 times in eggs
HY-PR8: high yield PR8 (H1N1)

Results

Y2017 virus was passaged 7 times in eggs (3 times in the amniotic cavity, followed by 4 times in the allantoic cavity). A progeny virus, Y2017-M3L4, grew efficiently in the allantoic cavity ($10^7$ to about $10^8$ PFU/mL), whereas the original Y2017 virus did not grow at all (<10 PFU/mL).

Mutations observed in Y2017-M3L4 virus were as follows:

TABLE 1

|  | PB2 | NA | NP | M1 |
|---|---|---|---|---|
| eggA | T147I, V344L and T147I, V344L, E358K | del 46-50aa, T32A, D147N, N329D, H347Q | none | E23Q |
| eggB | T147I | del 46-50aa, T32A, D147N, N329D, H347Q | D101N | none |
| eggC | T147I | del 46-50aa, T32A, D147N, N329D, H347Q | D101N | none |

A comparison of the growth ability of mutant Y2017 viruses, generated by reverse genetics, in allantoic fluid revealed that NA mutations were responsible for the high growth of Y2017-M3L4 virus (FIG. 4). A plasmid with PB2-T147I was used for virus generation (PB2-T147I, V344L and PB2-T147I, V344L, E358K were not analyzed). Mutations were not observed in the HA gene of the virus possessing a mutated NA segment and its other genes from wild-type Y2017 after replication in allantoic fluid (FIG. 4).

Figure 5A:
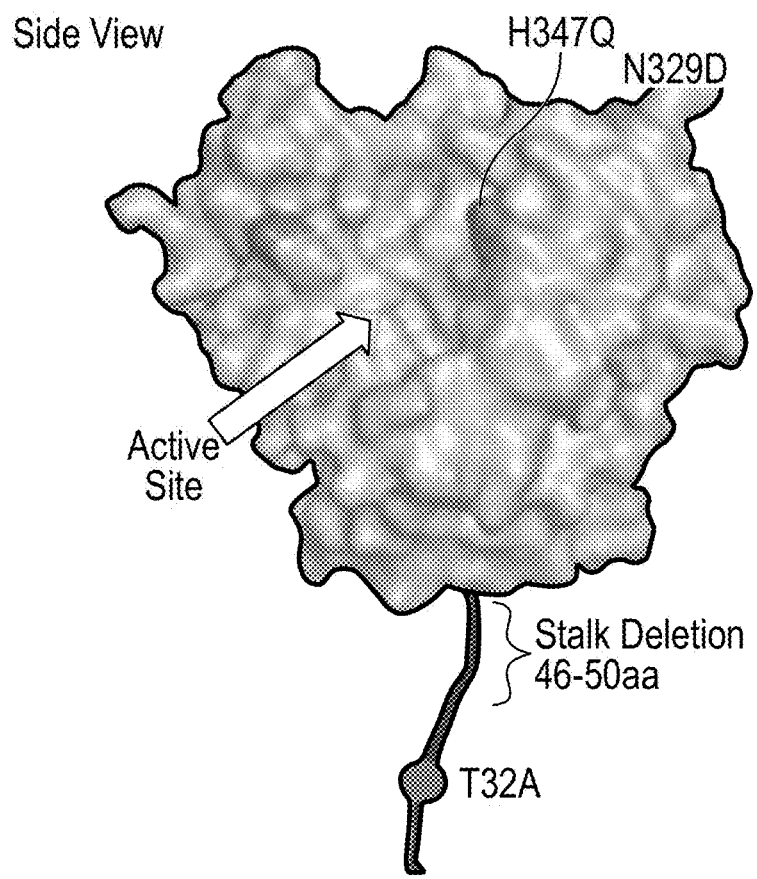
FIG. 5. Locations of the NA mutations on the 3D structure of N2 NA.
Figure 5B:
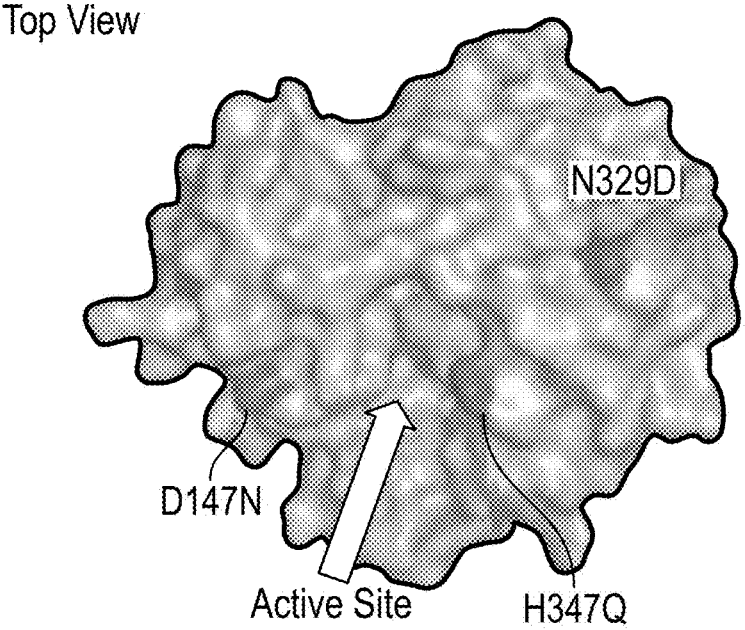

FIG. 5 shows the location of the NA mutations in Y2017-M3L4 in a 3D model.

Figure 6:
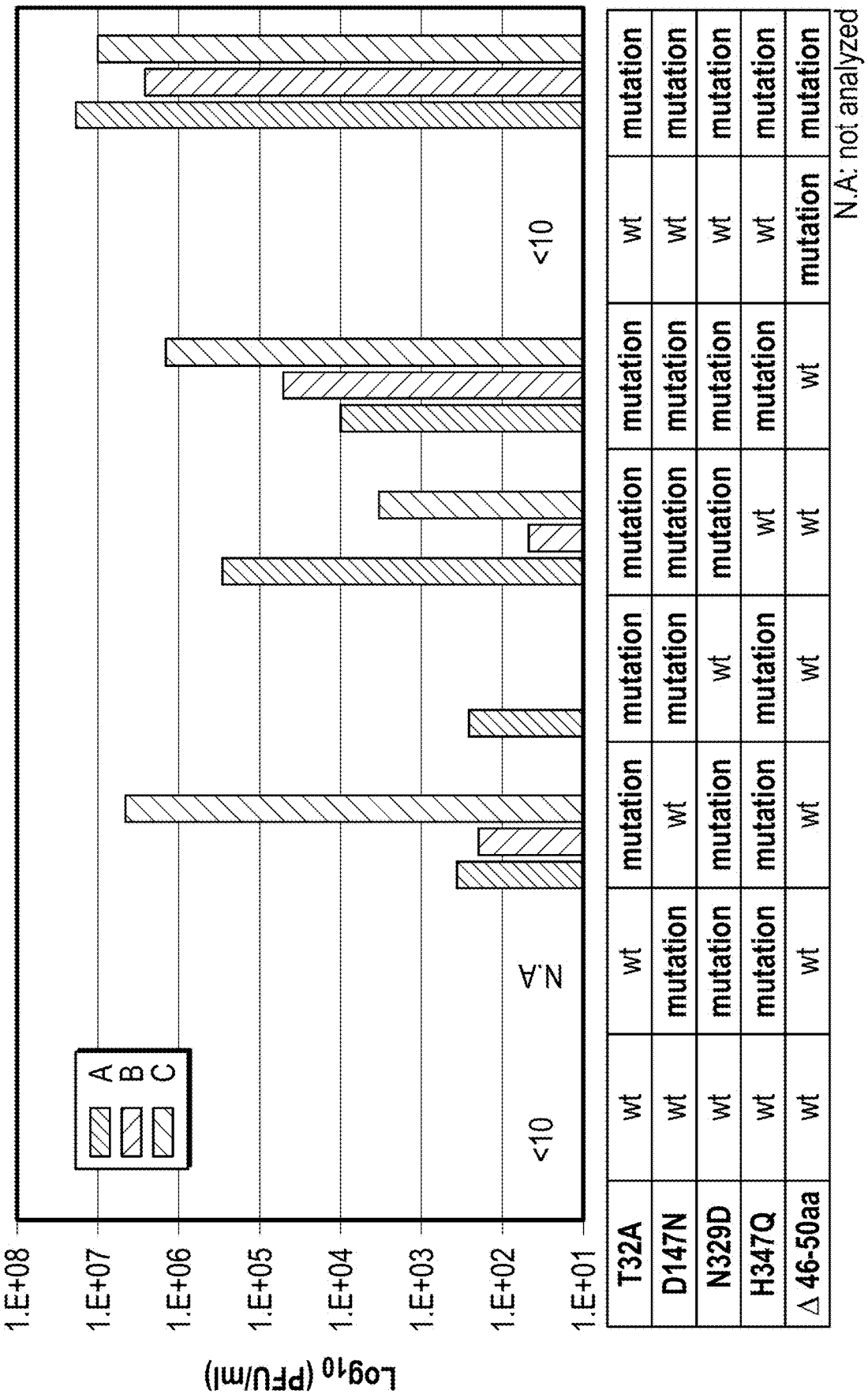
FIG. 6. Graph showing titers in eggs for recombinant viruses with specific mutations found in the mutant of A/Yokohama/2017/2003 ("Y2017-M3L4"). Virus inoculation: $2 \times 10^3$ pfu/egg into allantoic fluid, 72 h incubation at 37° C.

Comparison of the growth ability of Y2017 viruses with NA mutations revealed that NA-D147N, N329D, and H347Q generally contributed to the increased growth ability in allantoic fluid (FIG. 6).

The NA of Y2017-M3L4 allowed virus possessing HK4801HA to replicate efficiently in the allantoic cavity and the HY-PR8 backbone further enhanced the growth of this virus (FIG. 7).

In summary, described herein are influenza virus mutations that inhibit (e.g., prevent) the acquisition of antigenicity-compromising mutations in the hemagglutinin (HA) protein of influenza during growth in eggs and/or allow for enhanced replication. In one embodiment, the mutations are within the neuraminidase (NA) viral segment of human influenza viruses, and the mutant NA proteins stabilize the HA protein during egg-passages. Thus, in the presence of the mutant NA proteins, the HA protein does not acquire egg-adapting mutations. In some cases, the respective mutations in NA can also increase the yield of vaccine viruses.

EXAMPLE 3

Figure 12:
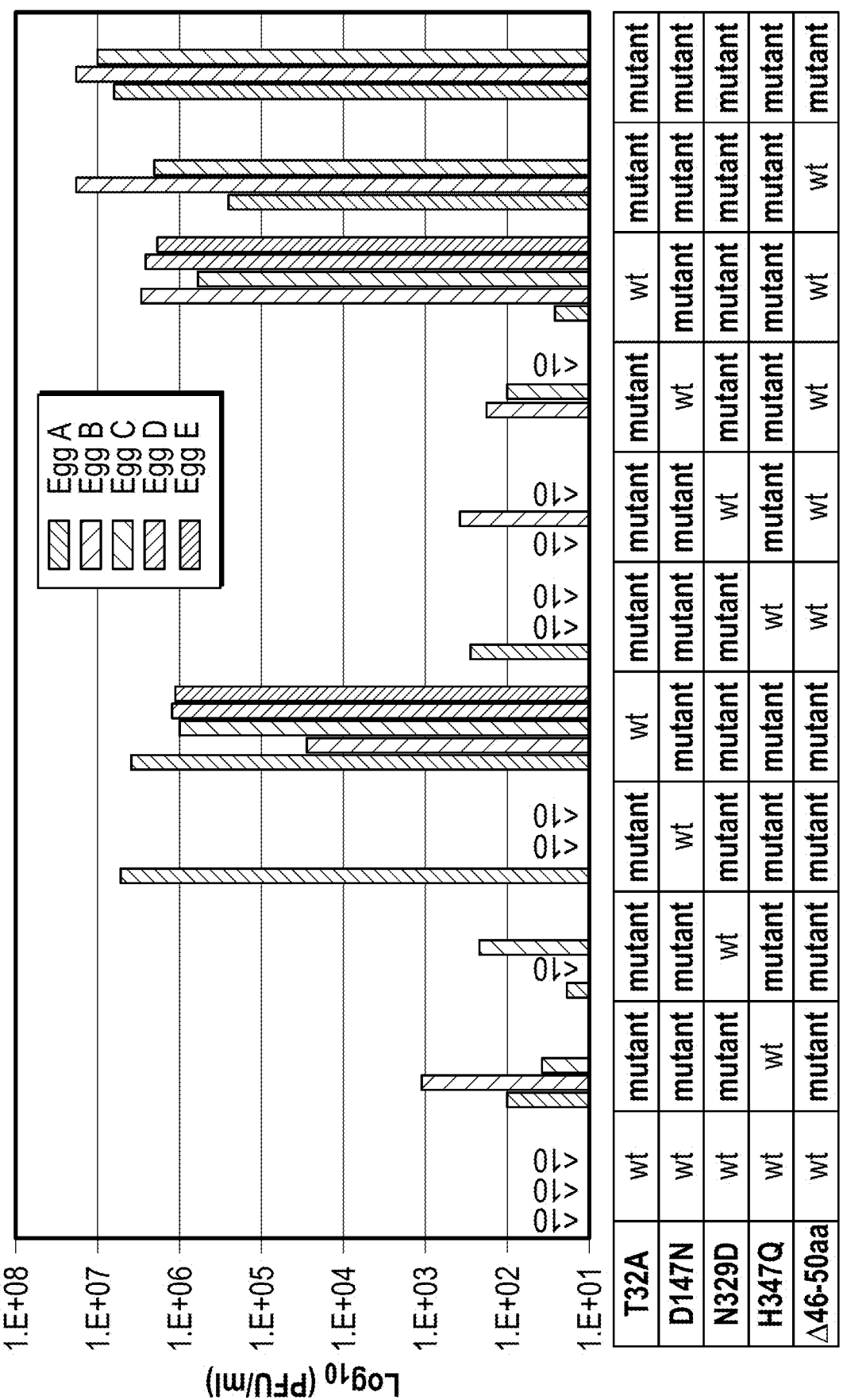
FIG. 12. Titers in eggs for various NA mutants.

Analysis of the growth capability of NA mutant viruses revealed that NA-D147N, N329D, and H347Q contribute to the increased growth capability of the viruses in allantoic fluid (FIG. 12). HA mutations were not observed in the virus possessing HK4801HA, Y2017-M3L4NA, and the HY-PR8 backbone (FIG. 13) after 3 passages in the allantoic cavity.

By passaging an HY-PR8 backbone virus possessing HK4801NA (T148K and the saturated mutations N329X and H347X) and HK4801HA in eggs, a virus possessing HK4801NA (T148K, D151E, H347G, and T369K) emerged that replicated efficiently in the allantoic cavity (FIG. 14; 4M=T148K, D151E, H347G, and T369K). HA mutations were not observed during passages in eggs (1× in the amniotic cavity then 5× in the allantoic cavity).

Figure 16:
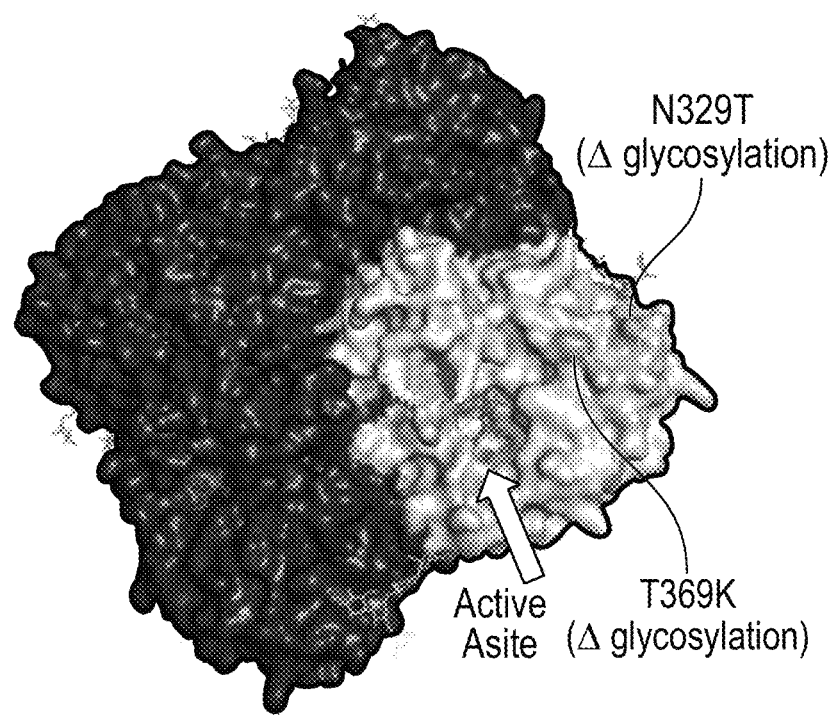
FIG. 16 is a schematic of the positions of certain NA residues.
Figure 17:
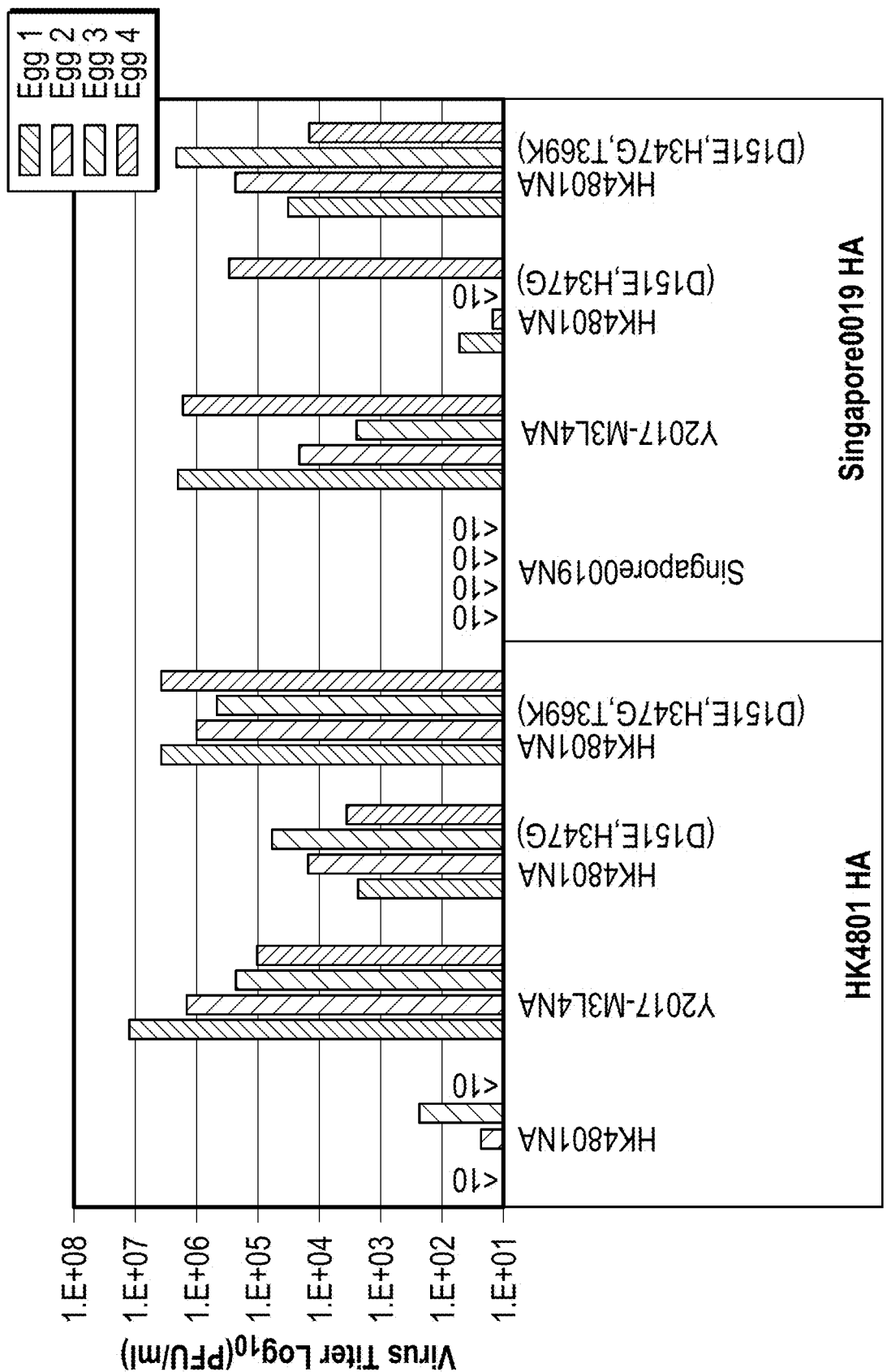
FIG. 17 shows virus titers for egg passaged isolates (HK4801NA (T148K, D151E, H347G, and T369K)) conferred efficient replication in the allantoic cavity to viruses possessing either HK4801HA or Singapore0019 HA (HY-PR8 backbone).

HK4801NA (T148K, D151E, H347G, and T369K) conferred efficient replication in the allantoic cavity to HY-PR8 backbone viruses possessing either HK4801HA or Singapore0019HA. Virus inoculation: 2×10$^3$ pfu/egg into allantoic fluid, 72 h incubation at 37° C. (FIG. 16).

The HA coding nucleic acid sequence and NA coding nucleic acid and amino acid sequences for Singapore0019 are as follows:

A/Singapore/INFINH-16-0019/2016(H3N2) HA (SEQ ID NO: 46)

atgaagactatcattgctttgagctacattctatgtctggttttcgctcaaaaaattcctggaaatgacaatagcacggcaacgctgt gccttgggcaccatgcagtaccaaacggaacgatagtgaaaacaatcacaaatgaccgaattgaagttactaatgctactgagtt ggttcagaattcctcaataggtgaaatatgcgacagtcctcatcagatccttgatggagagaactgcacactaatagatgctctatt gggagaccctcagtgtgatggctttcaaaataagaaatgggaccttttgttgaacgaaacaaagcctacagcaactgttaccctt atgatgtgccggattatgcctcccttaggtcactagttgcctcatccggcacactggagtttaaaaatgaaagcttcaattggactg gagtcactcaaaacggaacaagttctgcttgcataaggggatctagtagtagtttctttagtagattaaattggttgacccacttaaa ctacacatatccagcattgaacgtgactatgccaaacaaggaacaatttgacaaattgtacatttgggggttcaccacccgggta cggacaaggaccaaatcttcctgtatgctcaatcatcaggaagaatcacagtatctaccaaaagaagccaacaagctgtaatccc aaatatcggatctagacccagaataagggatatccctagcagaataagcatctattggacaatagtaaaaccgggagacatacttt tgattaacagcacagggaatctaattgctcctaagggttacttcaaaatacgaagtgggaaaagctcaataatgagatcagatgca cccattggcaaatgcaagtctgaatgcatcactccaaatggaagcattcccaatgacaaaccattccaaaatgtaaacaggatca catacgggcctgtcccagatatgttaagcatagcactctaaaattgacaacaggaatgcgaaatgtaccagagaaacaaacta gaggcatatttggcgcaatagcgggtttcatagaaaatggttgggagggaatggtggatggttggtacggtttcaggcatcaaaa ttctgagggaagaggacaagcagcagatctcaaaagcactcaagcagcaatcgatcaaatcaatgggaagctgaataggttga tcggaaaaaccaacgagaaattccatcagattgaaaagaattctcagaagtagaaggaagagttcaagaccttgagaaatatgt tgaggacactaaaatagatctctggtcatacaacgcggagcttcttgttgccctggagaaccaacatacaattgatctaactgactc agaaatgaacaaactgtttgaaaaacaaagaagcaactgagggaaaatgctgaggatatgggaaatggttgtttcaaaatatac cacaaatgtgacaatgcctgcatagaatcaataagaaatgaaacttatgaccacaatgtgtacagggatgaagcattgaacaacc -continued

```
ggttccagatcaagggagttgagctgaagtcaggatacaaagattggatcctatggatttccttgccatatcatgttttttgctttgtg ttgctttgttggggttcatcatgtgggcctgccaaaagggcaacattagatgcaacatttgcatttga
```

A/Singapore/INFINH-16-0019/2016(H3N2) NA (SEQ ID NO: 47)

```
atgaatccaaatcaaaagataataacgattggctctgtttctctcaccatttccacaatatgcttcttcatgcaaattgccatcctgata actactgtaacattgcatttcaagcaatatgaattcaactcccccccaaacaaccaagtgatgctgtgtgaaccaacaataatagaa agaaacataacagagatagtgtatttgaccaacaccaccatagaaaggaaatgccccaaaccagcagaatacagaaattg gtcaaaaccgcaatgtggcattacaggatttgcacctttctctaaggacaattcgattaggctttccgctggtggggacatctggt gacaagagaaccttatgtgtcatgcgatcctgacaagtgttatcaatttgcccttggacagggaacaacactaaacaacgtgcatt caaataacacagtacgtgatagaacccttatcggactctattgatgaatgagttgggtgttccttccatctggggaccaagcaag tgtgcatagcatggtccagctcaagttgtcacgatggaaaagcatggctgcatgtttgtataacgggggatgataaaaatgcaact gctagcttcatttacaatgggaggcttatagatagtgttgtttcatagtccaaagatattctcaggacccaggagtcagaatgcgttt gtatcaatggaacttgtacagtagtaatgactgatggaaatgctacaggaaaagctgatactaaaatactattcattgaggagggg aaaatcgttcatactagcaaattgtcaggaagtgctcagcatgtcgaagagtgctcttgctatcctcgatatcctggtgtcagatgtg tctgcagagacaactggaaaggatccaaccggcccatcgtagatataaacataaaggatcatagcattgtttccagttatgtgtgtt caggacttgttggagacacacccagaaaaaacgacagctccagcagtagccattgtttgaatcctaacaatgaagaaggtggtc atggagtgaaaggctgggcctttgatgatggaaatgacgtgtggatggggagaacaatcaacgagacgtcacgcttagggtat gaaaccttcaaagtcgttgaaggctggtccaaccctaagtccaaattgcagataaataggcaagtcatagttgacagaggtgata ggtccggttattctggtattttctctgttgaaggcaaaagctgcatcaatcggtgcttttatgtggagttgattaggggaagaaaga ggaaactgaagtcttgtggacctcaaacagtattgttgtgttttgtggcacctcaggtacatatggaacaggctcatggcctgatgg ggcggacctcaatctcatgcatatataa
``` which encodes (SEQ ID NO: 48)

```
M N P N Q K I I T I G S V S L T I S T I C F F M Q I A I L I T T V T L H F K
Q Y E F N S P P N N Q V M L C E P T I I E R N I T E I V Y L T N T T I E K
E I C P K P A E Y R N W S K P Q C G I T G F A P F S K D N S I R L S A G
G D I W V T R E P Y V S C D P D K C Y Q F A L G Q G T T L N N V H S N
N T V R D R T P Y R T L L M N E L G V P F H L G T K Q V C I A W S S S
S C H D G K A W L H V C I T G D D K N A T A S F I Y N G R L I D S V V
S W S K D I L R T Q E S E C V C I N G T C T V V M T D G N A T G K A D
T K I L F I E E G K I V H T S K L S G S A Q H V E E C S C Y P R Y P G V
R C V C R D N W K G S N R P I V D I N I K D H S I V S S Y V C S G L V G
D T P R K N D S S S S H C L N P N N E E G G H G V K G W A F D D G
N D V W M G R T I N E T S R L G Y E T F K V V E G W S N P K S L Q I
N R Q V I V D R G D R S G Y S G I F S V E G K S C I N R C F Y V E L I R
G R K E E T E V L W T S N S I V V F C G T S G T Y G T G S W P D G A D
L N L M H I.
```

Figure 18:
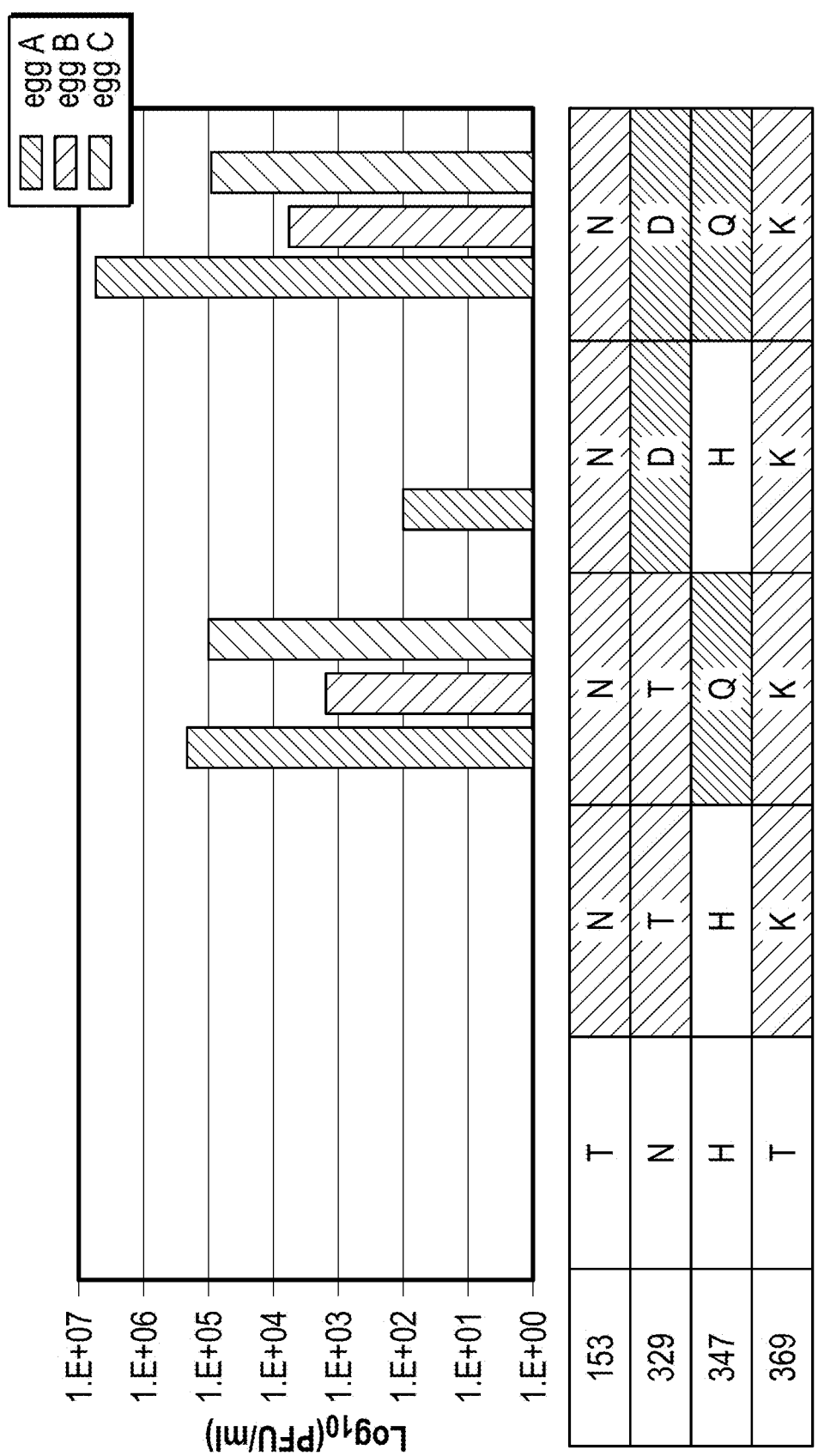
FIG. 18 shows egg titers for different combinations of selected residues at positions 153, 329, 347, and 369 in NA.

NA mutations T153N, N329T, and T369K allowed A/Saitama/102/2014 (H3N2) to replicate efficiently in the allantoic cavity (Kuwahara et al., 2018). Therefore, the effect of introducing NA-T153N, N329T (or D), T369K, and H347Q into HK4801NA(T148K) was examined. FIG. 18 reports on virus titers for different combinations of NA residues identified in screenings. FIGS. 19 and 20 report on virus titers for viruses with different combinations of selected NA residues.

EXAMPLE 4

A/Alaska/232/2015_HY-PR8 (H3N2) WT/mutant virus were passaged in eggs and HA and NA segments sequenced. Alaska WT (a more recent H3N2 virus where WT has 245N, prior to 2015 H3N2 WT viruses had 245S), HA-R142S, -K189E viruses did not get mutations in HA, even after 3 amniotic and 10 allantoic passages. HA-K189E/N158K/

A212T mutant did not get mutations in HA, but had some mutations in NA which exhibited improved growth in eggs since p6 (FIG. 21). The difference of NA mutations between p4(normal growth) (NA-N245S mutation, virus grows more than 1000 fold better than with NA-245N) and p6 (better growth) was G346V (FIG. 22). Therefore, G346V may also contribute to adaptation to eggs.

The NA for A/Alaska/232/2015 has the following sequence:

```
                                              (SEQ ID NO: 49)
mnpnqkiiti gsvsltisti cffmqiaili ttvtlhfkqy efnsppnnqv mlceptiier niteivyltn ttiekeicpk paeyrnwskp qcgitgfapf skdnsirlsa ggdiwvtrep yvscdpdkcy qfalgqgttl nnvhsnntvr drtpyrtllm nelgvpfhlg tkqvciawss sschdgkawl hvcitgddkn atasfiyngr lvdsvvswsk dilrtqesec vcingtctvv mtdgnatgka dtkilfieeg kivhtsklsg saqhveecsc yprypgvrcv crdnwkgsnr pivdinikdh sivssyvcsg lvgdtprknd ssssshclnp nneegghgvk gwafddgndv wmgrtinets rlgyetfkvv egwsnpkskl qinrqvivdr gdrsqysgif svegkscinr cfyvelirgr keetevlwts nsivvfcgts gtygtgswpd gadlnlmhi.
```

Figure 23B:
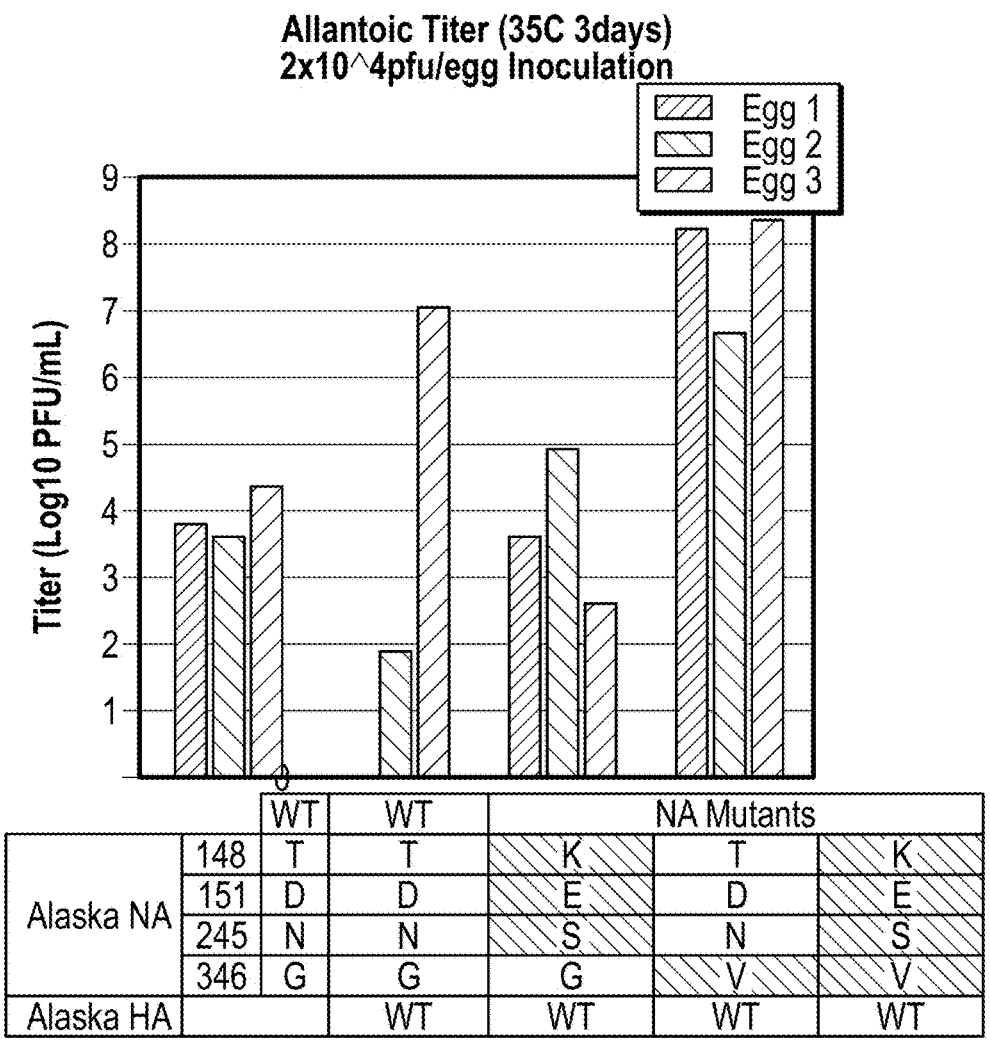
FIG. 23 shows egg titers for viruses with different NAs.
Figure 24:
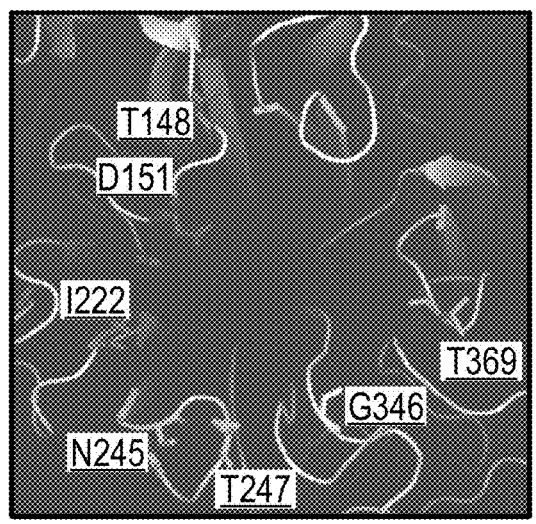
FIG. 24 is an enlarged view of the NA activity center. Most egg-adapted mutations are located in/around the NA active site.

NA pHH21 plasmids were constructed: Alaska NA-T148K/D151E/N245S (found in E4); Alaska NA-G346V; and Alaska NA-T148K/D151E/N245S/G346V (found in E6). Mutant NAs were combined with WT Alaska HA or HY-PR8 backbone. Eggs were inoculated with the same dosage of WT/mutant Alaska viruses and harvested viruses titrated (FIG. 23). NA-T148K/D151E/N245S/G346V mutant virus grew to a higher titer than WT virus but the single mutation G346V did not increase virus growth compared to WT. These results suggested that a combination of G346V and one (or two to three) other mutations, e.g., 3 mutations such as T148K, D151E and N245S, may be important for virus Alaska virus to grow efficiently in eggs.

Harvested virus samples with high titer (>5 Log10 PFU/mL) were sequenced however none had additional mutations in HA and NA.

References

Avery's Drug Treatment: Principles and Practice of Clinical Pharmacology and Therapeutics, 3rd edition, ADIS Press, Ltd Williams and Wilkins, Baltimore, Md. (1987).
Aymard-Henry et al., Virology: A Practical Approach, Oxford IRL Press, Oxford, 119-150 (1985).
Bachmeyer, Intervirology, 5:260 (1975).
Berkow et al., eds., The Merck Manual, 16th edition, Merck & Co., Rahway, N.J. (1992).
Hatta et al., Science, 293:1840 (2001).
Horimoto et al., J. Virol., 68:3120 (1994).
Horimoto et al., Vaccine 24:3669 (2006).
Keitel et al., in Textbook of Influenza, eds. Nickolson, K. G Webster, R. G., and Hay, A. (Blackwell, Oxford), pp. 373-390 (1998).
Kuwahara et al., Jpn. J. Infect. Dis., 71:234 (2018).
Laver & Webster, Virology, 69:511 (1976).
Neumann et al., Adv. Virus Res., 53:265 (1999).
Neumann et al., J. Gen. Virol., 83:2635 (2002).
Neumann et al., J. Virol., 71:9690 (1997).
Neumann et al., Proc. Natl. Acad. Sci. USA, 96:9345 (1999).
Neumann et al., Virology. 287:243 (2001).
Osol (ed.), Remington's Pharmaceutical Sciences, Mack Publishing Co., Easton, Pa. 1324-1341 (1980).
Sugawara et al., Biologicals, 30:303 (2002).
Webby & Webster et al., Science, 302:1519 (2003).
Wood & Robertson, Nat. Rev. Microbiol., 2:842 (2004).
World Health Organization TSR No. 673 (1982).
World Health Organization. Confirmed human cases of avian influenza A (H5N1). http://www.who.int/csr/disease/avian_influenza/country/en/index.html All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

SEQUENCE LISTING

```
<160> NUMBER OF SEQ ID NOS: 62

<210> SEQ ID NO 1
<211> LENGTH: 464
<212> TYPE: PRT
<213> ORGANISM: Influenza virus

<400> SEQUENCE: 1

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Ala
            20                  25                  30

Val Thr Leu His Phe Lys Gln Tyr Glu Phe Asn Ser Pro Met Leu Cys
        35                  40                  45

Glu Pro Thr Ile Ile Glu Arg Asn Ile Thr Glu Ile Val Tyr Leu Thr
    50                  55                  60

Asn Thr Thr Ile Glu Lys Glu Ile Cys Pro Lys Leu Ala Glu Tyr Arg
```

```
            65                  70                  75                  80
       Asn Trp Ser Lys Pro Gln Cys Asn Ile Thr Gly Phe Ala Pro Phe Ser
                        85                  90                  95
       Lys Asp Asn Ser Ile Arg Leu Ser Ala Gly Asp Ile Trp Val Thr
                   100                 105                 110
       Arg Glu Pro Tyr Val Ser Cys Asp Pro Asp Lys Cys Tyr Gln Phe Ala
                   115                 120                 125
       Leu Gly Gln Gly Thr Thr Leu Asn Asn Val His Ser Asn Asn Ile Val
                   130                 135                 140
       His Asp Arg Thr Pro Tyr Arg Thr Leu Leu Met Asn Glu Leu Gly Val
       145                 150                 155                 160
       Pro Phe His Leu Gly Thr Lys Gln Val Cys Ile Ala Trp Ser Ser Ser
                           165                 170                 175
       Ser Cys His Asp Gly Lys Ala Trp Leu His Val Cys Val Thr Gly Asp
                       180                 185                 190
       Asp Glu Asn Ala Thr Ala Ser Phe Ile Tyr Asn Gly Arg Leu Ala Asp
                       195                 200                 205
       Ser Ile Val Ser Trp Ser Lys Lys Ile Leu Arg Thr Gln Glu Ser Glu
                   210                 215                 220
       Cys Val Cys Ile Asn Gly Thr Cys Thr Val Val Met Thr Asp Gly Ser
       225                 230                 235                 240
       Ala Ser Gly Lys Ala Asp Thr Lys Ile Leu Phe Ile Glu Glu Gly Lys
                       245                 250                 255
       Ile Val His Thr Ser Thr Leu Ser Gly Ser Ala Gln His Val Glu Glu
                       260                 265                 270
       Cys Ser Cys Tyr Pro Arg Tyr Pro Gly Val Arg Cys Val Cys Arg Asp
                   275                 280                 285
       Asn Trp Lys Gly Ser Asn Arg Pro Ile Val Asp Ile Asn Ile Lys Asp
                   290                 295                 300
       Tyr Ser Ile Val Ser Ser Tyr Val Cys Ser Gly Leu Val Gly Asp Thr
       305                 310                 315                 320
       Pro Arg Lys Asp Asp Ser Ser Ser Ser His Cys Leu Asp Pro Asn
                       325                 330                 335
       Asn Glu Glu Gly Gly Gln Gly Val Lys Gly Trp Ala Phe Asp Asp Gly
                       340                 345                 350
       Asn Asp Val Trp Met Gly Arg Thr Ile Ser Glu Lys Leu Arg Ser Gly
                   355                 360                 365
       Tyr Glu Thr Phe Lys Val Ile Glu Gly Trp Ser Asn Pro Asn Ser Lys
                   370                 375                 380
       Leu Gln Ile Asn Arg Gln Val Ile Val Asp Arg Gly Asn Arg Ser Gly
       385                 390                 395                 400
       Tyr Ser Gly Ile Phe Ser Val Glu Gly Lys Ser Cys Ile Asn Arg Cys
                       405                 410                 415
       Phe Tyr Val Glu Leu Ile Arg Gly Arg Lys Gln Glu Thr Glu Val Leu
                       420                 425                 430
       Trp Thr Ser Asn Ser Ile Val Val Phe Cys Gly Thr Ser Gly Thr Tyr
                   435                 440                 445
       Gly Thr Gly Ser Trp Pro Asp Gly Ala Asp Ile Asn Leu Met Pro Ile
                   450                 455                 460

<210> SEQ ID NO 2
<211> LENGTH: 469
<212> TYPE: PRT
<213> ORGANISM: Influenza virus
```

```
<400> SEQUENCE: 2

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Val Thr Glu
    50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Val His
130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
            195                 200                 205

Gly Arg Leu Val Asp Ser Val Val Ser Trp Ser Lys Asp Ile Leu Arg
210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
            275                 280                 285

Cys Val Cys Arg Asp Asn Trp Lys Gly Ser Asn Arg Pro Ile Val Asp
290                 295                 300

Ile Asn Ile Lys Asp His Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Asn Glu
            355                 360                 365

Thr Ser Arg Leu Gly Tyr Glu Thr Phe Lys Val Glu Gly Trp Ser
370                 375                 380

Asn Pro Lys Ser Lys Leu Gln Ile Asn Arg Gln Val Ile Val Asp Arg
385                 390                 395                 400

Gly Asp Arg Ser Gly Tyr Ser Gly Ile Phe Ser Val Glu Gly Lys Ser
```

-continued

```
                405                 410                 415
Cys Ile Asn Arg Cys Phe Tyr Val Glu Leu Ile Arg Gly Arg Lys Glu
            420                 425                 430

Glu Thr Glu Val Leu Trp Thr Ser Asn Ser Ile Val Val Phe Cys Gly
            435                 440                 445

Thr Ser Gly Thr Tyr Gly Thr Gly Ser Trp Pro Asp Gly Ala Asp Leu
            450                 455                 460

Asn Leu Met Pro Ile
465

<210> SEQ ID NO 3
<211> LENGTH: 469
<212> TYPE: PRT
<213> ORGANISM: Influenza virus

<400> SEQUENCE: 3

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
            20                  25                  30

Val Thr Leu His Phe Lys Gln Tyr Glu Phe Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asp Ile Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Glu Asn Ala Thr Ala Ser Phe Ile Tyr Asn
        195                 200                 205

Gly Arg Leu Ala Asp Ser Ile Val Ser Trp Ser Lys Lys Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Thr Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300
```

```
Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser Ser His
            325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
            405                 410                 415

Cys Ile Asn Arg Cys Phe Tyr Val Glu Leu Ile Arg Gly Arg Lys Gln
            420                 425                 430

Glu Thr Glu Val Leu Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 4
<211> LENGTH: 2341
<212> TYPE: DNA
<213> ORGANISM: Influenza virus

<400> SEQUENCE: 4
agcaaaagca ggtcaattat attcagtatg gaaagaataa aagaactacg gaacctgatg      60
tcgcagtctc gcactcgcga gatactgaca aaaaccacag tggaccatat ggccataatt     120
aagaagtaca catcggggag acaggaaaag aacccgtcac ttaggatgaa atggatgatg     180
gcaatgaaat acccaatcac tgctgacaaa aggataacag aaatggttcc ggagagaaat     240
gaacaaggac aaactctatg gagtaaaatg agtgatgctg atcagatcg agtgatggta      300 tcacctttgg ctgtgacatg gtggaataga aatggacccg tgacaagtac ggtccattac     360
ccaaaagtat acaagactta ttttgacaaa gtcgaaggt aaaacatgg aacctttggc       420 cctgttcatt ttagaaatca gtcaagata cgccgaagag tagacacaaa ccctggtcat      480
gcggacctca gtgccaagga ggcacaagat gtaattatgg aagttgtttt tcccaatgaa     540
gtgggagcca ggatactaac atcagaatcg caattaacaa taactaaaga gaaaaagaa      600 gaactccgag attgcaaaat ttctcccttg atggttgcat acatgttaga gagagaactt     660
gtccgaaaaa caagatttct cccagttgct ggcggaacaa gcagtatata cattgaagtt     720
ttacatttga ctcaagggac gtgttgggaa caaatgtaca ctccaggtgg agaagtgagg     780
aatgacgatg ttgaccaaag cctaattatt gcagccagga acatagtaag aagagccgca     840
gtatcagcag atccactagc atctttattg gagatgtgcc acagcacaca aattggcggg     900
acaaggatgg tggacattct agacagaac ccgactgaag acaagctgt ggatatatgc       960 aaggctgcaa tgggattgag aatcagctca tccttcagct ttggtgggtt tacatttaaa    1020
agaacaagcg gtcatcagt caaaaaagag gaagaagtgc ttacaggcaa tctccaaaca    1080
ttgaagataa gagtacatga ggggtatgag gagttcacaa tggtggggaa aagagcaaca    1140
```

-continued

```
gctatactca gaaaagcaac cagaagattg gttcagctca tagtgagtgg aagagacgaa      1200
cagtcaatag ccgaagcaat aattgtggcc atggtgtttt cacaagagga ttgcatgata      1260
aaagcagtta gaggtgacct gaatttcgtc aacagagcaa atcagcggtt gaaccccatg      1320
catcagcttt taaggcattt tcagaaagat gcgaaagtgc ttttcagaa ttggggaatt       1380 gaacacatcg acagtgtaat gggaatggtt ggagtattac agatatgac tccaagcaca       1440 gagatgtcaa tgagaggaat aagagtcagc aaaatgggtg tggatgaata ctccagtaca      1500
gagagggtgg tggttagcat tgatcggttt ttgagagttc gagaccaacg cgggaatgta      1560
ttattatctc ctgaagaggt tagtgaaaca cagggaactg agagactgac aataacttat      1620
tcatcgtcga tgatgtggga gattaacggt cctgagtcgg ttttggtcaa tacttatcaa      1680
tggatcatca gaaattggga agctgtcaaa attcaatggt ctcagaatcc tgcaatgttg      1740
tacaacaaaa tggaatttga accatttcaa tctttagtcc caaggccat tagaagccaa       1800 tacagtgggt ttgtcagaac tctattccaa caaatgagag acgtacttgg gacatttgac      1860
accacccaga taataaagct tctcccttt gcagccgctc caccaaagca aagcagaatg       1920
cagttctctt cactgactgt aaatgtgagg ggatcaggga tgagaatact tgtaaggggc      1980
aattctcctg tattcaacta caacaagacc actaaaagac taacaattct cggaaaagat      2040
gccggcactt taattgaaga cccagatgaa agcacatccg gagtggagtc cgctgtattg      2100
agagggtttc tcattatagg taaggaagac agaagatacg gccagcatt aagcatcaat       2160 gaactgagta accttgcaaa aggggaaaag gctaatgtgc taatcgggca aggagacgtg      2220
gtgttggtaa tgaaacgaaa cgggactct agcatactta ctgacagcca gacagcgacc       2280 aaagaattc ggatggccat caattaatgt tgaatagttt aaaaacgacc ttgtttctac       2340
t                                                                      2341
```

<210> SEQ ID NO 5
<211> LENGTH: 2341
<212> TYPE: DNA
<213> ORGANISM: Influenza virus

<400> SEQUENCE: 5

```
agcaaaagca ggcaaaccat ttgaatggat gtcaatccga ctctactgtt cctaaaggtt       60
ccagcgcaaa atgccataag caccacattc ccttatactg gagatcctcc atacagccat      120
ggaacaggaa cagggtacac catggacaca gtcaacagaa cacaccaata ttcagataag      180
gggaagtgga cgacaaatac agaaactggg caccccaac tcaacccaat tgatggacca      240
ctacctgagg ataatgagcc aagtggatat gcacaaacag actgtgtcct ggaggctatg      300
gccttccttg aagaatccca cccaggtatc tttgagaact catgccttga acaatggaa       360 gtcgttcaac aaacaagggt ggacaaacta acccaaggtc gccagactta tgattggaca      420
ttaaacagaa atcaaccggc agcaactgca ttagccaaca ccatagaagt ttttagatcg      480
aatggactaa cagctaatga atcaggaagg ctaatagatt cctcaaggaa tgtgatggaa      540
tcaatggata agaggaaat ggagataaca acacactttc aaagaaaaag gagagtaaga      600
gacaacatga ccaagaaaat ggtcacacaa gaacaatag gaagaaaaa acaaagagtg       660 aataagagag gctatctaat aagagctttg acattgaaca cgatgaccaa agatgcagag      720
agaggtaaat taaaagaag gctattgca acacccggga tgcaaattag agggttcgtg       780
tacttcgttg aaactttagc tagaagcat tgcgaaaagc ttgaacagtc tggacttccg      840 gttggggta atgaaaagaa ggccaaactg gcaaatgttg tgagaaaaat gatgactaat       900
```

```
tcacaagaca cagagctttc tttcacaatc actggggaca acactaagtg aatgaaaat    960
caaaaccctc gaatgttttt ggcgatgatt acatatatca caaaaaatca acctgagtgg   1020
ttcagaaaca tcctgagcat cgcaccaata atgttctcaa acaaaatggc aagactggga   1080
aaaggataca tgttcgagag taagagaatg aaactccgaa cacaaatacc cgcagaaatg   1140
ctagcaaaca ttgacctgaa gtatttcaat gaatcaacaa ggaagaaaat tgagaaaata   1200
aggcctcttc taatagatgg cacagcatca ttgagccctg gatgatgat gggcatgttc    1260
aacatgctaa gtacggtttt aggagtctcg atactgaatc ttgggcaaaa gaaatacacc   1320
aagacaacat actggtggga tgggctccaa tcctccgacg attttgccct catagtgaat   1380
gcaccaaatc atgagggaat acaagcagga gtggatagat tttacaggac ctgcaagtta   1440
gtgggaatca acatgagcaa aaagaagtcc tatataaata aaacagggac atttgaattc   1500
acaagctttt tttatcgata tggatttgtg ctaattttta gcatggagct gcccagtttt   1560
ggagtgtctg gaataaacga gtcagctgat atgagcattg gagtaacagt gataaagaac   1620
aacatgataa acaatgacct tggaccagca acagcccaga tggctctcca attgttcatc   1680
aaagactaca gatatacata taggtgccat agaggagaca cacaaattca gacgagaaga   1740
tcattcgagc taaagaagct gtgggatcaa acccaatcaa gggcaggact attggtatca   1800
gatgggggac caaacttata caatatccgg aatcttcaca tccctgaagt ctgcttaaag   1860
tgggagctaa tggatgagaa ttatcgggga agactttgta atcccctgaa tccctttgtc   1920
agccataaag aaattgagtc tgtaaacaat gctgtagtga tgccagccca tggtccggcc   1980
aaaagtatgg aatatgatgc cgttgcaact acacactcct ggattcccaa gaggaaccgc   2040
tctattctca acacaagcca aggggaatt cttgaggatg aacagatgta ccagaagtgc   2100
tgcaacttgt tcgagaaatt tttccctagt agttcatata ggagaccgat tggaatttct   2160
agcatggtgg aggccatggt gtctagggcc cggattgatg ccagaattga cttcgagtct   2220
ggacggatta agaaggaaga gttctctgag atcatgaaga tctgttccac cattgaagaa   2280
ctcagacggc aaaaataatg aatttagctt gtccttcatg aaaaaatgcc ttgtttctac   2340
t                                                                  2341

<210> SEQ ID NO 6
<211> LENGTH: 2233
<212> TYPE: DNA
<213> ORGANISM: Influenza virus

<400> SEQUENCE: 6
agcaaaagca ggtactgatt cgaaatggaa gattttgtgc gacaatgctt caacccgatg    60
attgtcgaac ttgcagaaaa agcaatgaaa gagtatgggg aggatctgaa aattgaaaca    120
aacaaatttg cagcaatatg cactcacttg gaggtatgtt tcatgtattc agattttcat    180
ttcatcaatg aacaaggcga atcaatagtg gtagaacttg atgatccaaa tgcactgtta    240
aagcacagat ttgaaataat cgaggggaga gacagaacaa tggcctggac agtagtaaac    300
agtatctgca acactactgg agctgaaaaa ccgaagtttc taccagattt gtatgattac    360
aaggagaaca gattcatcga aattggagtg acaaggagaa gtccacat atattacctt     420
gaaaaggcca ataagattaa atctgagaac acacacattc acattttctc attcactggg    480
gaggaaatgg ccacaaaggc agactacact ctcgacgagg aaagcagggc taggattaag    540
accaggctat ttaccataag acaagaaatg gccaacagag gcctctggga ttcctttcgt    600
```

-continued

| | |
|---|---|
| cagtccgaaa gaggcgaaga acaattgaa gaaaaatttg aaatctcagg aactatgcgt | 660 |
| aggcttgccg accaaagtct cccaccgaac ttctcctgcc ttgagaattt tagagcctat | 720 |
| gtggatggat tcgaaccgaa cggctgcatt gagggcaagc tttctcaaat gtccaaagaa | 780 |
| gtgaatgccc aaattgaacc ttttctgaag acaacaccaa gaccaatcaa acttccgaat | 840 |
| ggacctcctt gttatcagcg gtccaagttc ctcctgatgg atgctttaaa attgagcatt | 900 |
| gaagacccaa gtcacgaagg agaagggatc ccattatatg atgcgatcaa gtgcataaaa | 960 |
| acattctttg gatggaaaga accttatata gtcaaaccac acgaaaaggg aataaattca | 1020 |
| aattacctgc tgtcatggaa gcaagtattg tcagaattgc aggacattga aaatgaggag | 1080 |
| aagattccaa ggactaaaaa catgaagaaa acgagtcaac taaagtgggc tcttggtgag | 1140 |
| aacatggcac cagagaaagt agactttgaa actgcagag acataagcga tttgaagcaa | 1200 |
| tatgatagtg acgaacctga attaaggtca cttttcaagct ggatacagaa tgagttcaac | 1260 |
| aaggcctgcg agctaactga ttcaatctgg atagagctcg atgaaattgg agaggacgta | 1320 |
| gcccccaattg aatacattgc aagcatgagg aggaattatt tcacagcaga ggtgtcccat | 1380 |
| tgtagagcca ctgagtacat aatgaagggg gtatacatta atactgccct gctcaatgca | 1440 |
| tcctgtgcag caatgacga ttttcaacta attcccatga taagcaagtg cagaactaaa | 1500 |
| gagggaaggc gaaaaaccaa tttatatgga ttcatcataa agggaagatc tcatttaagg | 1560 |
| aatgacacag atgtggtaaa cttttgtgagc atggagtttt ctctcactga cccgagactt | 1620 |
| gagccacata atgggagaa atactgtgtc cttgagatag agatatgtt actaagaagt | 1680 |
| gccataggcc aaatttcaag gcctatgttc ttgtatgtga ggacaaacgg aacatcaaag | 1740 |
| gtcaaaatga atgggggaat ggagatgaga cgttgcctcc ttcagtcact ccagcagatc | 1800 |
| gagagcatga ttgaagccga gtcctcggtt aaagagaaag acatgaccaa agagtttttt | 1860 |
| gagaataaat cagaagcatg gcccattggg gagtccccca agggagtgga agaaggttcc | 1920 |
| attgggaaag tctgtaggac tctattggct aagtcagtgt tcaatagcct gtatgcatca | 1980 |
| ccacaattgg aaggattttc agcggagtca agaaaactgc tccttgttgt tcaggctctt | 2040 |
| agggacaacc tcgaacctgg gaccttgat cttggggggc tatatgaagc aattgaggag | 2100 |
| tgcctgatta atgatccctg ggttttgctc aatgcgtctt ggttcaactc cttcctgaca | 2160 |
| catgcattaa aatagttatg gcagtgctac tatttgttat ccgtactgtc caaaaaagta | 2220 |
| ccttgtttct act | 2233 |

<210> SEQ ID NO 7
<211> LENGTH: 1762
<212> TYPE: DNA
<213> ORGANISM: Influenza virus

<400> SEQUENCE: 7

| | |
|---|---|
| agcaaaagca ggggataatt ctattaacca tgaagactat cattgctttg agctacattc | 60 |
| tatgtctggt tttcgctcaa aagcttcccg gaaatgacaa cagcacggca acgctgtgcc | 120 |
| ttgggcacca tgcagtacca acggaacga tagtgaaaac aatcacgaat gaccaaattg | 180 |
| aagttactaa tgctactgag ctggttcaga gttcctcaac aggtgaaata tgcgacagtc | 240 |
| ctcatcagat ccttgatgga gaaaactgca cactaataga tgctctattg ggagaccctc | 300 |
| agtgtgatgg cttccaaaat aagaaatggg accttttcgt tgaacgcagc aaagcctaca | 360 |
| gcaactgtta cccttatgat gtgccggatt atgcctccct taggtcacta gttgcctcat | 420 |
| ccggcacact ggagtttaac aatgaaagct tcaattggac tggagtcact cagaatggaa | 480 |

```
caagctctgc ttgcaaaagg agatctaata aaagtttctt tagtagattg aattggttga    540
cccacttaaa atacaaatac ccagcattga acgtgactat gccaaacaat gaaaaatttg    600
acaaattgta catttggggg gttcaccacc cgggtacgga cagtgatcaa atcagcctat    660
atgctcaagc atcaggaaga atcacagtct ctaccaaaag aagccaacaa actgtaatcc    720
cgaatatcgg atctagaccc agggtaaggg atgtctccag cagaataagc atctattgga    780
caatagtaaa accgggagac atacttttga ttaacagcac agggaatcta attgctcctc    840
ggggttactt caaaatacga agtgggaaaa gctcaataat gagatcagat gcacccattg    900
gcaaatgcaa ttctgaatgc atcactccaa atggaagcat tcccaatgac aaaccatttc    960
aaaatgtaaa caggatcaca tatggggcct gtcccagata tgttaagcaa acactctga    1020 aattggcaac agggatgcga atgtaccag agaaacaaac tagaggcata tttggcgcaa    1080
tcgcgggttt catagaaaat ggttgggagg gaatggtgga cggttggtac ggtttcaggc    1140
atcaaaattc tgagggcaca ggacaagcag cagatctcaa aagcactcaa gcagcaatca    1200
accaaatcaa tgggaaactg aataggttaa tcgggaaaac aaacgagaaa ttccatcaga    1260
ttgaaaaaga attctcagaa gtagaaggga gaattcagga cctcgagaaa tatgttgagg    1320
acactaaaat agatctctgg tcatacaacg cggagcttct tgttgccctg agaaccaac    1380 atacaattga tctaactgac tcagaaatga acaaactgtt tgaaagaaca agaagcaac    1440 tgagggaaaa tgctgaggat atgggcaatg gttgtttcaa aatataccac aaatgtgaca    1500
atgcctgcat agagtcaatc agaaatgaa cttatgacca tgatgtatac agagatgaag    1560
cattaaacaa ccggttccag atcaaggtg ttgagctgaa gtcaggatac aaagattgga    1620
tcctatggat ttcctttgcc atatcatgtt ttttgctctg tgttgctttg ttggggttca    1680
tcatgtgggc ctgccaaaaa ggcaacatta ggtgcaacat ttgcatttga gtgcattaat    1740
taaaaacacc cttgtttcta ct                                            1762
```

<210> SEQ ID NO 8
<211> LENGTH: 1565
<212> TYPE: DNA
<213> ORGANISM: Influenza virus

<400> SEQUENCE: 8

```
agcaaaagca gggttaataa tcactcactg agtgacatca aaatcatggc gtcccaaggc     60
accaaacggt cttatgaaca gatggaaact gatgggggatc gccagaatgc aactgagatt    120
agggcatccg tcgggaagat gattgatgga attgggagat tctacatcca atgtgcact    180 gaacttaaac tcagtgatta tgaagggcgg ttgatccaga acagcttgac aatagagaaa    240
atggtgctct ctgcttttga tgaaagaagg aataaatatc tggaagaaca ccccagcgcg    300
gggaaagatc ctaagaaaac tgggggggccc atatacagga gagtagatgg aaaatggatg    360
agggaactcg tcctttatga caagaagaa ataaggcgaa tctggcgcca agccaacaat    420
ggtgaggatg cgacagctgg tctaactcac ataatgatct ggcattccaa tttgaatgat    480
gcaacatacc agaggacaag agctcttgtt cgaaccggaa tggatccag atgtgctct    540 ctgatgcagg gctcgactct ccctagaagg tccgagctg caggtgctgc agtcaaagga    600
atcgggacaa tggtgatgga gctgatcaga atggtcaaac ggggggatcaa cgatcgaaat    660 ttctggagag gtgagaatgg gcggaaaaca agaagtgctt atgagagaat gtgcaacatt    720
cttaaaggaa aatttcaaac agctgcacaa agagcaatgg tggatcaagt gagagaaagt    780
```

-continued

| | |
|---|---|
| cggaacccag gaaatgctga gatcgaagat ctcatatttt tggcaagatc tgcattgata | 840 |
| ttgagaggat cagttgctca caaatcttgc ctacctgcct gtgtgtatgg acctgcagta | 900 |
| tccagtgggt acgacttcga aaaagaggga tattccttgg tgggaataga ccctttcaaa | 960 |
| ctacttcaaa atagccaagt atacagccta atcagaccta acgagaatcc agcacacaag | 1020 |
| agtcagctgg tatggatggc atgccattct gctgcatttg aagatttaag attgttaagc | 1080 |
| ttcatcagag ggacaaaagt atctccacga gggaaacttt caactagagg agtacaaatt | 1140 |
| gcttcaaatg agaacatgga taatatggga tcgagcactc ttgaactgag aagcgggtac | 1200 |
| tgggccataa ggaccaggag tggaggaaac actaatcaac agagggcctc cgcaggccaa | 1260 |
| accagtgtgc aacctacgtt ttctgtacaa agaaacctcc catttgaaaa gtcaaccatc | 1320 |
| atggcagcat tcactggaaa tacggaggga agaacttcag acatgagggc agaaatcata | 1380 |
| agaatgatgg aaggtgcaaa accagaagaa gtgtcgttcc gggggagggg agttttcgag | 1440 |
| ctctcagacg agaaggcaac gaacccgatc gtgccctctt ttgatatgag taatgaagga | 1500 |
| tcttatttct tcggagacaa tgcagaagag tacgacaatt aaggaaaaat accttgtttc | 1560 |
| ctact | 1565 |

<210> SEQ ID NO 9
<211> LENGTH: 1467
<212> TYPE: DNA
<213> ORGANISM: Influenza virus

<400> SEQUENCE: 9

| | |
|---|---|
| agcaaaagca ggagtaaaga tgaatccaaa tcaaaagata ataacgattg gctctgtttc | 60 |
| cctcaccatt tccacaatat gcttcttcat gcaaattgcc atcctgataa ctactgtaac | 120 |
| attgcatttc aagcaatatg aattcaactc cccccccaaac aaccaagtga tgctgtgtga | 180 |
| accaacaata atagaaagaa acataacaga gatagtgtat ctgaccaaca ccaccataga | 240 |
| gaaggaaata tgccccaaac tagcagaata cagaaattgg tcaaagccgc aatgtaacat | 300 |
| tacaggattt gcaccttttt ctaaggacaa ttcgattcgg ctttccgctg gtggggacat | 360 |
| ctgggtgaca agagaacctt atgtgtcatg cgatcctgac aagtgttatc aatttgccct | 420 |
| tggacaggga acaacactaa acaacgtgca ttcaaatgac atagtacatg ataggacccc | 480 |
| ttatcggacc ctattgatga atgagttggg tgttccattt catctgggga ccaagcaagt | 540 |
| gtgcatagca tggtccagct caagttgtca cgatggaaaa gcatggctgc atgtttgtgt | 600 |
| aacgggggat gatgaaaatg caactgctag cttcatttac aatgggaggc ttcagadatag | 660 |
| tattgtttca tggtccaaaa aaatcctcag gacccaggag tcagaatgcg tttgtatcaa | 720 |
| tggaacttgt acagtagtaa tgactgatgg gagtgcttca ggaaaagctg atactaaaat | 780 |
| actattcatt gaggagggga aaattgttca tactagcaca ttatcaggaa gtgctcagca | 840 |
| tgtcgaggag tgctcctgtt atcctcgata tcctggtgtc agatgtgtct gcagagacaa | 900 |
| ctggaaaggc tccaataggc ccatcgtaga tataaacata aaggattata gcattgtttc | 960 |
| cagttatgtg tgctcaggac ttgttggaga cacacccaga aaaaacgaca gctccagcag | 1020 |
| tagccattgc ttggatccaa acaatgagga aggtggtcat ggagtgaaag ctgggcctt | 1080 |
| tgatgatgga aatgacgtgt ggatgggaag aacgatcagc gagaagttac gctcaggata | 1140 |
| tgaaaccttc aaagtcattg aaggctggtc caacccaac tccaaattgc agataaatag | 1200 |
| gcaagtcata gttgacagag gtaacaggtc cggttattct ggtattttct ctgttgaagg | 1260 |
| caaaagctgc atcaatcggt gcttttatgt ggagttgata agggaagaa acaggaaac | 1320 |

-continued

| | |
|---|---|
| tgaagtcttg tggacctcaa acagtattgt tgtgttttgt ggcacctcag gtacatatgg | 1380 |
| aacaggctca tggcctgatg gggcggacat caatctcatg cctatataag ctttcgcaat | 1440 |
| tttagaaaaa aactccttgt ttctact | 1467 |

<210> SEQ ID NO 10
<211> LENGTH: 1027
<212> TYPE: DNA
<213> ORGANISM: Influenza virus

<400> SEQUENCE: 10

| | |
|---|---|
| agcaaaagca ggtagatatt gaaagatgag ccttctaacc gaggtcgaaa cgtatgttct | 60 |
| ctctatcgtt ccatcaggcc ccctcaaagc cgagatcgcg cagagacttg aagatgtctt | 120 |
| tgctgggaaa acacagatc ttgaggctct catggaatgg ctaaagacaa gaccaattct | 180 |
| gtcacctctg actaagggga ttctggggtt tgtgttcacg ctcaccgtgc ccagtgagcg | 240 |
| aggactgcag cgtagacgct ttgtccaaaa tgccctcaat gggaatggag atccaaataa | 300 |
| catggacaaa gcagttaaac tgtataggaa acttaagagg gagataacgt tccatggggc | 360 |
| caaagaaata gctctcagtt attctgctgg tgcacttgcc agttgcatgg gcctcatata | 420 |
| caataggatg ggggctgtaa ccactgaagt ggcatttggc ctggtatgtg caacatgtga | 480 |
| gcagattgct gactcccagc acaggtctca taggcaaatg gtggcaacaa ccaatccatt | 540 |
| aataaggcat gagaacagaa tggttttggc cagcactaca gctaaggcta tggagcaaat | 600 |
| ggctggatca agtgagcagg cagcggaggc catggagatt gctagtcagg ccaggcaaat | 660 |
| ggtgcaggca atgagagcca ttgggactca tcctagctcc agtactggtc taagagatga | 720 |
| tcttcttgaa aatttgcaga cctatcagaa acgaatgggg gtgcagatgc aacgattcaa | 780 |
| gtgacccact tgttgttgcc gcgagtatca ttgggatctt gcacttgata ttgtggattc | 840 |
| ttgatcgtct ttttttcaaa tgcgtctatc gactcttcaa acacggcctt aaaagaggcc | 900 |
| cttctacgga aggagtacct gagtctatga gggaagagta tcgaaggaa cagcagaatg | 960 |
| ctgtggatgc tgacgacagt cattttgtca gcatagagtt ggagtaaaaa actaccttgt | 1020 |
| ttctact | 1027 |

<210> SEQ ID NO 11
<211> LENGTH: 890
<212> TYPE: DNA
<213> ORGANISM: Influenza virus

<400> SEQUENCE: 11

| | |
|---|---|
| agcaaaagca gggtgacaaa gacataatgg attccaacac tgtgtcaagt ttccaggtag | 60 |
| attgctttct ttggcatatc cggaaacaag ttgtagacca agaactgagt gatgccccat | 120 |
| tccttgatcg gcttcgccga gatcagaggt ccctaagggg aagaggcaat actctcggtc | 180 |
| tagacatcaa agcagccacc catgttggaa agcaaattgt agaaaagatt ctgaaagaag | 240 |
| aatctgatga ggcacttaaa atgaccatgg tctccacacc tgcttcgcga tacataactg | 300 |
| acatgactat tgaggaattg tcaagaaact ggttcatgct aatgcccaag cagaaagtgg | 360 |
| aaggacctct tgcatcaga atggaccagg caatcatgga gaaaaacatc atgttgaaag | 420 |
| cgaatttcag tgtgattttt gaccgactag agaccatagt attactaagg ctttcaccg | 480 |
| aagagggagc aattgttggc gaatctcac cattgccttc ttttccagga catactattg | 540 |
| aggatgtcaa aaatgcaatt gggtcctca tcggaggact tgaatggaat gataacacag | 600 |

-continued

| | |
|---|---|
| ttcgagtctc taaaaatcta cagagattcg cttggagaag cagtaatgag aatgggggac | 660 |
| ctccacttac tccaaaacag aaacggaaaa tggcgagaac agctaggtca aaagtttgaa | 720 |
| gagataagat ggctgattga agaagtgaga cacagactaa aaacaactga aaatagcttt | 780 |
| gaacaaataa cattcatgca agcattacaa ctgctgtttg aagtggaaca ggagataaga | 840 |
| actttctcat ttcagcttat ttaatgataa aaaacaccct tgtttctact | 890 |

<210> SEQ ID NO 12
<211> LENGTH: 1433
<212> TYPE: DNA
<213> ORGANISM: Influenza virus

<400> SEQUENCE: 12

| | |
|---|---|
| atgaatccaa atcaaaagat aataacgatt ggctctgttt ccctcaccat ttccacaata | 60 |
| tgcttcttca tgcaaattgc catcctgata actgctgtaa cattgcattt caagcaatat | 120 |
| gaattcaact cccccatgct gtgtgaacca acaataatag aaagaaacat aacagagata | 180 |
| gtgtatctga ccaacaccac catagagaag gaaatatgcc ccaaactagc agaatacaga | 240 |
| aattggtcaa agccgcaatg taacattaca ggatttgcac cttttttctaa ggacaattcg | 300 |
| attcggcttt ccgctggtgg ggacatctgg gtgacaagaa acctatgt gtcatgcgat | 360 |
| cctgacaagt gttatcaatt tgcccttgga cagggaacaa cactaaacaa cgtgcattca | 420 |
| aataacatag tacatgatag accccctat cggaccctat tgatgaatga gttgggtgtt | 480 |
| ccatttcatc tggggaccaa gcaagtgtgc atagcatggt ccagctcaag ttgtcacgat | 540 |
| ggaaaagcat ggctgcatgt ttgtgtaacg ggggatgatg aaaatgcaac tgctagcttc | 600 |
| atttacaatg ggaggcttgc agatagtatt gtttcatggt ccaaaaaaat cctcaggacc | 660 |
| caggagtcag aatgcgtttg tatcaatgga acttgtacag tagtaatgac tgatgggagt | 720 |
| gcttcaggaa aagctgatac taaaatacta ttcattgagg aggggaaaat tgttcatact | 780 |
| agcacattat caggaagtgc tcagcatgtc gaggagtgct cctgttatcc tcgatatcct | 840 |
| ggtgtcagat gtgtctgcag agacaactgg aaaggctcca ataggcccat cgtagatata | 900 |
| aacataaagg attatagcat tgtttccagt tatgtgtgct caggacttgt ggagacaca | 960 |
| cccagaaaag acgacagctc cagcagtagc cattgcttgg atccaaacaa tgaggaaggt | 1020 |
| ggtcaaggag tgaaaggctg gccctttgat gatggaaatg acgtgtggat gggaagaacg | 1080 |
| atcagcgaga gttacgctc aggatatgaa accttcaaag tcattgaagg ctggtccaac | 1140 |
| cctaactcca aattgcagat aaataggcaa gtcatagttg acagaggtaa caggtccggt | 1200 |
| tattctggta ttttctctgt tgaaggcaaa agctgcatca atcggtgctt ttatgtggag | 1260 |
| ttgataaggg gaagaaaaca ggaaactgaa gtcttgtgga cctcaaacag tattgttgtg | 1320 |
| ttttgtggca cctcaggtac atatggaaca ggctcatggc ctgatggggc ggacatcaat | 1380 |
| ctcatgccta taagctttt cgcaattta gaaaaaaact ccttgttctt act | 1433 |

<210> SEQ ID NO 13
<211> LENGTH: 1733
<212> TYPE: DNA
<213> ORGANISM: Influenza virus

<400> SEQUENCE: 13

| | |
|---|---|
| atgaagacta tcattgcttt gagctacatt ctatgtctgg ttttcgctca aaagcttccc | 60 |
| ggaaatgaca acagcacggc aacgctgtgc cttgggcacc atgcagtacc aaacggaacg | 120 |
| atagtgaaaa caatcacgaa tgaccaaatt gaagttacta atgctactga gctggttcag | 180 |

| | |
|---|---|
| agttcctcaa caggtggaat atgcgacagt cctcatcaga tccttgatgg agaaaactgc | 240 |
| acactaatag atgctctatt gggagaccct cagtgtgatg gcttccaaaa taagaaatgg | 300 |
| gaccttttg ttgaacgcag caaagcctac agcaactgtt acccttatga tgtgccggat | 360 |
| tatgcctccc ttaggtcact agttgcctca tccggcacac tggagtttaa caatgaaagc | 420 |
| ttcaattgga ctggagtcac tcagaatgga acaagctctg cttgcaaaag agatctaat | 480 |
| aaaagtttct ttagtagatt gaattggttg acccacttaa aatacaaata cccagcattg | 540 |
| aacgtgacta tgccaaacaa tgaaaaattt gacaaattgt acatttgggg ggttcaccac | 600 |
| ccgggtacgg acagtgatca aatcagccta tatgctcaag catcaggaag aatcacagtc | 660 |
| tctaccaaaa gaagccaaca aactgtaatc ccgaatatcg atctagacc cagggtaagg | 720 |
| gatgtctcca gcagaataag catctattgg acaatagtaa accgggaga catacttttg | 780 |
| attaacagca cagggaatct aattgctcct cggggttact tcaaaatacg aagtgggaaa | 840 |
| agctcaataa tgagatcaga tgcacccatt ggcaaatgca attctgaatg catcactcca | 900 |
| aatggaagca ttcccaatga caaaccattt caaaatgtaa acaggatcac atatgggggc | 960 |
| tgtcccagat atgttaagca aaacactctg aaattggcaa cagggatgcg aaatgtacca | 1020 |
| gagaaacaaa ctagaggcat atttggcgca atcgcgggtt tcatagaaaa tggttgggag | 1080 |
| ggaatggtgg acgttggta cggtttcagg catcaaaatt ctgagggcac aggacaagca | 1140 |
| gcagatctca aaagcactca agcagcaatc aaccaaatca tgggaaact gaataggtta | 1200 |
| atcgggaaaa caacgagaa attccatcag attgaaaag aattctcaga gtgaagggg | 1260 |
| agaattcagg acctcgagaa atatgttgag gacactaaaa tagatctctg gtcatacaac | 1320 |
| gcggagcttc ttgttgccct ggagaaccaa catacaattg atctaactga ctcagaaatg | 1380 |
| aacaaactgt ttgaaagaac aaagaagcaa ctgagggaaa atgctgagga tatgggcaat | 1440 |
| ggttgtttca aaatatacca caatgtgac aatgcctgca tagagtcaat cagaaatgga | 1500 |
| acttatgacc atgatgtata cagagatgaa gcattaaaca accggttcca gatcaaaggt | 1560 |
| gttgagctga gtcaggata caaagattgg atcctatgga tttcctttgc catatcatgt | 1620 |
| ttttgctct gtgttgcttt gttggggttc atcatgtggg cctgccaaaa aggcaacatt | 1680 |
| aggtgcaaca tttgcatttg agtgcattaa ttaaaaacac ccttgtttct act | 1733 |

<210> SEQ ID NO 14
<211> LENGTH: 1002
<212> TYPE: DNA
<213> ORGANISM: Influenza virus

<400> SEQUENCE: 14

| | |
|---|---|
| atgagccttc taaccgaggt cgaaacgtat gttctctcta tcgttccatc aggccccctc | 60 |
| aaagcccaga tcgcgcagag acttgaagat gtctttgctg gaaaaacac agatcttgag | 120 |
| gctctcatgg aatggctaaa gacaagacca attctgtcac ctctgactaa ggggattctg | 180 |
| gggtttgtgt tcacgctcac cgtgcccagt gagcgaggac tgcagcgtag acgctttgtc | 240 |
| caaaatgccc tcaatgggaa tggagatcca aataacatgg acaaagcagt taaactgtat | 300 |
| aggaaactta gagggagat aacgttccat ggggccaaag aaatagctct cagttattct | 360 |
| gctggtgcac ttgccagttg catgggcctc atatacaata ggatgggggc tgtaaccact | 420 |
| gaagtggcat ttgcctggt atgtgcaaca tgtgagcaga ttgctgactc ccagcacagg | 480 |
| tctcataggc aaatggtggc aacaaccaat ccattaataa ggcatgagaa cagaatggtt | 540 |

| | |
|---|---|
| ttggccagca ctacagctaa ggctatggag caaatggctg atcaagtga gcaggcagcg | 600 |
| gaggccatgg agattgctag tcaggccagg caaatggtgc aggcaatgag agccattggg | 660 |
| actcatccta gctccagtac tggtctaaga gatgatcttc ttgaaaattt gcagacctat | 720 |
| cagaaacgaa tggggtgca gatgcaacga ttcaagtgac ccacttgttg ttgccgcgag | 780 |
| tatcattggg atcttgcact tgatattgtg gattcttgat cgtctttttt tcaaatgcgt | 840 |
| ctatcgactc ttcaaacacg gccttaaaag aggcccttct acggaaggag tacctgagtc | 900 |
| tatgagggaa gagtatcgaa aggaacagca gaatgctgtg gatgctgacg acagtcattt | 960 |
| tgtcagcata gagttggagt aaaaaactac cttgtttcta ct | 1002 |

```
<210> SEQ ID NO 15
<211> LENGTH: 1520
<212> TYPE: DNA
<213> ORGANISM: Influenza virus

<400> SEQUENCE: 15
```

| | |
|---|---|
| atggcgtccc aaggcaccaa acggtcttat gaacagatgg aaactgatgg ggatcgccag | 60 |
| aatgcaactg agattagggc atccgtcggg aagatgattg atggaattgg gagattctac | 120 |
| atccaaatgt gcactgaact aaactcagt gattatgaag gcggttgat ccagaacagc | 180 |
| ttgacaatag agaaaatggt gctctctgct tttgatgaaa aaggaataa atatctggaa | 240 |
| gaacacccca gcgcgggga agatcctaag aaaactgggg ggcccatata caggagagta | 300 |
| aatggaaaat ggatgaggga actcgtcctt tatgacaaag agaaataag gcgaatctgg | 360 |
| cgccaagcca acaatggtga ggatgcgaca gctggtctaa ctcacataat gatctggcat | 420 |
| tccaatttga atgatgcaac ataccagagg acaagagctc ttgttcgaac cggaatggat | 480 |
| cccagaatgt gctctctgat gcagggctcg actctcccta aaggtccgg agctgcaggt | 540 |
| gctgcagtca aggaatcgg acaatggtg atggagctga tcagaatggt caaacggggg | 600 |
| atcaacgatc gaaatttctg gagaggtgag atgggcgga aaacaagaag tgcttatgag | 660 |
| agaatgtgca acattcttaa aggaaaattt caaacagctg cacaaagagc aatggtggat | 720 |
| caagtgagag aaagtcggaa cccaggaaat gctgagatcg aagatctcat attttttggca | 780 |
| agatctgcat tgatattgag aggatcagtt gctcacaaat cttgcctacc tgcctgtgtg | 840 |
| tatgacctg cagtatccag tgggtacgac ttcgaaaaag agggatattc cttggtggga | 900 |
| atagaccctt tcaaactact tcaaaatagc caagtataca gcctaatcag acctaacgag | 960 |
| aatccagcac acaagagtca gctggtatgg atggcatgcc attctgctgc atttgaagat | 1020 |
| ttaagattgt taagcttcat cagagggaca aaagtatctc cacgagggaa actttcaact | 1080 |
| agaggagtac aaattgcttc aaatgagaac atggataata tgggatcgag cactcttgaa | 1140 |
| ctgagaagcg ggtactgggc cataaggacc aggagtggag gaaacactaa tcaacagagg | 1200 |
| gcctccgcag gccaaaccag tgtgcaacct acgttttctg tacaaagaaa cctcccattt | 1260 |
| gaaaagtcaa ccatcatggc agcattcact ggaaatacgg agggaagaac ttcagacatg | 1320 |
| agggcagaaa tcataagaat gatggaaggt gcaaaaccag aagaagtgtc gttccggggg | 1380 |
| aggggagttt tcgagctctc agacgagaag gcaacgaacc cgatcgtgcc ctcttttgat | 1440 |
| atgagtaatg aaggatctta tttcttcgga gacaatgcag aagagtacga caattaagga | 1500 |
| aaaatacct tgtttctact | 1520 |

```
<210> SEQ ID NO 16
<211> LENGTH: 864
```

<212> TYPE: DNA
<213> ORGANISM: Influenza virus

<400> SEQUENCE: 16
atggattcca acactgtgtc aagtttccag gtagattgct ttctttggca tatccggaaa 60
caagttgtag accaagaact gagtgatgcc ccattccttg atcggcttcg ccgagatcag 120
aggtccctaa ggggaagagg caatactctc ggtctagaca tcaaagcagc cacccatgtt 180
ggaaagcaaa ttgtagaaaa gattctgaaa gaagaatctg atgaggcact taaaatgacc 240
atggtctcca cacctgcttc gcgatacata actgacatga ctattgagga attgtcaaga 300
aactggttca tgctaatgcc caagcagaaa gtggaaggac ctctttgcat cagaatggac 360
caggcaatca tggagaaaaa catcatgttg aaagcgaatt tcagtgtgat ttttgaccga 420
ctagagacca tagtattact aagggctttc accgaagagg gagcaattgt tggcgaaatc 480
tcaccattgc cttcttttcc aggacatact attgaggatg tcaaaaatgc aattggggtc 540
ctcatcggag gacttgaatg gaatgataac acagttcgag tctctaaaaa tctacagaga 600
ttcgcttgga gaagcagtaa tgagaatggg ggacctccac ttactccaaa acagaaacgg 660
aaaatggcga gaacagctag gtcaaaagtt tgaagagata agatggctga ttgaagaagt 720
gagacacaga ctaaaaacaa ctgaaaatag ctttgaacaa ataacattca tgcaagcatt 780
acaactgctg tttgaagtgg aacaggagat aagaactttc tcatttcagc ttatttaatg 840
ataaaaaaca cccttgtttc tact 864

<210> SEQ ID NO 17
<211> LENGTH: 2317
<212> TYPE: DNA
<213> ORGANISM: Influenza virus

<400> SEQUENCE: 17
atggatgtca atccgactct actgttccta aaggttccag cgcaaaatgc cataagcacc 60
acattccctt atactggaga tcctccatac agccatggaa caggaacagg gtacaccatg 120
gacacagtca acagaacaca ccaatattca gataagggga agtggacgac aaatacagaa 180
actggggcac cccaactcaa cccaattgat ggaccactac ctgaggataa tgagccaagt 240
ggatatgcac aaacagactg tgtcctggag gctatggcct tccttgaaga atcccaccca 300
ggtatctttg agaactcatg ccttgaaaca atggaagtcg ttcaacaaac aagggtggac 360
aaactaaccc aaggtcgcca gacttatgat tggacattaa acagaaatca accggcagca 420
actgcattag ccaacaccat agaagttttt agatcgaatg gactaacagc taatgaatca 480
ggaaggctaa tagatttcct caaggatgtg atggaatcaa tggataaaga ggaaatggag 540
ataacaacac actttcaaag aaaaaggaga gtaagagaca acatgaccaa gaaaatggtc 600
acacaaagaa caatagggaa gaaaaaacaa agagtaaata agagaggcta tctaataaga 660
gctttgacat tgaacacgat gaccaaagat gcagagagag gtaaattaaa aagaagggct 720
attgcaacac ccgggatgca aattagaggg ttcgtgtact tcgttgaaac tttagctaga 780
agcatttgcg aaaagcttga acagtctgga cttccggttg gggtaatga aaagaaggcc 840
aaactggcaa atgttgtgag aaaaatgatg actaattcac aagacacaga gctttctttc 900
acaatcactg ggacaacac taagtggaat gaaaatcaaa accctcgaat gtttttggcg 960
atgattacat atatcacaaa aaatcaacct gagtggttca gaaacatcct gagcatcgca 1020
ccaataatgt tctcaaacaa aatggcaaga ctgggaaaag gatacatgtt cgagagtaag 1080

| | |
|---|---|
| agaatgaaac tccgaacaca aatacccgca gaaatgctag caaacattga cctgaagtat | 1140 |
| ttcaatgaat caacaaggaa gaaaattgag aaaataaggc ctcttctaat agatggcaca | 1200 |
| gcatcattga gccctgggat gatgatgggc atgttcaaca tgctaagtac ggttttagga | 1260 |
| gtctcgatac tgaatcttgg gcaaaagaaa tacaccaaga caacatactg gtgggatggg | 1320 |
| ctccaatcct ccgacgattt tgccctcata gtgaatgcac caaatcatga gggaatacaa | 1380 |
| gcaggagtgg atagatttta caggacctgc aagttagtgg gaatcaacat gagcaaaaag | 1440 |
| aagtcctata taaataaaac agggacattt gaattcacaa gcttttttta tcgatatgga | 1500 |
| tttgtggcta attttagcat ggagctgccc agttttggag tgtctggaat aaacgagtca | 1560 |
| gctgatatga gcattggagt aacagtgata agaacaaca tgataaacaa tgaccttgga | 1620 |
| ccagcaacag cccagatggc tctccaattg ttcatcaaag actacagata tacatatagg | 1680 |
| tgccatagag gagacacaca aattcagacg agaagatcat tcgagctaaa gaagctgtgg | 1740 |
| gatcaaaccc aatcaagggc aggactattg gtatcagatg ggggaccaaa cttatacaat | 1800 |
| atccggaatc ttcacatccc tgaagtctgc ttaaagtggg agctaatgga tgagaattat | 1860 |
| cggggaagac tttgtaatcc cctgaatccc tttgtcagcc ataaagaaat tgagtctgta | 1920 |
| aacaatgctg tagtgatgcc agcccatggt ccggccaaaa gtatggaata tgatgccgtt | 1980 |
| gcaactacac actcctggat tcccaagagg aaccgctcta ttctcaacac aagccaaagg | 2040 |
| ggaattcttg aggatgaaca gatgtaccag aagtgctgca cttgttcga gaattttttc | 2100 |
| cctagtagtt catataggag accgattgga atttctagca tggtggaggc catggtgtct | 2160 |
| agggcccgga ttgatgccag aattgacttc gagtctggac ggattaagaa ggaagagttc | 2220 |
| tctgagatca tgaagatctg ttccaccatt gaagaactca gacggcaaaa ataatgaatt | 2280 |
| tagcttgtcc ttcatgaaaa aatgccttgt ttctact | 2317 |

<210> SEQ ID NO 18
<211> LENGTH: 2209
<212> TYPE: DNA
<213> ORGANISM: Influenza virus

<400> SEQUENCE: 18

| | |
|---|---|
| atggaagatt ttgtgcgaca atgcttcaac ccgatgattg tcgaacttgc agaaaaagca | 60 |
| atgaaagagt atggggagga tctgaaaatt gaaacaaaca atttgcagc aatatgcact | 120 |
| cacttggagg tatgtttcat gtattcagat tttcatttca tcaatgaaca aggcgaatca | 180 |
| atagtggtag aacttgatga tccaaatgca ctgttaaagc acagatttga ataatcgag | 240 |
| gggagagaca gaacaatggc ctggacagta gtaaacagta tctgcaacac tactggagct | 300 |
| gaaaaaccga gtttctacc agatttgtat gattacaagg agaacagatt catcgaaatt | 360 |
| ggagtgacaa ggagagaagt ccacatatat taccttgaaa aggccaataa gattaaatct | 420 |
| gagaacacac acattcacat tttctcattc actggggagg aaatggccac aaaggcagac | 480 |
| tacactctcg acgaggaaag cagggctagg attaagacca ggctatttac cataagacaa | 540 |
| gaaatggcca acagaggcct ctgggattcc tttcgtcagt ccgaaagagg cgaagaaaca | 600 |
| attgaagaaa aatttgaaat ctcaggaact atgcgtagc ttgccgacca agtctccca | 660 |
| ccgaacttct cctgccttga aatttttaga gcctatgtgg atggattcga accgaacggc | 720 |
| tgcattgagg gcaagctttc tcaaatgtcc aaagaagtga atgcccaaat tgaaccttt | 780 |
| ctgaagacaa caccaagacc aatcaaactt ccgaatggac ctccttgtta tcagcggtcc | 840 |
| aagttcctcc tgatggatgc tttaaaattg agcattgaag acccaagtca cgaaggagaa | 900 |

-continued

```
gggatcccat tatatgatgc gatcaagtgc ataaaaacat tctttggatg gaaagaacct      960
tatatagtca aaccacacga aaagggaata aattcaaatt acctgctgtc atggaagcaa     1020
gtattgtcag aattgcagga cattgaaaat gaggagaaga ttccaaggac taaaaacatg     1080
aagaaaacga gtcaactaaa gtgggctctt ggtgagaaca tggcaccaga gaaagtagac     1140
tttgaaaact gcagagacat aagcgatttg aagcaatatg atagtgacga acctgaatta     1200
aggtcacttt caagctggat acagaatgag ttcaacaagg cctgcgagct aactgattca     1260
atctggatag agctcgatga aattggagag gacgtagccc caattgaata cattgcaagc     1320
atgaggagga attatttcac agcagaggtg tcccattgta gagccactga gtacataatg     1380
aaggggtat acattaatac tgccctgctc aatgcatcct gtgcagcaat ggacgatttt     1440
caactaattc ccatgataag caagtgcaga actaaagagg gaaggcgaaa aaccaattta     1500
tatggattca tcataaaggg aagatctcat ttaaggaatg acacagatgt ggtaaacttt     1560
gtgagcatgg agttttctct cactgacccg agacttgagc cacataaatg ggagaaatac     1620
tgtgtccttg agataggaga tatgttacta agaagtgcca taggccaaat ttcaaggcct     1680
atgttcttgt atgtgaggac aaacggaaca tcaaaggtca aaatgaaatg gggaatggag     1740
atgagacgtt gcctccttca gtcactccag cagatcgaga gcatgattga agccgagtcc     1800
tcggttaaag agaaagacat gaccaaagag ttttttgaga ataaatcaga agcatggccc     1860
attggggagt cccccaaggg agtggaagaa ggttccattg ggaaagtctg taggactcta     1920
ttggctaagt cagtgttcaa tagcctgtat gcatcaccac aattggaagg attttcagcg     1980
gagtcaagaa aactgctcct tgttgttcag gctcttaggg acaacctcga acctgggacc     2040
tttgatcttg ggggctata tgaagcaatt gaggagtgcc tgattaatga tccctgggtt     2100
ttgctcaatg cgtcttggtt caactccttc ctgacacatg cattaaaata gttatggcag     2160
tgctactatt tgttatccgt actgtccaaa aaagtacctt gtttctact                2209
```

<210> SEQ ID NO 19
<211> LENGTH: 2314
<212> TYPE: DNA
<213> ORGANISM: Influenza virus

<400> SEQUENCE: 19

```
atggaaagaa taaagaaact acggaacctg atgtcgcagt ctcgcactcg cgagatactg      60
acaaaaacca cagtggacca tatggccata attaagaagt acacatcggg gagacaggaa     120
aagaacccgt cacttaggat gaaatggatg atggcaatga aatacccaat cactgctgac     180
aaaaggataa cagaaatggt tccggagaga aatgaacaag gacaaactct atggagtaaa     240
atgagtgatc tggatcaga tcgagtgatg gtatcacctt ggctgtgac atggtggaat     300
agaaatggac ccgtgacaag tacggtccat acccaaaaag tatacaagac ttattttgac     360
aaagtcgaaa ggtaaaaaca tggaaccttt ggccctgttc attttagaaa tcaagtcaag     420
atacgccgaa gagtagacat aaaccctggt catgcggacc tcagtgccaa ggaggcacaa     480
gatgtaatta tggaagttgt ttttcccaat gaagtgggag ccaggatact aacatcagaa     540
tcgcaattaa caataactaa agagaaaaaa gaagaactcc gagattgcaa aatttctccc     600
ttgatggttg catacatgtt agagagagaa cttgtccgaa aaacaagatt tctcccagtt     660
gctggcggaa caagcagtat atacattgaa gttttacatt tgactcaagg acgtgttgg     720
gaacaaatgt acactccagg tggagaagtg aggaatgacg atgttgacca aagcctaatt     780
```

| | |
|---|---:|
| attgcagcca ggaacatagt aagaagagcc gcagtatcag cagatccact agcatcttta | 840 |
| ttggagatgt gccacagcac acaaattggc gggacaagga tggtggacat tcttagacag | 900 |
| aacccgactg aagaacaagc tgtggatata tgcaaggctg caatgggatt gagaatcagc | 960 |
| tcatccttca gctttggtgg gtttacattt aaaagaacaa gcgggtcatc agtcaaaaaa | 1020 |
| gaggaagaag tgcttacagg caatctccaa acattgaaga taagagtaca tgagggtat | 1080 |
| gaggagttca atggtggg gaaaagagca acagctatac tcagaaaagc aaccagaaga | 1140 |
| ttggttcagc tcatagtgag tggaagagac gaacagtcaa tagccgaagc aataattgtg | 1200 |
| gccatggtgt tttcacaaga ggattgcatg ataaaagcag ttagaggtga cctgaatttc | 1260 |
| gtcaacagag caaatcagcg gttgaacccc atgcatcagc ttttaaggca ttttcagaaa | 1320 |
| gatgcgaaag tgcttttca gaattgggga attgagcaca tcgacagtgt aatgggaatg | 1380 |
| gttggagtat accagatat gactccaagc acagagatgt caatgagagg aataagagtc | 1440 |
| agcaaaatgg gtgtggatga atactccagt acagagaggg tggtggttag cattgatcgg | 1500 |
| tttttgagag ttcgagacca acgcgggaat gtattattat ctcctgaaga ggttagtgaa | 1560 |
| acacagggaa ctgagagact gacaataact tattcatcgt cgatgatgtg ggagattaac | 1620 |
| ggtcctgagt cggttttggt caatacttat caatggatca tcagaaattg ggaagctgtc | 1680 |
| aaaattcaat ggtctcagaa tcctgcaatg ttgtacaaca aaatggaatt tgaaccattt | 1740 |
| caatctttag tccccaaggc cattagaagc caatacagtg gtttgtcag aactctattc | 1800 |
| caacaaatga gagacgtact gggacatttt gacaccaccc agataataaa gcttctccct | 1860 |
| tttgcagccg ctccaccaaa gcaaagcaga atgcagttct cttcactgac tgtaaatgtg | 1920 |
| aggggatcag ggatgagaat acttgtaagg gcaattctc ctgtattcaa ctacaacaag | 1980 |
| accactaaaa gactaacaat tctcggaaaa gatgccggca cttaattga agacccagat | 2040 |
| gaaagcacat ccggagtgga gtccgctgta ttgagagggt ttctcattat aggtaaggaa | 2100 |
| gacagaagat acgggccagc attaagcatc aatgaactga gtaaccttgc aaaaggggaa | 2160 |
| aaggctaatg tgctaatcgg gcaaggagac gtggtgttgg taatgaaacg aaaacgggac | 2220 |
| tctagcatac ttactgacag ccagacagcg accaaaagaa ttcggatggc catcaattaa | 2280 |
| tgttgaatag tttaaaaacg accttgtttc tact | 2314 |

<210> SEQ ID NO 20
<211> LENGTH: 2314
<212> TYPE: DNA
<213> ORGANISM: Influenza virus

<400> SEQUENCE: 20

| | |
|---|---:|
| atggaaagaa taaagaaact acggaacctg atgtcgcagt ctcgcactcg cgagatactg | 60 |
| acaaaaacca cagtggacca tatggccata attaagaagt acacatcggg gagacaggaa | 120 |
| aagaacccgt cacttaggat gaaatggatg atggcaatga aatacccaat cactgctgac | 180 |
| aaaaggataa cagaaatggt tccggagaga atgaacaag acaaactct atggagtaaa | 240 |
| atgagtgatg ctggatcaga tcgagtgatg gtatcacctt ggctgtgac atggtggaat | 300 |
| agaaatggac ccgtgacaag tacggtccat tacccaaaag tatacaagac ttattttgac | 360 |
| aaagtcgaaa ggttaaaaca tggaaccttt ggccctgttc attttagaaa tcaagtcaag | 420 |
| atacgccgaa gagtagacat aaaccctggt catgcggacc tcagtgccaa ggaggcacaa | 480 |
| gatgtaatta tggaagttgt ttttcccaat gaagtgggag ccaggatact aacatcagaa | 540 |
| tcgcaattaa caataactaa agagaaaaaa gaagaactcc gagattgcaa aatttctccc | 600 |

```
ttgatggttg catacatgtt agagagagaa cttgtccgaa aaacaagatt cctcccagtt    660
gctggcggaa caagcagtat atacattgaa gttttacatt tgactcaagg gacgtgttgg    720
gaacaaatgt acactccagg tggagaagtg aggaatgacg atgttgacca aagcctaatt    780
attgcagcca ggaacatagt aagaagagcc gcagtatcag cagatccact agcatttta    840 ttggagatgt gccacagcac acaaattggc gggacaagga tggtggacat tcttagacag    900
aacccgactg aagaacaagc tgtggatata tgcaaggctg caatgggatt gagaatcagc    960
tcatccttca gctttggtgg gtttacattt aaaagaacaa gcgggtcatc agtcaaaaaa   1020
gaggaagaac tgcttacagg caatctccaa acattgaaga taagagtaca tgagggtat    1080 gaggagttca caatggtggg gaaaagagca acagctatac tcagaaaagc aaccagaaga   1140
ttggttcagc tcatagtgag tggaagagac gaacagtcaa tagccgaagc aataattgtg   1200
gccatggtgt tttcacaaga ggattgcatg ataaaagcag ttagaggtga cctgaatttc   1260
gtcaacagag caaatcagcg gttgaacccc atgcatcagc ttttaaggca ttttcagaaa   1320
gatgcgaaag tgcttttttca gaattgggga attgagcaca tcgacagtgt aatgggaatg   1380
gttggagtat taccagatat gactccaagc acagagatgt caatgagagg aataagagtc   1440
agcaaaatgg gtgtggatga atactccagt acagagaggg tggtggttag cattgatcgg   1500
tttttgagag ttcagaccca acgcgggaat gtattattat ctcctgaaga ggttagtgaa   1560
acacagggaa ctgagagact gacaataact tattcatcgt cgatgatgtg ggagattaac   1620
ggtcctgagt cggttttggt caatacttat caatggatca tcagaaattg ggaagctgtc   1680
aaaattcaat ggtctcagaa tcctgcaatg ttgtacaaca aaatggaatt tgaaccattt   1740
caatctttag tccccaaggc cattagaagc aatacagtg ggtttgtcag aactctattc   1800
caacaaatga gagacgtact gggacatttt gacaccaccc agataataaa gcttctccct   1860
tttgcagccg ctccaccaaa gcaaagcaga atgcagttct cttcactgac tgtaaatgtg   1920
aggggatcag ggatgagaat acttgtaagg gcaattctc ctgtattcaa ctacaacaag   1980
accactaaaa gactaacaat tctcggaaaa gatgccggca ctttaattga agacccagat   2040
gaaagcacat ccggagtgga gtccgctgta ttgagagggt ttctcattat aggtaaggaa   2100
gacagaagat acgggccagc attaagcatc aatgaactga gtaaccttgc aaaagggaa    2160 aaggctaatg tgctaatcgg gcaaggagac gtggtgttgg taatgaaacg aaaacgggac   2220
tctagcatac ttactgacag ccagacagcg accaaaagaa ttcggatggc catcaattaa   2280
tgttgaatag tttaaaaacg accttgtttc tact                                2314
```

<210> SEQ ID NO 21
<211> LENGTH: 2314
<212> TYPE: DNA
<213> ORGANISM: Influenza virus

<400> SEQUENCE: 21

```
atggaaagaa taaagaaact acggaacctg atgtcgcagt ctcgcactcg cgagatactg     60
acaaaaacca cagtggacca tatggccata attaagaagt acacatcggg gagacaggaa    120
aagaacccgt cacttaggat gaatggatg atggcaatga ataccaat cactgctgac       180 aaaaggataa cagaaatggt tccggagaga atgaacaag acaaactct atggagtaaa      240 atgagtgatg ctggatcaga tcgagtgatg gtatcacctt tggctgtgac atggtggaat    300
agaaatggac ccgtgacaag tacggtccat tacccaaaag tatacaagac ttattttgac    360
```

| | |
|---|---|
| aaagtcgaaa ggttaaaaca tggaacccttt ggccctgttc attttagaaa tcaagtcaag | 420 |
| atacgccgaa gagtagacat aaaccctggt catgcggacc tcagtgccaa ggaggcacaa | 480 |
| gatgtaatta tggaagttgt ttttcccaat gaagtgggag ccaggatact aacatcagaa | 540 |
| tcgcaattaa caataactaa agagaaaaaa gaagaactcc gagattgcaa aatttctccc | 600 |
| ttgatggttg catacatgtt agagagagaa cttgtccgaa aacaagatt cctcccagtt | 660 |
| gctggcggaa caagcagtat atacattgaa gttttacatt tgactcaagg gacgtgttgg | 720 |
| gaacaaatgt acactccagg tggagaagtg aggaatgacg atgttgacca aagcctaatt | 780 |
| attgcagcca ggaacatagt aagaagagcc gcagtatcag cagatccact agcatcttta | 840 |
| ttggagatgt gccacagcac acaaattggc gggacaagga tggtggacat tcttagacag | 900 |
| aacccgactg aagaacaagc tgtggatata tgcaaggctg caatgggatt gagaatcagc | 960 |
| tcatccttca gctttggtgg gtttacattt aaaagaacaa gcgggtcatc agtcaaaaaa | 1020 |
| gaggaagaac tgcttacagg caatctccaa acattgaaga taagagtaca taagggtat | 1080 |
| gaggagttca caatggtggg gaaaagagca acagctatac tcagaaaagc aaccagaaga | 1140 |
| ttggttcagc tcatagtgag tggaagagac gaacagtcaa tagccgaagc aataattgtg | 1200 |
| gccatggtgt tttcacaaga ggattgcatg ataaaagcgt tagaggtgaa cctgaatttc | 1260 |
| gtcaacagag caaatcagcg gttgaacccc atgcatcagc ttttaaggca ttttcagaaa | 1320 |
| gatgcgaaag tgctttttca gaattgggga attgagcaca tcgacagtgt aatgggaatg | 1380 |
| gttggagtat taccagatat gactccaagc acagagatgt caatgagagg aataagagtc | 1440 |
| agcaaaatgg gtgtggatga atactccagt acagagaggt ggtggttag cattgatcgg | 1500 |
| tttttgagag ttcgagacca acgcgggaat gtattattat ctcctgaaga ggttagtgaa | 1560 |
| acacagggaa ctgagagact gacaataact tattcatcgt cgatgatgtg ggagattaac | 1620 |
| ggtcctgagt cggttttggt caatacttat caatggatca tcagaaattg ggaagctgtc | 1680 |
| aaaattcaat ggtctcagaa tcctgcaatg ttgtacaaca aaatggaatt tgaaccattt | 1740 |
| caatctttag tccccaaggc cattagaagc caatacagtg ggtttgtcag aactctattc | 1800 |
| caacaaatga gagacgtact tgggacattt gacaccaccc agataataaa gcttctccct | 1860 |
| tttgcagccg ctccaccaaa gcaaagcaga atgcagttct cttcactgac tgtaaatgtg | 1920 |
| aggggatcag ggatgagaat acttgtaagg ggcaattctc ctgtattcaa ctacaacaag | 1980 |
| accactaaaa gactaacaat tctcggaaaa gatgccggca ctttaattga agacccagat | 2040 |
| gaaagcacat ccggagtgga gtccgctgta ttgagagggt ttctcattat aggtaaggaa | 2100 |
| gacagaagat acgggccagc attaagcatc aatgaactga gtaaccttgc aaaaggggaa | 2160 |
| aaggctaatg tgctaatcgg gcaagggac gtggtgttgg taatgaaacg aaaacgggac | 2220 |
| tctagcatac ttactgacag ccagacagcg accaaaagaa ttcggatggc catcaattaa | 2280 |
| tgttgaatag tttaaaaacg accttgtttc tact | 2314 |

<210> SEQ ID NO 22
<211> LENGTH: 1775
<212> TYPE: DNA
<213> ORGANISM: Influenza virus

<400> SEQUENCE: 22

| | |
|---|---|
| agcaaaagca ggggaaaata aaaacaacca aaatgaaggc aaacctactg gtcctgttat | 60 |
| gtgcacttgc agctgcagat gcagcacaca atatgtatag gctaccatgcg aacaattcaa | 120 |
| ccgacactgt tgacacagta ctcgagaaga atgtgacagt gacacactct gttaacctgc | 180 |

-continued

```
tcgaagacag ccacaacgga aaactatgta gattaaaagg aatagcccca ctacaattgg      240
ggaaatgtaa catcgccgga tggctcttgg gaaacccaga atgcgaccca ctgcttccag      300
tgagatcatg gtcctacatt gtagaaacac caaactctga aatggaata tgttatccag      360 gagatttcat cgactatgag gagctgaggg agcaattgag ctcagtgtca tcattcgaaa      420
gattcgaaat atttcccaaa gaaagctcat ggcccaacca caacacaaac ggagtaacgg      480
cagcatgctc ccatgagggg aaaagcagtt tttacagaaa tttgctatgg ctgacggaga      540
aggagggctc atacccaaag ctgaaaaatt cttatgtgaa caaaaaggg aagaagtcc        600 ttgtactgtg gggtattcat cacccgccta acagtaagga caacagaat ctctatcaga       660 atgaaaatgc ttatgtctct gtagtgactt caaattataa caggagattt accccggaaa     720
tagcagaaag acccaaagta agagatcaag ctgggaggat gaactattac tggaccttgc     780
taaaacccgg agacacaata atatttgagg caaatggaaa tctaatagca ccaatgtatg     840
ctttcgcact gagtagaggc tttgggtccg gcatcatcac ctcaaacgca tcaatgcatg     900
agtgtaacac gaagtgtcaa acacccctgg gagctataaa cagcagtctc ccttaccaga     960
atatacaccc agtcacaata ggagagtgcc caaaatacgt caggagtgcc aaattgagga   1020
tggttacagg actaaggaac attccgtcca ttcaatccag aggtctattt ggagccattg   1080
ccggttttat tgaaggggga tggactggaa tgatagatgg atggtatggt tatcatcatc   1140
agaatgaaca gggatcaggc tatgcagcgg atcaaaaaag cacacaaaat gccattaacg   1200
ggattacaaa caaggtgaac actgttatcg agaaaatgaa cattcaattc acagctgtgg   1260
gtaaagaatt caacaaatta gaaaaaagga tggaaaattt aaataaaaaa gttgatgatg   1320
gatttctgga catttggaca tataatgcag aattgttagt tctactggaa atgaaagga    1380 ctctggattt ccatgactca aatgtgaaga atctgtatga gaaagtaaaa agccaattaa   1440
agaataatgc caaagaaatc ggaaatggat gttttgagtt ctaccacaag tgtgacaatg   1500
aatgcatgga aagtgtaaga aatgggactt atgattatcc caaatattca gaagagtcaa   1560
agttgaacag ggaaaaggta gatggagtga aattggaatc aatggggatc tatcagattc   1620
tggcgatcta ctcaactgtc gccagttcac tggtgctttt ggtctccctg ggggcaatca   1680
gtttctggat gtgttctaat ggatctttgc agtgcagaat atgcatctga gattagaatt   1740
tcagagatat gaggaaaaac accttgttt ctact                                 1775
```

<210> SEQ ID NO 23
<211> LENGTH: 1413
<212> TYPE: DNA
<213> ORGANISM: Influenza virus

<400> SEQUENCE: 23

```
agcaaaagca ggggtttaaa atgaatccaa atcagaaaat aataaccatt ggatcaatct      60
gtctggtagt cggactaatt agcctaatat tgcaaatagg aatataatc tcaatatgga     120 ttagccattc aattcaaact ggaagtcaaa accatactgg aatatgcaac caaaacatca     180
ttacctataa aaatagcacc tgggtaaagg acacaacttc agtgatatta accggcaatt     240
catctctttg tccatccgt gggtgggcta tatacagcaa agacaatagc ataagaattg      300
gttccaaagg agacgttttt gtcataagag agccctttat ttcatgttct cacttggaat     360 gcaggaccctt ttttctgacc caaggtgcct tactgaatga caagcattca gtgggactg     420 ttaaggacag aagcccttat agggccttaa tgagctgccc tgtcggtgaa gctccgtccc    480
```

-continued

```
cgtacaattc aagatttgaa tcggttgctt ggtcagcaag tgcatgtcat gatggcatgg      540
gctggctaac aatcggaatt tcaggtccag ataatggagc agtggctgta ttaaaataca      600
acggcataat aactgaaacc ataaaaagtt ggaggaagaa atattgagg acacaagagt       660
ctgaatgtgc ctgtgtaaat ggttcatgtt ttactataat gactgatggc ccgagtgatg      720
ggctggcctc gtacaaaatt ttcaagatcg aaaagggaa ggttactaaa tcaatagagt       780
tgaatgcacc taattctcac tatgaggaat gttcctgtta ccctgatacc ggcaaagtga      840
tgtgtgtgtg cagagacaat tggcatggtt cgaaccggcc atgggtgtct ttcgatcaaa      900
acctggatta tcaaatagga tacatctgca gtggggtttt cggtgacaac ccgcgtcccg      960
aagatggaac aggcagctgt ggtccagtgt atgttgatgg agcaaacgga gtaaagggat     1020
tttcatatag gtatggtaat ggtgtttgga taggaaggac caaaagtcac agttccagac     1080
atgggtttga tgatgatttgg gatcctaatg gatggacaga gactgatagt aagttctctg    1140
tgaggcaaga tgttgtggca atgactgatt ggtcagggta tagcggaagt ttcgttcaac     1200
atcctgagct gacagggcta gactgtatga ggccgtgctt ctgggttgaa ttaatcaggg     1260
gacgacctaa agaaaaaaca atctggacta gtgcgagcag catttctttt tgtggcgtga     1320
atagtgatac tgtagattgg tcttggccag acggtgctga gttgccattc agcattgaca    1380
agtagtctgt tcaaaaaact ccttgtttct act                                  1413

<210> SEQ ID NO 24
<211> LENGTH: 2233
<212> TYPE: DNA
<213> ORGANISM: Influenza virus

<400> SEQUENCE: 24
agcgaaagca ggtactgatc caaaatggaa gattttgtgc gacaatgctt caatccgatg       60
attgtcgagc ttgcggaaaa aacaatgaaa gagtatgggg aggacctgaa atcgaaaca      120
aacaaatttg cagcaatatg cactcacttg gaagtatgct tcatgtattc agattttcac     180
ttcatcaatg agcaaggcga gtcaataatc gtagaacttg gtgatccaaa tgcacttttg     240
aagcacagat ttgaaataat cgagggaaga gatcgcacaa tggcctggac agtagtaaac    300
agtatttgca acactacagg ggctgagaaa ccaaagttc taccagattt gtatgattac     360
aaggagaata gattcatcga aattggagta acaaggagaa agttcacat atactatctg     420
gaaaaggcca ataaaattaa atctgagaaa acacacatcc acattttctc gttcactggg    480
gaagaaatgg ccacaaaggc agactacact ctcgatgaag aaagcagggc taggatcaaa    540
accagactat tcaccataag acaagaaatg gccagcagag gcctctggga ttccttttcgt    600
cagtccgaga gaggagaaga gacaattgaa gaaaggtttg aaatcacagg aacaatgcgc    660
aagcttgccg accaaagtct cccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc ttttttgaaa acaacaccac gaccacttag acttccgaat    840
gggcctccct gttctcagcg gtccaaattc ctgctgatgg atgccttaaa attaagcatt    900
gaggacccaa gtcatgaagg agagggaata ccgctatatg atgcaatcaa atgcatgaga    960
acattctttg gatggaagga acccaatgtt gttaaaccac acgaaaaggg aataaatcca   1020
aattatcttc tgtcatggaa gcaagtactg gcagaactgc aggacattga gaatgaggag   1080
aaaattccaa agactaaaaa tatgaagaaa acaagtcagc taaagtgggc acttggtgag   1140
aacatggcac cagaaaaggt agactttgac gactgtaaag atgtaggtga tttgaagcaa   1200
```

-continued

```
tatgatagtg atgaaccaga attgaggtcg cttgcaagtt ggattcagaa tgagtttaac   1260
aaggcatgcg aactgacaga ttcaagctgg atagagctcg atgagattgg agaagatgtg   1320
gctccaattg aacacattgc aagcatgaga aggaattatt tcacatcaga ggtgtctcac   1380
tgcagagcca cagaatacat aatgaaggga gtgtacatca atactgcctt gcttaatgca   1440
tcttgtgcag caatggatga tttccaatta attccaatga taagcaagtg tagaactaag   1500
gagggaaggc gaaagaccaa cttgtatggt ttcatcataa aaggaagatc ccacttaagg   1560
aatgacaccg acgtggtaaa ctttgtgagc atggagtttt ctctcactga cccaagactt   1620
gaaccacata aatgggagaa gtactgtgtt cttgagatag gagatatgct tataagaagt   1680
gccataggcc aggtttcaag gcccatgttc ttgtatgtga gaacaaatgg aacctcaaaa   1740
attaaaatga aatggggaat ggagatgagg cgttgcctcc tccagtcact tcaacaaatt   1800
gagagtatga ttgaagctga gtcctctgtc aaagagaaag acatgaccaa agagttcttt   1860
gagaacaaat cagaaacatg gcccattgga gagtccccca aaggagtgga ggaaagttcc   1920
attgggaagg tctgcaggac tttattagca aagtcggtat tcaacagctt gtatgcatct   1980
ccacaactag aaggattttc agctgaatca agaaaactgc ttcttatcgt tcaggctctt   2040
agggacaacc tggaacctgg gacctttgat cttgggggc tatatgaagc aattgaggag    2100
tgcctgatta atgatccctg ggttttgctt aatgcttctt ggttcaactc cttccttaca   2160
catgcattga gttagttgtg gcagtgctac tatttgctat ccatactgtc caaaaaagta   2220
ccttgtttct act                                                      2233
```

<210> SEQ ID NO 25
<211> LENGTH: 2341
<212> TYPE: DNA
<213> ORGANISM: Influenza virus

<400> SEQUENCE: 25

```
agcgaaagca ggcaaaccat ttgaatggat gtcaatccga ccttactttt cttaaaagtg     60
ccagcacaaa atgctataag cacaactttc ccttatactg gagaccctcc ttacagccat    120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga aacgatggag    360
gttgttcagc aaacacgagt agacaagctg acacaaggcc gacagaccta tgactggact    420
ctaaatagaa accaacctgc tgcaacagca ttggccaaca caatagaagt gttcagatca    480
aatggcctca cggccaatga gtctggaagg ctcatagact tccttaagga tgtaatggag    540
tcaatgaaca aagaagaaat ggggatcaca actcattttc agagaaagag acgggtgaga    600
gacaatatga ctaagaaaat gataacacag agaacaatgg gtaaaaagaa gcagagattg    660
aacaaaagga gttatctaat tagagcattg accctgaaca caatgaccaa agatgctgag    720
agagggaagc taaaacggag agcaattgca accccaggga tgcaaataag gggggtttgta    780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttcaccatc actggagata acaccaaatg gaacgaaaat    960
cagaatcctc ggatgttttt ggccatgatc acatatatga ccagaaatca gcccgaatgg   1020

| | |
|---|---:|
| ttcagaaatg ttctaagtat tgctccaata atgttctcaa acaaaatggc gagactggga | 1080 |
| aaagggtata tgtttgagag caagagtatg aaacttagaa ctcaaatacc tgcagaaatg | 1140 |
| ctagcaagca tcgatttgaa atatttcaat gattcaacaa gaaagaagat tgaaaaaatc | 1200 |
| cgaccgctct aatagaggg gactgcatca ttgagccctg aatgatgat gggcatgttc | 1260 |
| aatatgttaa gcactgtatt aggcgtctcc atcctgaatc ttggacaaaa gagatacacc | 1320 |
| aagactactt actggtggga tggtcttcaa tcctctgacg attttgctct gattgtgaat | 1380 |
| gcacccaatc atgaagggat tcaagccgga gtcgacaggt tttatcgaac ctgtaagcta | 1440 |
| cttggaatca atatgagcaa gaaaaagtct tacataaaca gaacaggtac atttgaattc | 1500 |
| acaagttttt tctatcgtta tgggtttgtt gccaatttca gcatggagct tcccagtttt | 1560 |
| ggggtgtctg gatcaacga gtcagcggac atgagtattg gagttactgt catcaaaaac | 1620 |
| aatatgataa acaatgatct tggtccagca acagctcaaa tggcccttca gttgttcatc | 1680 |
| aaagattaca ggtacacgta ccgatgccat ataggtgaca cacaaataca aacccgaaga | 1740 |
| tcatttgaaa taagaaact gtgggagcaa acccgttcca agctggact gctggtctcc | 1800 |
| gacggaggcc caaatttata caacattaga atctccaca ttcctgaagt ctgcctaaaa | 1860 |
| tgggaattga tggatgagga ttaccagggg cgtttatgca accccactga cccatttgtc | 1920 |
| agccataaag aaattgaatc aatgaacaat gcagtgatga tgccagcaca tggtccagcc | 1980 |
| aaaaacatgg agtatgatgc tgttgcaaca acacactcct ggatcccccaa agaaatcga | 2040 |
| tccatcttga atacaagtca agaggagta cttgaggatg aacaaatgta ccaaaggtgc | 2100 |
| tgcaatttat ttgaaaaatt cttccccagc agttcataca aagaccagt cgggatatcc | 2160 |
| agtatggtgg aggctatggt ttccagagcc cgaattgatg cacggattga tttcgaatct | 2220 |
| ggaaggataa agaagaaga gttcactgag atcatgaaga tctgttccac cattgaagag | 2280 |
| ctcagacggc aaaaaatagtg aatttagctt gtccttcatg aaaaaatgcc ttgtttctac | 2340 |
| t | 2341 |

<210> SEQ ID NO 26
<211> LENGTH: 2341
<212> TYPE: DNA
<213> ORGANISM: Influenza virus

<400> SEQUENCE: 26

| | |
|---|---:|
| agcgaaagca ggtcaattat attcaatatg gaaagaataa agaactacg aaatctaatg | 60 |
| tcgcagtctc gcacccgcga gatactcaca aaaaccaccg tggaccatat ggccataatc | 120 |
| aagaagtaca catcaggaag acaggagaag aacccagcac ttaggatgaa atggatgatg | 180 |
| gcaatgaaat atccaattac agcagacaag aggataacgg aaatgattcc tgagagaaat | 240 |
| gagcaaggac aaactttatg gagtaaaatg aatgatgccg atcagaccg agtgatggta | 300 |
| tcacctctgg ctgtgacatg gtggaatagg aatggaccaa taacaaatac agttcattat | 360 |
| ccaaaaatct acaaaactta ttttgaaaga gtcgaaggc taaagcatgg aaccttggc | 420 |
| cctgtccatt ttagaaacca agtcaaaata cgtcggagag ttgacataaa tcctggtcat | 480 |
| gcagatctca gtgccaagga ggcacaggat gtaatcatgg aagttgtttt ccctaacgaa | 540 |
| gtgggagcca ggatactaac atcggaatcg caactaacga taaccaaaga gaagaaagaa | 600 |
| gaactccagg attgcaaaat ttctcctttg atggttgcat acatgttgga gagagaactg | 660 |
| gtccgcaaaa cgagattcct cccagtggct ggtggaacaa gcagtgtgta cattgaagtg | 720 |
| ttgcatttga ctcaaggaac atgctgggaa cagatgtata ctccaggagg ggaagtgagg | 780 |

```
aatgatgatg ttgatcaaag cttgattatt gctgctagga acatagtgag aagagctgca      840
gtatcagcag atccactagc atctttattg gagatgtgcc acagcacaca gattggtgga      900
attaggatgg tagacatcct taggcagaac ccaacagaag agcaagccgt ggatatatgc      960
aaggctgcaa tgggactgag aattagctca tccttcagtt ttggtggatt cacatttaag     1020
agaacaagcg gatcatcagt caagagagag gaagaggtgc ttacgggcaa tcttcaaaca     1080
ttgaagataa gagtgcatga gggatatgaa gagttcacaa tggttgggag aagagcaaca     1140
gccatactca gaaaagcaac caggagattg attcagctga tagtgagtgg gagagacgaa     1200
cagtcgattg ccgaagcaat aattgtggcc atggtatttt cacaagagga ttgtatgata     1260
aaagcagtca gaggtgatct gaatttcgtc aatagggcga atcaacgatt gaatcctatg     1320
catcaacttt taagacattt tcagaaggat gcgaaagtgc tttttcaaaa ttggggagtt     1380
gaacctatcg acaatgtgat gggaatgatt gggatattgc cgacatgac tccaagcatc      1440 gagatgtcaa tgagaggagt gagaatcagc aaaatgggtg tagatgagta ctccagcacg     1500
gagagggtag tggtgagcat tgaccgtttt ttgagaatcc gggaccaacg aggaaatgta     1560
ctactgtctc ccgaggaggt cagtgaaaca cagggaacag agaaactgac aataacttac     1620
tcatcgtcaa tgatgtggga gattaatggt cctgaatcag tgttggtcaa tacctatcaa     1680
tggatcatca gaaactggga aactgttaaa attcagtggt cccagaaccc tacaatgcta     1740
tacaataaaa tggaatttga accatttcag tctttagtac ctaaggccat tagaggccaa     1800
tacagtgggt ttgtaagaac tctgttccaa caaatgaggg atgtgcttgg gacatttgat     1860
accgcacaga taataaaact tcttcccttc gcagccgctc caccaaagca agtagaatg      1920 cagttctcct catttactgt gaatgtgagg ggatcaggaa tgagaatact tgtaaggggc     1980
aattctcctg tattcaacta taacaaggcc acgaagagac tcacagttct cggaaaggat     2040
gctggcactt taactgaaga cccagatgaa ggcacagctg gagtggagtc cgctgttctg     2100
aggggattcc tcattctggg caaagaagac aagagatatg gccagcact aagcatcaat      2160 gaactgagca accttgcgaa aggagagaag gctaatgtgc taattgggca aggagacgtg     2220
gtgttggtaa tgaaacggaa acgggactct agcatactta ctgacagcca gacagcgacc     2280
aaaagaattc ggatggccat caattagtgt cgaatagttt aaaaacgacc ttgtttctac     2340
t                                                                   2341
```

<210> SEQ ID NO 27
<211> LENGTH: 1565
<212> TYPE: DNA
<213> ORGANISM: Influenza virus

<400> SEQUENCE: 27

```
agcaaaagca gggtagataa tcactcactg agtgacatca aaatcatggc gtctcaaggc       60
accaaacgat cttacgaaca gatggagact gatggagaac gccagaatgc cactgaaatc      120
agagcatccg tcggaaaaat gattggtgga attggacgat tctacatcca aatgtgcacc      180
gaactcaaac tcagtgatta tgagggacgg ttgatccaaa acagcttaac aatagagaga      240
atggtgctct ctgcttttga cgaaaggaga aataaatacc ttgaagaaca tcccagtgcg      300
gggaaagatc ctaagaaaac tggaggacct atatacagga gagtaaacgg aaagtggatg      360
agagaactca tcctttatga caagaaggaa ataaggcgaa tctggcgcca agctaataat      420
ggtgacgatg caacggctgg tctgactcac atgatgatct ggcattccaa tttgaatgat      480
```

-continued

| | |
|---|---|
| gcaacttatc agaggacaag agctcttgtt cgcaccggaa tggatcccag gatgtgctct | 540 |
| ctgatgcaag gttcaactct ccctaggagg tctggagccg caggtgctgc agtcaaagga | 600 |
| gttggaacaa tggtgatgga attggtcaga atgatcaaac gtgggatcaa tgatcggaac | 660 |
| ttctggaggg gtgagaatgg acgaaaaaca agaattgctt atgaaagaat gtgcaacatt | 720 |
| ctcaaaggga aatttcaaac tgctgcacaa aaagcaatga tggatcaagt gagagagagc | 780 |
| cggaacccag ggaatgctga gttcgaagat ctcacttttc tagcacggtc tgcactcata | 840 |
| ttgagagggt cggttgctca caagtcctgc ctgcctgcct gtgtgtatgg acctgccgta | 900 |
| gccagtgggt acgactttga agggaggga tactctctag tcggaataga cccttttcaga | 960 |
| ctgcttcaaa acagccaagt gtacagccta atcagaccaa atgagaatcc agcacacaag | 1020 |
| agtcaactgg tgtggatggc atgccattct gccgcatttg aagatctaag agtattaagc | 1080 |
| ttcatcaaag ggacgaaggt gctcccaaga gggaagcttt ccactagagg agttcaaatt | 1140 |
| gcttccaatg aaaatatgga gactatggaa tcaagtacac ttgaactgag aagcaggtac | 1200 |
| tgggccataa ggaccagaag tggaggaaac accaatcaac agagggcatc tgcgggccaa | 1260 |
| atcagcatac aacctacgtt ctcagtacag agaaatctcc cttttgacag aacaaccatt | 1320 |
| atggcagcat tcaatgggaa tacagagggg agaacatctg acatgaggac cgaaatcata | 1380 |
| aggatgatgg aaagtgcaag accagaagat gtgtctttcc aggggcgggg agtcttcgag | 1440 |
| ctctcggacg aaaaggcagc gagcccgatc gtgccttcct ttgacatgag taatgaagga | 1500 |
| tcttatttct tcggagacaa tgcagaggag tacgacaatt aaagaaaaat accccttgttt | 1560 |
| ctact | 1565 |

<210> SEQ ID NO 28
<211> LENGTH: 1027
<212> TYPE: DNA
<213> ORGANISM: Influenza virus

<400> SEQUENCE: 28

| | |
|---|---|
| agcaaaagca ggtagatatt gaaagatgag tcttctaacc gaggtcgaaa cgtacgtact | 60 |
| ctctatcatc ccgtcaggcc ccctcaaagc cgagatcgca cagagacttg aagatgtctt | 120 |
| tgcagggaag aacaccgatc ttgaggttct catggaatgg ctaaagacaa gaccaatcct | 180 |
| gtcacctctg actaaggga ttttaggatt tgtgttcacg ctcaccgtgc ccagtgagcg | 240 |
| aggactgcag cgtagacgct ttgtccaaaa tgccctta at gggaacgggg atccaaataa | 300 |
| catggacaaa gcagttaaac tgtataggaa gctcaagagg gagataacat tccatgggc | 360 |
| caaagaaatc tcactcagtt attctgctgg tgcacttgcc agttgtatgg gcctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaatccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctagacaaat | 660 |
| ggtgcaagcg atgagaacca ttgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cactattgcc gcaaatatca ttgggatctt gcacttgaca ttgtggattc | 840 |
| ttgatcgtct ttttttcaaa tgcatttacc gtcgctttaa atacggactg aaaggagggc | 900 |
| cttctacgga aggagtgcca aagtctatga gggaagaata tcgaaggaa cagcagagtg | 960 |
| ctgtggatgc tgacgatggt cattttgtca gcatagagct ggagtaaaaa actaccttgt | 1020 |

-continued

```
ttctact                                                            1027
```

<210> SEQ ID NO 29
<211> LENGTH: 890
<212> TYPE: DNA
<213> ORGANISM: Influenza virus

<400> SEQUENCE: 29

```
agcaaaagca gggtgacaaa aacataatgg atccaaacac tgtgtcaagc tttcaggtag    60
attgctttct ttggcatgtc cgcaaacgag ttgcagacca agaactaggc gatgccccat   120
tccttgatcg gcttcgccga gatcagaaat ccctaagagg aagggcagt actctcggtc    180
tggacatcaa gacagccaca cgtgctggaa agcagatagt ggagcggatt ctgaaagaag   240
aatccgatga ggcacttaaa atgaccatgg cctctgtacc tgcgtcgcgt tacctaactg   300
acatgactct tgaggaaatg tcaagggact ggtccatgct catacccaag cagaaagtgg   360
caggccctct ttgtatcaga atggaccagg cgatcatgga taagaacatc atactgaaag   420
cgaacttcag tgtgattttt gaccggctgg agactctaat attgctaagg gctttcaccg   480
aagagggagc aattgttggc gaaatttcac cattgccttc tcttccagga catactgctg   540
aggatgtcaa aaatgcagtt ggagtcctca tcggaggact tgaatggaat gataacacag   600
ttcgagtctc tgaaactcta cagagattcg cttggagaag cagtaatgag atgggagac   660
ctccactcac tccaaaacag aaacgagaaa tggcgggaac aattaggtca gaagtttgaa   720
gaaataagat ggttgattga agaagtgaga cacaaactga agataacaga gaatagtttt   780
gagcaaataa catttatgca agccttacat ctattgcttg aagtggagca agagataaga   840
actttctcgt ttcagcttat ttagtactaa aaacacccct tgtttctact              890
```

<210> SEQ ID NO 30
<211> LENGTH: 468
<212> TYPE: PRT
<213> ORGANISM: Influenza virus

<400> SEQUENCE: 30

```
Met Asn Pro Asn Gln Lys Ile Ile Thr Ile Gly Val Val Asn Thr Thr
  1               5                  10                  15

Leu Ser Thr Ile Ala Leu Leu Ile Gly Val Gly Asn Leu Ile Phe Asn
             20                  25                  30

Thr Val Ile His Glu Lys Ile Gly Asp His Gln Thr Val Ile His Pro
         35                  40                  45

Thr Thr Thr Thr Pro Ala Ile Pro Asn Cys Ser Asp Thr Ile Ile Thr
     50                  55                  60

Tyr Asn Asn Thr Val Ile Asn Asn Ile Thr Thr Ile Ile Thr Glu Ala
 65                  70                  75                  80

Glu Arg Leu Phe Lys Pro Pro Leu Pro Leu Cys Pro Phe Arg Gly Phe
                 85                  90                  95

Phe Pro Phe His Lys Asp Asn Ala Ile Arg Leu Gly Glu Asn Lys Asp
            100                 105                 110

Val Ile Val Thr Arg Glu Pro Tyr Val Ser Cys Asp Asn Asp Asn Cys
        115                 120                 125

Trp Ser Phe Ala Leu Ala Gln Gly Ala Leu Leu Gly Thr Lys His Ser
    130                 135                 140

Asn Gly Thr Ile Lys Asp Arg Thr Pro Tyr Arg Ser Leu Ile Gln Phe
145                 150                 155                 160
```

```
Pro Ile Gly Thr Ala Pro Val Leu Gly Asn Tyr Lys Glu Ile Cys Ile
            165                 170                 175

Ala Trp Ser Ser Ser Cys Phe Asp Gly Lys Glu Trp Met His Val
        180                 185                 190

Cys Met Thr Gly Asn Asp Asn Asp Ala Ser Ala Gln Ile Ile Tyr Ala
            195                 200                 205

Gly Arg Met Thr Asp Ser Ile Lys Ser Trp Lys Arg Asp Ile Leu Arg
        210                 215                 220

Thr Gln Glu Ser Glu Cys Gln Cys Ile Asp Gly Thr Cys Val Val Ala
225                 230                 235                 240

Val Thr Asp Gly Pro Ala Ala Asn Ser Ala Asp His Arg Val Tyr Trp
            245                 250                 255

Ile Arg Glu Gly Arg Ile Val Lys Tyr Glu Asn Val Pro Lys Thr Lys
            260                 265                 270

Ile Gln His Leu Glu Glu Cys Ser Cys Tyr Val Asp Ile Asp Val Tyr
        275                 280                 285

Cys Ile Cys Arg Asp Asn Trp Lys Gly Ser Asn Arg Pro Trp Met Arg
        290                 295                 300

Ile Asn Asn Glu Thr Ile Leu Glu Thr Gly Tyr Val Cys Ser Lys Phe
305                 310                 315                 320

His Ser Asp Thr Pro Arg Pro Ala Asp Pro Ser Thr Val Ser Cys Asp
            325                 330                 335

Ser Pro Ser Asn Val Asn Gly Gly Pro Gly Val Lys Gly Phe Gly Phe
        340                 345                 350

Lys Val Gly Asn Asp Val Trp Leu Gly Arg Thr Met Ser Thr Ser Gly
        355                 360                 365

Arg Ser Gly Phe Glu Ile Ile Lys Val Ala Glu Gly Trp Ile Asn Ser
        370                 375                 380

Pro Asn His Ala Lys Ser Val Thr Gln Thr Leu Val Ser Asn Asn Asp
385                 390                 395                 400

Trp Ser Gly Tyr Ser Gly Ser Phe Ile Val Lys Thr Lys Ala Cys Phe
            405                 410                 415

Gln Pro Cys Phe Tyr Val Glu Leu Ile Arg Gly Arg Pro Asn Lys Asn
            420                 425                 430

Asp Asp Val Ser Trp Thr Ser Asn Ser Ile Val Thr Phe Cys Gly Leu
            435                 440                 445

Asp Asn Glu Pro Gly Ser Gly Asn Trp Pro Asp Gly Ser Asn Ile Gly
            450                 455                 460

Phe Met Pro Lys
465

<210> SEQ ID NO 31
<211> LENGTH: 470
<212> TYPE: PRT
<213> ORGANISM: Influenza virus

<400> SEQUENCE: 31

Met Asn Pro Asn Gln Lys Ile Ile Thr Ile Gly Ser Val Ser Ile Ile
1               5                   10                  15

Leu Thr Thr Ile Gly Leu Leu Leu Gln Ile Thr Ser Leu Cys Ser Ile
            20                  25                  30

Trp Phe Ser His Tyr Asn Gln Val Thr Gln Thr His Glu Gln Pro Cys
        35                  40                  45

Ser Asn Asn Thr Thr Asn Tyr Tyr Asn Glu Thr Phe Val Asn Val Thr
    50                  55                  60
```

```
Asn Val Gln Asn Asn Tyr Thr Thr Val Ile Glu Pro Ser Ala Pro Asp
 65                  70                  75                  80

Val Val His Tyr Ser Gly Arg Asp Leu Cys Pro Ile Arg Gly Trp
             85                  90                  95

Ala Pro Leu Ser Lys Asp Asn Gly Ile Arg Ile Gly Ser Arg Gly Glu
            100                 105                 110

Val Phe Val Ile Arg Glu Pro Phe Ile Ser Cys Ser Ile Ser Glu Cys
            115                 120                 125

Arg Thr Phe Phe Leu Thr Gln Gly Ala Leu Leu Asn Asp Lys His Ser
            130                 135             140

Asn Gly Thr Val Lys Asp Arg Ser Pro Phe Arg Thr Leu Met Ser Cys
145                 150                 155                 160

Pro Ile Gly Val Ala Pro Ser Pro Ser Asn Ser Arg Phe Glu Ser Val
                165                 170                 175

Ala Trp Ser Ala Thr Ala Cys Ser Asp Gly Pro Gly Trp Leu Thr Leu
            180                 185                 190

Gly Ile Thr Gly Pro Asp Ala Thr Ala Val Ala Val Leu Lys Tyr Asn
            195                 200                 205

Gly Ile Ile Thr Asp Thr Leu Lys Ser Trp Lys Gly Asn Ile Met Arg
210                 215                 220

Thr Gln Glu Ser Glu Cys Val Cys Gln Asp Glu Phe Cys Tyr Thr Leu
225                 230                 235                 240

Ile Thr Asp Gly Pro Ser Asp Ala Gln Ala Phe Tyr Lys Ile Leu Lys
                245                 250                 255

Ile Arg Lys Gly Lys Ile Val Ser Met Lys Asp Val Asp Ala Thr Gly
            260                 265                 270

Phe His Phe Glu Glu Cys Ser Cys Tyr Pro Ser Gly Thr Asp Ile Glu
            275                 280                 285

Cys Val Cys Arg Asp Asn Trp Arg Gly Ser Asn Arg Pro Trp Ile Arg
            290                 295                 300

Phe Asn Ser Asp Leu Asp Tyr Gln Ile Gly Tyr Val Cys Ser Gly Ile
305                 310                 315                 320

Phe Gly Asp Asn Pro Arg Pro Val Asp Gly Thr Gly Ser Cys Asn Ser
                325                 330                 335

Pro Val Asn Asn Gly Lys Gly Arg Tyr Gly Val Lys Gly Phe Ser Phe
            340                 345                 350

Arg Tyr Gly Asp Gly Val Trp Ile Gly Arg Thr Lys Ser Leu Glu Ser
            355                 360                 365

Arg Ser Gly Phe Glu Met Val Trp Asp Ala Asn Gly Trp Val Ser Thr
            370                 375                 380

Asp Lys Asp Ser Asn Gly Val Gln Asp Ile Ile Asp Asn Asp Asn Trp
385                 390                 395                 400

Ser Gly Tyr Ser Gly Ser Phe Ser Ile Arg Gly Glu Thr Thr Gly Arg
                405                 410                 415

Asn Cys Thr Val Pro Cys Phe Trp Val Glu Met Ile Arg Gly Gln Pro
            420                 425                 430

Lys Glu Lys Thr Ile Trp Thr Ser Gly Ser Ser Ile Ala Phe Cys Gly
            435                 440                 445

Val Asn Ser Asp Thr Thr Gly Trp Ser Trp Pro Asp Gly Ala Leu Leu
            450                 455                 460

Pro Phe Asp Ile Asp Lys
465                 470
```

<210> SEQ ID NO 32
<211> LENGTH: 470
<212> TYPE: PRT
<213> ORGANISM: Influenza virus

<400> SEQUENCE: 32

| | | | | | | | | | | | | | | |
|---|---|---|---|---|---|---|---|---|---|---|---|---|---|---|
| Met | Asn | Pro | Asn | Gln | Lys | Ile | Ile | Cys | Ile | Ser | Ala | Thr | Gly | Met | Thr |
| 1 | | | | 5 | | | | | 10 | | | | | 15 | |
| Leu | Ser | Val | Val | Ser | Leu | Leu | Ile | Gly | Ile | Ala | Asn | Leu | Gly | Leu | Asn |
| | | | 20 | | | | | 25 | | | | | 30 | | |
| Ile | Gly | Leu | His | Tyr | Lys | Met | Gly | Asp | Thr | Pro | Asp | Val | Asn | Ile | Pro |
| | | | 35 | | | | | 40 | | | | | 45 | | |
| Asn | Met | Asn | Glu | Thr | Asn | Ser | Thr | Thr | Thr | Ile | Ile | Asn | Asn | His | Thr |
| | 50 | | | | | 55 | | | | | 60 | | | | |
| Gln | Asn | Asn | Phe | Thr | Asn | Ile | Thr | Asn | Ile | Ile | Val | Asn | Lys | Asn | Glu |
| 65 | | | | | 70 | | | | | 75 | | | | | 80 |
| Glu | Gly | Thr | Phe | Leu | Asn | Leu | Thr | Lys | Pro | Leu | Cys | Glu | Val | Asn | Ser |
| | | | | 85 | | | | | 90 | | | | | 95 | |
| Trp | His | Ile | Leu | Ser | Lys | Asp | Asn | Ala | Ile | Arg | Ile | Gly | Glu | Asp | Ala |
| | | | 100 | | | | | 105 | | | | | 110 | | |
| His | Ile | Leu | Val | Thr | Arg | Glu | Pro | Tyr | Leu | Ser | Cys | Asp | Pro | Gln | Gly |
| | | | 115 | | | | | 120 | | | | | 125 | | |
| Cys | Arg | Met | Phe | Ala | Leu | Ser | Gln | Gly | Thr | Thr | Leu | Arg | Gly | Arg | His |
| | 130 | | | | | 135 | | | | | 140 | | | | |
| Ala | Asn | Gly | Thr | Ile | His | Asp | Arg | Ser | Pro | Phe | Arg | Ala | Leu | Ile | Ser |
| 145 | | | | | 150 | | | | | 155 | | | | | 160 |
| Trp | Glu | Met | Gly | Gln | Ala | Pro | Ser | Pro | Tyr | Asn | Val | Arg | Val | Glu | Cys |
| | | | | 165 | | | | | 170 | | | | | 175 | |
| Ile | Gly | Trp | Ser | Ser | Thr | Ser | Cys | His | Asp | Gly | Ile | Ser | Arg | Met | Ser |
| | | | 180 | | | | | 185 | | | | | 190 | | |
| Ile | Cys | Met | Ser | Gly | Ala | Asn | Asn | Ala | Ser | Ala | Val | Val | Trp | Tyr |
| | | | 195 | | | | | 200 | | | | | 205 | | |
| Gly | Gly | Arg | Pro | Val | Thr | Glu | Ile | Pro | Ser | Trp | Ala | Gly | Asn | Ile | Leu |
| | 210 | | | | | 215 | | | | | 220 | | | | |
| Arg | Thr | Gln | Glu | Ser | Glu | Cys | Val | Cys | His | Lys | Gly | Ile | Cys | Pro | Val |
| 225 | | | | | 230 | | | | | 235 | | | | | 240 |
| Val | Met | Thr | Asp | Gly | Pro | Ala | Asn | Asn | Arg | Ala | Ala | Thr | Lys | Ile | Ile |
| | | | | 245 | | | | | 250 | | | | | 255 | |
| Tyr | Phe | Lys | Glu | Gly | Lys | Ile | Gln | Lys | Ile | Glu | Glu | Leu | Ala | Gly | Asn |
| | | | 260 | | | | | 265 | | | | | 270 | | |
| Thr | Gln | His | Ile | Glu | Glu | Cys | Ser | Cys | Tyr | Gly | Ala | Val | Gly | Val | Ile |
| | | | 275 | | | | | 280 | | | | | 285 | | |
| Lys | Cys | Ile | Cys | Arg | Asp | Asn | Trp | Lys | Gly | Ala | Asn | Arg | Pro | Val | Ile |
| | 290 | | | | | 295 | | | | | 300 | | | | |
| Thr | Ile | Asp | Pro | Glu | Met | Met | Thr | His | Thr | Ser | Lys | Tyr | Leu | Cys | Ser |
| 305 | | | | | 310 | | | | | 315 | | | | | 320 |
| Lys | Ile | Leu | Thr | Asp | Thr | Ser | Arg | Pro | Asn | Asp | Pro | Thr | Asn | Gly | Asn |
| | | | | 325 | | | | | 330 | | | | | 335 | |
| Cys | Asp | Ala | Pro | Ile | Thr | Gly | Gly | Ser | Pro | Asp | Pro | Gly | Val | Lys | Gly |
| | | | 340 | | | | | 345 | | | | | 350 | | |
| Phe | Ala | Phe | Leu | Asp | Arg | Glu | Asn | Ser | Trp | Leu | Gly | Arg | Thr | Ile | Ser |
| | | | 355 | | | | | 360 | | | | | 365 | | |
| Lys | Asp | Ser | Arg | Ser | Gly | Tyr | Glu | Met | Leu | Lys | Val | Pro | Asn | Ala | Glu |
| | 370 | | | | | 375 | | | | | 380 | | | | |

Thr Asp Thr Gln Ser Gly Pro Ile Ser His Gln Val Ile Val Asn Asn
385                 390                 395                 400

Gln Asn Trp Ser Gly Tyr Ser Gly Ala Phe Ile Asp Tyr Trp Ala Asn
            405                 410                 415

Lys Glu Cys Phe Asn Pro Cys Phe Tyr Val Glu Leu Ile Arg Gly Arg
        420                 425                 430

Pro Lys Glu Ser Ser Val Leu Trp Thr Ser Asn Ser Ile Val Ala Leu
    435                 440                 445

Cys Gly Ser Lys Glu Arg Leu Gly Ser Trp Ser Trp His Asp Gly Ala
450                 455                 460

Glu Ile Ile Tyr Phe Lys
465                 470

<210> SEQ ID NO 33
<211> LENGTH: 470
<212> TYPE: PRT
<213> ORGANISM: Influenza virus

<400> SEQUENCE: 33

Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
            20                  25                  30

Val Ser Leu His Leu Lys Gly Ser Ser Asp Gln Asp Lys Asn Trp Thr
        35                  40                  45

Cys Thr Ser Val Thr Gln Asn Asn Thr Thr Leu Ile Glu Asn Thr Tyr
    50                  55                  60

Val Asn Asn Thr Thr Val Ile Asp Lys Glu Thr Gly Thr Ala Lys Pro
65                  70                  75                  80

Asn Tyr Leu Met Leu Asn Lys Ser Leu Cys Lys Val Glu Gly Trp Val
                85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
        115                 120                 125

Met Tyr Ala Leu His Gln Gly Thr Thr Ile Arg Asn Lys His Ser Asn
130                 135                 140

Gly Thr Ile His Asp Arg Thr Ala Phe Arg Gly Leu Ile Ser Thr Pro
145                 150                 155                 160

Leu Gly Ser Pro Pro Val Val Ser Asn Ser Asp Phe Leu Cys Val Gly
                165                 170                 175

Trp Ser Ser Thr Ser Cys His Asp Gly Ile Gly Arg Met Thr Ile Cys
            180                 185                 190

Val Gln Gly Asn Asn Asp Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
210                 215                 220

Gln Glu Ser Glu Cys Val Cys His Asn Gly Thr Cys Val Val Ile Met
225                 230                 235                 240

Thr Asp Gly Ser Ala Ser Ser Gln Ala Tyr Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys

```
              275                 280                 285
Val Cys Arg Asp Asn Trp Gln Gly Ala Asn Arg Pro Val Ile Glu Ile
290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Met Gly Asp Cys Asn
                325                 330                 335

Asn Pro Ile Thr Gly Ser Pro Gly Ala Pro Gly Val Lys Gly Phe Gly
                340                 345                 350

Phe Leu Asp Ser Ser Asn Thr Trp Leu Gly Arg Thr Ile Ser Pro Arg
                355                 360                 365

Ser Arg Ser Gly Phe Glu Met Leu Lys Ile Pro Asn Ala Glu Thr Asp
370                 375                 380

Pro Asn Ser Lys Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415

Glu Cys Tyr Asn Pro Cys Phe Tyr Val Glu Leu Ile Arg Gly Arg Pro
                420                 425                 430

Glu Glu Ala Lys Tyr Val Gly Trp Thr Ser Asn Ser Leu Ile Ala Leu
                435                 440                 445

Cys Gly Ser Pro Ile Ser Val Gly Ser Gly Ser Phe Pro Asp Gly Ala
450                 455                 460

Gln Ile Gln Tyr Phe Ser
465                 470

<210> SEQ ID NO 34
<211> LENGTH: 470
<212> TYPE: PRT
<213> ORGANISM: Influenza virus

<400> SEQUENCE: 34

Met Asn Pro Asn Gln Lys Ile Ile Thr Val Gly Ser Val Ser Leu Gly
1               5                   10                  15

Leu Val Val Leu Asn Ile Leu Leu His Ile Val Ser Ile Thr Val Thr
                20                  25                  30

Val Leu Val Leu Pro Gly Asn Gly Asn Asn Lys Asn Cys Asn Glu Thr
                35                  40                  45

Val Ile Arg Glu Tyr Asn Glu Thr Val Arg Ile Glu Lys Val Thr Gln
                50                  55                  60

Trp His Asn Thr Asn Val Ile Glu Tyr Ile Glu Lys Pro Glu Ser Gly
65                  70                  75                  80

His Phe Met Asn Asn Thr Glu Ala Leu Cys Asp Ala Lys Gly Phe Ala
                85                  90                  95

Pro Phe Ser Lys Asp Asn Gly Ile Arg Ile Gly Ser Arg Gly His Val
                100                 105                 110

Phe Val Ile Arg Glu Pro Phe Val Ser Cys Ser Pro Thr Glu Cys Arg
                115                 120                 125

Thr Phe Phe Leu Thr Gln Gly Ser Leu Leu Asn Asp Lys His Ser Asn
                130                 135                 140

Gly Thr Val Lys Asp Arg Ser Pro Tyr Arg Thr Leu Met Ser Val Glu
145                 150                 155                 160

Ile Gly Gln Ser Pro Asn Val Tyr Gln Ala Arg Phe Glu Ala Val Ala
                165                 170                 175
```

```
Trp Ser Ala Thr Ala Cys His Asp Gly Lys Lys Trp Met Thr Ile Gly
                180                 185                 190

Val Thr Gly Pro Asp Ala Lys Ala Val Ala Val Val His Tyr Gly Gly
            195                 200                 205

Ile Pro Thr Asp Val Ile Asn Ser Trp Ala Gly Asp Ile Leu Arg Thr
        210                 215                 220

Gln Glu Ser Ser Cys Thr Cys Ile Gln Gly Glu Cys Tyr Trp Val Met
225                 230                 235                 240

Thr Asp Gly Pro Ala Asn Arg Gln Ala Gln Tyr Arg Ala Phe Lys Ala
                245                 250                 255

Lys Gln Gly Lys Ile Val Gly Gln Thr Glu Ile Ser Phe Asn Gly Ser
            260                 265                 270

His Ile Glu Glu Cys Ser Cys Tyr Pro Asn Glu Gly Lys Val Glu Cys
        275                 280                 285

Val Cys Arg Asp Asn Trp Thr Gly Thr Asn Arg Pro Val Leu Val Ile
        290                 295                 300

Ser Pro Asp Leu Ser Tyr Arg Ala Gly Tyr Leu Cys Ala Gly Leu Pro
305                 310                 315                 320

Ser Asp Thr Pro Arg Gly Glu Asp Ser Gln Phe Thr Gly Ser Cys Thr
                325                 330                 335

Ser Pro Val Gly Asn Gln Gly Tyr Gly Val Lys Gly Phe Gly Phe Arg
            340                 345                 350

Gln Gly Asn Asp Val Trp Met Gly Arg Thr Ile Ser Arg Thr Ser Arg
        355                 360                 365

Ser Gly Phe Glu Ile Leu Lys Val Arg Asn Gly Trp Val Gln Asn Ser
        370                 375                 380

Lys Glu Gln Ile Lys Arg Gln Val Val Asp Asn Leu Lys Trp Ser
385                 390                 395                 400

Gly Tyr Ser Gly Ser Phe Thr Leu Pro Val Glu Leu Thr Lys Arg Asn
                405                 410                 415

Cys Leu Val Pro Cys Phe Trp Val Glu Met Ile Arg Gly Lys Pro Glu
            420                 425                 430

Glu Lys Thr Ile Trp Thr Ser Ser Ser Ile Val Met Cys Gly Val
        435                 440                 445

Asp His Glu Ile Ala Asp Trp Ser Trp His Asp Gly Ala Ile Leu Pro
        450                 455                 460

Phe Asp Ile Asp Lys Met
465                 470

<210> SEQ ID NO 35
<211> LENGTH: 465
<212> TYPE: PRT
<213> ORGANISM: Influenza virus

<400> SEQUENCE: 35

Met Asn Pro Asn Gln Lys Ile Leu Cys Thr Ser Ala Thr Ala Ile Ile
1               5                   10                  15

Ile Gly Ala Ile Ala Val Leu Ile Gly Ile Ala Asn Leu Gly Leu Asn
            20                  25                  30

Ile Gly Leu His Leu Lys Pro Gly Cys Asn Cys Ser His Ser Gln Pro
        35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80
```

-continued

```
Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Thr Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240

Gly Ser Ala Thr Gly Pro Ala Asp Thr Arg Ile Tyr Tyr Phe Lys Glu
                245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
        275                 280                 285

Arg Asp Asn Trp Gln Gly Ser Asn Arg Pro Val Ile Gln Ile Asp Pro
    290                 295                 300

Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
                325                 330                 335

Tyr Pro Gly Asn Asn Asn Gly Val Lys Gly Phe Ser Tyr Leu Asp
            340                 345                 350

Gly Ala Asn Thr Trp Leu Gly Arg Thr Ile Ser Thr Ala Ser Arg Ser
        355                 360                 365

Gly Tyr Glu Met Leu Lys Val Pro Asn Ala Leu Thr Asp Asp Arg Ser
    370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
        435                 440                 445

Phe Leu Gly Gln Trp Asn Trp Pro Asp Gly Ala Lys Ile Glu Tyr Phe
    450                 455                 460

Leu
465

<210> SEQ ID NO 36
```

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39
<211> LENGTH: 2341
<212> TYPE: DNA
<213> ORGANISM: Influenza virus

<400> SEQUENCE: 39

```
agcgaaagca ggtcaattat attcaatatg gaaagaataa aagaactaag aaatctaatg      60
tcgcagtctc gcacccgcga gatactcaca aaaaccaccg tggaccatat ggccataatc     120
aagaagtaca catcaggaag acaggagaag aacccagcac ttaggatgaa atggatgatg     180
gcaatgaaat atccaattac agcagacaag aggataacgg aaatgattcc tgagagaaat     240
gagcaaggac aaactttatg gagtaaaatg aatgatgccg atcagaccg  agtgatggta     300
tcacctctgg ctgtgacatg gtggaatagg aatggaccaa tgacaaatac agttcattat     360
ccaaaaatct acaaaactta ttttgaaaga gtcgaaaggc taaagcatgg aaccttttggc    420
cctgtccatt ttagaaacca agtcaaaata cgtcggagag ttgacataaa tcctggtcat     480
gcagatctca gtgccaagga ggcacaggat gtaatcatgg aagttgtttt ccctaacgaa     540
gtgggagcca ggatactaac atcggaatcg caactaacga taaccaaaga gaagaaagaa     600
gaactccagg attgcaaaat ttctcctttg atggttgcat acatgttgga gagagaactg     660
gtccgcaaaa cgagattcct cccagtggct ggtggaacaa gcagtgtgta cattgaagtg     720
ttgcatttga ctcaaggaac atgctgggaa cagatgtata ctccaggagg ggaagtgaag     780
aatgatgatg ttgatcaaag cttgattatt gctgctagga catagtgag  aagagctgca     840
gtatcagcag acccactagc atctttattg agatgtgcc  acagcacaca gattggtgga     900
attaggatgg tagacatcct taagcagaac ccaacagaag agcaagccgt ggatatatgc     960
aaggctgcaa tgggactgag aattagctca tccttcagtt ttggtggatt cacatttaag    1020
agaacaagcg gatcatcagt caagagagag gaagaggtgc ttacgggcaa tcttcaaaca    1080
ttgaagataa gagtgcatga gggatctgaa gagttcacaa tggttgggag aagagcaaca    1140
gccatactca gaaaagcaac caggagattg attcagctga tagtgagtgg gagagacgaa    1200
cagtcgattg ccgaagcaat aattgtggcc atggtatttt cacaagagga ttgtatgata    1260
aaagcagtta gaggtgatct gaatttcgtc aataggggcga atcagcgact gaatcctatg    1320
catcaacttt taagacattt tcagaaggat gcgaaagtgc ttttttcaaaa ttggggagtt    1380
gaacctatcg acaatgtgat gggaatgatt gggatattgc ccgacatgac tccaagcatc    1440
gagatgtcaa tgagaggagt gagaatcagc aaaatgggtg tagatgagta ctccagcacg    1500
gagagggtag tggtgagcat tgaccggttc ttgagagtca gggaccaacg aggaaatgta    1560
ctactgtctc ccgaggaggt cagtgaaaca caggggaacag agaaactgac aataacttac    1620
```

-continued

```
tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg gacatttgat    1860
accgcacaga taataaaact tcttcccttc gcagccgctc caccaaagca agtagaatg     1920 cagttctcct catttactgt gaatgtgagg ggatcaggaa tgagaatact tgtaaggggc    1980
aattctcctg tattcaacta caacaaggcc acgaagagac tcacagttct cggaaaggat    2040
gctggcactt taaccgaaga cccagatgaa ggcacagctg gagtggagtc cgctgttctg    2100
aggggattcc tcattctggg caaagaagac aggagatatg gccagcattt aagcatcaat    2160
gaactgagca accttgcgaa aggagagaag gctaatgtgc taattgggca aggagacgtg    2220
gtgttggtaa tgaaacgaaa acgggactct agcatactta ctgacagcca gacagcgacc    2280
aaaagaattc ggatggccat caattagtgt cgaatagttt aaaaacgacc ttgtttctac    2340
t                                                                    2341
```

<210> SEQ ID NO 40
<211> LENGTH: 2341
<212> TYPE: DNA
<213> ORGANISM: Influenza virus

<400> SEQUENCE: 40

```
agcgaaagca ggcaaaccat ttgaatggat gtcaatccga ccttactttt cttaaaagtg      60
ccagcacaaa atgctataag cacaactttc ccttataccg gagaccctcc ttacagccat     120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaagcaatg    300
gctttccttg aggaatccca tcctggtatt tttgaaaact cgtgtattga acgatggag     360 gttgttcagc aaacacgagt agacaagctg acacaaggcc gacagaccta tgactggact    420
ttaaatagaa accagcctgc tgcaacagca ttggccaaca caatagaagt gttcagatca    480
aatggcctca cggccaatga gtcaggaagg ctcatagact tccttaagga tgtaatggag    540
tcaatgaaaa aagaagaaat ggggatcaca actcattttc agagaaagag acgggtgaga    600
gacaatatga ctaagaaaat gataacacag agaacaatag gtaaaaggaa acagagattg    660
aacaaaaggg gttatctaat tagagcattg accctgaaca caatgaccaa agatgctgag    720
agagggaagc taaaacggag agcaattgca ccccaggga tgcaaataag ggggtttgta    780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttcaccatc actggagata caccaaatg gaacgaaaat    960 cagaatcctc ggatgttttt ggccatgatc acatatatga ccagaaatca gcccgaatgg   1020
ttcagaaatg ttctaagtat tgctccaata atgttctcaa acaaaatggc gagactggga   1080
aaagggtata tgtttgagag caagagtatg aaacttagaa ctcaaatacc tgcagaaatg   1140
ctagcaagca ttgatttgaa atatttcaat gattcaacaa gaagaagat tgaaaaaatc   1200 cgaccgctct aatagagggg gactgcatca ttgagccctg aatgatgat gggcatgttc   1260 aatatgttaa gcactgtatt aggcgtctcc atcctgaatc ttggacaaaa gagatacacc   1320
```

-continued

| | |
|---|---|
| aagactactt actggtggga tggtcttcaa tcctctgacg attttgctct gattgtgaat | 1380 |
| gcacccaatc atgaagggat tcaagccgga gtcgacaggt tttatcgaac ctgtaagcta | 1440 |
| cttggaatca atatgagcaa gaaaaagtct tacataaaca gaacaggtac atttgaattc | 1500 |
| acaagttttt tctatcgtta tgggtttgtt gccaatttca gcatggagct tcccagtttt | 1560 |
| ggggtgtctg ggatcaacga gtcagcggac atgagtattg gagttactgt catcaaaaac | 1620 |
| aatatgataa acaatgatct tggtccagca acagctcaaa tggcccttca gttgttcatc | 1680 |
| aaagattaca ggtacacgta ccgatgccat agaggtgaca cacaaataca aacccgaaga | 1740 |
| tcatttgaaa taaagaaact gtgggagcaa acccgttcca agctggact gctggtctcc | 1800 |
| gacggaggcc caaatttata caacattaga atctccaca ttcctgaagt ctgcctaaaa | 1860 |
| tgggaattga tggatgagga ttaccagggg cgtttatgca cccactgaa cccatttgtc | 1920 |
| agccataaag aaattgaatc aatgaacaat gcagtgatga tgccagcaca tggtccagcc | 1980 |
| aaaaacatgg agtatgatgc tgttgcaaca acacactcct ggatcccca aagaaatcga | 2040 |
| tccatcttga atacaagtca agaggagta cttgaagatg aacaaatgta ccaaaggtgc | 2100 |
| tgcaatttat ttgaaaaatt cttccccagc agttcataca aagaccagt cgggatatcc | 2160 |
| agtatggtgg aggctatggt ttccagagcc cgaattgatg cacggattga tttcgaatct | 2220 |
| ggaaggataa agaaagaaga gttcactgag atcatgaaga tctgttccac cattgaagag | 2280 |
| ctcgagacgg caaaaatagtg aatttagctt gtccttcatg aaaaaatgcc ttgtttctac | 2340 |
| t | 2341 |

<210> SEQ ID NO 41
<211> LENGTH: 2233
<212> TYPE: DNA
<213> ORGANISM: Influenza virus

<400> SEQUENCE: 41

| | |
|---|---|
| agcgaaagca ggtactgatt caaaatggaa gattttgtgc gacaatgctt caatccgatg | 60 |
| attgtcgagc ttgcggaaaa aacaatgaaa gagtatgggg aggacctgaa atcgaaaca | 120 |
| aacaaatttg cagcaatatg cactcacttg gaagtatgct tcatgtattc agatttccac | 180 |
| ttcatcaatg agcaaggcga gtcaataatc gtagaacttg gtgatcctaa tgcacttttg | 240 |
| aagcacagat ttgaaataat cgagggaaga gatcgcacaa tggcctggac agtagtaaac | 300 |
| agtatttgca acactacagg ggctgagaaa ccaaagtttc taccagattt gtatgattac | 360 |
| aaggaaaata gattcatcga aattggagta acaaggagag aagttcacat atactatctg | 420 |
| gaaaaggcca ataaaattaa atctgagaaa acacacatcc acattttctc gttcactggg | 480 |
| gaagaaatgg ccacaagggc cgactacact ctcgatgaag aaagcagggc taggatcaaa | 540 |
| accaggctat tcaccataag acaagaaatg gccagcagag gcctctggga ttcctttcgt | 600 |
| cagtccgaga gaggagaaga gacaattgaa gaaaggtttg aatcacagg acaatgcgc | 660 |
| aagcttgccg accaaagtct cccgccgaac ttctccagcc ttgaaaattt tagagcctat | 720 |
| gtggatggat tcgaaccgaa cggctacatt gagggcaagc tgtctcaaat gtccaaagaa | 780 |
| gtaaatgcta gaattgaacc ttttttgaaa acaacaccac gaccacttag acttccgaat | 840 |
| gggcctccct gttctcagcg gtccaaattc ctgctgatgg atgccttaaa attaagcatt | 900 |
| gaggacccaa gtcatgaagg agagggaata ccgctatatg atgcaatcaa atgcatgaga | 960 |
| acattctttg gatggaagga acccaatgtt gttaaaccac acgaaaaggg aataaatcca | 1020 |
| aattatcttc tgtcatggaa gcaagtactg gcagaactgc aggacattga gaatgaggag | 1080 |

| | | | | |
|---|---|---|---|---|
| aaaattccaa | agactaaaaa | tatgaaaaaa | acaagtcagc | taaagtgggc | acttggtgag | 1140 |
| aacatggcac | cagaaaaggt | agactttgac | gactgtaaag | atgtaggtga | tttgaagcaa | 1200 |
| tatgatagtg | atgaaccaga | attgaggtcg | cttgcaagtt | ggattcagaa | tgagttcaac | 1260 |
| aaggcatgcg | aactgacaga | ttcaagctgg | atagagcttg | atgagattgg | agaagatgtg | 1320 |
| gctccaattg | aacacattgc | aagcatgaga | aggaattatt | tcacatcaga | ggtgtctcac | 1380 |
| tgcagagcca | cagaatacat | aatgaagggg | gtgtacatca | atactgcctt | acttaatgca | 1440 |
| tcttgtgcag | caatggatga | tttccaatta | attccaatga | taagcaagtg | tagaactaag | 1500 |
| gagggaaggc | gaaagaccaa | cttgtatggt | ttcatcataa | aaggaagatc | ccacttaagg | 1560 |
| aatgacaccg | acgtggtaaa | ctttgtgagc | atggagtttt | ctctcactga | cccaagactt | 1620 |
| gaaccacaca | aatgggagaa | gtactgtgtt | cttgagatag | agatatgct | tctaagaagt | 1680 |
| gccataggcc | aggtttcaag | gcccatgttc | ttgtatgtga | ggacaaatgg | aacctcaaaa | 1740 |
| attaaaatga | aatggggaat | ggagatgagg | cgttgtctcc | tccagtcact | tcaacaaatt | 1800 |
| gagagtatga | ttgaagctga | gtcctctgtc | aaagagaaag | acatgaccaa | agagttcttt | 1860 |
| gagaacaaat | cagaaacatg | gcccattgga | gagtctccca | aggagtggga | ggaaagttcc | 1920 |
| attgggaagg | tctgcaggac | tttattagca | aagtcggtat | ttaacagctt | gtatgcatct | 1980 |
| ccacaactag | aaggattttc | agctgaatca | agaaaactgc | ttcttatcgt | tcaggctctt | 2040 |
| agggacaatc | tggaacctgg | gacctttgat | cttggggggc | tatatgaagc | aattgaggag | 2100 |
| tgcctaatta | atgatccctg | ggttttgctt | aatgcttctt | ggttcaactc | cttccttaca | 2160 |
| catgcattga | gttagttgtg | gcagtgctac | tatttgctat | ccatactgtc | caaaaaagta | 2220 |
| ccttgtttct | act | | | | | 2233 |

<210> SEQ ID NO 42
<211> LENGTH: 1565
<212> TYPE: DNA
<213> ORGANISM: Influenza virus

<400> SEQUENCE: 42

| | | | | | | |
|---|---|---|---|---|---|---|
| agcaaaagca | gggtagataa | tcactcactg | agtgacatca | aaatcatggc | gtcccaaggc | 60 |
| accaaacggt | cttacgaaca | gatggagact | gatggagaac | gccagaatgc | cactgaaatc | 120 |
| agagcatccg | tcgaaaaaat | gattggtgga | attggacgat | tctacatcca | aatgtgcaca | 180 |
| gaacttaaac | tcagtgatta | tgagggacgg | ttgatccaaa | acagcttaac | aatagagaga | 240 |
| atggtgctct | ctgcttttga | cgaaaggaga | aataaatacc | tggaagaaca | tcccagtgcg | 300 |
| gggaaagatc | ctaagaaaac | tggaggacct | atatacagaa | gagtaaacgg | aaagtggatg | 360 |
| agagaactca | tcctttatga | caagaagaa | ataaggcgaa | tctggcgcca | agctaataat | 420 |
| ggtgacgatg | caacggctgg | tctgactcac | atgatgatct | ggcattccaa | tttgaatgat | 480 |
| gcaacttatc | agaggacaag | ggctcttgtt | cgcaccggaa | tggatcccag | gatgtgctct | 540 |
| ctgatgcaag | gttcaactct | ccctaggagg | tctggagccg | caggtgctgc | agtcaaagga | 600 |
| gttggaacaa | tggtgatgga | attggtcagg | atgatcaaac | gtgggatcaa | tgatcggaac | 660 |
| ttctggaggg | gtgagaatgg | acgaaaaaca | agaattgctt | atgaaagaat | gtgcaacatt | 720 |
| ctcaaaggga | aatttcaaac | tgctgcacaa | aaagcaatga | tggatcaagt | gagagagagc | 780 |
| cggaacccag | gaatgctga | gttcgaagat | ctcactttc | tagcacgtc | tgcactcata | 840 |
| ttgagagggt | cggttgctca | caagtcctgc | ctgcctgcct | gtgtgtatgg | acctgccgta | 900 |

| | |
|---|---:|
| gccagtgggt acgactttga agagaggga tactctctag tcggaataga ccctttcaga | 960 |
| ctgcttcaaa acagccaagt gtacagccta atcagaccaa atgagaatcc agcacacaag | 1020 |
| agtcaactgg tgtggatggc atgccattct gccgcatttg aagatctaag agtattgagc | 1080 |
| ttcatcaaag ggacgaaggt ggtcccaaga gggaagcttt ccactagagg agttcaaatt | 1140 |
| gcttccaatg aaaatatgga gactatggaa tcaagtacac ttgaactgag aagcaggtac | 1200 |
| tgggccataa ggaccagaag tggaggaaac accaatcaac agagggcatc tgcgggccaa | 1260 |
| atcagcatac aacctacgtt ctcagtacag agaaatctcc cttttgacag aacaaccgtt | 1320 |
| atggcagcat tcactgggaa tacagagggg agaaacatctg acatgaggac cgaaatcata | 1380 |
| aggatgatgg aaagtgcaag accagaagat gtgtctttcc aggggcgggg agtcttcgag | 1440 |
| ctctcggacg aaaaggcagc gagcccgatc gtgccttcct ttgacatgag taatgaagga | 1500 |
| tcttatttct tcggagacaa tgcagaggag tacgacaatt aaagaaaaat acccttgttt | 1560 |
| ctact | 1565 |

<210> SEQ ID NO 43
<211> LENGTH: 1027
<212> TYPE: DNA
<213> ORGANISM: Influenza virus

<400> SEQUENCE: 43

| | |
|---|---:|
| agcaaaagca ggtagatatt gaaagatgag tcttctaacc gaggtcgaaa cgtacgttct | 60 |
| ctctatcatc ccgtcaggcc cctcaaagc cgagatcgca cagagacttg aagatgtctt | 120 |
| tgcagggaag aacaccgatc ttgaggttct catggaatgg ctaaagacaa gaccaatcct | 180 |
| gtcacctctg actaagggga ttttaggatt tgtgttcacg ctcaccgtgc ccagtgagcg | 240 |
| aggactgcag cgtagacgct ttgtccaaaa tgcccttaat gggaacgggg atccaaataa | 300 |
| catggacaaa gcagttaaac tgtataggaa gctcaagagg gagataacat tccatggggc | 360 |
| caaagaaatc tcactcagtt attctgctgg tgcacttgcc agttgtatgg gcctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaacccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctaggcaaat | 660 |
| ggtgcaagcg atgagaacca ttgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cgctattgcc gcaaatatca ttgggatctt gcacttgata ttgtggattc | 840 |
| ttgatcgtct ttttttcaaa tgcatttacc gtcgctttaa atacggactg aaaggagggc | 900 |
| cttctacgga aggagtgcca aagtctatga gggaagaata tcgaaggaa cagcagagtg | 960 |
| ctgtggatgc tgacgatggt cattttgtca gcatagagct ggagtaaaaa actaccttgt | 1020 |
| ttctact | 1027 |

<210> SEQ ID NO 44
<211> LENGTH: 890
<212> TYPE: DNA
<213> ORGANISM: Influenza virus

<400> SEQUENCE: 44

| | |
|---|---:|
| agcaaaagca gggtgacaaa gacataatgg atccaaacac tgtgtcaagc tttcaggtag | 60 |
| attgctttct ttggcatgtc cgcaaacgag ttgcagacca agaactaggt gatgccccat | 120 |

```
tccttgatcg gcttcgccga gatcagaaat ccctaagagg aaggggcagc actcttggtc    180
tggacatcga gacagccaca cgtgctggaa agcagatagt ggagcggatt ctgaaagaag    240
aatccgatga ggcacttaaa atgaccatgg cctctgtacc tgcgtcgcgt tacctaaccg    300
acatgactct tgaggaaatg tcaagggaat ggtccatgct catacccaag cagaaagtgg    360
caggccctct ttgtatcaga atggaccagg cgatcatgga taaaaacatc atactgaaag    420
cgaacttcag tgtgattttt gaccggctgg agactctaat attgctaagg gctttcaccg    480
aagagggagc aattgttggc gaaatttcac cattgccttc tcttccagga catactgctg    540
aggatgtcaa aaatgcagtt ggagtcctca tcggaggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga aggtaacaga aatagttttt    780
gagcaaataa catttatgca agccttacat ctattgcttg aagtggagca agagataaga    840
actttctcat ttcagcttat ttaataataa aaaacaccct tgtttctact    890

<210> SEQ ID NO 45

<400> SEQUENCE: 45

000

<210> SEQ ID NO 46
<211> LENGTH: 1701
<212> TYPE: DNA
<213> ORGANISM: Influenza virus

<400> SEQUENCE: 46
atgaagacta tcattgcttt gagctacatt ctatgtctgg ttttcgctca aaaaattcct     60
ggaaatgaca atagcacggc aacgctgtgc cttgggcacc atgcagtacc aaacggaacg    120
atagtgaaaa caatcacaaa tgaccgaatt gaagttacta atgctactga gttggttcag    180
aattcctcaa taggtgaaat atgcgacagt cctcatcaga tccttgatgg agagaactgc    240
acactaatag atgctctatt gggagaccct cagtgtgatg gctttcaaaa taagaaatgg    300 gaccttttg ttgaacgaag caaagcctac agcaactgtt accctatga tgtgccggat    360 tatgcctccc ttaggtcact agttgcctca tccggcacac tggagtttaa aaatgaaagc    420
ttcaattgga ctggagtcac tcaaaacgga acaagttctg cttgcataag gggatctagt    480 agtagttct ttagtagatt aaattggttg acccacttaa actacacata tccagcattg    540
aacgtgacta tgccaaacaa ggaacaattt gacaaattgt acatttgggg ggttcaccac    600
ccgggtacgg acaaggacca atcttcctg tatgctcaat catcaggaag aatcacagta    660
tctaccaaaa gaagccaaca agctgtaatc ccaaatatcg gatctagacc cagaataagg    720
gatatcccta gcagaataag catctattgg acaaatagta aaccgggaga catactttg    780 attaacagca cagggaatct aattgctcct agggggttact tcaaaatacg aagtgggaaa    840
agctcaataa tgagatcaga tgcacccatt ggcaaatgca gtctgaatg catcactcca    900 aatggaagca ttcccaatga caaaccattc caaaatgtaa acaggatcac atacggggcc    960
tgtcccagat atgttaagca tagcactctg aaattggcaa caggaatgcg aaatgtacca   1020
gagaaacaaa ctagaggcat atttggcgca atagcgggtt tcatagaaaa tggttgggag   1080
ggaatggtgg atggttggta cggtttcagg catcaaaatt ctgagggaag aggacaagca   1140
```

| | |
|---|---|
| gcagatctca aaagcactca agcagcaatc gatcaaatca atgggaagct gaataggttg | 1200 |
| atcggaaaaa ccaacgagaa attccatcag attgaaaaag aattctcaga agtagaagga | 1260 |
| agagttcaag accttgagaa atatgttgag gacactaaaa tagatctctg gtcatacaac | 1320 |
| gcggagcttc ttgttgccct ggagaaccaa catacaattg atctaactga ctcagaaatg | 1380 |
| aacaaactgt ttgaaaaaac aagaagcaa ctgagggaaa atgctgagga tatgggaaat | 1440 |
| ggttgtttca aaatatacca caaatgtgac aatgcctgca tagaatcaat aagaaatgaa | 1500 |
| acttatgacc acaatgtgta cagggatgaa gcattgaaca accggttcca gatcaaggga | 1560 |
| gttgagctga agtcaggata caaagattgg atcctatgga tttcctttgc catatcatgt | 1620 |
| tttttgcttt gtgttgcttt gttggggttc atcatgtggg cctgccaaaa gggcaacatt | 1680 |
| agatgcaaca tttgcattg a | 1701 |

<210> SEQ ID NO 47
<211> LENGTH: 1410
<212> TYPE: DNA
<213> ORGANISM: Influenza virus
<400> SEQUENCE: 47

| | |
|---|---|
| atgaatccaa atcaaaagat aataacgatt ggctctgttt ctctcaccat ttccacaata | 60 |
| tgcttcttca tgcaaattgc catcctgata actactgtaa cattgcattt caagcaatat | 120 |
| gaattcaact cccccccaaa caaccaagtg atgctgtgtg aaccaacaat aatagaaaga | 180 |
| aacataacag atagtgtata tttgaccaac accaccatag agaaggaaat atgccccaaa | 240 |
| ccagcagaat acagaaattg gtcaaaaccg caatgtggca ttacaggatt tgcacctttc | 300 |
| tctaaggaca attcgattag ctttccgct ggtggggaca tctgggtgac aagagaacct | 360 |
| tatgtgtcat gcgatcctga caagtgttat caatttgccc ttggacaggg aacaacacta | 420 |
| aacaacgtgc attcaaataa cacagtacgt gataggaccc cttatcggac tctattgatg | 480 |
| aatgagttgg gtgttccttt ccatctgggg accaagcaag tgtgcatagc atggtccagc | 540 |
| tcaagttgtc acgatggaaa agcatggctg catgtttgta taacggggga tgataaaaat | 600 |
| gcaactgcta gcttcattta caatgggagg cttatagata gtgttgtttc atggtccaaa | 660 |
| gatattctca ggacccagga gtcagaatgc gtttgtatca atggaacttg tacagtagta | 720 |
| atgactgatg gaaatgctac aggaaaagct gatactaaaa tactattcat tgaggagggg | 780 |
| aaaatcgttc atactagcaa attgtcagga agtgctcagc atgtcgaaga gtgctcttgc | 840 |
| tatcctcgat atcctggtgt cagatgtgtc tgcagagaca actggaaagg atccaaccgg | 900 |
| cccatcgtag atataaacat aaaggatcat agcattgttt ccagttatgt gtgttcagga | 960 |
| cttgttggag acacacccag aaaaaacgac agctccagca gtagccattg tttgaatcct | 1020 |
| aacaatgaag aaggtggtca tggagtgaaa ggctgggcct ttgatgatgg aaatgacgtg | 1080 |
| tggatgggga gaacaatcaa cgagacgtca cgcttaggt atgaaaccttt caaagtcgtt | 1140 |
| gaaggctggt ccaaccctaa gtccaaattg cagataaata ggcaagtcat agttgacaga | 1200 |
| ggtgataggt ccggttattc tggtattttc tctgttgaag caaaagctg catcaatcgg | 1260 |
| tgcttttatg tggagttgat taggggaaga aagaggaaa ctgaagtctt gtggaccctca | 1320 |
| aacagtattg ttgtgttttg tggcacctca ggtacatatg gaacaggctc atggcctgat | 1380 |
| ggggcggacc tcaatctcat gcatatataa | 1410 |

<210> SEQ ID NO 48

<211> LENGTH: 469
<212> TYPE: PRT
<213> ORGANISM: Influenza virus

<400> SEQUENCE: 48

```
Met Asn Pro Asn Gln Lys Ile Ile Thr Ile Gly Ser Val Ser Leu Thr
1               5                   10                  15
Ile Ser Thr Ile Cys Phe Phe Met Gln Ile Ala Ile Leu Ile Thr Thr
                20                  25                  30
Val Thr Leu His Phe Lys Gln Tyr Glu Phe Asn Ser Pro Pro Asn Asn
            35                  40                  45
Gln Val Met Leu Cys Glu Pro Thr Ile Ile Glu Arg Asn Ile Thr Glu
    50                  55                  60
Ile Val Tyr Leu Thr Asn Thr Thr Ile Glu Lys Glu Ile Cys Pro Lys
65                  70                  75                  80
Pro Ala Glu Tyr Arg Asn Trp Ser Lys Pro Gln Cys Gly Ile Thr Gly
                85                  90                  95
Phe Ala Pro Phe Ser Lys Asp Asn Ser Ile Arg Leu Ser Ala Gly Gly
            100                 105                 110
Asp Ile Trp Val Thr Arg Glu Pro Tyr Val Ser Cys Asp Pro Asp Lys
        115                 120                 125
Cys Tyr Gln Phe Ala Leu Gly Gln Gly Thr Thr Leu Asn Asn Val His
130                 135                 140
Ser Asn Asn Thr Val Arg Asp Arg Thr Pro Tyr Arg Thr Leu Leu Met
145                 150                 155                 160
Asn Glu Leu Gly Val Pro Phe His Leu Gly Thr Lys Gln Val Cys Ile
                165                 170                 175
Ala Trp Ser Ser Ser Ser Cys His Asp Gly Lys Ala Trp Leu His Val
            180                 185                 190
Cys Ile Thr Gly Asp Asp Lys Asn Ala Thr Ala Ser Phe Ile Tyr Asn
        195                 200                 205
Gly Arg Leu Ile Asp Ser Val Val Ser Trp Ser Lys Asp Ile Leu Arg
    210                 215                 220
Thr Gln Glu Ser Glu Cys Val Cys Ile Asn Gly Thr Cys Thr Val Val
225                 230                 235                 240
Met Thr Asp Gly Asn Ala Thr Gly Lys Ala Asp Thr Lys Ile Leu Phe
                245                 250                 255
Ile Glu Glu Gly Lys Ile Val His Thr Ser Lys Leu Ser Gly Ser Ala
            260                 265                 270
Gln His Val Glu Glu Cys Ser Cys Tyr Pro Arg Tyr Pro Gly Val Arg
        275                 280                 285
Cys Val Cys Arg Asp Asn Trp Lys Gly Ser Asn Arg Pro Ile Val Asp
    290                 295                 300
Ile Asn Ile Lys Asp His Ser Ile Val Ser Ser Tyr Val Cys Ser Gly
305                 310                 315                 320
Leu Val Gly Asp Thr Pro Arg Lys Asn Asp Ser Ser Ser Ser His
                325                 330                 335
Cys Leu Asn Pro Asn Asn Glu Glu Gly Gly His Gly Val Lys Gly Trp
            340                 345                 350
Ala Phe Asp Asp Gly Asn Asp Val Trp Met Gly Arg Thr Ile Asn Glu
        355                 360                 365
Thr Ser Arg Leu Gly Tyr Glu Thr Phe Lys Val Val Glu Gly Trp Ser
    370                 375                 380
Asn Pro Lys Ser Lys Leu Gln Ile Asn Arg Gln Val Ile Val Asp Arg
```

```
385                 390                 395                 400
Gly Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Glu
                420                 425                 430

Glu Thr Glu Val Leu Trp Thr Ser Asn Ser Ile Val Phe Cys Gly
                435                 440                 445

Thr Ser Gly Thr Tyr Gly Thr Gly Ser Trp Pro Asp Gly Ala Asp Leu
    450                 455                 460

Asn Leu Met His Ile
465

<210> SEQ ID NO 49
<211> LENGTH: 469
<212> TYPE: PRT
<213> ORGANISM: Influenza virus

<400> SEQUENCE: 49

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
                20                  25                  30

Val Thr Leu His Phe Lys Gln Tyr Glu Phe Asn Ser Pro Pro Asn Asn
            35                  40                  45

Gln Val Met Leu Cys Glu Pro Thr Ile Ile Glu Arg Asn Ile Thr Glu
        50                  55                  60

Ile Val Tyr Leu Thr Asn Thr Thr Ile Glu Lys Glu Ile Cys Pro Lys
65                  70                  75                  80

Pro Ala Glu Tyr Arg Asn Trp Ser Lys Pro Gln Cys Gly Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Val His
    130                 135                 140

Ser Asn Asn Thr Val Arg Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
            180                 185                 190

Cys Ile Thr Gly Asp Asp Lys Asn Ala Thr Ala Ser Phe Ile Tyr Asn
        195                 200                 205

Gly Arg Leu Val Asp Ser Val Val Ser Trp Ser Lys Asp Ile Leu Arg
    210                 215                 220

Thr Gln Glu Ser Glu Cys Val Cys Ile Asn Gly Thr Cys Thr Val Val
225                 230                 235                 240

Met Thr Asp Gly Asn Ala Thr Gly Lys Ala Asp Thr Lys Ile Leu Phe
                245                 250                 255

Ile Glu Glu Gly Lys Ile Val His Thr Ser Lys Leu Ser Gly Ser Ala
            260                 265                 270

Gln His Val Glu Glu Cys Ser Cys Tyr Pro Arg Tyr Pro Gly Val Arg
        275                 280                 285
```

```
Cys Val Cys Arg Asp Asn Trp Lys Gly Ser Asn Arg Pro Ile Val Asp
    290                 295                 300
Ile Asn Ile Lys Asp His Ser Ile Val Ser Ser Tyr Val Cys Ser Gly
305                 310                 315                 320
Leu Val Gly Asp Thr Pro Arg Lys Asn Asp Ser Ser Ser Ser His
                325                 330                 335
Cys Leu Asn Pro Asn Asn Glu Glu Gly Gly His Gly Val Lys Gly Trp
                340                 345                 350
Ala Phe Asp Asp Gly Asn Asp Val Trp Met Gly Arg Thr Ile Asn Glu
                355                 360                 365
Thr Ser Arg Leu Gly Tyr Glu Thr Phe Lys Val Val Glu Gly Trp Ser
370                 375                 380
Asn Pro Lys Ser Lys Leu Gln Ile Asn Arg Gln Val Ile Val Asp Arg
385                 390                 395                 400
Gly Asp Arg Ser Gly Tyr Ser Gly Ile Phe Ser Val Glu Gly Lys Ser
                405                 410                 415
Cys Ile Asn Arg Cys Phe Tyr Val Glu Leu Ile Arg Gly Arg Lys Glu
                420                 425                 430
Glu Thr Glu Val Leu Trp Thr Ser Asn Ser Ile Val Val Phe Cys Gly
                435                 440                 445
Thr Ser Gly Thr Tyr Gly Thr Gly Ser Trp Pro Asp Gly Ala Asp Leu
    450                 455                 460
Asn Leu Met His Ile
465

<210> SEQ ID NO 50

<400> SEQUENCE: 50

000

<210> SEQ ID NO 51
<211> LENGTH: 469
<212> TYPE: PRT
<213> ORGANISM: Influenza virus

<400> SEQUENCE: 51

Met Asn Pro Asn Gln Lys Ile Ile Thr Ile Gly Ser Val Cys Met Thr
1               5                   10                  15
Ile Gly Met Ala Asn Leu Ile Leu Gln Ile Gly Asn Ile Ile Ser Ile
                20                  25                  30
Trp Ile Ser His Ser Ile Gln Leu Gly Asn Gln Asn Gln Ile Glu Thr
            35                  40                  45
Cys Asn Gln Ser Val Ile Thr Tyr Glu Asn Asn Thr Trp Val Asn Gln
    50                  55                  60
Thr Tyr Val Asn Ile Ser Asn Thr Asn Phe Ala Ala Gly Gln Ser Val
65                  70                  75                  80
Val Ser Val Lys Leu Ala Gly Asn Ser Ser Leu Cys Pro Val Ser Gly
                85                  90                  95
Trp Ala Ile Tyr Ser Lys Asp Asn Ser Val Arg Ile Gly Ser Lys Gly
                100                 105                 110
Asp Val Phe Val Ile Arg Glu Pro Phe Ile Ser Cys Ser Pro Leu Glu
            115                 120                 125
Cys Arg Thr Phe Phe Leu Thr Gln Gly Ala Leu Leu Asn Asp Lys His
    130                 135                 140
Ser Asn Gly Thr Ile Lys Asp Arg Ser Pro Tyr Arg Thr Leu Met Ser
```

```
                145                 150                 155                 160
Cys Pro Ile Gly Glu Val Pro Ser Pro Tyr Asn Ser Arg Phe Glu Ser
                165                 170                 175
Val Ala Trp Ser Ala Ser Ala Cys His Asp Gly Ile Asn Trp Leu Thr
                180                 185                 190
Ile Gly Ile Ser Gly Pro Asp Asn Gly Ala Val Ala Val Leu Lys Tyr
                195                 200                 205
Asn Gly Ile Ile Thr Asp Thr Ile Lys Ser Trp Arg Asn Asn Ile Leu
            210                 215                 220
Arg Thr Gln Glu Ser Glu Cys Ala Cys Val Asn Gly Ser Cys Phe Thr
225                 230                 235                 240
Val Met Thr Asp Gly Pro Ser Asn Gly Gln Ala Ser Tyr Lys Ile Phe
                245                 250                 255
Arg Ile Glu Lys Gly Lys Ile Val Lys Ser Val Glu Met Asn Ala Pro
                260                 265                 270
Asn Tyr His Tyr Glu Glu Cys Ser Cys Tyr Pro Asp Ser Ser Glu Ile
                275                 280                 285
Thr Cys Val Cys Arg Asp Asn Trp His Gly Ser Asn Arg Pro Trp Val
            290                 295                 300
Ser Phe Asn Gln Asn Leu Glu Tyr Gln Ile Gly Tyr Ile Cys Ser Gly
305                 310                 315                 320
Ile Phe Gly Asp Asn Pro Arg Pro Asn Asp Lys Thr Gly Ser Cys Gly
                325                 330                 335
Pro Val Ser Ser Asn Gly Ala Asn Gly Val Lys Gly Phe Ser Phe Lys
                340                 345                 350
Tyr Gly Asn Gly Val Trp Ile Gly Arg Thr Lys Ser Ile Ser Ser Arg
                355                 360                 365
Asn Gly Phe Glu Met Ile Trp Asp Pro Asn Gly Trp Thr Gly Thr Asp
            370                 375                 380
Asn Asn Phe Ser Ile Lys Gln Asp Ile Val Gly Ile Asn Glu Trp Ser
385                 390                 395                 400
Gly Tyr Ser Gly Ser Phe Val Gln His Pro Glu Leu Thr Gly Leu Asp
                405                 410                 415
Cys Ile Arg Pro Cys Phe Trp Val Glu Leu Ile Arg Gly Arg Pro Lys
                420                 425                 430
Glu Asn Thr Ile Trp Thr Ser Gly Ser Ser Ile Ser Phe Cys Gly Val
                435                 440                 445
Asn Ser Asp Thr Val Gly Trp Ser Trp Pro Asp Gly Ala Glu Leu Pro
            450                 455                 460
Phe Thr Ile Asp Lys
465

<210> SEQ ID NO 52
<211> LENGTH: 470
<212> TYPE: PRT
<213> ORGANISM: Influenza virus

<400> SEQUENCE: 52

Met Asn Pro Asn Gln Lys Leu Phe Ala Leu Ser Gly Val Ala Ile Ala
1               5                   10                  15

Leu Ser Ile Leu Asn Leu Leu Ile Gly Ile Ser Asn Val Gly Leu Asn
                20                  25                  30

Val Ser Leu His Leu Lys Gly Ser Ser Asp Gln Asp Lys Asn Trp Thr
            35                  40                  45
```

```
Cys Thr Ser Val Thr Gln Asn Asn Thr Thr Leu Ile Glu Asn Thr Tyr
 50                  55                  60

Val Asn Asn Thr Thr Val Ile Asp Lys Glu Thr Gly Thr Ala Lys Pro
 65                  70                  75                  80

Asn Tyr Leu Met Leu Asn Lys Ser Leu Cys Lys Val Glu Gly Trp Val
                 85                  90                  95

Val Val Ala Lys Asp Asn Ala Ile Arg Phe Gly Glu Ser Glu Gln Ile
            100                 105                 110

Ile Val Thr Arg Glu Pro Tyr Val Ser Cys Asp Pro Leu Gly Cys Lys
            115                 120                 125

Met Tyr Ala Leu His Gln Gly Thr Thr Ile Arg Asn Lys His Ser Asn
    130                 135                 140

Gly Thr Ile His Asp Arg Thr Ala Phe Arg Gly Leu Ile Ser Thr Pro
145                 150                 155                 160

Leu Gly Ser Pro Pro Val Val Ser Asn Ser Asp Phe Leu Cys Val Gly
                165                 170                 175

Trp Ser Ser Thr Ser Cys His Asp Gly Ile Gly Arg Met Thr Ile Cys
            180                 185                 190

Val Gln Gly Asn Asn Asp Asn Ala Thr Ala Thr Val Tyr Tyr Asp Arg
        195                 200                 205

Arg Leu Thr Thr Thr Ile Lys Thr Trp Ala Gly Asn Ile Leu Arg Thr
        210                 215                 220

Gln Glu Ser Glu Cys Val Cys His Asn Gly Thr Cys Val Val Ile Met
225                 230                 235                 240

Thr Asp Gly Ser Ala Ser Ser Gln Ala Tyr Thr Lys Val Leu Tyr Phe
                245                 250                 255

His Lys Gly Leu Val Ile Lys Glu Glu Ala Leu Lys Gly Ser Ala Arg
            260                 265                 270

His Ile Glu Glu Cys Ser Cys Tyr Gly His Asn Ser Lys Val Thr Cys
        275                 280                 285

Val Cys Arg Asp Asn Trp Gln Gly Ala Asn Arg Pro Val Ile Glu Ile
        290                 295                 300

Asp Met Asn Ala Met Glu His Thr Ser Gln Tyr Leu Cys Thr Gly Val
305                 310                 315                 320

Leu Thr Asp Thr Ser Arg Pro Ser Asp Lys Ser Met Gly Asp Cys Asn
                325                 330                 335

Asn Pro Ile Thr Gly Ser Pro Gly Ala Pro Gly Val Lys Gly Phe Gly
            340                 345                 350

Phe Leu Asp Ser Ser Asn Thr Trp Leu Gly Arg Thr Ile Ser Pro Arg
        355                 360                 365

Ser Arg Ser Gly Phe Glu Met Leu Lys Ile Pro Asn Ala Glu Thr Asp
        370                 375                 380

Pro Asn Ser Lys Ile Thr Glu Arg Gln Glu Ile Val Asp Asn Asn Asn
385                 390                 395                 400

Trp Ser Gly Tyr Ser Gly Ser Phe Ile Asp Tyr Trp Asp Glu Ser Ser
                405                 410                 415

Glu Cys Tyr Asn Pro Cys Phe Tyr Val Glu Leu Ile Arg Gly Arg Pro
            420                 425                 430

Glu Glu Ala Lys Tyr Val Gly Trp Thr Ser Asn Ser Leu Ile Ala Leu
        435                 440                 445

Cys Gly Ser Pro Ile Ser Val Gly Ser Gly Ser Phe Pro Asp Gly Ala
450                 455                 460

Gln Ile Gln Tyr Phe Ser
```

```
                       465                 470

<210> SEQ ID NO 53
<211> LENGTH: 465
<212> TYPE: PRT
<213> ORGANISM: Influenza virus

<400> SEQUENCE: 53

Met Asn Pro Asn Gln Lys Ile Leu Cys Thr Ser Ala Thr Ala Ile Ile
1               5                   10                  15

Ile Gly Ala Ile Ala Val Leu Ile Gly Ile Ala Asn Leu Gly Leu Asn
            20                  25                  30

Ile Gly Leu His Leu Lys Pro Gly Cys Asn Cys Ser His Ser Gln Pro
        35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240

Gly Ser Ala Thr Gly Pro Ala Asp Thr Arg Ile Tyr Tyr Phe Lys Glu
                245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
        275                 280                 285

Arg Asp Asn Trp Gln Gly Ser Asn Arg Pro Val Ile Gln Ile Asp Pro
    290                 295                 300

Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
                325                 330                 335

Tyr Pro Gly Asn Asn Asn Asn Gly Val Lys Gly Phe Ser Tyr Leu Asp
            340                 345                 350

Gly Ala Asn Thr Trp Leu Gly Arg Thr Ile Ser Thr Ala Ser Arg Ser
        355                 360                 365
```

```
Gly Tyr Glu Met Leu Lys Val Pro Asn Ala Leu Thr Asp Asp Arg Ser
    370             375                 380
Lys Pro Ile Gln Gly Gln Thr Ile Val Leu Asn Ala Asp Trp Ser Gly
385             390                 395                 400
Tyr Ser Gly Ser Phe Met Asp Tyr Trp Ala Glu Gly Asp Cys Tyr Arg
                405                 410                 415
Ala Cys Phe Tyr Val Glu Leu Ile Arg Gly Arg Pro Lys Glu Asp Lys
                420                 425                 430
Val Trp Trp Thr Ser Asn Ser Ile Val Ser Met Cys Ser Ser Thr Glu
            435                 440                 445
Phe Leu Gly Gln Trp Asn Trp Pro Asp Gly Ala Lys Ile Glu Tyr Phe
450                 455                 460
Leu
465

<210> SEQ ID NO 54
<211> LENGTH: 469
<212> TYPE: PRT
<213> ORGANISM: Influenza virus

<400> SEQUENCE: 54

Met Asn Pro Asn Gln Lys Ile Ile Thr Ile Gly Ser Val Ser Leu Thr
1               5                   10                  15
Ile Ser Thr Ile Cys Phe Phe Met Gln Ile Ala Ile Leu Ile Thr Thr
            20                  25                  30
Val Thr Leu His Phe Lys Gln Tyr Glu Phe Asn Ser Pro Pro Asn Asn
        35                  40                  45
Gln Val Met Leu Cys Glu Pro Thr Ile Ile Glu Arg Asn Ile Thr Glu
    50                  55                  60
Ile Val Tyr Leu Thr Asn Thr Thr Ile Glu Lys Glu Ile Cys Pro Lys
65                  70                  75                  80
Leu Ala Glu Tyr Arg Asn Trp Ser Lys Pro Gln Cys Asn Ile Thr Gly
                85                  90                  95
Phe Ala Pro Phe Ser Lys Asp Asn Ser Ile Arg Leu Ser Ala Gly Gly
            100                 105                 110
Asp Ile Trp Val Thr Arg Glu Pro Tyr Val Ser Cys Asp Pro Asp Lys
        115                 120                 125
Cys Tyr Gln Phe Ala Leu Gly Gln Gly Thr Thr Leu Asn Asn Val His
    130                 135                 140
Ser Asn Asp Ile Val His Asp Arg Thr Pro Tyr Arg Thr Leu Leu Met
145                 150                 155                 160
Asn Glu Leu Gly Val Pro Phe His Leu Gly Thr Lys Gln Val Cys Ile
                165                 170                 175
Ala Trp Ser Ser Ser Cys His Asp Gly Lys Ala Trp Leu His Val
            180                 185                 190
Cys Val Thr Gly Asp Asp Glu Asn Ala Thr Ala Ser Phe Ile Tyr Asn
        195                 200                 205
Gly Arg Leu Ala Asp Ser Ile Val Ser Trp Ser Lys Lys Ile Leu Arg
    210                 215                 220
Thr Gln Glu Ser Glu Cys Val Cys Ile Asn Gly Thr Cys Thr Val Val
225                 230                 235                 240
Met Thr Asp Gly Ser Ala Ser Gly Lys Ala Asp Thr Lys Ile Leu Phe
                245                 250                 255
Ile Glu Glu Gly Lys Ile Val His Thr Ser Thr Leu Ser Gly Ser Ala
            260                 265                 270
```

-continued

```
Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
290                 295                 300

Ile Asn Ile Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
                340                 345                 350

Ala Phe Asp Asp Gly Asn Asp Val Trp Met Gly Arg Thr Ile Ser Glu
                355                 360                 365

Lys Leu Arg Ser Gly Tyr Glu Thr Phe Lys Val Ile Glu Gly Trp Ser
370                 375                 380

Asn Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
                420                 425                 430

Glu Thr Glu Val Leu Trp Thr Ser Asn Ser Ile Val Val Phe Cys Gly
                435                 440                 445

Thr Ser Gly Thr Tyr Gly Thr Gly Ser Trp Pro Asp Gly Ala Asp Ile
450                 455                 460

Asn Leu Met Pro Ile
465

<210> SEQ ID NO 55
<211> LENGTH: 469
<212> TYPE: PRT
<213> ORGANISM: Influenza virus

<400> SEQUENCE: 55

Met Asn Pro Asn Gln Lys Ile Ile Thr Ile Gly Ser Val Ser Leu Thr
1               5                   10                  15

Ile Ser Thr Ile Cys Phe Phe Met Gln Ile Ala Ile Leu Ile Thr Thr
                20                  25                  30

Val Thr Leu His Phe Lys Gln Tyr Glu Phe Asn Ser Pro Pro Asn Asn
            35                  40                  45

Gln Val Met Leu Cys Glu Pro Thr Ile Ile Glu Arg Asn Ile Thr Glu
50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Val His
        130                 135                 140

Ser Asn Asp Ile Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
```

```
                  165                 170                 175
Ala Trp Ser Ser Ser Cys His Asp Gly Lys Ala Trp Leu His Val
            180                 185                 190
Cys Val Thr Gly Asp Asp Glu Asn Ala Thr Ala Ser Phe Ile Tyr Asn
            195                 200                 205
Gly Arg Leu Ala Asp Ser Ile Val Ser Trp Ser Lys Lys Ile Leu Arg
            210                 215                 220
Thr Gln Glu Ser Glu Cys Val Cys Ile Asn Gly Thr Cys Thr Val Val
225                 230                 235                 240
Met Thr Asp Gly Ser Ala Ser Gly Lys Ala Asp Thr Lys Ile Leu Phe
            245                 250                 255
Ile Glu Glu Gly Lys Ile Val His Thr Ser Thr Leu Ser Gly Ser Ala
            260                 265                 270
Gln His Val Glu Glu Cys Ser Cys Tyr Pro Arg Tyr Pro Gly Val Arg
            275                 280                 285
Cys Val Cys Arg Asp Asn Trp Lys Gly Ser Asn Arg Pro Ile Val Asp
            290                 295                 300
Ile Asn Ile Lys Asp Tyr Ser Ile Val Ser Ser Tyr Val Cys Ser Gly
305                 310                 315                 320
Leu Val Gly Asp Thr Pro Arg Lys Asn Asp Ser Ser Ser Ser His
            325                 330                 335
Cys Leu Asp Pro Asn Asn Glu Glu Gly Gly His Gly Val Lys Gly Trp
            340                 345                 350
Ala Phe Asp Asp Gly Asn Asp Val Trp Met Gly Arg Thr Ile Ser Glu
            355                 360                 365
Lys Leu Arg Ser Gly Tyr Glu Thr Phe Lys Val Ile Glu Gly Trp Ser
            370                 375                 380
Asn Pro Asn Ser Lys Leu Gln Ile Asn Arg Gln Val Ile Val Asp Arg
385                 390                 395                 400
Gly Asn Arg Ser Gly Tyr Ser Gly Ile Phe Ser Val Glu Gly Lys Ser
            405                 410                 415
Cys Ile Asn Arg Cys Phe Tyr Val Glu Leu Ile Arg Gly Arg Lys Gln
            420                 425                 430
Glu Thr Glu Val Leu Trp Thr Ser Asn Ser Ile Val Val Phe Cys Gly
            435                 440                 445
Thr Ser Gly Thr Tyr Gly Thr Gly Ser Trp Pro Asp Gly Ala Asp Ile
            450                 455                 460
Asn Leu Met Pro Ile
465

<210> SEQ ID NO 56
<211> LENGTH: 1467
<212> TYPE: DNA
<213> ORGANISM: Influenza virus

<400> SEQUENCE: 56
agcaaaagca ggagtaaaga tgaatccaaa tcaaaagata taacgattg gctctgtttc      60 cctcaccatt tccacaatat gcttcttcat gcaaattgcc atcctgataa ctactgtaac    120
attgcatttc aagcaatatg aattcaactc ccccccaaac aaccaagtga tgctgtgtga    180
accaacaata atagaaagaa acataacaga gatagtgtat ctgaccaaca ccaccataga    240
gaaggaaata tgccccaaac tagcagaata cagaaattgg tcaaagccgc aatgtaacat    300
tacaggattt gcacctttttt ctaaggacaa ttcgattcgg ctttccgctg gtggggacat    360
```

```
ctgggtgaca agagaaccct tatgtgtcatg cgatcctgac aagtgttatc aatttgccct    420
tggacaggga acaacactaa acaacgtgca ttcaaatgac atagtacatg ataggacccc    480
ttatcggacc ctattgatga atgagttggg tgttccattt catctgggga ccaagcaagt    540
gtgcatagca tggtccagct caagttgtca cgatggaaaa gcatggctgc atgtttgtgt    600
aacgggggat gatgaaaatg caactgctag cttcatttac aatgggaggc ttgcagatag    660
tattgtttca tggtccaaaa aaatcctcag gacccaggag tcagaatgcg tttgtatcaa    720
tggaacttgt acagtagtaa tgactgatgg gagtgcttca ggaaaagctg atactaaaat    780
actattcatt gaggagggga aaattgttca ctactagcaca ttatcaggaa gtgctcagca    840
tgtcgaggag tgctcctgtt atcctcgata tcctggtgtc agatgtgtct gcagagacaa    900
ctggaaaggc tccaataggc ccatcgtaga tataaacata aaggattata gcattgtttc    960
cagttatgtg tgctcaggac ttgttggaga cacacccaga aaaaacgaca gctccagcag   1020
tagccattgc ttggatccaa acaatgagga aggtggtcat ggagtgaaag gctgggcctt   1080
tgatgatgga aatgacgtgt ggatgggaag aacgatcagc gagaagttac gctcaggata   1140
tgaaaccttc aaagtcattg aaggctggtc caaccctaac tccaaattgc agataaatag   1200
gcaagtcata gttgacagag gtaacaggtc cggttattct ggtatttttct ctgttgaagg   1260
caaaagctgc atcaatcggt gcttttatgt ggagttgata aggggaagaa acaggaaac    1320
tgaagtcttg tggacctcaa acagtattgt tgtgttttgt ggcacctcag gtacatatgg   1380
aacaggctca tggcctgatg gggcggacat caatctcatg cctatataag ctttcgcaat   1440
tttagaaaaa aactccttgt ttctact                                       1467
```

<210> SEQ ID NO 57
<211> LENGTH: 469
<212> TYPE: PRT
<213> ORGANISM: Influenza virus

<400> SEQUENCE: 57

Met Asn Pro Asn Gln Lys Ile Ile Thr Ile Gly Ser Val Ser Leu Thr
1               5                   10                  15

Ile Ala Thr Ile Cys Phe Leu Met Gln Ile Ala Ile Leu Val Thr Thr
            20                  25                  30

Val Thr Leu His Phe Lys Gln Tyr Glu Cys Asn Ser Pro Pro Asn Asn
        35                  40                  45

Gln Val Met Leu Cys Glu Pro Thr Ile Ile Glu Arg Asn Ile Thr Glu
    50                  55                  60

Ile Val Tyr Leu Thr Asn Thr Thr Ile Glu Lys Glu Ile Cys Pro Lys
65                  70                  75                  80

Leu Ala Glu Tyr Arg Asn Trp Ser Lys Pro Gln Cys Asn Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asp Lys
        115                 120                 125

Cys Tyr Gln Phe Ala Leu Gly Gln Gly Thr Thr Leu Asn Asn Gly His
    130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Ser Cys His Asp Gly Lys Ala Trp Leu His Val
            180                 185                 190

Cys Val Thr Gly Asp Asp Gly Asn Ala Thr Ala Ser Phe Ile Tyr Asn
            195                 200                 205

Gly Arg Leu Val Asp Ser Ile Gly Ser Trp Ser Lys Lys Ile Leu Arg
        210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Lys Ile Leu Phe
                245                 250                 255

Ile Glu Glu Gly Lys Ile Val His Thr Ser Leu Leu Ser Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
    290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asn Asp Ser Ser Ser Ser His
                325                 330                 335

Cys Leu Asp Pro Asn Asn Glu Glu Gly Gly His Gly Val Lys Gly Trp
            340                 345                 350

Ala Phe Asp Asp Gly Asn Asp Val Trp Met Gly Arg Thr Ile Ser Glu
        355                 360                 365

Lys Leu Arg Ser Gly Tyr Glu Thr Phe Lys Val Ile Glu Gly Trp Ser
    370                 375                 380

Lys Pro Asn Ser Lys Leu Gln Ile Asn Arg Gln Val Ile Val Asp Arg
385                 390                 395                 400

Gly Asn Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Asn Gln
            420                 425                 430

Glu Thr Glu Val Leu Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 58
<211> LENGTH: 759
<212> TYPE: PRT
<213> ORGANISM: Influenza virus

<400> SEQUENCE: 58

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

```
Met Asn Asp Ala Gly Ser Asp Arg Val Met Val Ser Pro Leu Ala Val
                85                  90                  95

Thr Trp Trp Asn Arg Asn Gly Pro Met Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Lys Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Asp Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Val Leu Thr Gly Asn Leu Gln Thr Leu
            340                 345                 350

Lys Ile Arg Val His Glu Gly Ser Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495
```

-continued

```
Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
        530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Ala Gln Ile Ile Lys Leu Leu Pro Phe Ala Ala Ala
610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Arg Arg Tyr
690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
            755

<210> SEQ ID NO 59
<211> LENGTH: 757
<212> TYPE: PRT
<213> ORGANISM: Influenza virus

<400> SEQUENCE: 59

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110
```

```
Val Val Gln Gln Thr Arg Val Asp Lys Leu Thr Gln Gly Arg Gln Thr
            115                 120                 125

Tyr Asp Trp Thr Leu Asn Arg Asn Gln Pro Ala Ala Thr Ala Leu Ala
        130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Val Arg
            180                 185                 190

Asp Asn Met Thr Lys Lys Met Ile Thr Gln Arg Thr Ile Gly Lys Arg
            195                 200                 205

Lys Gln Arg Leu Asn Lys Arg Gly Tyr Leu Ile Arg Ala Leu Thr Leu
        210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
        290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365

Pro Ala Glu Met Leu Ala Ser Ile Asp Leu Lys Tyr Phe Asn Asp Ser
        370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Gly Met Phe Asn Met Leu Ser
            405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Glu Gly Ile Gln Ala Gly Val Asp
        450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525
```

```
Val Ile Lys Asn Asn Met Ile Asn Asn Asp Leu Gly Pro Ala Thr Ala
        530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
                580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
        610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Val Leu Glu Asp Glu Gln Met
            675                 680                 685

Tyr Gln Arg Cys Cys Asn Leu Phe Glu Lys Phe Phe Pro Ser Ser Ser
        690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
                740                 745                 750

Leu Arg Arg Gln Lys
            755

<210> SEQ ID NO 60
<211> LENGTH: 716
<212> TYPE: PRT
<213> ORGANISM: Influenza virus

<400> SEQUENCE: 60

Met Glu Asp Phe Val Arg Gln Cys Phe Asn Pro Met Ile Val Glu Leu
1               5                   10                  15

Ala Glu Lys Thr Met Lys Glu Tyr Gly Glu Asp Leu Lys Ile Glu Thr
                20                  25                  30

Asn Lys Phe Ala Ala Ile Cys Thr His Leu Glu Val Cys Phe Met Tyr
            35                  40                  45

Ser Asp Phe His Phe Ile Asn Glu Gln Gly Glu Ser Ile Ile Val Glu
        50                  55                  60

Leu Gly Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140
```

```
Ile His Ile Phe Ser Phe Thr Gly Glu Glu Met Ala Thr Arg Ala Asp
145                 150                 155                 160

Tyr Thr Leu Asp Glu Glu Ser Arg Ala Arg Ile Lys Thr Arg Leu Phe
            165                 170                 175

Thr Ile Arg Gln Glu Met Ala Ser Arg Gly Leu Trp Asp Ser Phe Arg
            180                 185                 190

Gln Ser Glu Arg Gly Glu Glu Thr Ile Glu Glu Arg Phe Glu Ile Thr
            195                 200                 205

Gly Thr Met Arg Lys Leu Ala Asp Gln Ser Leu Pro Pro Asn Phe Ser
            210                 215                 220

Ser Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Arg
                245                 250                 255

Ile Glu Pro Phe Leu Lys Thr Thr Pro Arg Pro Leu Arg Leu Pro Asn
            260                 265                 270

Gly Pro Pro Cys Ser Gln Arg Ser Lys Phe Leu Leu Met Asp Ala Leu
            275                 280                 285

Lys Leu Ser Ile Glu Asp Pro Ser His Glu Gly Glu Gly Ile Pro Leu
290                 295                 300

Tyr Asp Ala Ile Lys Cys Met Arg Thr Phe Phe Gly Trp Lys Glu Pro
305                 310                 315                 320

Asn Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Lys Thr Lys Asn Met Lys Lys Thr Ser Gln Leu Lys Trp
            355                 360                 365

Ala Leu Gly Glu Asn Met Ala Pro Glu Lys Val Asp Phe Asp Asp Cys
            370                 375                 380

Lys Asp Val Gly Asp Leu Lys Gln Tyr Asp Ser Asp Glu Pro Glu Leu
385                 390                 395                 400

Arg Ser Leu Ala Ser Trp Ile Gln Asn Glu Phe Asn Lys Ala Cys Glu
                405                 410                 415

Leu Thr Asp Ser Ser Trp Ile Glu Leu Asp Glu Ile Gly Glu Asp Val
            420                 425                 430

Ala Pro Ile Glu His Ile Ala Ser Met Arg Arg Asn Tyr Phe Thr Ser
            435                 440                 445

Glu Val Ser His Cys Arg Ala Thr Glu Tyr Ile Met Lys Gly Val Tyr
            450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
            485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
            515                 520                 525

Asp Pro Arg Leu Glu Pro His Lys Trp Glu Lys Tyr Cys Val Leu Glu
            530                 535                 540

Ile Gly Asp Met Leu Leu Arg Ser Ala Ile Gly Gln Val Ser Arg Pro
545                 550                 555                 560
```

```
Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Ser Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Ile Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Leu Ser
705                 710                 715

<210> SEQ ID NO 61
<211> LENGTH: 498
<212> TYPE: PRT
<213> ORGANISM: Influenza virus

<400> SEQUENCE: 61

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220
```

-continued

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
            245                 250                 255

Thr Phe Leu Ala Arg Ser Ala Leu Ile Leu Arg Gly Ser Val Ala His
        260                 265                 270

Lys Ser Cys Leu Pro Ala Cys Val Tyr Gly Pro Ala Val Ala Ser Gly
    275                 280                 285

Tyr Asp Phe Glu Arg Glu Gly Tyr Ser Leu Val Gly Ile Asp Pro Phe
290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Val Pro Arg Gly Lys Leu Ser Thr Arg Gly Val Gln Ile Ala Ser Asn
        355                 360                 365

Glu Asn Met Glu Thr Met Glu Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Val Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 62
<211> LENGTH: 252
<212> TYPE: PRT
<213> ORGANISM: Influenza virus

<400> SEQUENCE: 62

Met Ser Leu Leu Thr Glu Val Glu Thr Tyr Val Leu Ser Ile Ile Pro
1               5                   10                  15

Ser Gly Pro Leu Lys Ala Glu Ile Ala Gln Arg Leu Glu Asp Val Phe
            20                  25                  30

Ala Gly Lys Asn Thr Asp Leu Glu Val Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
65                  70                  75                  80

Gln Asn Ala Leu Asn Gly Asn Gly Asp Pro Asn Asn Met Asp Lys Ala
                85                  90                  95

-continued

```
Val Lys Leu Tyr Arg Lys Leu Lys Arg Glu Ile Thr Phe His Gly Ala
                100             105             110

Lys Glu Ile Ser Leu Ser Tyr Ser Ala Gly Ala Leu Ala Ser Cys Met
            115             120             125

Gly Leu Ile Tyr Asn Arg Met Gly Ala Val Thr Thr Glu Val Ala Phe
        130             135             140

Gly Leu Val Cys Ala Thr Cys Glu Gln Ile Ala Asp Ser Gln His Arg
145             150             155             160

Ser His Arg Gln Met Val Thr Thr Thr Asn Pro Leu Ile Arg His Glu
                165             170             175

Asn Arg Met Val Leu Ala Ser Thr Thr Ala Lys Ala Met Glu Gln Met
            180             185             190

Ala Gly Ser Ser Glu Gln Ala Ala Glu Ala Met Glu Val Ala Ser Gln
        195             200             205

Ala Arg Gln Met Val Gln Ala Met Arg Thr Ile Gly Thr His Pro Ser
    210             215             220

Ser Ser Ala Gly Leu Lys Asn Asp Leu Leu Glu Asn Leu Gln Ala Tyr
225             230             235             240

Gln Lys Arg Met Gly Val Gln Met Gln Arg Phe Lys
                245             250
```

What is claimed is:

1. An isolated recombinant influenza virus comprising a selected NA viral segment encoding at least three selected residues in NA, wherein the residues are selected from residue A, I, G, or L at position 32; the residue N or Q at position 147: residue K, R or H at position 148: residue E, N or Q at position 151: residue S, T, I, L, A, N, W, Y, P, V, or G at position 245; residue D or E at position 329: residue S, T, P, Y, W, A, N, I, L, or V at position 346: residue G, Q, S, T, Y, C or W at position 347, or any combination thereof, wherein the numbering is relative to SEQ ID NO:3, wherein the recombinant influenza virus has enhanced replication in avian eggs or has a reduction in HA mutations when grown in avian eggs relative to a corresponding influenza virus that has a NA that encodes a threonine at residue 32, does not have a deletion of residues 46 to 50, encodes an aspartic acid at position 147, encodes a threonine at residue 148, encodes an aspartic acid at residue 151, encodes an asparagine at residue 245, encodes an asparagine at residue 329, encodes a glycine at residue 346, encodes a histidine at residue 347, or any combination thereof.

2. The isolated recombinant influenza virus of claim 1 wherein the NA viral segment encodes a NA that has at least 90% amino acid sequence identity to SEQ ID NO:1, SEQ ID NO:2, SEQ ID NO:3, SEQ ID NO:48, SEQ ID NO:49, SEQ ID NO:50 or SEQ ID NO:54.

3. The isolated recombinant influenza virus of claim 1 wherein the NA viral segment encodes a N2, N3, N7, or N9.

4. The isolated recombinant influenza virus of claim 1 wherein the residue at position 32 is A; the residue at position 147 is N; the residue at position 148 is K; the residue at position 151 is E; the residue at position 245 is S; the residue at position 329 is D; the residue at position 346 is V; the residue at position 347 is Q; or any combination thereof.

5. The isolated recombinant influenza virus of claim 1 wherein the residue at position 147 is N or Q, the residue at position 329 is D or E, the residue at position 347 is G or Q, or any combination thereof.

6. The isolated recombinant influenza virus of claim 1 wherein the residue at position 148 is K, R or H, the residue at position 151 is E, N or Q, the residue at position 245 is S, T, I, L, A, or V, or any combination thereof.

7. The isolated recombinant influenza virus of claim 1 which comprises PA, PB1, PB2, NP, M, and NS viral segments having at least 85% nucleic acid sequence identity to SEQ ID NOS: 24 to 29 or 39 to 44 or encoding a polypeptide having at least 80% amino acid sequence identity to a polypeptide encoded by SEQ ID NOS: 24 to 29 or 39 to 44.

8. A method to prepare influenza virus, comprising: contacting a cell with:
a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS DNA linked to a transcription termination sequence, wherein the PB1, PB2, PA, NP, NS, and M DNAs in the vectors for vRNA production are from one or more influenza vaccine virus isolates, wherein the NA DNA in the vector for vRNA production encodes a NA having at least three residues selected from residue A, I, G, L at position 32: the residue N or Q at position 147; residue K, R or H at position 148; residue E, N or Q at position 151; residue S, T, I, L, A, N, W, Y, P, V, or G at position 245; residue D or E at position 329; residue S, T, P, Y, W, A, N, I, L, or V at position 346; residue G, Q, S, T, Y, C or W at position 347, or any combination thereof, wherein the numbering for NA residues is relative to SEQ ID NO:3; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1 a vector for mRNA production comprising a promoter operably linked to a DNA segment encoding influenza virus M2, or a vector for mRNA production comprising a promoter operably linked to a DNA segment encoding influenza virus NS2; in an amount effective to yield infectious influenza virus.

9. The method of claim 8 wherein the NA has at least 90% amino acid sequence identity to SEQ ID NO:1, SEQ ID NO:2, SEQ ID NO:3, SEQ ID NO:48, SEQ ID NO:49, or SEQ ID NO:54.

10. The method of claim 8 wherein the residue at position 147 is N; the residue at position 329 is D; the residue at position 347 is Q; the residue at position 151 is E; the residue at position 148 is K; or the residue at position 245 is S.

11. The method of claim 8 wherein the virus comprises PA, PB1, PB2, NP, M, and NS viral segments having at least 85% nucleic acid sequence identity to SEQ ID NOS: 24 to 29 or 39 to 44 or encoding a polypeptide having at least 80% amino acid sequence identity to a polypeptide encoded by SEQ ID NOS: 24 to 29 or 39 to 44.

12. An isolated virus prepared by the method of claim 8.

13. A method of immunizing an avian or a mammal, comprising: administering to the avian or the mammal a composition having an effective amount of the virus of claim 1.

14. The method of claim 13 wherein the composition comprises at least one other different influenza virus.

15. The method of claim 13 wherein the mammal is a human.

16. The method of claim 13 wherein the composition is administered intranasally.

17. The method of claim 13 wherein the composition is administered via injection.

18. A method comprising passaging the virus of claim 1 in eggs.

* * * * *